United States Patent
Chin et al.

(10) Patent No.: US 11,827,609 B2
(45) Date of Patent: Nov. 28, 2023

(54) TOLL LIKE RECEPTOR MODULATOR COMPOUNDS

(71) Applicant: GILEAD SCIENCES, INC., Foster City, CA (US)

(72) Inventors: Gregory Chin, San Francisco, CA (US); Richard L. Mackman, Millbrae, CA (US); Michael R. Mish, Foster City, CA (US); Jeff Zablocki, Los Altos, CA (US)

(73) Assignee: Gilead Sciences, Inc., Foster City, CA (US)

( * ) Notice: Subject to any disclaimer, the term of this patent is extended or adjusted under 35 U.S.C. 154(b) by 0 days.

(21) Appl. No.: 17/399,984

(22) Filed: Aug. 11, 2021

(65) Prior Publication Data

US 2022/0073473 A1    Mar. 10, 2022

Related U.S. Application Data

(62) Division of application No. 16/441,339, filed on Jun. 14, 2019, now Pat. No. 11,124,487, which is a division of application No. 15/692,093, filed on Aug. 31, 2017, now Pat. No. 10,370,342.

(60) Provisional application No. 62/383,162, filed on Sep. 2, 2016.

(51) Int. Cl.
| | |
|---|---|
| *C07D 239/95* | (2006.01) |
| *A61P 31/18* | (2006.01) |
| *A61P 35/00* | (2006.01) |
| *A61K 31/517* | (2006.01) |
| *A61K 31/519* | (2006.01) |
| *A61K 45/06* | (2006.01) |
| *C07D 471/04* | (2006.01) |
| *C07D 487/04* | (2006.01) |
| *C07D 495/04* | (2006.01) |

(52) U.S. Cl.
CPC .......... *C07D 239/95* (2013.01); *A61K 31/517* (2013.01); *A61K 31/519* (2013.01); *A61K 45/06* (2013.01); *A61P 31/18* (2018.01); *A61P 35/00* (2018.01); *C07D 471/04* (2013.01); *C07D 487/04* (2013.01); *C07D 495/04* (2013.01)

(58) Field of Classification Search
CPC .................................................... C07D 239/95
See application file for complete search history.

(56) References Cited

U.S. PATENT DOCUMENTS

| | | |
|---|---|---|
| 2,512,572 A | 6/1950 | Smith, Jr. et al. |
| 2,581,889 A | 1/1952 | Millward |
| 2,665,275 A | 1/1954 | Robert et al. |
| 2,667,486 A | 1/1954 | Cain |
| 2,740,784 A | 4/1956 | Meyer et al. |
| 2,939,882 A | 6/1960 | Mecorney |
| 2,940,972 A | 6/1960 | Josef |
| 3,071,587 A | 1/1963 | Curran et al. |
| 3,081,230 A | 3/1963 | Joseph et al. |
| 3,122,546 A | 2/1964 | Osdene |
| 3,159,628 A | 12/1964 | Pachter et al. |
| 3,162,635 A | 12/1964 | Schroeder Elmer F |
| 3,475,425 A | 10/1969 | Roch Josef |
| 3,843,791 A | 10/1974 | Mcfarland |
| 3,859,287 A | 1/1975 | Parish et al. |
| 4,438,128 A | 3/1984 | Wiedemann et al. |
| 4,608,383 A | 8/1986 | Wiedemann et al. |
| 5,047,405 A | 9/1991 | Gennari |
| 5,064,833 A | 11/1991 | Ife et al. |
| 5,281,603 A | 1/1994 | Venkatesan et al. |
| 5,300,509 A | 4/1994 | Block et al. |
| 5,354,776 A | 10/1994 | Chandraratna |
| 5,380,724 A | 1/1995 | Zubovics et al. |
| 5,500,428 A | 3/1996 | Block et al. |
| 5,534,518 A | 7/1996 | Henrie et al. |
| 5,641,783 A | 6/1997 | Klein et al. |
| 5,665,772 A | 9/1997 | Cottens et al. |
| 5,707,998 A | 1/1998 | Takase et al. |
| 5,780,462 A | 7/1998 | Lee et al. |
| 5,843,943 A | 12/1998 | Carson et al. |
| 5,866,572 A | 2/1999 | Barker et al. |
| 5,929,046 A | 7/1999 | Mcmurry et al. |
| 5,955,464 A | 9/1999 | Barker |
| 5,992,713 A | 11/1999 | Manabat |
| 6,043,228 A | 3/2000 | Mcmurry et al. |
| 6,203,723 B1 | 3/2001 | Hsu |
| 6,331,547 B1 | 12/2001 | Zhu et al. |
| 6,440,991 B1 | 8/2002 | Zhu et al. |
| 6,559,149 B1 | 5/2003 | Matsuoka et al. |
| 6,844,343 B1 | 1/2005 | Pfleiderer et al. |
| 6,946,465 B2 | 9/2005 | Waer et al. |
| 7,074,801 B1 | 7/2006 | Yoshida et al. |

(Continued)

FOREIGN PATENT DOCUMENTS

| | | |
|---|---|---|
| CH | 231852 A | 4/1944 |
| CN | 1583747 A | 2/2005 |

(Continued)

OTHER PUBLICATIONS

American Chemical Society, 2022, Chemical Abstracts Service Registry Nos. 106941-25-7 and 142340-99-6, 1 page.
Balbach, et al. "Pharmaceutical evaluation of early development candidates "the 100-mg approach1"", International J. Pharmaceutics, vol. 275, pp. 1-12 (2004).
"International Nonproprietary Names for Pharmaceutical Substances (INN)", Who Drug Information, 2018, 32, 4, 559-690.
"Selgantolimod (GS-9688)", MedChemExpress 2022, 3 pages.
"Selgantolimod", PubChem CID 122585078, 15 pages, Mar. 14, 2022.

(Continued)

*Primary Examiner* — Susanna Moore
(74) *Attorney, Agent, or Firm* — Mintz, Levin, Cohn, Ferris, Glovsky and Popeo, P.C.

(57) ABSTRACT

This application relates generally to toll like receptor modulator compounds and pharmaceutical compositions which, among other things, modulate toll-like receptors (e.g. TLR8), and methods of making and using them.

11 Claims, No Drawings

(56) References Cited

U.S. PATENT DOCUMENTS

| | | |
|---|---|---|
| 7,276,506 B2 | 10/2007 | Waer et al. |
| 7,501,513 B2 | 3/2009 | Waer et al. |
| 7,928,111 B2 | 4/2011 | Tachdjian et al. |
| 8,143,394 B2 | 3/2012 | Watkins et al. |
| 8,232,278 B2 | 7/2012 | De et al. |
| 8,338,435 B2 | 12/2012 | Herdewijn et al. |
| 8,367,670 B2 | 2/2013 | Desai et al. |
| 8,536,187 B2 | 9/2013 | Zhang et al. |
| 8,541,421 B2 | 9/2013 | Tachdjian et al. |
| 8,633,186 B2 | 1/2014 | Tachdjian et al. |
| 8,637,531 B2 | 1/2014 | Bondy et al. |
| 8,673,929 B2 | 3/2014 | Gao et al. |
| 8,729,089 B2 | 5/2014 | Bondy et al. |
| 8,901,133 B2 | 12/2014 | Ren et al. |
| 8,916,575 B2 | 12/2014 | Mcgowan et al. |
| 8,969,363 B2 | 3/2015 | Castro et al. |
| 9,181,276 B2 | 11/2015 | Tachdjian et al. |
| 9,259,426 B2 | 2/2016 | Gao et al. |
| 9,603,848 B2 | 3/2017 | Servant et al. |
| 9,670,205 B2 | 6/2017 | Aktoudianakis et al. |
| 10,144,736 B2 | 12/2018 | Herdewijn et al. |
| 10,285,990 B2 | 5/2019 | Aktoudianakis et al. |
| 10,370,342 B2 | 8/2019 | Chin et al. |
| 10,640,499 B2 | 5/2020 | Chin et al. |
| 10,882,851 B2 | 1/2021 | Gao et al. |
| 11,124,487 B2 | 9/2021 | Chin et al. |
| 11,286,257 B2 | 3/2022 | Ambrosi et al. |
| 11,396,509 B2 | 7/2022 | Asselin et al. |
| 11,517,567 B2 | 12/2022 | Li |
| 11,583,531 B2 | 2/2023 | Asselin et al. |
| 2003/0236255 A1 | 12/2003 | Waer et al. |
| 2004/0030156 A1 | 2/2004 | Maul et al. |
| 2004/0038856 A1 | 2/2004 | Chakravarty et al. |
| 2004/0102447 A1 | 5/2004 | Bonnert et al. |
| 2004/0167121 A1 | 8/2004 | Aronov et al. |
| 2004/0167198 A1 | 8/2004 | Wrasidlo et al. |
| 2005/0054626 A1 | 3/2005 | Cherney et al. |
| 2005/0054653 A1 | 3/2005 | Eisenbrand et al. |
| 2005/0191238 A1 | 9/2005 | Casebier et al. |
| 2005/0282814 A1 | 12/2005 | Wrasidlo et al. |
| 2006/0116371 A1 | 6/2006 | Martyres et al. |
| 2007/0004721 A1 | 1/2007 | Waer et al. |
| 2007/0043000 A1 | 2/2007 | Waer et al. |
| 2007/0054916 A1 | 3/2007 | Patel et al. |
| 2007/0287704 A1 | 12/2007 | Dollinger et al. |
| 2008/0004285 A1 | 1/2008 | De et al. |
| 2008/0027062 A1 | 1/2008 | Doblhofer et al. |
| 2008/0096883 A1 | 4/2008 | Caravatti et al. |
| 2008/0112884 A1 | 5/2008 | Casebier et al. |
| 2008/0182870 A1 | 7/2008 | Bondy et al. |
| 2008/0234251 A1 | 9/2008 | Doherty et al. |
| 2008/0306053 A1 | 12/2008 | Tachdjian et al. |
| 2008/0306093 A1 | 12/2008 | Servant et al. |
| 2008/0312227 A1 | 12/2008 | De et al. |
| 2009/0036430 A1 | 2/2009 | De et al. |
| 2009/0131414 A1 | 5/2009 | De et al. |
| 2009/0253696 A1 | 10/2009 | Herdewijn et al. |
| 2009/0318456 A1 | 12/2009 | Herdewijn et al. |
| 2009/0318471 A1 | 12/2009 | Sieger et al. |
| 2010/0029585 A1 | 2/2010 | Howbert et al. |
| 2010/0143299 A1 | 6/2010 | Gao et al. |
| 2010/0143301 A1 | 6/2010 | Desai et al. |
| 2010/0305117 A1 | 12/2010 | Herdewijn et al. |
| 2011/0053997 A1 | 3/2011 | Beliaev et al. |
| 2011/0098248 A1 | 4/2011 | Halcomb et al. |
| 2011/0224155 A1 | 9/2011 | Tachdjian et al. |
| 2011/0230502 A1 | 9/2011 | Tachdjian et al. |
| 2012/0122838 A1 | 5/2012 | Ren et al. |
| 2012/0238587 A1 | 9/2012 | Lee et al. |
| 2013/0029982 A1 | 1/2013 | Castro et al. |
| 2013/0109693 A1 | 5/2013 | Routier et al. |
| 2014/0235623 A1 | 8/2014 | Tachdjian et al. |
| 2016/0289229 A1 | 10/2016 | Aktoudianakis et al. |
| 2017/0071944 A1 | 3/2017 | Geleziunas et al. |
| 2019/0152974 A1 | 5/2019 | Herdewijn et al. |
| 2020/0017451 A1 | 1/2020 | Chin et al. |
| 2020/0345738 A1 | 11/2020 | Asselin et al. |
| 2020/0347051 A1 | 11/2020 | Asselin et al. |
| 2021/0017170 A1 | 1/2021 | Aktoudianakis et al. |
| 2021/0276988 A1 | 9/2021 | Gao et al. |
| 2022/0218709 A1 | 7/2022 | Aktoudianakis et al. |
| 2022/0274985 A1 | 9/2022 | Ambrosi et al. |

FOREIGN PATENT DOCUMENTS

| | | |
|---|---|---|
| DE | 1921308 A1 | 1/1971 |
| DE | 267495 A1 | 5/1989 |
| DE | 4009941 A1 | 10/1991 |
| EP | 0042593 A1 | 12/1981 |
| EP | 0108890 A2 | 5/1984 |
| EP | 0134922 A1 | 3/1985 |
| EP | 0185259 A2 | 6/1986 |
| EP | 0290819 A2 | 11/1988 |
| EP | 0322133 A1 | 6/1989 |
| EP | 0362645 A2 | 4/1990 |
| EP | 0404322 A1 | 12/1990 |
| EP | 0404355 A1 | 12/1990 |
| EP | 0544445 A2 | 6/1993 |
| EP | 0574906 A2 | 12/1993 |
| EP | 0837063 A1 | 4/1998 |
| EP | 0956855 A1 | 11/1999 |
| EP | 1144412 A1 | 10/2001 |
| EP | 1382603 A1 | 1/2004 |
| EP | 1479682 A1 | 11/2004 |
| EP | 1724268 A1 | 11/2006 |
| EP | 3097102 B1 | 10/2017 |
| EP | 2709989 B1 | 12/2017 |
| EP | 3321265 A1 | 5/2018 |
| GB | 677342 A | 8/1952 |
| GB | 763044 A | 12/1956 |
| GB | 785353 A | 10/1957 |
| GB | 1301319 A | 12/1972 |
| GB | 2143232 A | 2/1985 |
| GB | 2405793 A | 3/2005 |
| JP | H07138238 A | 5/1995 |
| JP | 2000038350 A | 2/2000 |
| JP | 2000053653 A | 2/2000 |
| JP | 2000053654 A | 2/2000 |
| WO | 9307124 A1 | 4/1993 |
| WO | 9325712 A1 | 12/1993 |
| WO | 9406431 A1 | 3/1994 |
| WO | 9411001 A1 | 5/1994 |
| WO | 9414065 A1 | 6/1994 |
| WO | 9422449 A1 | 10/1994 |
| WO | 9422855 A1 | 10/1994 |
| WO | 9427439 A1 | 12/1994 |
| WO | 9513075 A1 | 5/1995 |
| WO | 9531469 A1 | 11/1995 |
| WO | 9531987 A1 | 11/1995 |
| WO | 9532203 A2 | 11/1995 |
| WO | 9610568 A1 | 4/1996 |
| WO | 9616960 A1 | 6/1996 |
| WO | 9620710 A1 | 7/1996 |
| WO | 9723616 A1 | 7/1997 |
| WO | 9730034 A1 | 8/1997 |
| WO | 9731920 A1 | 9/1997 |
| WO | 9739358 A1 | 10/1997 |
| WO | 9804558 A1 | 2/1998 |
| WO | 9808516 A1 | 3/1998 |
| WO | 9852948 A1 | 11/1998 |
| WO | 9950264 A1 | 10/1999 |
| WO | 0039129 A1 | 7/2000 |
| WO | 0045800 A2 | 8/2000 |
| WO | 0119825 A1 | 3/2001 |
| WO | 0121619 A1 | 3/2001 |
| WO | 0232507 A1 | 4/2002 |
| WO | 03001887 A2 | 1/2003 |
| WO | 03031406 A2 | 4/2003 |
| WO | 03062240 A1 | 7/2003 |
| WO | 2004026307 A1 | 4/2004 |
| WO | 2004065392 A1 | 8/2004 |
| WO | 2004072033 A2 | 8/2004 |
| WO | 2004104005 A2 | 12/2004 |
| WO | 2005020899 A2 | 3/2005 |

(56) References Cited

FOREIGN PATENT DOCUMENTS

| | | | |
|---|---|---|---|
| WO | 2005021003 A2 | 3/2005 |
| WO | 2005025574 A2 | 3/2005 |
| WO | 2005028444 A1 | 3/2005 |
| WO | 2005039587 A1 | 5/2005 |
| WO | 2005046698 A1 | 5/2005 |
| WO | 2005063752 A1 | 7/2005 |
| WO | 2005073204 A1 | 8/2005 |
| WO | 2005079391 A2 | 9/2005 |
| WO | 2005080377 A1 | 9/2005 |
| WO | 2005105761 A1 | 11/2005 |
| WO | 2006015859 A1 | 2/2006 |
| WO | 2006039718 A2 | 4/2006 |
| WO | 2006050843 A1 | 5/2006 |
| WO | 2006058867 A2 | 6/2006 |
| WO | 2006058869 A2 | 6/2006 |
| WO | 2006069805 A2 | 7/2006 |
| WO | 2006120251 A1 | 11/2006 |
| WO | 2006135993 A1 | 12/2006 |
| WO | 2007093901 A1 | 8/2007 |
| WO | 2007135026 A2 | 11/2007 |
| WO | 2007135027 A1 | 11/2007 |
| WO | 2008003149 A2 | 1/2008 |
| WO | 2008009076 A2 | 1/2008 |
| WO | 2008009077 A2 | 1/2008 |
| WO | 2008009078 A2 | 1/2008 |
| WO | 2008009079 A2 | 1/2008 |
| WO | 2008009706 A1 | 1/2008 |
| WO | 2008024977 A2 | 2/2008 |
| WO | 2008030455 A2 | 3/2008 |
| WO | 2008077649 A1 | 7/2008 |
| WO | 2008077651 A1 | 7/2008 |
| WO | 2008154221 A2 | 12/2008 |
| WO | 2009003669 A2 | 1/2009 |
| WO | 2010002877 A2 | 1/2010 |
| WO | 2010002998 A1 | 1/2010 |
| WO | 2010042489 A2 | 4/2010 |
| WO | 2010046639 A1 | 4/2010 |
| WO | 2010092340 A1 | 8/2010 |
| WO | 2011057148 A1 | 5/2011 |
| WO | 2011072275 A2 | 6/2011 |
| WO | 2011097607 A1 | 8/2011 |
| WO | 2011135259 A1 | 11/2011 |
| WO | 2012058601 A1 | 5/2012 |
| WO | 2012136834 A1 | 10/2012 |
| WO | 2012156498 A1 | 11/2012 |
| WO | 2013060881 A1 | 5/2013 |
| WO | 2013090840 A1 | 6/2013 |
| WO | 2013117615 A1 | 8/2013 |
| WO | 2013174947 A1 | 11/2013 |
| WO | 2014023813 A1 | 2/2014 |
| WO | 2014056953 A1 | 4/2014 |
| WO | 2014076221 A1 | 5/2014 |
| WO | 2014078778 A2 | 5/2014 |
| WO | 2014116755 A1 | 7/2014 |
| WO | 2014120995 A2 | 8/2014 |
| WO | 2014128189 A1 | 8/2014 |
| WO | 2015014815 A1 | 2/2015 |
| WO | 2015168269 A1 | 11/2015 |
| WO | 2015191752 A1 | 12/2015 |
| WO | 2016141092 A1 | 9/2016 |
| WO | 2017048727 A1 | 3/2017 |
| WO | 2018002319 A1 | 1/2018 |
| WO | 2018045144 A1 | 3/2018 |
| WO | 2018045150 A1 | 3/2018 |
| WO | 2020214652 A1 | 10/2020 |
| WO | 2020214663 A1 | 10/2020 |
| WO | 2022241134 A1 | 11/2022 |

OTHER PUBLICATIONS

Database Beilstein, Accession Nos. 285496, 252276, and 250719, Beilstein Institute for Organic Chemistry, Angew. Chem. 73:695, 704, 1961; Ber. Bunsen-Ges. Phys. Chem. 69:458, 462, 465, 1965; Chem. Ber. 90:2631, 2633, 2635, 1957; Chem. Ber. 95:755, 762, 1962; Chem. Ber. 106:3203, 3205, 1973; Chem. Ber. 114:699-706, 1981; Heterocycles 24:1565-1566, 1986; Heterocycles 41:781-788, 1995; J. Chem. Soc. Perkin Trans. 2:35-36, 1979; Justus Liebigs Ann. Chem. 547:180, 183, 1941; Liebigs Ann. Chem. 11:11798-1814, 1984; Zh. Org. Khim. RU 32:455-460, 1996. (XP-002296934, 22 pages).
Dominican Patent Office, Office Action for DO Application No. P2017-0203, dated Oct. 8, 2020 with English translation, 4 pages.
Australian Patent Office, Examination Report No. 2 for Australian Patent Application No. 2016216673, dated Nov. 14, 2016, 3 pages.
Examination Report for EP Patent Application No. 16711723.3, dated Nov. 29, 2016.
Australian Patent Office, Examination Report No. 1 for Australian Patent Application No. 2016216673, dated Sep. 5, 2016, 7 pages.
Gulf Cooperation Council Patent Office, Examination Report for GC application No. GC 2016-30932, dated Jul. 6, 2020, 4 pages.
European Patent Office, International Preliminary Report on Patentability for International Application No. PCT/BE2007/000092, dated Apr. 7, 2009, 13 pages.
International Preliminary Report on Patentability and Written Opinion for International Application No. PCT/BE2007/000091, dated Jan. 20, 2009, 14 pages.
International Preliminary Report on Patentability received for PCT Application No. PCT/US2017/049562, dated Mar. 5, 2019, 8 pages.
European Patent Office, International Search Report and Written Opinion for International Application No. PCT/US2016/020499, dated Jul. 25, 2016, 18 pages.
International Search Report and Written Opinion for International Application No. PCT/US2017/049573, dated Oct. 25, 2017, 12 pages.
International Search Report and Written Opinion received for PCT Application No. PCT/US2016/051545, dated Dec. 8, 2016, 13 pages.
International Search Report received for PCT Patent Application No. PCT/US2020/028237, dated Jun. 30, 2020, 8 pages.
International Search Report received for PCT Patent Application No. PCT/US2020/028257, dated Jun. 26, 2020, 8 pages.
Invitation to Pay Additional Fees (PCT/BE2007/000091), dated Jun. 6, 2008.
European Patent Office, Invitation to Pay Additional Fees and Partial Search Report (PCT/BE2007/000092), dated Oct. 16, 2008.
Israel Patent Office, Office Action for IL Application No. 254164, dated Sep. 21, 2020, 2 pages.
Mexico Patent Office, Notice of Allowance for MX application No. MX/a/2017011307, dated Oct. 14, 2020, 2 pages.
Notice of Preliminary Rejection for Korean Patent Application No. 10-2016-7023289, dated Nov. 2, 2016, 7 pages.
Office Action for U.S. Appl. No. 15/264,401, dated Dec. 27, 2016, 11 pages.
Office Action for U.S. Appl. No. 12/374,242, dated Apr. 9, 2012, 20 pages.
Search Report for Korean Patent Application 10-2016-7023289 with English translation, dated Aug. 25, 2016, 14 pages.
Ukraine Patent Office, Notice of Allowance for UA Application No. a210708923, dated Nov. 5, 2020, 17 pages.
Abou-Hedeed et al. (1996) "Pteridines CVIII Reactions of 6, 7-Dichloro-1, 3-Dimethyllumazine with Sulfur-Nucleophiles", Pteridines, 7:113-122.
Anonymous, (Jul. 27, 2007) "Ankylosing Spondylitis", Retrieved Online on from http://www.nlm.nih.gov/medicineplus/print/ankylosingspondylitis.html, 3 pages.
Anonymous, (Sep. 24, 2003) "FDA mulls drug to slow late-stage Alzheimer's", Retrieved from CNN.com, 2 pages.
Armarego et al. (1967) "Quinazolines. Part IX. Covalent hydration in the neutral species of substituted quinazolines", Journal ofthe Chemical Society B: Physical Organic, 449-454.
Australian Patent Office "Examination Report No. 1 for Australian Patent Application No. 2016322763", dated Nov. 28, 2018, 5 pages.
Baba et al. (Apr. 1984) "Synergistic Antiviral Effects of Antiherpes Compounds and Human Leukocyte Interferon on Varicella-Zoster Virus in Vitro", Antimicrobial Agents and Chemotherapy, 25(4):515-517.
Banker et al. (1996) "Modern Pharmaceutics", Third Edition, Revised and Expanded, 596 (3 pages).

(56) References Cited

OTHER PUBLICATIONS

Barl et al. (Apr. 2014) "The Halogen/Magnesium-Exchange using iPrMgCl LiCl and related exchange reagents", Heterocycles, 45(13) 827-844.
Beers et al. (1999) "The Merck Manual of Diagnosis and Therapy, Merck Research Laboratories", Whitehouse Station, N.J Neurologic Disorders, Sec. 14, 1474-1476.
Beers et al. (1999) "The Merck Manual of Diagnosis and Therapy, Merck Research Laboratories", Whitehouse Station, N.J Leukemias, Chapter 138, 953-954.
Bennett et al. (1996) "Cecil Textbook of Medicine, 20th Ed.", 20th Edition, 2:1992-1996.
Bennett et al. (1996) "Cecil Textbook of Medicine, 20th Ed.", 20th Edition, 2:2050-2057.
Bigorgne et al. (Aug. 30, 2010) "TLRs in Hepatic Cellular Crosstalk, Gastroenterology Research and Practice", Article ID 618260, 1-7.
Black et al. (1997) "Agents that Block TNF-a Synthesis or Activity", Annual Reports in Medicinal Chemistry, 32:241-250.
Boon (1957) "Pteridines. Part IV.' Derivatives of 2:4-Diaminopteridine and Related Compounds", Journal of the Chemical Society, 2146-2158.
Brown et al. (1961) "Pteridine Studies. Part XIV. Methylation of 2-Amino-4-hydroxypteridine and Related Compounds", Journal of the Chemical Society, 869:4413- 4420.
Buitendijk et al. (May 2014) "Toll-Like Receptor Agonists Are Potent Inhibitors of Human Immunodeficiency Virus-Type 1 Replication in Peripheral Blood Mononuclear Cells", AIDS Research and Human Retroviruses, 30(5):457-467.
Bundgaard Hans, (Nov. 1, 1985) "Design of Prodrugs: Bioreversible Derivatives for Various Functional Groups and Chemical Entities", Elsevier, 3 pages.
Buu-Hoi et al. (Aug. 1968) "Phthalonimides (1,3,4-Trioxo-1,2,3,4-Tetrahydroisoquinolines) of Potential Biological Interest", Journal of Heterocyclic Chemistry, 5:545-546.
Cairo, (Sep. 30, 2003) "Immunology Lecture #20: Transplantation", Columbia University [online] Retrieved Jul. 12, 2005 from http://healthsciences.columbia.edu/depUps/2007/immuno/2006/IM20.pdf, 6 pages.
Cervantes et al. (2012) "TLR8: the forgotten relative revindicated", Cellular & Molecular Immunology, 9:434-438.
Chantry (1999) "Tumour Necrosis Factor Antagonists", Expert Opinion on Emerging Drugs, 1:5-13.
Chapman et al. (1947) "Synthetic Antimalarials. Part XVI. 4 Dialkylaminoalkylaminoquinazolines; Variation of Substituents in the 6-and 7-Positions", Journal ofthe Chemical Society, 890-899.
Chilean Patent Office,"Chilean Patent Office Official Action for CL Application No. 201702225 with English Translation", Dec. 4, 2018, 11 pages.
Bennett, et al. (1996) Cecil Textbook of Medicine, 20th Ed vol. 1, 1004-1010.
Cho, (Mar. 8, 2012) "Synthesis and antiviral activity of a series of 1'-substituted 4-aza-7,9-dideazaadenosince C-nucleosides", Bioorganic & Medicinal Chemistry Letters, 2705-2707.
Chou et al. (1984) "Quantitative Analysis of Dose-Effect Relationships: The Combined Effects of Multiple Drugs or Enzyme Inhibitors", Advances in Enzyme Regulation, 22:27-55.
Cohen et al. (1999) "The Development and Therapeutic Potential of Protein Kinase Inhibitors", Current Opinion in Chemical Biology, 3:459-465.
Colonna et al. (2004) "Plasmacytoid dendritic cells in immunity", Nature Immunology, 5(12):1219-1226.
Cottam et al. (1996) "Substituted Xanthines, Pteridinediones and Related Compounds as Potential Anti-Inflammatory Agents. Synthesis and Biological Evaluation of Inhibitors of Tumor Necrosis Factor Alpha", Journal of Medicinal Chemistry, 39:2-9.
Database Beilstein, (Jan. 1, 1900) "Accession Nos. 1184281", XP002324247, 2 pages.
Database Beilstein, (Jan. 1, 1900) "Accession Nos. 533693 and 540145", XP002296935, 4 pages.
Database Beilstein, (Jan. 1, 1900) "Accession Nos. 6337777 and 6373242", XP002296933, 6 pages.
Database Beilstein, (Jan. 1, 1900) "Accession Nos. 7216143", 3 pages.
Database Beilstein, (Jan. 1, 1900) "Accession Nos. 7928670", XP002296938, 2 pages.
Database Beilstein (2003) "Accession Nos. 9571456 and 9570157", XP002296936, 11 pages.
Database WPI, (Feb. 23, 2005) "Week 2005", Thompson Scientific, London, GB (XP002498175).
Dempcy et al. (1991) "Regioselective Synthesis of Imidazo[4,5-g] quinazoline Quinone Nucleosides and Quinazoline Amino Nucleosides. Studies of their Xanthine Oxidase and Purine Nucleoside Phosphorylase Substrate Activity", The Journal of Organic Chemistry, 56:776-785.
Dermer (Mar. 1, 1994) "Another Anniversary for the War on Cancer", Bio/Technology, 12:320.
Deuis (2017) "Pharmacological characterization of the highly Nav1.7 selective spider venom peptide Pn3a", Scientific Reports, 1-18.
Dimauro et al. (2006) "Microwave-assisted preparation of fused bicyclic heteroaryl boronates: application in one-pot Suzuki couplings", The Journal of Organic Chemistry, 71(10):3959-3962.
Ding et al. (Feb. 2005) "Parallel Synthesis of Pteridine Derivatives as Potent Inhibitors for Hepatitis C Virus NS5B RNA-Dependent RNA Polymerase", Bioorganic & Medicinal Chemistry Letters, 15(3):675-678.
Elion et al. (Jun. 1954) "Antagonists of Nucleic Acid Derivatives. VIII. Synergism in Combinations of Biochemically Related Antimetabolites", Journal of Biological Chemistry, 208(2):477-488.
Elliott et al. (May 1975) "Synthesis of N-10-Methyl-4-Thiofolic Acid and Related Compounds", Journal of Medicinal Chemistry, 18(5):492-496.
Freshney (1983) "Culture of Animal Cells", Alan R. Liss, Inc. 1 page.
Frohlich et al. (1999) "Inhibition of Neuronal Nitric Oxide Synthase by 4-Amino Pteridine Derivatives: Structure-Activity Relationship of Antagonists of (6R)-5, 6, 7, 8-Tetrahydrobiopterin Cofactor", Journal of Medicinal Chemistry, 42:4108-4121.
Ganellin (2002) "Final Report on the Activities ofthe Medicinal Chemistry Section", Retrieved Jun. 2, 2004 from www.iupac.org/divisions/VII/VII.M/VIIM-ReportDec2001.pdf, 4 pages.
Gerlach et al. (1965) "Influence of Pyrimidopyrimidine and Pteridine Derivatives on Phosphate and Adenosine Permeability in Human Erythrocytes", Arzneimittelforschung (English Abstract), 15:558-563.
Giori (Dec. 1986) "Reactivity of 3H-Pyrimido [5, 4-c] [1, 2, 5] Oxadiazin-3-0ne Towards Carbanions: Synthesis of Pteridine-2, 4-Diones", Journal of Heterocyclic Chemistry, 23:1661-1665.
Golub et al. (Oct. 15, 1999) "Molecular Classification of Cancer: Class Discovery and Class Prediction by Gene Expression Monitoring", Science, 286(5439):531-537.
Gonzalez-Rodriguez et al. (Jan. 2017) "Synergistic Combinations ofthe Dual Enkephalinase Inhibitor PL265 given Orally with Various Analgesic Compounds Acting on Different Targets, in a Murine Model of Cancer-Induced Bone Pain", Scandinavian Journal of Pain, 14:25-38.
Guillermo et al. (Apr. 1, 2007) "Targeting Cell Cycle Kinases for Cancer Therapy", Current Medicinal Chemistry, 14(9):969-985.
Hayakawa et al. (Oct. 15, 2006) "Synthesis and Biological Evaluation of 4-Morpholino-2-Phenylquinazolines and Related Derivatives as Novel PI3 Kinase p11Oalpha Inhibitors", Bioorganic & Medicinal Chemistry, 14(20):6847-6858.
Hayden (2001) "Antimicrobial Agents (Continued) Antiviral Agents (Nonretroviral)", Goodman and Gilman's The Pharmacological Basis for Therapeutics, 10th Edition, Chapter 50, 1313-1315.
Higuchi et al. (1976) "A Disproportionation of 6-Amino-5-Benzylideneamino-1,3-dimethyl uracils in Formamide. Formation of 6,7-Diaryl-1,3-dimethyllumazines and Theophylline", Heterocycles, 4:977-980.
Horner et al. (1968) "Analogs of 3 Amino-7-chloro-1,2,4-benzotriazine 1-0xide as Antimalarial Agents", Journal of Medicinal Chemistry, 11(5):946-949.

(56) References Cited

OTHER PUBLICATIONS

Illei et al. (Dec. 2000) "Novel, Non-Antigen-Specific Therapeutic Approaches to Autoimmune/Inflammatory Diseases", Current Opinion in Immunology, 12(6):712-718.
Isensee (Jan. 10, 2017) "Synergistic Regulation of Serotonin and Opioid Signaling Contribute to Pain Insensitivity in Nav1.7 Knockout Mice", Neuroscience, Science Signaling, 10(461):eaah4874 (11 pages).
Israel et al. (Nov. 1965) "Pyrimidine Derivatives. VII. Some Condensed Derivatives of 2, 4, 5-Triamino-6-Methylthiopyrimidine", Journal of Pharmaceutical Sciences, 54(11):1626-1632.
Iwagaki et al. (Mar. 1995) "Decreased Serum Tryptophan in Patients with Cancer Cachexia Correlates with Increased Serum Neopterin", Immunological Investigations, 24(3):467-478.
Jackson et al. (Jun. 1996) "6,7-Disubstituted 2,4-Diaminoteridines: Novel Inhibitors of Pneumocystis carinii and Toxoplasma gondii Dihydrofolate Reductase", Antimicrobial Agents and Chemotherapy, 40(6):1371-1375.
Jo et al. (Jun. 26, 2014) "Toll Like Receptor 8 Agonist and Bacteria Trigger Potent Activation of Innate Immune Cells in Human Liver", PLOS Pathogens, 13 pages.
Kaczanowska et al. (Jun. 2013) "TLR agonists: our best frenemy in cancer immunotherapy", Journal of Leukocyte Biology, 93(6):847-863.
Kaldrikyan et al. (1976) "Pteridine Derivatives. I. Synthesis of Some Substituted 6,7-Diarylpteridines", Armyanskii Khimicheskii Zhumat, (8 pages including English translation on pp. 6-8), 29:337-341.
Kandror et al. (Sep. 1, 1982) "Radical Arylation of N-Substituted Carboxylic Acid Thioamides and Cyclic Thioamides", Russian Chemical Bulletin (Abstract only), 31:1873-1876.
Kikelj, (2004) "From 2-Aminobenzonitriles and Carbon Dioxide, Carbon Monoxide, Carbon Disulfide, or Potassium 0-Ethyl Dithiocarbonate", Science of Synthesis, 573-749.
Kujime et al. (Oct. 1, 2010) "Regioselective Preparation of Pterin 6-Triflate and Its Application to 6-Substituted Pterin Synthesis", Heterocycles, 57:1841-1850.
Landauer et al. (1953) "A Convenient Synthesis of Some 4-Substituted 5-Aminopyrimidines", Journal of the Chemical Society, 3721-3722.
Landry et al. (2003) "Pharmacologie Des Cibles Vers L'Indication Therapeutique", Cours et Exercices, 177(1 page).
Leguen (Jul. 2003) "Pain management by a new series of dual inhibitors of enkephalin degrading enzymes: long lasting antinociceptive properties and potentiation by CCK2 antagonist or methadone", Pain, 104(1-2):139-148.
Lensink Cornelis, (Feb. 1998) "Synthesis and Structure of Sulfonamido Cyclopentadiene Titanium Complexes: X-ray Structure of Ti(ri5:o-C5H4CH2CH2NS02C6H4CH3)Cl2", Journal of Organometallic Chemistry, 553:387-392.
Lin et al. (Jun. 27, 1997) "Use ofthe Methylxanthine Derivative A802715 in Transplantation Immunology, I. Strong in Vitro Inhibitory Effects on CD28-Costimulated T Cell", Transplantation, 63:1813-1818.
Lin, et al. (Jun. 27, 1997) "Use ofthe Methylxanthine Derivative A802715 in Transplantation Immunology, II. In Vivo Experiments" Transplantation, 63(12):1734-1738.
Magnus et al. (2005) "Neural Stem Cells in Inflammatory CNS Diseases: Mechanisms and Therapy", Journal of Cellular and Molecular Medicine, 9(2):303-319.
Matter et al. (2002) "Structural Requirements for Inhibition ofthe Neuronal Nitric Oxide Synthase (Nos. I): 3D-QSAR Analysis of 4-0xo-and 4-Amino-Pteridine-Based Inhibitors", Journal of Medicinal Chemistry, 45 (14):2923-2941.
Merz et al. (1998) "Synthesis of 7-Benzylamino-6-chloro-2-piperazino-4-pyrrolidinopteridine and Novel Derivatives Free of Positional Isomers. Potent Inhibitors of cAMP-Specific Phosphodiesterase and of Malignant Tumor Cell Growth", Journal of Medicinal Chemistry, 41(24):4733-4743.
Minett (Dec. 4, 2015) "Endogenous opioids contribute to insensitivity to pain in humans and mice lacking sodium channel Nav1.7", Nature Communciations, 8 pages.
Mohr et al. (Nov. 11, 1992) "Pteridines. Part XCVII. Synthesis and Properties of 6-thioxanthopterine and 7-thioisoxanthopterin", Helvetica Chimica Acta, 75:2317-2326.
Moody et al. (Mar. 15, 2014) "Toll-Like Receptor 718 (TLR7/8) and TLR9 Agonists Cooperate to Enhance HIV-1 Envelope Antibody Responses in Rhesus Macaques", Journal of Virology, 88(6):3329-3339.
Moreb et al. (Nov. 1992) "The Therapeutic Potential of Interleukin-1 and Tumor Necrosis Factor on Hematopoietic Stem Cells", Leukemia & Lymphoma, 8(4-5):267-275. (Abstract Only).
Murata et al. (Sep. 2000) "A Facile Method for Regioselective 6,7-Disubstitution of Pleridine,", Heterocycles, 53:1259-1262.
Neilsen et al. (Nov. 1, 1987) "Unequivocal Syntheses of 6-Methyl-and 6-Phenylisoxanthoterin", Journal of Heterocyclic Chemistry, 24:1621-1628.
Nicolaus (1983) "Symbiotic Approach to Drug Design", Decision Making in Drug Research, Gross (Ed.) Raven Press: New York, 173-186.
Novis et al. (Oct. 24, 2013) "Reactivation of latent HIV-1 in central memory CD4+ T cells through TLR-1/2 stimulation", Retrovirology, 10(119):15 pages.
Obach (May 2003) "Drug-drug Interactions: An Important Negative Attribute in Drugs", Drugs Today, 39(5):301-338.
Ochoa et al. (1997) "Application of Neural Networks to the Study of Structure-Activity Relationships of 6,7-Diarylpteridines as Nematocides", Medicinal Chemistry Research, 7:530-545.
Ohto et al. (Feb. 8, 2014) "Structure and function of toll-like receptor 8", Microbes and Infection, 16(4):273-282.
O'Neill et al. (May 17, 2013) "The history of Toll-like receptors-redefining innate immunity", Nat Rev Immunol, 13:453-460.
Patani et al. (1996) "Bioisosterism: A Rational Approach in Drug Design", Chemical Reviews, 96(8):3147-3176.
Peng et al. (Aug. 26, 2005) "Toll-Like Receptor 8-Mediated Reversal of CD4+ Regulatory T Cell Function", Science, 1380-1384.
Pfleiderer et al. (Jan. 1961) "Pteridine, XII: Synthese von 2-Amino-4-Alkoxy-Pteridinen", Chemische Berichte, 94:12-18.
Ramu et al. (Mar. 15, 1989) "Circumvention of Adriamycin Resistance by Dipyridamole Analogues: A Structure-activity Relationship Study", International Journal of Cancer, 43:487-491.
Rodrigues, E. L., and J. M. C. Bueno. (Jan. 2004) "Co/SiO2 catalysts for selective hydrogenation of crotonaldehyde: III. Promoting effect of zinc." Applied Catalysis A: General, 257(2):201-211.
Roethle et al. (Aug. 20, 2013) "Identification and Optimization of Pteridinone Toll-Like Receptor 7 (TLR7) Agonists for the Oral Treatment of Viral Hepatitis", Journal of Medicinal Chemistry, 56(18): 7324-7333.
Rosowsky et al. (Jan. 1995) "Structure-activity and structure-selectivity studies on diaminoquinozolines and other inhibitors of Pneumocystis carnii and Toxoplasma gondii dihydrofolate reductase", Antimicrobial Agents and Chemotherapy, 39(1):79-86.
Sasse Klaus, (1978) "A Simple New Method for Preparation of 2-Substituted Quinazolines", Synthesis, 379-382.
Sato et al. (Dec. 24, 1999) "Studies on Pyrazines. Part 37. Synthesis of 6-Propionylpteridine-2.4 (1 H,3H)-dione and its 1-and/or 3-Methyl Derivatives from Marine Natural Products", Journal ofthe Chemical Society, Perkins Transactions 1, 1:89-95.
Schlaepfer et al. (Apr. 1, 2011) "TLR8 Activates HIV from Latently Infected Cells of Myeloid-Monocytic Origin Directly via the MAPK Pathway and from Latently Infected CD4+ T Cells Indirectly via TNF-a", Journal of Immunology, 186(7):4314-4324.
Sielecki et al. (May 7, 2001) "Quinazolines as Cyclin Dependent Kinase Inhibitors", Bioorganic & Medicinal Chemistry Letters, 11(9):1157-1160.
Spickett et al. (1954) "The Synthesis of Compounds with Potential Anti-Folic Acid Activity. Part I 7-Amino-And 7-Hydroxy-Pteridines", Journal ofthe Chemical Society, 2887-2895.
Sugimoto et al. (1997) "Regioselective Arylation of 1,3-Dimethyllumazine and Its 5-Oxide by Diazonium Salts", Pteridines, 8:188-194.

(56) References Cited

OTHER PUBLICATIONS

Sun (Sep. 2014) "Inhibitors of voltage-gated sodium channel $Na_v1.7$: patent applications since 2010", Pharmaceutical Patent Analyst, 3(5)509-521.
Taghavi-Moghadam (Sep. 29, 1997) "A New, General, and Regioselective Method for the Synthesis of 2, 6-Disubstituted 4-Aminopteridines", Tetrahedron Letters, 38:6835-6836.
Taylor et al. (Mar. 13, 2013) "Opioid antagonists for pain", Expert Opinion on Investigational Drugs, 22(4):517-525.
Ulrich (2002) "Kirk-Othmer Encyclopedia of Chemical Technology", Wiley, Chapter 4: Crystallization, 7 pages.
Urakov et al. (1995) "Multiple Reactivity and Tautomerism of Substituted Pyrimidines. IV. Multiple Reactivity of 2-Acetamido-4-Quinazolinones", Uzbek Chemical Journal, 5-6:37-41.
Vema et al. (Sep. 10, 2003) "Design of EGFR Kinase Inhibitors: A Ligand-Based Approach and its Confirmation with Structure-Based Studies", Bioorganic & Medicinal Chemistry, 11:4643-4653.
Vinot, Nicole P. (1973) "No. 505.—Etude de Pteridiones-2,4 III Orientation de la reaction de condensation d'a-dicetones avec le diamino-4,5 dimethyl-1,3 uracile", Bulletin de la Societe Chimique de France, 9-10:2752-2755.
Vippagunta et al. (Apr. 20, 2001) "Crystalline Solids", Advanced Drug Delivery Reviews, 48:3-26.
Wang et al. (2004) "Use of Polymer-supported Pd Reagents for Rapid and Efficient Suzuki Reactions Using Microwave Heating", Organic Letters, 6(16):2793-2796.
Warren et al. (Mar. 2, 2016) "Therapeutic Efficacy of the Small Molecule GS-5734 Against Ebola Virus in Rhesus Monkeys", Nature, 531(7594):381-385.
Watashi et al. (Sep. 11, 2013) "Interleukin-1 and Tumor Necrosis Factor Triggeer Restriction of Hepatitis B Virus Infection Via a Cytidine Deaminase Activation-induced Cytidine Deaminase (AID)", The Journal of Biological Chemistry, 288(44):31715-31727.
Weinstock et al. (May 1, 1968) "Pteridines. XII. Structure-Activity Relationships of Some Pteridine Diuretics", Journal of Medicinal Chemistry, 11:573-579.
West (1984) "Solid State Chemistry and its Applications", Wiley, 3 pages.
Wikipedia, (Dec. 28, 2006) "Wikipedia entries for Anthistamine, Autoimmunity, List of Autoimmune Diseases, Lupus Erythematosus, and Sjogren's Syndrome", retrieved Dec. 28, 2006 from http://en.wikipedia.org, 23 pages.
Wille-Reece et al. (Apr. 24, 2006) "Toll-like receptor agonists infl uence the magnitude and quality of memory T cell responses after prime-boost immunization in nonhuman primates", The Journal of Experimental Medicine, 203(5):1249-1258.
Wolff, (1995) "Burger's Medicinal Chemistry and Drug Discovery: Fifth Edition", Principles and Practice, 1:783-802.
Wolff (1995) "Some Considerations for Prodrug Design", Burger's Medicinal Chemistry and Drug Discovery: Fifth Edition, Principles and Practice, 1:975-977.
Xagorari (2008) "Toll-Like Receptors and Viruses: Induction of Innate Antiviral Immune Responses", The Open Microbiology Journal, 2:49-59.
Yao et al. (2003) "Pteridines, Part CXIII: Protection of Pteridines", Helvetica Chimica Acta 86:1-12.
Yin et al. (2012) "Synthesis of 2,4-Diaminoquinazolines and Tricyclic Quinazolines by Cascade Reductive Cyclization of Methyl N-Cyano-2-nitrobenzimidates", The Journal of Organic Chemistry, 77(6):2649-2658.
Yu et al. (Apr. 2013) "Dual Character of Toll-like Receptor Signaling: Pro-tumorigenic Effects and Anti-Tumor Functions", Biochimica et Biophysica Acta, 1835(2):144-154.
Zhao et al. (Jul. 2014) "Toll-like Receptors and Prostate Cancer", Frontiers in Immunology, Article 352, 5:1-6.

TOLL LIKE RECEPTOR MODULATOR COMPOUNDS

CROSS REFERENCE TO RELATED APPLICATIONS

This application is a Divisional of U.S. application Ser. No. 16/441,339, filed on Jun. 14, 2019, which is a Divisional of U.S. application Ser. No. 15/692,093, filed on Aug. 31, 2017, which claims priority benefit to U.S. Provisional Application Ser. No. 62/383,162, filed on Sep. 2, 2016, the disclosure of which are incorporated by reference in their entirety.

FIELD

This application relates generally to toll like receptor modulator compounds and pharmaceutical compositions which, among other things, modulate toll-like receptors (e.g. TLR8), and methods of making and using them.

BACKGROUND

The toll-like receptor (TLR) family plays a fundamental role in pathogen recognition and activation of innate immunity. Toll-like receptor 8 (TLR8) is predominantly expressed by myeloid immune cells and activation of this receptor stimulates a broad immunological response. Agonists of TLR8 activate myeloid dendritic cells, monocytes, monocyte-derived dendridic cells and Kupffer cells leading to the production of proinflammatory cytokines and chemokines, such as interleukin-18 (IL-18), interleukin-12 (IL-12), tumor necrosis factor-alpha (TNF-α), and interferon-gamma (IFN-γ). Such agonists also promote the increased expression of co-stimulatory molecules such as CD8+ cells, major histocompatibility complex molecules (MAIT, NK cells), and chemokine receptors.

Collectively, activation of these innate and adaptive immune responses induces an immune response and provides a therapeutic benefit in various conditions involving autoimmunity, inflammation, allergy, asthma, graft rejection, graft versus host disease (GVHD), infection, cancer, and immunodeficiency. For example, with respect to hepatitis B, activation of TLR8 on professional antigen presenting cells (pAPCs) and other intrahepatic immune cells is associated with induction of IL-12 and proinflammatory cytokines, which is expected to augment HBV-specific T cell responses, activate intrahepatic NK cells and drive reconstitution of antiviral immunity. See e.g. Wille-Reece, U. et al. *J Exp Med* 203, 1249-1258 (2006); Peng, G. et al., *Science* 309, 1380-1384 (2005); Jo, J. et al., *PLoS Pathogens* 10, e1004210 (2014) and Watashi, K. et al., *J Biol Chem* 288, 31715-31727 (2013).

Given the potential to treat a wide array of diseases, there remains a need for novel modulators of toll like receptors, for example TLR8. Potent and selective modulators of TLR8 that have reduced potential for off target liabilities are particularly desirable.

SUMMARY

The present disclosure provides a compound of Formula I

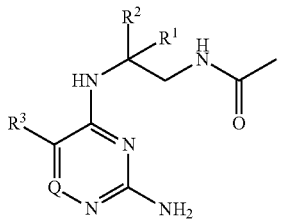

Formula I or a pharmaceutically acceptable salt thereof, wherein:
$R^1$ is —H, $C_{1-4}$ alkyl, or $C_{1-4}$ haloalkyl;
$R^2$ is $C_{1-6}$ alkyl or $C_{1-6}$ haloalkyl;
$R^3$ is $C_{1-4}$ alkoxy optionally substituted with 1 $R^X$;
  each $R^X$ is independently —$OR^Y$, 5 to 6 membered heterocyclyl having 1 to 3 heteroatoms selected from oxygen, nitrogen, and sulfur optionally substituted with 1 to 3 $R^Z$; phenyl optionally substituted with 1 to 3 $R^Z$; or 5 to 6 membered heteroaryl having 1 to 3 heteroatoms selected from oxygen, nitrogen, and sulfur optionally substituted with 1 to 3 $R^Z$;
  $R^Y$ is $C_{1-4}$ alkyl, $C_{1-4}$ haloalkyl, or 5 to 10 membered heteroaryl having 1 to 3 heteroatoms selected from oxygen, nitrogen, and sulfur optionally substituted with 1 to 3 $R^Z$;
Q is N, CH, or $CR^4$;
or $R^3$ and $R^4$ are taken together to form $C_{5-6}$ cycloalkyl; 5 to 6 membered heterocyclyl having 1 to 3 heteroatoms selected from oxygen, nitrogen, and sulfur; phenyl; or 5 to 6 membered heteroaryl having 1 to 3 heteroatoms selected from oxygen, nitrogen, and sulfur, wherein:
  $C_{5-6}$ cycloalkyl and phenyl are each independently optionally substituted with 1 to 3 $R^5$;
  each $R^5$ is independently halogen, —OH, —$NH_2$, —CN, $C_{1-4}$ alkyl optionally substituted with 1 to 3 $R^Z$, $C_{1-4}$ haloalkyl, $C_{1-4}$ alkoxy, —C(O)OH, —C(O)$C_{1-4}$ alkyl, —C(O)O$C_{1-4}$ alkyl, —C(O)$NH_2$, —C(O)NH($C_{1-4}$ alkyl), —C(O)N($C_{1-4}$ alkyl)$_2$, —N(H)C(O)$C_{1-4}$ alkyl, —S(O)$_2C_{1-4}$ alkyl, or 5 to 6 membered heteroaryl having 1 to 3 heteroatoms selected from oxygen, nitrogen, and sulfur optionally substituted with 1 to 3 $R^Z$;
  5 to 6 membered heteroaryl is optionally substituted with 1 to 3 $R^6$;
  each $R^6$ is independently halogen, —OH, —$NH_2$, —CN, $C_{1-4}$ alkyl optionally substituted with 1 phenyl optionally substituted with 1 to 3 $R^Z$; $C_{1-4}$ haloalkyl, $C_{1-4}$ alkoxy, —S(O)$_2C_{1-4}$ alkyl; 5 to 6 membered heterocyclyl having 1 to 3 heteroatoms selected from oxygen, nitrogen, and sulfur optionally substituted with 1 to 3 $R^Z$; phenyl optionally substituted with 1 to 3 $R^Z$; or 5 to 6 membered heteroaryl having 1 to 3 heteroatoms selected from oxygen, nitrogen, and sulfur optionally substituted with 1 to 3 $R^Z$;
  5 to 6 membered heterocyclyl is optionally substituted with 1 to 3 $R^7$ R⁷ is halogen, —OH, $C_{1-4}$ alkyl, $C_{1-4}$ alkoxy, or —C(O)R⁸;

each R⁸ is independently $C_{1-4}$ alkyl optionally substituted with —CN or —NH₂; $C_{1-4}$ haloalkyl; $C_{5-6}$ cycloalkyl, 5 to 6 membered heterocyclyl having 1 to 3 heteroatoms selected from oxygen, nitrogen, and sulfur optionally substituted with 1 to 3 $R^Z$; or 5 to 10 membered heteroaryl having 1 to 3 heteroatoms selected from oxygen, nitrogen, and sulfur optionally substituted with 1 to 3 $R^Z$;

and each $R^Z$ is independently —NH₂, $C_{1-4}$ alkyl, halogen, —CN, —$OC_{1-4}$ alkyl, $C_{1-4}$ haloalkyl, or —C(O)NH₂;

with the proviso that Formula I is not

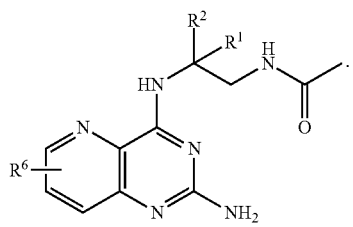

In certain embodiments, the present disclosure provides a pharmaceutical composition comprising a compound of the present disclosure, or a pharmaceutically acceptable salt thereof, and a pharmaceutically acceptable excipient. In certain embodiments, the pharmaceutical composition comprises one or more additional therapeutic agents.

In certain embodiments, a method of modulating TLR8 is provided, comprising administering a compound of the present disclosure, or a pharmaceutically acceptable salt thereof, to an individual (e.g. a human).

In certain embodiments, a method of treating or preventing a disease or condition responsive to the modulation of TLR8 is provided, comprising administering to an individual (e.g. a human) in need thereof a therapeutically effective amount of a compound of the present disclosure, or a pharmaceutically acceptable salt thereof. In certain embodiments, the method of treating or preventing a disease or condition responsive to the modulation of TLR8, comprises administering one or more additional therapeutic agents.

In certain embodiments, a method of treating or preventing a viral infection is provided, comprising administering to an individual (e.g. a human) in need thereof a therapeutically effective amount a compound of the present disclosure, or a pharmaceutically acceptable salt thereof.

In certain embodiments, a method of treating or preventing a hepatitis B viral infection is provided, comprising administering to an individual (e.g. a human) in need thereof a therapeutically effective amount of a compound of the present disclosure, or a pharmaceutically acceptable salt thereof. In certain embodiments, the method of treating or preventing a hepatitis B viral infection comprises administering one or more additional therapeutic agents. In certain embodiments, the individual is a human infected with hepatitis B.

In certain embodiments, a method of treating or preventing a HIV infection is provided, comprising administering to an individual (e.g. a human) in thereof a therapeutically effective amount a compound of the present disclosure, or a pharmaceutically acceptable salt thereof. In certain embodiments, the method of treating or preventing a HIV infection comprises administering one or more additional therapeutic agents. In certain embodiments, the individual is a human infected with HIV (e.g. HIV-1).

In certain embodiments, a method of treating a hyperproliferative disease (e.g. cancer) is provided, comprising administering to an individual (e.g. a human) in thereof a therapeutically effective amount a compound of the present disclosure, or a pharmaceutically acceptable salt thereof. In certain embodiments, the method of treating a hyperproliferative disease (e.g. cancer) comprises administering one or more additional therapeutic agents. In certain embodiments, the individual is a human.

In certain embodiments, a compound of the present disclosure, or a pharmaceutically acceptable salt thereof, for use in medical therapy is provided.

In certain embodiments, a compound of the present disclosure, or a pharmaceutically acceptable salt thereof, for use in treating or preventing a disease or condition responsive to the modulation of TLR8, is provided. In certain embodiments, the disease or condition is a viral infection.

In certain embodiments, a compound of the present disclosure, or a pharmaceutically acceptable salt thereof, for use in treating or preventing hepatitis B, is provided In certain embodiments, the use of a compound of the present disclosure, or a pharmaceutically acceptable salt thereof, for the manufacture of a medicament for treating or preventing a disease or condition responsive to the modulation of TLR8, is provided.

In certain embodiments, the use of a compound of the present disclosure, or a pharmaceutically acceptable salt thereof, for the manufacture of a medicament for treating or preventing hepatitis B, is provided.

Kits comprising the compounds, or pharmaceutically acceptable salts thereof, or pharmaceutical compositions of the foregoing are also provided. Articles of manufacture comprising a unit dose of the compounds, or pharmaceutically acceptable salts thereof, of the foregoing are also provided. Methods of preparing compounds of the present disclosure are also provided.

DETAILED DESCRIPTION

The description below is made with the understanding that the present disclosure is to be considered as an exemplification of the claimed subject matter, and is not intended to limit the appended claims to the specific embodiments illustrated. The headings used throughout this disclosure are provided for convenience and are not to be construed to limit the claims in any way. Embodiments illustrated under any heading may be combined with embodiments illustrated under any other heading.

I. DEFINITIONS

Unless defined otherwise, all technical and scientific terms used herein have the same meaning as commonly understood by one of ordinary skill in the art. A dash at the front or end of a chemical group is a matter of convenience to indicate the point of attachment to a parent moiety; chemical groups may be depicted with or without one or more dashes without losing their ordinary meaning. A prefix such as "$C_{u-v}$" or ($C_u$-$C_v$) indicates that the following group has from u to v carbon atoms, where u and v are integers. For example, "$C_{1-6}$alkyl" indicates that the alkyl group has from 1 to 6 carbon atoms.

"Alkyl" is a linear or branched saturated monovalent hydrocarbon. For example, an alkyl group can have 1 to 10 carbon atoms (i.e., ($C_{1-10}$)alkyl) or 1 to 8 carbon atoms (i.e., ($C_{1-8}$)alkyl) or 1 to 6 carbon atoms (i.e., ($C_{1-6}$ alkyl) or 1 to 4 carbon atoms (i.e., ($C_{1-4}$)alkyl). Examples of alkyl groups include, but are not limited to, methyl (Me, —$CH_3$), ethyl (Et, —$CH_2CH_3$), 1-propyl (n-Pr, n-propyl, —$CH_2CH_2CH_3$), 2-propyl (i-Pr, i-propyl, —$CH(CH_3)_2$), 1-butyl (n-Bu, n-butyl, —$CH_2CH_2CH_2CH_3$), 2-methyl-1-propyl (i-Bu, i-butyl, —$CH_2CH(CH_3)_2$), 2-butyl (s-Bu, s-butyl, —$CH(CH_3)CH_2CH_3$), 2-methyl-2-propyl (t-Bu, t-butyl, —$C(CH_3)_3$), 1-pentyl (n-pentyl, —$CH_2CH_2CH_2CH_2CH_3$), 2-pentyl (—$CH(CH_3)CH_2CH_2CH_3$), 3-pentyl (—$CH(CH_2CH_3)_2$), 2-methyl-2-butyl (—$C(CH_3)_2CH_2CH_3$), 3-methyl-2-butyl (—$CH(CH_3)CH(CH_3)_2$), 3-methyl-1-butyl (—$CH_2CH_2CH(CH_3)_2$), 2-methyl-1-butyl (—$CH_2CH(CH_3)CH_2CH_3$), 1-hexyl (—$CH_2CH_2CH_2CH_2CH_2CH_3$), 2-hexyl (—$CH(CH_3)CH_2CH_2CH_2CH_3$), 3-hexyl (—$CH(CH_2CH_3)(CH_2CH_2CH_3)$), 2-methyl-2-pentyl (—$C(CH_3)_2CH_2CH_2CH_3$), 3-methyl-2-pentyl (—$CH(CH_3)CH(CH_3)CH_2CH_3$), 4-methyl-2-pentyl (—$CH(CH_3)CH_2CH(CH_3)_2$), 3-methyl-3-pentyl (—$C(CH_3)(CH_2CH_3)_2$), 2-methyl-3-pentyl (—$CH(CH_2CH_3)CH(CH_3)_2$), 2,3-dimethyl-2-butyl (—$C(CH_3)_2CH(CH_3)_2$), 3,3-dimethyl-2-butyl (—$CH(CH_3)C(CH_3)_3$), and octyl (—$(CH_2)_7CH_3$).

The term "halo" or "halogen" as used herein refers to fluoro (—F), chloro (—$C_1$), bromo (—Br) and iodo (—I).

The term "haloalkyl" as used herein refers to an alkyl as defined herein, wherein one or more hydrogen atoms of the alkyl are independently replaced by a halo substituent, which may be the same or different. For example, $C_{1-8}$haloalkyl is a $C_{1-8}$ alkyl wherein one or more of the hydrogen atoms of the $C_{1-8}$ alkyl have been replaced by a halo substituent. Examples of haloalkyl groups include but are not limited to fluoromethyl, fluorochloromethyl, difluoromethyl, difluorochloromethyl, trifluoromethyl, 1,1,1-trifluoroethyl and pentafluoroethyl.

The term "aryl" as used herein refers to a single all carbon aromatic ring or a multiple condensed all carbon ring system wherein at least one of the rings is aromatic. For example, in certain embodiments, an aryl group has 6 to 20 carbon atoms, 6 to 14 carbon atoms, or 6 to 12 carbon atoms. Aryl includes a phenyl radical. Aryl also includes multiple condensed ring systems (e.g., ring systems comprising 2, 3 or 4 rings) having about 9 to 20 carbon atoms in which at least one ring is aromatic and wherein the other rings may be aromatic or not aromatic (i.e., carbocycle). Such multiple condensed ring systems are optionally substituted with one or more (e.g., 1, 2 or 3) oxo groups on any carbocycle portion of the multiple condensed ring system. The rings of the multiple condensed ring system can be connected to each other via fused, spiro and bridged bonds when allowed by valency requirements. It is also to be understood that when reference is made to a certain atom-range membered aryl (e.g., 6-10 membered aryl), the atom range is for the total ring atoms of the aryl. For example, a 6-membered aryl would include phenyl and a 10-membered aryl would include naphthyl and 1, 2, 3, 4-tetrahydronaphthyl. Non-limiting examples of aryl groups include, but are not limited to, phenyl, indenyl, naphthyl, 1, 2, 3, 4-tetrahydronaphthyl, anthracenyl, and the like.

The term "heteroaryl" as used herein refers to a single aromatic ring that has at least one atom other than carbon in the ring, wherein the atom is selected from the group consisting of oxygen, nitrogen and sulfur; "heteroaryl" also includes multiple condensed ring systems that have at least one such aromatic ring, which multiple condensed ring systems are further described below. Thus, "heteroaryl" includes single aromatic rings of from about 1 to 6 carbon atoms and about 1-4 heteroatoms selected from the group consisting of oxygen, nitrogen and sulfur. The sulfur and nitrogen atoms may also be present in an oxidized form provided the ring is aromatic. Exemplary heteroaryl ring systems include but are not limited to pyridyl, pyrimidinyl, oxazolyl or furyl. "Heteroaryl" also includes multiple condensed ring systems (e.g., ring systems comprising 2, 3 or 4 rings) wherein a heteroaryl group, as defined above, is condensed with one or more rings selected from heteroaryls (to form for example 1,8-naphthyridinyl), heterocycles, (to form for example 1,2,3,4-tetrahydro-1,8-naphthyridinyl), carbocycles (to form for example 5,6,7,8-tetrahydroquinolyl) and aryls (to form for example indazolyl) to form the multiple condensed ring system. Thus, a heteroaryl (a single aromatic ring or multiple condensed ring system) has about 1-20 carbon atoms and about 1-6 heteroatoms within the heteroaryl ring. Such multiple condensed ring systems may be optionally substituted with one or more (e.g., 1, 2, 3 or 4) oxo groups on the carbocycle or heterocycle portions of the condensed ring. The rings of the multiple condensed ring system can be connected to each other via fused, spiro and bridged bonds when allowed by valency requirements. It is to be understood that the individual rings of the multiple condensed ring system may be connected in any order relative to one another. It is to be understood that the point of attachment for a heteroaryl or heteroaryl multiple condensed ring system can be at any suitable atom of the heteroaryl or heteroaryl multiple condensed ring system including a carbon atom and a heteroatom (e.g., a nitrogen). It also to be understood that when a reference is made to a certain atom-range membered heteroaryl (e.g., a 5 to 10 membered heteroaryl), the atom range is for the total ring atoms of the heteroaryl and includes carbon atoms and heteroatoms. For example, a 5-membered heteroaryl would include a thiazolyl and a 10-membered heteroaryl would include a quinolinyl. Exemplary heteroaryls include but are not limited to pyridyl, pyrrolyl, pyrazinyl, pyrimidinyl, pyridazinyl, pyrazolyl, thienyl, indolyl, imidazolyl, oxazolyl, isoxazolyl, thiazolyl, furyl, oxadiazolyl, thiadiazolyl, quinolyl, isoquinolyl, benzothiazolyl, benzoxazolyl, indazolyl, quinoxalyl, quinazolyl, 5,6,7,8-tetrahydroisoquinolinyl benzofuranyl, benzimidazolyl, thianaphthenyl, pyrrolo[2,3-b]pyridinyl, quinazolinyl-4(3H)-one, triazolyl, 4,5,6,7-tetrahydro-1H-indazole and 3b,4,4a,5-tetrahydro-1H-cyclopropa[3,4]cyclopenta[1,2-c]pyrazole.

The term "cycloalkyl" refers to a single saturated or partially unsaturated all carbon ring having 3 to 20 annular carbon atoms (i.e., $C_{3-20}$ cycloalkyl), for example from 3 to 12 annular atoms, for example from 3 to 10 annular atoms. The term "cycloalkyl" also includes multiple condensed, saturated and partially unsaturated all carbon ring systems (e.g., ring systems comprising 2, 3 or 4 carbocyclic rings). Accordingly, cycloalkyl includes multicyclic carbocycles such as a bicyclic carbocycles (e.g., bicyclic carbocycles having about 6 to 12 annular carbon atoms such as bicyclo [3.1.0]hexane and bicyclo[2.1.1]hexane), and polycyclic carbocycles (e.g tricyclic and tetracyclic carbocycles with up to about 20 annular carbon atoms). The rings of a multiple condensed ring system can be connected to each other via fused, spiro and bridged bonds when allowed by valency requirements. Non-limiting examples of monocyclic cycloalkyl include cyclopropyl, cyclobutyl, cyclopentyl, 1-cyclopent-1-enyl, 1-cyclopent-2-enyl, 1-cyclopent-3-enyl, cyclohexyl, 1-cyclohex-1-enyl, 1-cyclohex-2-enyl and 1-cyclohex-3-enyl.

The term "heterocyclyl" or "heterocycle" as used herein refers to a single saturated or partially unsaturated non-aromatic ring or a non-aromatic multiple ring system that has at least one heteroatom in the ring (i.e., at least one annular heteroatom selected from oxygen, nitrogen, and sulfur). Unless otherwise specified, a heterocyclyl group has from 5 to about 20 annular atoms, for example from 3 to 12 annular atoms, for example from 5 to 10 annular atoms. Thus, the term includes single saturated or partially unsaturated rings (e.g., 3, 4, 5, 6 or 7-membered rings) having from about 1 to 6 annular carbon atoms and from about 1 to 3 annular heteroatoms selected from the group consisting of oxygen, nitrogen and sulfur in the ring. The rings of the multiple condensed ring system can be connected to each other via fused, spiro and bridged bonds when allowed by valency requirements. Heterocycles include, but are not limited to, azetidine, aziridine, imidazolidine, morpholine, oxirane (epoxide), oxetane, piperazine, piperidine, pyrazolidine, piperidine, pyrrolidine, pyrrolidinone, tetrahydrofuran, tetrahydrothiophene, dihydropyridine, tetrahydropyridine, quinuclidine, N-bromopyrrolidine, N-chloropiperidine, and the like.

As used herein, "treatment" or "treating" is an approach for obtaining beneficial or desired results. For purposes of the present disclosure, beneficial or desired results include, but are not limited to, alleviation of a symptom and/or diminishment of the extent of a symptom and/or preventing a worsening of a symptom associated with a disease or condition. In one embodiment, "treatment" or "treating" includes one or more of the following: a) inhibiting the disease or condition (e.g., decreasing one or more symptoms resulting from the disease or condition, and/or diminishing the extent of the disease or condition); b) slowing or arresting the development of one or more symptoms associated with the disease or condition (e.g., stabilizing the disease or condition, delaying the worsening or progression of the disease or condition); and c) relieving the disease or condition, e.g., causing the regression of clinical symptoms, ameliorating the disease state, delaying the progression of the disease, increasing the quality of life, and/or prolonging survival.

A "compound of the present disclosure" includes compounds disclosed herein, for example a compound of the present disclosure includes compounds of Formula (I), (II), (III), and the compounds listed in Table 1. A compound of the present disclosure also includes compounds of Formula (I), (II), (III), the compounds of Examples 1-14, and the compounds listed in Tables 1. A compound of the present disclosure also includes the compounds of Examples 1-14

As used herein, "delaying" development of a disease or condition means to defer, hinder, slow, retard, stabilize and/or postpone development of the disease or condition. This delay can be of varying lengths of time, depending on the history of the disease and/or individual being treated. As is evident to one skilled in the art, a sufficient or significant delay can, in effect, encompass prevention, in that the individual does not develop the disease or condition. For example, a method that "delays" development of AIDS is a method that reduces the probability of disease development in a given time frame and/or reduces extent of the disease in a given time frame, when compared to not using the method. Such comparisons may be based on clinical studies, using a statistically significant number of subjects. For example, the development of AIDS can be detected using known methods, such as confirming an individual's HIV$^+$ status and assessing the individual's T-cell count or other indication of AIDS development, such as extreme fatigue, weight loss, persistent diarrhea, high fever, swollen lymph nodes in the neck, armpits or groin, or presence of an opportunistic condition that is known to be associated with AIDS (e.g., a condition that is generally not present in individuals with functioning immune systems but does occur in AIDS patients). Development may also refer to disease progression that may be initially undetectable and includes occurrence, recurrence and onset.

As used herein, "prevention" or "preventing" refers to a regimen that protects against the onset of the disease or disorder such that the clinical symptoms of the disease do not develop. Thus, "prevention" relates to administration of a therapy (e.g., administration of a therapeutic substance) to a subject before signs of the disease are detectable in the subject (e.g., administration of a therapeutic substance to a subject in the absence of detectable infectious agent (e.g., virus) in the subject). The subject may be an individual at risk of developing the disease or disorder, such as an individual who has one or more risk factors known to be associated with development or onset of the disease or disorder. Thus, in certain embodiments, the term "preventing HBV infection" refers to administering to a subject who does not have a detectable HBV infection an anti-HBV therapeutic substance. It is understood that the subject for anti-HBV preventative therapy may be an individual at risk of contracting the HBV virus. Thus, in certain embodiments, the term "preventing HIV infection" refers to administering to a subject who does not have a detectable HIV infection an anti-HIV therapeutic substance. It is understood that the subject for anti-HIV preventative therapy may be an individual at risk of contracting the HIV virus.

As used herein, an "at risk" individual is an individual who is at risk of developing a condition to be treated. An individual "at risk" may or may not have detectable disease or condition, and may or may not have displayed detectable disease prior to the treatment of methods described herein. "At risk" denotes that an individual has one or more so-called risk factors, which are measurable parameters that correlate with development of a disease or condition and are known in the art. An individual having one or more of these risk factors has a higher probability of developing the disease or condition than an individual without these risk factor(s). For example, individuals at risk for AIDS are those having HIV.

As used herein, the term "therapeutically effective amount" or "effective amount" refers to an amount that is effective to elicit the desired biological or medical response, including the amount of a compound that, when administered to a subject for treating a disease, is sufficient to effect such treatment for the disease. The effective amount will vary depending on the compound, the disease, and its severity and the age, weight, etc., of the subject to be treated. The effective amount can include a range of amounts. As is understood in the art, an effective amount may be in one or more doses, i.e., a single dose or multiple doses may be required to achieve the desired treatment endpoint. An effective amount may be considered in the context of administering one or more therapeutic agents, and a single agent may be considered to be given in an effective amount if, in conjunction with one or more other agents, a desirable or beneficial result may be or is achieved. Suitable doses of any co-administered compounds may optionally be lowered due to the combined action (e.g., additive or synergistic effects) of the compounds.

As used herein, an "agonist" is a substance that stimulates its binding partner, typically a receptor. Stimulation is defined in the context of the particular assay, or may be apparent in the literature from a discussion herein that makes a comparison to a factor or substance that is accepted as an "agonist" or an "antagonist" of the particular binding partner under substantially similar circumstances as appreciated by those of skill in the art. Stimulation may be defined with respect to an increase in a particular effect or function that is induced by interaction of the agonist or partial agonist with a binding partner and can include allosteric effects.

As used herein, an "antagonist" is a substance that inhibits its binding partner, typically a receptor. Inhibition is defined in the context of the particular assay, or may be apparent in the literature from a discussion herein that makes a comparison to a factor or substance that is accepted as an "agonist" or an "antagonist" of the particular binding partner under substantially similar circumstances as appreciated by those of skill in the art. Inhibition may be defined with respect to a decrease in a particular effect or function that is induced by interaction of the antagonist with a binding partner, and can include allosteric effects.

As used herein, a "partial agonist" or a "partial antagonist" is a substance that provides a level of stimulation or inhibition, respectively, to its binding partner that is not fully or completely agonistic or antagonistic, respectively. It will be recognized that stimulation, and hence, inhibition is defined intrinsically for any substance or category of substances to be defined as agonists, antagonists, or partial agonists.

As used herein, "intrinsic activity" or "efficacy" relates to some measure of biological effectiveness of the binding partner complex. With regard to receptor pharmacology, the context in which intrinsic activity or efficacy should be defined will depend on the context of the binding partner (e.g., receptor/ligand) complex and the consideration of an activity relevant to a particular biological outcome. For example, in some circumstances, intrinsic activity may vary depending on the particular second messenger system involved. Where such contextually specific evaluations are relevant, and how they might be relevant in the context of the present disclosure, will be apparent to one of ordinary skill in the art.

"Pharmaceutically acceptable excipient" includes without limitation any adjuvant, carrier, excipient, glidant, sweetening agent, diluent, preservative, dye/colorant, flavor enhancer, surfactant, wetting agent, dispersing agent, suspending agent, stabilizer, isotonic agent, solvent, or emulsifier which has been approved by the United States Food and Drug Administration as being acceptable for use in humans or domestic animals As used herein, modulation of a receptor includes agonism, partial agonism, antagonism, partial antagonism, or inverse agonism of a receptor.

The nomenclature used herein to name the subject compounds is illustrated in the Examples and elsewhere herein.

As used herein, "co-administration" includes administration of unit dosages of the compounds disclosed herein before or after administration of unit dosages of one or more additional therapeutic agents, for example, administration of the compound disclosed herein within seconds, minutes, or hours of the administration of one or more additional therapeutic agents. For example, in some embodiments, a unit dose of a compound of the present disclosure is administered first, followed within seconds or minutes by administration of a unit dose of one or more additional therapeutic agents. Alternatively, in other embodiments, a unit dose of one or more additional therapeutic agents is administered first, followed by administration of a unit dose of a compound of the present disclosure within seconds or minutes. In some embodiments, a unit dose of a compound of the present disclosure is administered first, followed, after a period of hours (e.g., 1-12 hours), by administration of a unit dose of one or more additional therapeutic agents. In other embodiments, a unit dose of one or more additional therapeutic agents is administered first, followed, after a period of hours (e.g., 1-12 hours), by administration of a unit dose of a compound of the present disclosure.

Provided are also pharmaceutically acceptable salts, hydrates, solvates, tautomeric forms, polymorphs, and prodrugs of the compounds described herein. "Pharmaceutically acceptable" or "physiologically acceptable" refer to compounds, salts, compositions, dosage forms and other materials which are useful in preparing a pharmaceutical composition that is suitable for veterinary or human pharmaceutical use.

The compounds of described herein may be prepared and/or formulated as pharmaceutically acceptable salts. Pharmaceutically acceptable salts are non-toxic salts of a free base form of a compound that possesses the desired pharmacological activity of the free base. These salts may be derived from inorganic or organic acids or bases. For example, a compound that contains a basic nitrogen may be prepared as a pharmaceutically acceptable salt by contacting the compound with an inorganic or organic acid. Non-limiting examples of pharmaceutically acceptable salts include sulfates, pyrosulfates, bisulfates, sulfites, bisulfites, phosphates, monohydrogen-phosphates, dihydrogenphosphates, metaphosphates, pyrophosphates, chlorides, bromides, iodides, acetates, propionates, decanoates, caprylates, acrylates, formates, isobutyrates, caproates, heptanoates, propiolates, oxalates, malonates, succinates, suberates, sebacates, fumarates, maleates, butyne-1,4-dioates, hexyne-1,6-dioates, benzoates, chlorobenzoates, methylbenzoates, dinitrobenzoates, hydroxybenzoates, methoxybenzoates, phthalates, sulfonates, methylsulfonates, propylsulfonates, besylates, xylenesulfonates, naphthalene-1-sulfonates, naphthalene-2-sulfonates, phenylacetates, phenylpropionates, phenylbutyrates, citrates, lactates, γ-hydroxybutyrates, glycolates, tartrates, and mandelates. Lists of other suitable pharmaceutically acceptable salts are found in Remington: The Science and Practice of Pharmacy, $21^{st}$ Edition, Lippincott Wiliams and Wilkins, Philadelphia, Pa., 2006.

Examples of "pharmaceutically acceptable salts" of the compounds disclosed herein also include salts derived from an appropriate base, such as an alkali metal (for example, sodium, potassium), an alkaline earth metal (for example, magnesium), ammonium and $NX_4^+$ (wherein X is $C_1$-$C_4$ alkyl). Also included are base addition salts, such as sodium or potassium salts.

Provided are also compounds described herein or pharmaceutically acceptable salts, isomers, or a mixture thereof, in which from 1 to n hydrogen atoms attached to a carbon atom may be replaced by a deuterium atom or D, in which n is the number of hydrogen atoms in the molecule. As known in the art, the deuterium atom is a non-radioactive isotope of the hydrogen atom. Such compounds may increase resistance to metabolism, and thus may be useful for increasing the half-life of the compounds described herein or pharmaceutically acceptable salts, isomer, or a mixture thereof when administered to a mammal. See, e.g., Foster, "Deuterium Isotope Effects in Studies of Drug Metabolism", Trends Pharmacol. Sci., 5(12):524-527 (1984). Such compounds are synthesized by means well known in the art, for example by employing starting materials in which one or more hydrogen atoms have been replaced by deuterium.

Examples of isotopes that can be incorporated into the disclosed compounds also include isotopes of hydrogen, carbon, nitrogen, oxygen, phosphorous, fluorine, chlorine, and iodine, such as $^2$H, $^3$H, $^{11}$C, $^{13}$C, $^{14}$C, $^{13}$N, $^{15}$N, $^{15}$O, $^{17}$O, $^{18}$O, $^{31}$P, $^{32}$P, $^{35}$S, $^{18}$F, $^{36}$Cl, $^{123}$I, and $^{125}$I, respectively. Substitution with positron emitting isotopes, such as $^{11}$C, $^{18}$F, $^{15}$O and $^{13}$N, can be useful in Positron Emission Topography (PET) studies for examining substrate receptor occupancy. Isotopically-labeled compounds of Formula (I), can generally be prepared by conventional techniques known to those skilled in the art or by processes analogous to those described in the Examples as set out below using an appropriate isotopically-labeled reagent in place of the non-labeled reagent previously employed.

The compounds of the embodiments disclosed herein, or their pharmaceutically acceptable salts may contain one or more asymmetric centers and may thus give rise to enantiomers, diastereomers, and other stereoisomeric forms that may be defined, in terms of absolute stereochemistry, as (R)- or (S)- or, as (D)- or (L)- for amino acids. The present disclosure is meant to include all such possible isomers, as well as their racemic and optically pure forms. Optically active (+) and (−), (R)- and (S)-, or (D)- and (L)-isomers may be prepared using chiral synthons or chiral reagents, or resolved using conventional techniques, for example, chromatography and fractional crystallization. Conventional techniques for the preparation/isolation of individual enantiomers include chiral synthesis from a suitable optically pure precursor or resolution of the racemate (or the racemate of a salt or derivative) using, for example, chiral high pressure liquid chromatography (HPLC). When the compounds described herein contain olefinic double bonds or other centres of geometric asymmetry, and unless specified otherwise, it is intended that the compounds include both E and Z geometric isomers. Likewise, all tautomeric forms are also intended to be included. Where compounds are represented in their chiral form, it is understood that the embodiment encompasses, but is not limited to, the specific diastereomerically or enantiomerically enriched form. Where chirality is not specified but is present, it is understood that the embodiment is directed to either the specific diastereomerically or enantiomerically enriched form; or a racemic or scalemic mixture of such compound(s). As used herein, "scalemic mixture" is a mixture of stereoisomers at a ratio other than 1:1.

A "stereoisomer" refers to a compound made up of the same atoms bonded by the same bonds but having different three-dimensional structures, which are not interchangeable. The present disclosure contemplates various stereoisomers and mixtures thereof and includes "enantiomers", which refers to two stereoisomers whose molecules are non-superimposable mirror images of one another.

A "tautomer" refers to a proton shift from one atom of a molecule to another atom of the same molecule. The present disclosure includes tautomers of any said compounds.

A "solvate" is formed by the interaction of a solvent and a compound. Solvates of salts of the compounds described herein are also provided. Hydrates of the compounds described herein are also provided.

The term "prodrug" is defined in the pharmaceutical field as a biologically inactive derivative of a drug that upon administration to the human body is converted to the biologically active parent drug according to some chemical or enzymatic pathway.

The terms "combination antiretroviral therapy" ("cART") refers to combinations or "cocktails" of antiretroviral medications used to treat human viral infections, including HIV infections. As used herein, the terms "combination antiretroviral therapy" and "cART include combinations and regimens often referred to as Highly Active Antiretroviral Therapy (HAART). HAART and cART combinations and regimens commonly include multiple, often two or more, drugs such as nucleoside reverse transcriptase inhibitors (NRTIs), non-nucleoside reverse transcriptase inhibitors (NNRTIs), protease inhibitors (PIs), fusion inhibitors, CCR5 agonists, and/or integrase inhibitors.

The terms "latent HIV reservoir", "HIV latent reservoir", "HIV reservoir", "latent reservoir", and "latent HIV infection" refer to a condition in which resting CD4+T lymphocytes or other cells are infected with HIV but are not actively producing HIV. The presently inactive HIV infected cells are referred to as "latently infected cells". Antiretroviral therapy (ART) can reduce the level of HIV in the blood to an undetectable level, while latent reservoirs of HIV continue to survive. When a latently infected cell is reactivated, the cell begins to produce HIV (HIV replication).

II. COMPOUNDS

The present disclosure provides a compound of Formula I

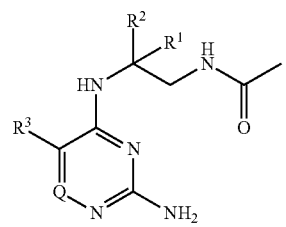

Formula I or a pharmaceutically acceptable salt thereof,
wherein:
$R^1$ is —H, $C_{1-4}$ alkyl, or $C_{1-4}$ haloalkyl;
$R^2$ is $C_{1-6}$ alkyl or $C_{1-6}$ haloalkyl;
$R^3$ is $C_{1-4}$ alkoxy optionally substituted with 1 $R^X$;
  each $R^X$ is independently —OR$^Y$, 5 to 6 membered heterocyclyl having 1 to 3 heteroatoms selected from oxygen, nitrogen, and sulfur optionally substituted with 1 to 3 $R^Z$; phenyl optionally substituted with 1 to 3 $R^Z$; or 5 to 6 membered heteroaryl having 1 to 3 heteroatoms selected from oxygen, nitrogen, and sulfur optionally substituted with 1 to 3 $R^Z$;
    $R^Y$ is $C_{1-4}$ alkyl, $C_{1-4}$ haloalkyl, or 5 to 10 membered heteroaryl having 1 to 3 heteroatoms selected from oxygen, nitrogen, and sulfur optionally substituted with 1 to 3 $R^Z$;
Q is N, CH, or CR$^4$;
or $R^3$ and $R^4$ are taken together to form $C_{5-6}$ cycloalkyl; 5 to 6 membered heterocyclyl having 1 to 3 heteroatoms selected from oxygen, nitrogen, and sulfur; phenyl; or 5 to 6 membered heteroaryl having 1 to 3 heteroatoms selected from oxygen, nitrogen, and sulfur, wherein:
  $C_{5-6}$ cycloalkyl and phenyl are each independently optionally substituted with 1 to 3 $R^5$;
    each $R^5$ is independently halogen, —OH, —NH$_2$, —CN, $C_{1-4}$ alkyl optionally substituted with 1 to 3 $R^Z$, $C_{1-4}$ haloalkyl, $C_{1-4}$ alkoxy, —C(O)OH, —C(O)$C_{1-4}$ alkyl, —C(O)O$C_{1-4}$ alkyl, —C(O)NH$_2$, —C(O)NH($C_{1-4}$ alkyl), —C(O)N($C_{1-4}$ alkyl)$_2$, —N(H)C(O)$C_{1-4}$ alkyl, —S(O)$_2$$C_{1-4}$ alkyl, or 5 to 6 membered heteroaryl having 1 to 3 heteroatoms selected from oxygen, nitrogen, and sulfur optionally substituted with 1 to 3 $R^Z$;

5 to 6 membered heteroaryl is optionally substituted with 1 to 3 $R^6$;

each $R^6$ is independently halogen, —OH, —NH$_2$, —CN, $C_{1-4}$ alkyl optionally substituted with 1 phenyl optionally substituted with 1 to 3 $R^Z$; $C_{1-4}$ haloalkyl, $C_{1-4}$ alkoxy, —S(O)$_2$$C_{1-4}$ alkyl; 5 to 6 membered heterocyclyl having 1 to 3 heteroatoms selected from oxygen, nitrogen, and sulfur optionally substituted with 1 to 3 $R^Z$; phenyl optionally substituted with 1 to 3 $R^Z$; or 5 to 6 membered heteroaryl having 1 to 3 heteroatoms selected from oxygen, nitrogen, and sulfur optionally substituted with 1 to 3 $R^Z$;

5 to 6 membered heterocyclyl is optionally substituted with 1 to 3 $R^7$ $R^7$ is halogen, —OH, $C_{1-4}$ alkyl, $C_{1-4}$ alkoxy, or —C(O)$R^8$;

each $R^8$ is independently $C_{1-4}$ alkyl optionally substituted with —CN or —NH$_2$; $C_{1-4}$ haloalkyl; $C_{5-6}$ cycloalkyl, 5 to 6 membered heterocyclyl having 1 to 3 heteroatoms selected from oxygen, nitrogen, and sulfur optionally substituted with 1 to 3 $R^Z$; or 5 to 10 membered heteroaryl having 1 to 3 heteroatoms selected from oxygen, nitrogen, and sulfur optionally substituted with 1 to 3 $R^Z$;

and each $R^Z$ is independently —NH$_2$, $C_{1-4}$ alkyl, halogen, —CN, —O$C_{1-4}$ alkyl, $C_{1-4}$ haloalkyl, or —C(O)NH$_2$;

with the proviso that Formula I is not

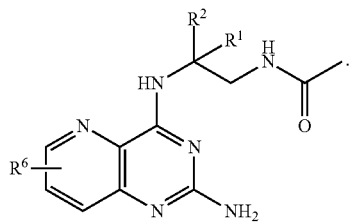

In certain embodiments of Formula (I), Q is N, CH, or $CR^4$. In certain embodiments of Formula (I), Q is N. In certain embodiments of Formula (I), Q is CH. In certain embodiments of Formula (I), Q is $CR^4$. In certain embodiments of Formula (I), Q is CH or $CR^4$.

In certain embodiments of Formula (I), $R^1$ is —H, $C_{1-4}$ alkyl, or $C_{1-4}$ haloalkyl. In certain embodiments of Formula (I), $R^1$ is —H or $C_{1-4}$ alkyl. In certain embodiments of Formula (I), $R^1$ is methyl. In certain embodiments of Formula (I), $R^1$ is ethyl. In certain embodiments of Formula (I), $R^1$ is propyl. In certain embodiments of Formula (I), $R^1$ is trifluoromethyl.

In certain embodiments of Formula (I), $R^2$ is $C_{1-6}$ alkyl or $C_{1-6}$ haloalkyl. In certain embodiments of Formula (I), $R^2$ is $C_{3-6}$ alkyl. In certain embodiments of Formula (I), $R^2$ is methyl. In certain embodiments of Formula (I), $R^2$ is ethyl. In certain embodiments of Formula (I), $R^2$ is propyl. In certain embodiments of Formula (I), $R^2$ is butyl. In certain embodiments of Formula (I), $R^2$ is pentyl. In certain embodiments of Formula (I), $R^2$ is hexyl.

In certain embodiments of Formula (I), $R^1$ is —H or $C_{1-4}$ alkyl; $R^2$ is $C_{3-6}$ alkyl; Q is $CR^4$; $R^3$ and $R^4$ are taken together to form $C_{5-6}$ cycloalkyl; 5 to 6 membered heterocyclyl having 1 to 3 heteroatoms selected from oxygen, nitrogen, and sulfur; phenyl; or 5 to 6 membered heteroaryl having 1 to 3 heteroatoms selected from oxygen, nitrogen, and sulfur, wherein: phenyl is optionally substituted with 1 to 3 halogen; 5 to 6 membered heteroaryl is optionally substituted with 1 to 3 $R^6$; each $R^6$ is independently halogen, —OH, $C_{1-4}$ alkyl, or $C_{1-4}$ alkoxy; and 5 to 6 membered heterocyclyl is optionally substituted with 1 to 3 —C(O)$C_{1-4}$ alkyl.

In certain embodiments of Formula (I), $R^1$ is —H or $C_{1-4}$ alkyl; $R^2$ is $C_{3-6}$ alkyl; $R^3$ and $R^4$ are taken together to form $C_{5-6}$ cycloalkyl; 5 to 6 membered heterocyclyl having 1 to 3 heteroatoms selected from oxygen, nitrogen, and sulfur; phenyl; or 5 to 6 membered heteroaryl having 1 to 3 heteroatoms selected from oxygen, nitrogen, and sulfur, wherein phenyl is optionally substituted with 1 to 3 halogen; 5 to 6 membered heteroaryl is optionally substituted with 1 to 3 $R^6$; each $R^6$ is independently halogen, —OH, $C_{1-4}$ alkyl, or $C_{1-4}$ alkoxy; and 5 to 6 membered heterocyclyl is optionally substituted with 1 to 3 —C(O)$R^8$ wherein each $R^8$ is independently $C_{1-4}$ alkyl optionally substituted with —CN or —NH$_2$, $C_{1-3}$ haloalkyl, cyclopropyl, cyclobutyl, tetrahydropyranyl, thienyl optionally substituted with 1 to 3 $C_{1-3}$ alkyl; thiazolyl, imidazolyl optionally substituted with 1 to 3 $C_{1-2}$ alkyl; oxazolyl, isoxazolyl optionally substituted with 1 to 3 $C_{1-2}$ alkyl; thiadiazolyl, phenyl, pyrazinyl, or quinolinyl.

In certain embodiments of Formula (I), $R^1$ is —H or $C_{1-4}$ alkyl; $R^2$ is $C_{3-6}$ alkyl; $R^3$ and $R^4$ are taken together to form $C_{5-6}$ cycloalkyl; 5 to 6 membered heterocyclyl having 1 to 3 heteroatoms selected from oxygen, nitrogen, and sulfur; phenyl; or 5 to 6 membered heteroaryl having 1 to 3 heteroatoms selected from oxygen, nitrogen, and sulfur, wherein phenyl is optionally substituted with 1 to 3 halogen; 5 to 6 membered heteroaryl is optionally substituted with 1 to 3 $R^6$; each $R^6$ is independently halogen, —OH, $C_{1-4}$ alkyl, or $C_{1-4}$ alkoxy; and 5 to 6 membered heterocyclyl is optionally substituted with 1 to 3 —C(O)$C_{1-4}$ alkyl.

In certain embodiments of Formula (I), (II), or (III), $R^3$ is $C_{1-4}$ alkoxy optionally substituted with 1 to 3 $R^X$, wherein $R^X$ is defined in this application. In certain embodiments of Formula (I), (II), or (III), $R^3$ is $C_{1-4}$ alkoxy optionally substituted with 1 $R^X$, wherein $R^X$ is defined in this application. In certain embodiments of Formula (I), (II), or (III), $R^3$ is $C_{1-2}$ alkoxy optionally substituted with 1 to 3 $R^X$, wherein $R^X$ is defined in this application.

In certain embodiments of Formula (I), (II), or (III), each $R^X$ is independently —O$R^Y$, 5 to 6 membered heterocyclyl having 1 to 3 heteroatoms selected from oxygen, nitrogen, and sulfur optionally substituted with 1 to 3 $R^Z$; phenyl optionally substituted with 1 to 3 $R^Z$; or 5 to 6 membered heteroaryl having 1 to 3 heteroatoms selected from oxygen, nitrogen, and sulfur optionally substituted with 1 to 3 $R^Z$, wherein $R^Y$ and $R^Z$ are defined in this application. In certain embodiments of Formula (I), (II), or (III), each $R^X$ is independently O$R^Y$, morpholino, phenyl, pyridinyl, pyrazolyl, or pyridazinyl, wherein each morpholino, phenyl, pyridinyl, pyrazolyl, and pyridazinyl are independently optionally substituted with —OCH$_3$, $C_{1-3}$ alkyl, chloro, or fluoro; wherein $R^Y$ is —CH$_3$, —CH$_2$CF$_3$, or quinolinyl optionally substituted with —OCH$_3$, C$_{1-3}$ alkyl, chloro, or fluoro.

In certain embodiments of Formula (I), (II), or (III), each $R^Y$ is independently C$_{1-4}$ alkyl, C$_{1-4}$ haloalkyl, or 5 to 10 membered heteroaryl having 1 to 3 heteroatoms selected from oxygen, nitrogen, and sulfur optionally substituted with 1 to 3 $R^Z$ wherein $R^Z$ is defined in this application. In certain embodiments of Formula (I), (II), or (III), each $R^Y$ is independently $R^Y$ is —CH$_3$, —CH$_2$CF$_3$, or quinolinyl optionally substituted with —OCH$_3$, C$_{1-3}$ alkyl, chloro, or fluoro.

In certain embodiments of Formula (I), (II), or (III), $R^3$ and $R^4$ are taken together to form C$_{5-6}$ cycloalkyl; 5 to 6 membered heterocyclyl having 1 to 3 heteroatoms selected from oxygen, nitrogen, and sulfur; phenyl; or 5 to 6 membered heteroaryl having 1 to 3 heteroatoms selected from oxygen, nitrogen, and sulfur, wherein C$_{5-6}$ cycloalkyl and phenyl are each independently optionally substituted with 1 to 3 $R^5$; 5 to 6 membered heteroaryl is optionally substituted with 1 to 3 $R^6$; 5 to 6 membered heterocyclyl is optionally substituted with 1 to 3 $R^7$; wherein $R^5$, $R^6$, and $R^7$ are defined in this application.

In certain embodiments of Formula (I), (II), or (III), $R^3$ and $R^4$ are taken together to form C$_{5-6}$ cycloalkyl optionally substituted with 1 to 3 $R^5$, wherein $R^5$ is defined in this application. In certain embodiments of Formula (I), (II), or (III), $R^3$ and $R^4$ are taken together to form C$_{5-6}$ cycloalkyl. In certain embodiments of Formula (I), (II), or (III), $R^3$ and $R^4$ are taken together to form a 6 membered cycloalkyl.

In certain embodiments of Formula (I), (II), or (III), $R^3$ and $R^4$ are taken together to form a 5 to 6 membered heterocyclyl having 1 to 3 heteroatoms selected from oxygen, nitrogen, and sulfur optionally substituted with 1 to 3 $R^7$, wherein $R^7$ is defined in this application. In certain embodiments of Formula (I), (II), or (III), each $R^7$ is —C(O)$R^8$ wherein $R^8$ is C$_{1-4}$ alkyl optionally substituted with —CN or —NH$_2$, C$_{1-3}$ haloalkyl, cyclopropyl, cyclobutyl, tetrahydropyranyl, thienyl optionally substituted with 1 to 3 C$_{1-3}$ alkyl; thiazolyl, imidazolyl optionally substituted with 1 to 3 C$_{1-2}$ alkyl; oxazolyl, isoxazolyl optionally substituted with 1 to 3 C$_{1-2}$ alkyl; thiadiazolyl, phenyl, pyrazinyl, or quinolinyl. In certain embodiments of Formula (I), (II), or (III), $R^7$ is —C(O)C$_{1-4}$alkyl. In certain embodiments of Formula (I), (II), or (III), $R^7$ is —C(O)CH$_3$. In certain embodiments of Formula (I), (II), or (III), $R^3$ and $R^4$ are taken together to form a tetrahydropyridinyl optionally substituted with —C(O)$R^8$ wherein $R^8$ is C$_{1-4}$ alkyl optionally substituted with —CN or —NH$_2$, C$_{1-3}$ haloalkyl, cyclopropyl, cyclobutyl, tetrahydropyranyl, thienyl optionally substituted with 1 to 3 C$_{1-3}$ alkyl; thiazolyl, imidazolyl optionally substituted with 1 to 3 C$_{1-2}$ alkyl; oxazolyl, isoxazolyl optionally substituted with 1 to 3 C$_{1-2}$ alkyl; thiadiazolyl, phenyl, pyrazinyl, or quinolinyl.

In certain embodiments of Formula (I), (II), or (III), $R^3$ and $R^4$ are taken together to form a phenyl optionally substituted with 1 to 3 $R^5$, wherein $R^5$ is defined in this application. In certain embodiments of Formula (I), (II), or (III), $R^3$ and $R^4$ are taken together to form a phenyl. In certain embodiments of Formula (I), (II), or (III), $R^3$ and $R^4$ are taken together to form a phenyl optionally substituted with 1 to 3 chloro, fluoro, bromo, —CN, C$_{1-2}$ alkyl optionally substituted with —OH, C$_{1-2}$ alkoxy, —C(O)C$_{1-2}$ alkyl, —C(O)OC$_{1-2}$ alkyl, or pyrazolyl optionally substituted with 1 to 3 C$_{1-2}$ alkyl; or imidazolyl optionally substituted with 1 to 3 C$_{1-2}$ alkyl.

In certain embodiments of Formula (I), (II), or (III), each $R^5$ is independently halogen, —OH, —NH$_2$, —CN, C$_{1-4}$ alkyl, C$_{1-2}$ haloalkyl, C$_{1-4}$ alkoxy, —C(O)OH, —C(O)C$_{1-4}$ alkyl, —C(O)OC$_{1-4}$ alkyl, —C(O)NH$_2$, —C(O)NH(C$_{1-4}$ alkyl), —C(O)N(C$_{1-4}$ alkyl)$_2$, —N(H)C(O)C$_{1-4}$ alkyl, —S(O)$_2$C$_{1-4}$ alkyl. In certain embodiments of Formula (I), (II), or (III), each $R^5$ is independently chloro, fluoro, bromo, —CN, C$_{1-2}$ alkyl optionally substituted with —OH, C$_{1-2}$ alkoxy, —C(O)C$_{1-2}$ alkyl, —C(O)OC$_{1-2}$ alkyl, or pyrazolyl optionally substituted with 1 to 3 C$_{1-2}$ alkyl; or imidazolyl optionally substituted with 1 to 3 C$_{1-2}$ alkyl. In certain embodiments of Formula (I), (II), or (III), each $R^5$ is independently chloro, fluoro, bromo, —CN, —CH$_3$, —CF$_3$, —OCH$_3$, —C(O)CH$_3$, or —C(O)OCH$_3$. In certain embodiments of Formula (I), (II), or (III), each $R^5$ is independently chloro, fluoro, bromo, —CN, —CH$_3$, —OCH$_3$, —C(O)CH$_3$, or —C(O)OCH$_3$.

In certain embodiments of Formula (I), (II), or (III), $R^3$ and $R^4$ are taken together to form a 5 to 6 membered heteroaryl having 1 to 3 heteroatoms selected from oxygen, nitrogen, and sulfur optionally substituted with 1 to 3 $R^6$, wherein $R^6$ is defined in the application. In certain embodiments of Formula (I), (II), or (III), each $R^6$ is independently halogen, —OH, C$_{1-4}$ alkyl, or C$_{1-4}$ alkoxy. In certain embodiments of Formula (I), (II), or (III), each $R^6$ is independently halogen, —OH, —CH$_3$, or —OCH$_3$. In certain embodiments of Formula (I), (II), or (III), $R^3$ and $R^4$ are taken together to form a 5 to 6 membered heteroaryl having 1 to 3 heteroatoms selected from oxygen, nitrogen, and sulfur. In certain embodiments of Formula (I), (II), or (III), $R^3$ and $R^4$ are taken together to form pyrazinyl, pyridinyl or thienyl optionally substituted with 1 to 3 C$_{1-2}$ alkyl.

In certain embodiments of a compound of Formula (I), (II), or (III), $R^3$ and $R^4$ are taken together to form:

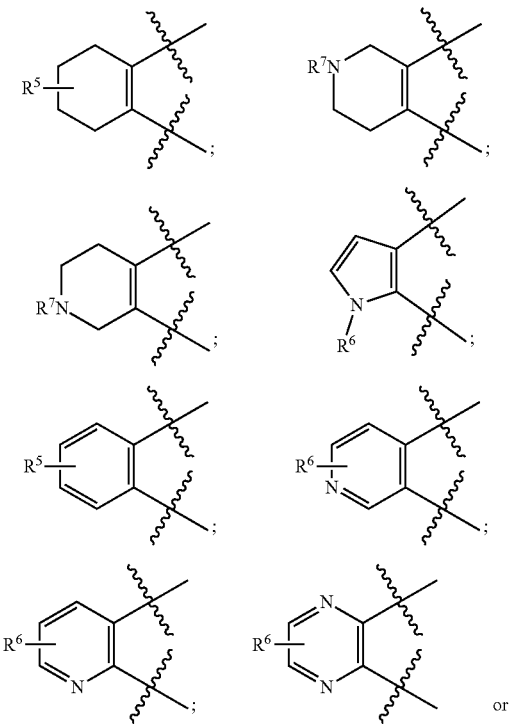

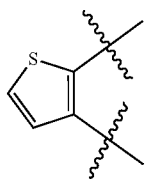

wherein each $R^5$, $R^6$, or $R^7$ is optionally present and as defined herein.

In certain embodiments, the compound of Formula (I) is a compound of Formula (II)

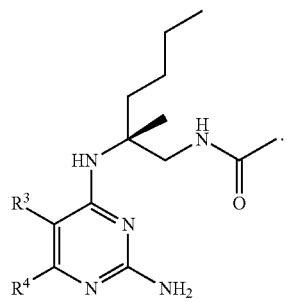

Formula II

In certain embodiments of a compound of Formula (I), (II), or (III), $R^3$ and $R^4$ are taken together to form a 6 membered cycloalkyl. In certain embodiments of a compound of Formula (I), (II), or (III), $R^3$ and $R^4$ are taken together to form tetrahydropyridinyl optionally substituted with 1 to 3 $C(O)C_{1-2}$ alkyl. In certain embodiments of a compound of Formula (I), (II), or (III), $R^3$ and $R^4$ are taken together to form phenyl optionally substituted with 1 to 3 fluoro. In certain embodiments of a compound of Formula (I), (II), or (III), $R^3$ and $R^4$ are taken together to form pyrazinyl, thienyl or pyridinyl.

In certain embodiments of a compound of Formula (I), (II), or (III), $R^3$ and $R^4$ are taken together to form phenyl optionally substituted with 1 to 3 chloro, fluoro, bromo, —CN, $C_{1-2}$ alkyl optionally substituted with —OH, $C_{1-2}$ alkoxy, —$C(O)C_{1-2}$ alkyl, or —$C(O)OC_{1-2}$ alkyl.

In certain embodiments of a compound of Formula (II), $R^3$ and $R^4$ are taken together to form:

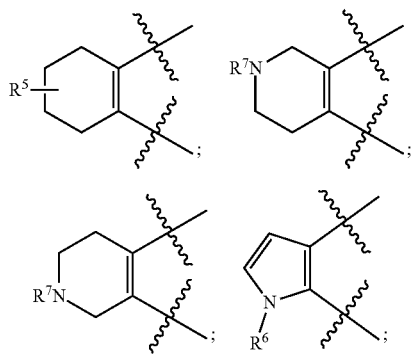

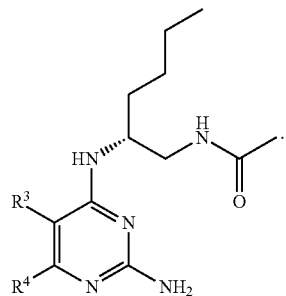

wherein each $R^5$, $R^6$, or $R^7$ is optionally present and as defined herein.

In certain embodiments of a compound of Formula (I), the compound is a compound of Formula (III)

Formula III

The groups $R^3$, $R^4$, $R^5$, $R^6$, $R^7$, $R^8$, $R^X$, $R^Y$, and $R^Z$ are as defined for Formula (I) above, or as defined below, or any combination thereof. Accordingly, in certain embodiments of Formula (I), (II), or (III), $R^3$ is $C_{1-4}$ alkoxy optionally substituted with 1 to 3 $R^X$, wherein $R^X$ is defined in this application. Accordingly, in certain embodiments of Formula (I), (II), or (III), $R^3$ is $C_{1-4}$ alkoxy optionally substituted with 1 $R^X$, wherein $R^X$ is defined in this application. In certain embodiments of Formula (I), (II), or (III), $R^3$ is $C_{1-2}$ alkoxy optionally substituted with 1 to 3 $R^X$, wherein $R^X$ is defined in this application.

In certain embodiments of Formula (I), (II), or (III), each $R^X$ is independently —$OR^Y$, 5 to 6 membered heterocyclyl having 1 to 3 heteroatoms selected from oxygen, nitrogen, and sulfur optionally substituted with 1 to 3 $R^Z$; phenyl optionally substituted with 1 to 3 $R^Z$; or 5 to 6 membered heteroaryl having 1 to 3 heteroatoms selected from oxygen, nitrogen, and sulfur optionally substituted with 1 to 3 $R^Z$, wherein $R^Y$ and $R^Z$ are defined in this application. In certain embodiments of Formula (I), (II), or (III), each $R^X$ is independently $OR^Y$, morpholino, phenyl, pyridinyl, pyrazolyl, or pyridazinyl, wherein each morpholino, phenyl, pyridinyl, pyrazolyl, and pyridazinyl are independently optionally substituted with —$OCH_3$, $C_{1-3}$ alkyl, chloro, or fluoro; wherein $R^Y$ is —$CH_3$, —$CH_2CF_3$, or quinolinyl optionally substituted with —$OCH_3$, $C_{1-3}$ alkyl, chloro, or fluoro.

In certain embodiments of Formula (I), (II), or (III), each $R^Y$ is independently $C_{1-4}$ alkyl, $C_{1-4}$ haloalkyl, or 5 to 10 membered heteroaryl having 1 to 3 heteroatoms selected from oxygen, nitrogen, and sulfur optionally substituted with 1 to 3 $R^Z$ wherein $R^Z$ is defined in this application. In certain embodiments of Formula (I), (II), or (III), each $R^Y$ is independently $R^Y$ is —$CH_3$, —$CH_2CF_3$, or quinolinyl optionally substituted with —$OCH_3$, $C_{1-3}$ alkyl, chloro, or fluoro.

In certain embodiments of Formula (I), (II), or (III), $R^3$ and $R^4$ are taken together to form $C_{5-6}$ cycloalkyl; 5 to 6 membered heterocyclyl having 1 to 3 heteroatoms selected from oxygen, nitrogen, and sulfur; phenyl; or 5 to 6 membered heteroaryl having 1 to 3 heteroatoms selected from oxygen, nitrogen, and sulfur, wherein $C_{5-6}$ cycloalkyl and phenyl are each independently optionally substituted with 1 to 3 $R^5$, 5 to 6 membered heteroaryl is optionally substituted with 1 to 3 $R^6$; 5 to 6 membered heterocyclyl is optionally substituted with 1 to 3 $R^7$; wherein $R^5$, $R^6$, and $R^7$ are defined in this application.

In certain embodiments of Formula (I), (II), or (III), $R^3$ and $R^4$ are taken together to form $C_{5-6}$ cycloalkyl optionally substituted with 1 to 3 $R^5$, wherein $R^5$ is defined in this application. In certain embodiments of Formula (I), (II), or (III), $R^3$ and $R^4$ are taken together to form $C_{5-6}$ cycloalkyl. In certain embodiments of Formula (I), $R^3$ and $R^4$ are taken together to form a 6 membered cycloalkyl.

In certain embodiments of Formula (I), (II), or (III), $R^3$ and $R^4$ are taken together to form a 5 to 6 membered heterocyclyl having 1 to 3 heteroatoms selected from oxygen, nitrogen, and sulfur optionally substituted with 1 to 3 $R^7$, wherein $R^7$ is defined in this application. In certain embodiments of Formula (I), (II), or (III), $R^3$ and $R^4$ are taken together to form a 5 to 6 membered heterocyclyl having 1 to 3 heteroatoms selected from oxygen, nitrogen, and sulfur optionally substituted with 1 to 3 —$C(O)R^8$ wherein $R^8$ is $C_{1-4}$ alkyl optionally substituted with —CN or —$NH_2$, $C_{1-3}$ haloalkyl, cyclopropyl, cyclobutyl, tetrahydropyranyl, thienyl optionally substituted with 1 to 3 $C_{1-3}$ alkyl; thiazolyl, imidazolyl optionally substituted with 1 to 3 $C_{1-2}$ alkyl; oxazolyl, isoxazolyl optionally substituted with 1 to 3 $C_{1-2}$ alkyl; thiadiazolyl, phenyl, pyrazinyl, or quinolinyl. In certain embodiments of Formula (I), (II), or (III), $R^3$ and $R^4$ are taken together to form a tetrahydropyridinyl optionally substituted with —$C(O)R^8$ wherein $R^8$ is $C_{1-4}$ alkyl optionally substituted with —CN or —$NH_2$, $C_{1-3}$ haloalkyl, cyclopropyl, cyclobutyl, tetrahydropyranyl, thienyl optionally substituted with 1 to 3 $C_{1-3}$ alkyl; thiazolyl, imidazolyl optionally substituted with 1 to 3 $C_{1-2}$ alkyl; oxazolyl, isoxazolyl optionally substituted with 1 to 3 $C_{1-2}$ alkyl; thiadiazolyl, phenyl, pyrazinyl, or quinolinyl.

In certain embodiments of Formula (I), (II), or (III), $R^3$ and $R^4$ are taken together to form a phenyl optionally substituted with 1 to 3 $R^5$, wherein $R^5$ is defined in this application. In certain embodiments of Formula (I), (II), or (III), $R^3$ and $R^4$ are taken together to form a phenyl. In certain embodiments of Formula (I), (II), or (III), $R^3$ and $R^4$ are taken together to form a phenyl optionally substituted with 1 to 3 chloro, fluoro, bromo, —CN, $C_{1-2}$ alkyl optionally substituted with —OH, $C_{1-2}$ alkoxy, —$C(O)C_{1-2}$ alkyl, —$C(O)OC_{1-2}$ alkyl, or pyrazolyl optionally substituted with 1 to 3 $C_{1-2}$ alkyl; or imidazolyl optionally substituted with 1 to 3 $C_{1-2}$ alkyl.

In certain embodiments of Formula (I), (II), or (III), $R^3$ and $R^4$ are taken together to form a 5 to 6 membered heteroaryl having 1 to 3 heteroatoms selected from oxygen, nitrogen, and sulfur optionally substituted with 1 to 3 $R^6$, wherein $R^6$ is defined in the application. In certain embodiments of Formula (I), (II), or (III), $R^3$ and $R^4$ are taken together to form a 5 to 6 membered heteroaryl having 1 to 3 heteroatoms selected from oxygen, nitrogen, and sulfur. In certain embodiments of Formula (I), (II), or (III), $R^3$ and $R^4$ are taken together to form pyrazinyl, pyridinyl or thienyl optionally substituted with 1 to 3 $C_{1-2}$ alkyl.

In certain embodiments of a compound of Formula (I), (II), or (III), $R^3$ and $R^4$ are taken together to form:

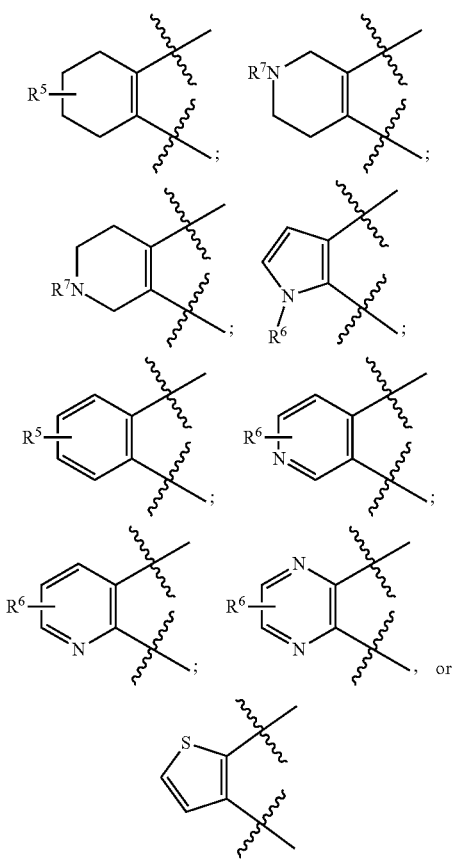

wherein each $R^5$, $R^6$, or $R^7$ is optionally present and as defined herein.

In certain embodiments of a compound of Formula (I), (II), or (III), $R^3$ and $R^4$ are taken together to form:

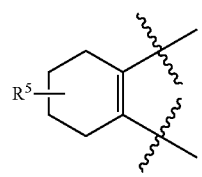

wherein $R^5$ is optionally present and as defined herein.

In certain embodiments of a compound of Formula (I), (II), or (III), $R^3$ and $R^4$ are taken together to form:

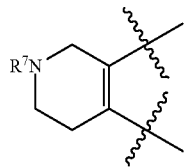

wherein R⁷ is optionally present and as defined herein.

In certain embodiments of a compound of Formula (I), (II), or (III), R³ and R⁴ are taken together to form:

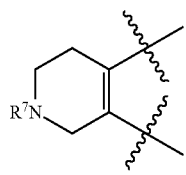

wherein R⁷ is optionally present and as defined herein.

In certain embodiments of a compound of Formula (I), (II), or (III), R³ and R⁴ are taken together to form:

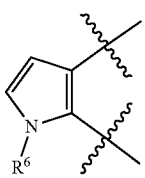

wherein R⁶ is optionally present and as defined herein.

In certain embodiments of a compound of Formula (I), (II), or (III), R³ and R⁴ are taken together to form:

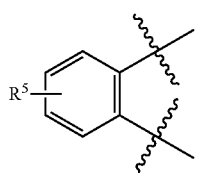

wherein R⁵ is optionally present and as defined herein.

In certain embodiments of a compound of Formula (I), (II), or (III), R³ and R⁴ are taken together to form:

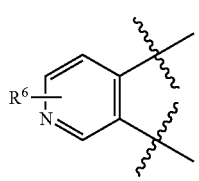

wherein R⁶ is optionally present and as defined herein.

In certain embodiments of a compound of Formula (I), (II), or (III), R³ and R⁴ are taken together to form:

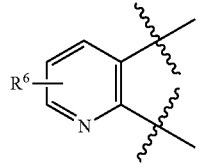

wherein R⁶ is optionally present and as defined herein.

In certain embodiments of a compound of Formula (I), (II), or (III), R³ and R⁴ are taken together to form:

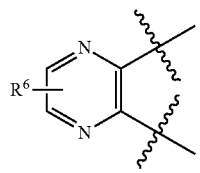

wherein R⁶ is optionally present and as defined herein.

In certain embodiments of a compound of Formula (I), (II), or (III), R³ and R⁴ are taken together to form:

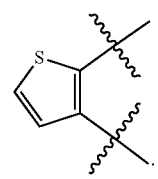 [SMILES: *c1ccsc1*]

In certain embodiments of a compound of Formula (I), (II), or (III), each R⁵ is independently halogen, —OH, —NH₂, —CN, $C_{1-4}$ alkyl optionally substituted with 1 to 3 $R^Z$, $C_{1-4}$ haloalkyl, $C_{1-4}$ alkoxy, —C(O)OH, —C(O)$C_{1-4}$ alkyl, —C(O)O$C_{1-4}$ alkyl, —C(O)NH₂, —C(O)NH($C_{1-4}$ alkyl), —C(O)N($C_{1-4}$ alkyl)₂, —N(H)C(O)$C_{1-4}$ alkyl, —S(O)₂$C_{1-4}$ alkyl, or 5 to 6 membered heteroaryl having 1 to 3 heteroatoms selected from oxygen, nitrogen, and sulfur optionally substituted with 1 to 3 $R^Z$, wherein $R^Z$ is defined in this application. In certain embodiments of a compound of Formula (I), (II), or (III), each R⁵ is independently chloro, fluoro, bromo, —CN, $C_{1-2}$ alkyl optionally substituted with —OH, $C_{1-2}$ alkoxy, —C(O)$C_{1-2}$ alkyl, —C(O)O$C_{1-2}$ alkyl, or pyrazolyl optionally substituted with 1 to 3 $C_{1-2}$ alkyl; or imidazolyl optionally substituted with 1 to 3 $C_{1-2}$ alkyl In certain embodiments of a compound of Formula (I), (II), or (III), each R⁶ is independently halogen, —OH, —NH₂, —CN, $C_{1-4}$ alkyl optionally substituted with 1 phenyl optionally substituted with 1 to 3 $R^Z$; $C_{1-4}$ haloalkyl, $C_{1-4}$ alkoxy, —S(O)₂$C_{1-4}$ alkyl; 5 to 6 membered heterocyclyl having 1 to 3 heteroatoms selected from oxygen, nitrogen, and sulfur optionally substituted with 1 to 3 $R^Z$; phenyl optionally substituted with 1 to 3 $R^Z$; or 5 to 6 membered heteroaryl having 1 to 3 heteroatoms selected from oxygen, nitrogen, and sulfur optionally substituted with 1 to 3 $R^Z$, wherein $R^Z$ is defined in this application. In certain embodiments of a compound of Formula (I), (II), or (III), each R⁶ is independently $C_{1-2}$ alkyl.

In certain embodiments of a compound of Formula (I), (II), or (III), each R⁷ is independently halogen, —OH, $C_{1-4}$ alkyl, $C_{1-4}$ alkoxy, or —C(O)R⁸ wherein R⁸ is defined in this application. In certain embodiments of a compound of Formula (I), (II), or (III), each $R^7$ is independently —C(O)$R^8$ wherein $R^8$ is $C_{1-4}$ alkyl optionally substituted with —CN or —$NH_2$, $C_{1-3}$ haloalkyl, cyclopropyl, cyclobutyl, tetrahydropyranyl, thienyl optionally substituted with 1 to 3 $C_{1-3}$ alkyl; thiazolyl, imidazolyl optionally substituted with 1 to 3 $C_{1-2}$ alkyl; oxazolyl, isoxazolyl optionally substituted with 1 to 3 $C_{1-2}$ alkyl; thiadiazolyl, phenyl, pyrazinyl, or quinolinyl.

In certain embodiments of a compound of Formula (I), (II), or (III), each $R^8$ is independently $C_{1-4}$ alkyl optionally substituted with —CN or —$NH_2$; $C_{1-4}$ haloalkyl; $C_{5-6}$ cycloalkyl, 5 to 6 membered heterocyclyl having 1 to 3 heteroatoms selected from oxygen, nitrogen, and sulfur optionally substituted with 1 to 3 $R^Z$; or 5 to 10 membered heteroaryl having 1 to 3 heteroatoms selected from oxygen, nitrogen, and sulfur optionally substituted with 1 to 3 $R^Z$, wherein $R^Z$ is defined in this application. In certain embodiments of a compound of Formula (I), (II), or (III), each $R^8$ is independently $C_{1-4}$ alkyl optionally substituted with —CN or —$NH_2$, $C_{1-3}$ haloalkyl, cyclopropyl, cyclobutyl, tetrahydropyranyl, thienyl optionally substituted with 1 to 3 $C_{1-3}$ alkyl; thiazolyl, imidazolyl optionally substituted with 1 to 3 $C_{1-2}$ alkyl; oxazolyl, isoxazolyl optionally substituted with 1 to 3 $C_{1-2}$ alkyl; thiadiazolyl, phenyl, pyrazinyl, or quinolinyl In certain embodiments of a compound of Formula (I), (II), or (III), each $R^Z$ is independently —$NH_2$, $C_{1-4}$ alkyl, halogen, —CN, —$OC_{1-4}$ alkyl, $C_{1-4}$ haloalkyl, or —C(O)$NH_2$.

In certain embodiments, the compound of Formula (I) is selected from:

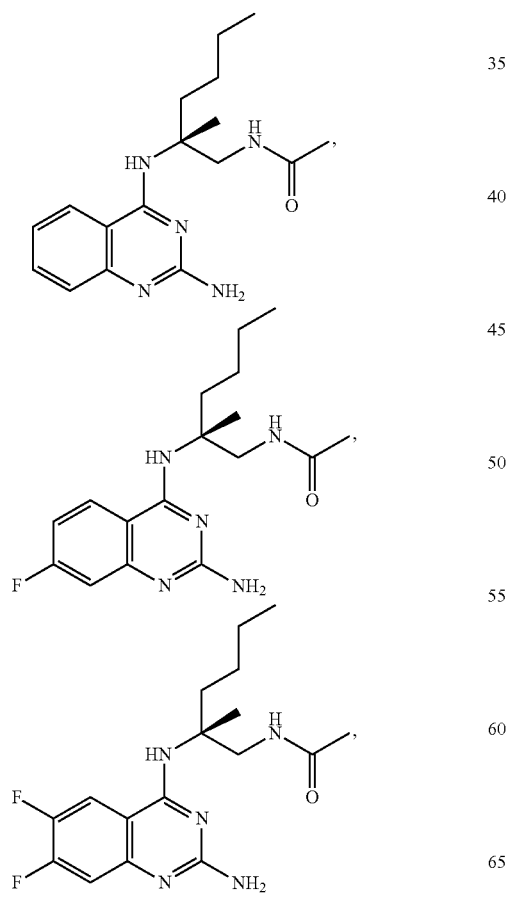

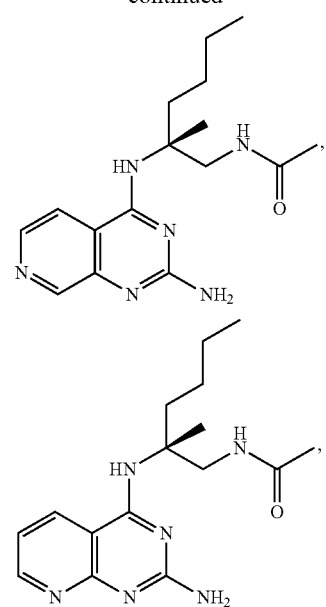

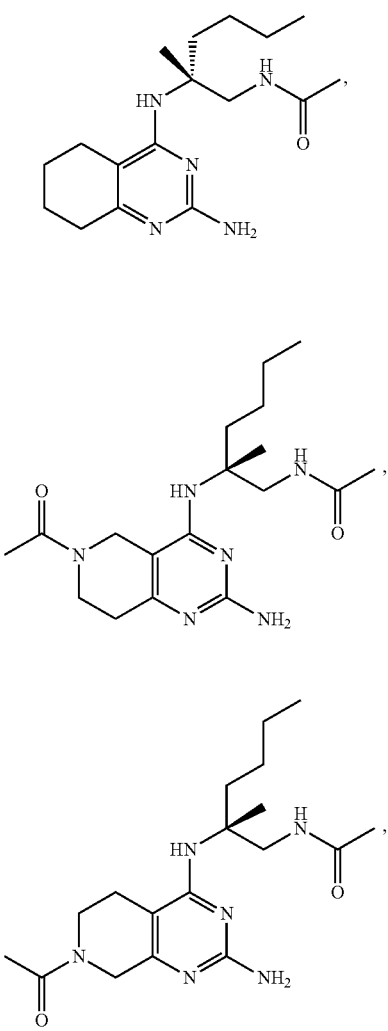

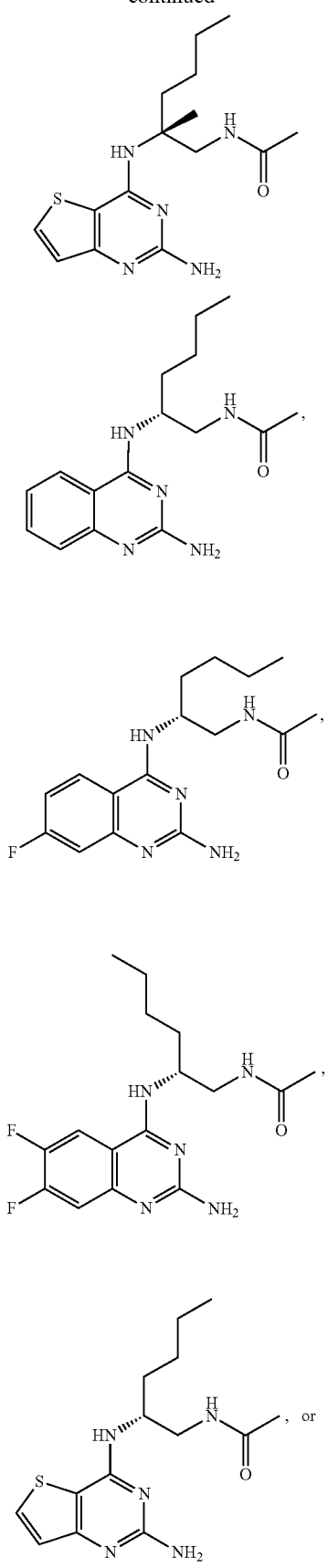
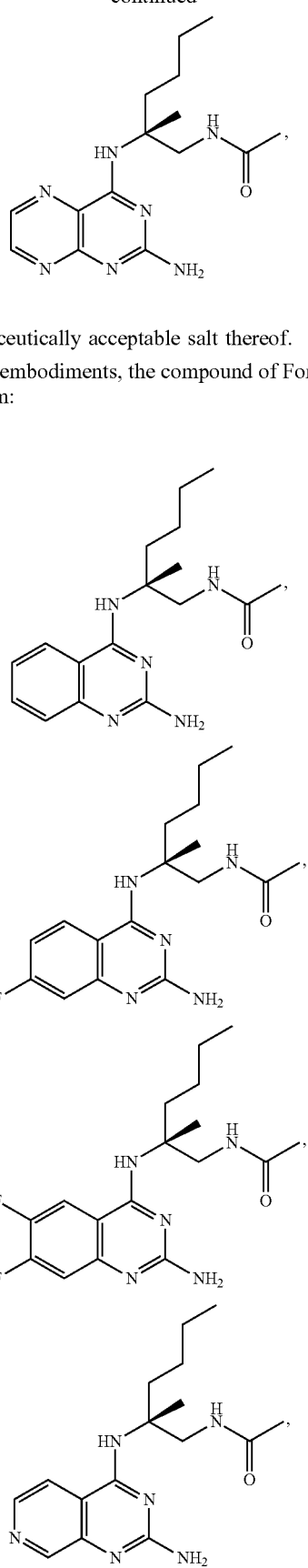
or a pharmaceutically acceptable salt thereof.
In certain embodiments, the compound of Formula (II) is selected from:

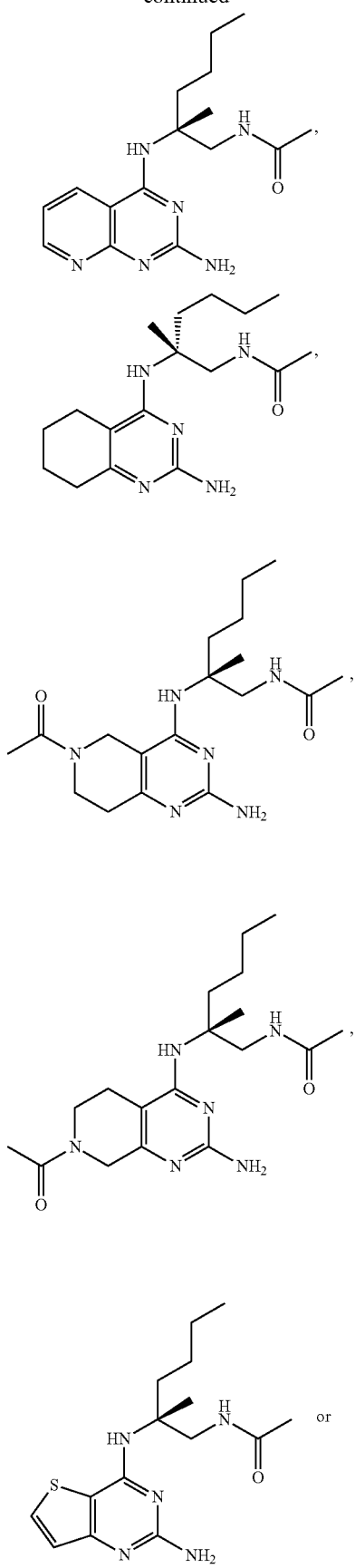
or a pharmaceutically acceptable salt thereof.
In certain embodiments, the compound of Formula (III) is selected from:
or a pharmaceutically acceptable salt thereof.
As used herein, "a compound of Formula (I)" includes compounds for Formula (II), or (III).

III. COMPOSITIONS

In certain embodiments, the present disclosure provides a pharmaceutical composition comprising a compound of the present disclosure (e.g. a compound of Formula (I), (II), or (III), or a pharmaceutically acceptable salt thereof, and a pharmaceutically acceptable excipient.

In certain embodiments, the pharmaceutical composition comprises one or more additional therapeutic agent, as more fully set forth below.

Pharmaceutical compositions comprising the compounds disclosed herein, or pharmaceutically acceptable salts thereof, may be prepared with one or more pharmaceutically acceptable excipients which may be selected in accord with ordinary practice. Tablets may contain excipients including glidants, fillers, binders and the like. Aqueous compositions may be prepared in sterile form, and when intended for delivery by other than oral administration generally may be isotonic. All compositions may optionally contain excipients such as those set forth in the Rowe et al, Handbook of Pharmaceutical Excipients, $6^{th}$ edition, American Pharmacists Association, 2009. Excipients can include ascorbic acid and other antioxidants, chelating agents such as EDTA, carbohydrates such as dextrin, hydroxyalkylcellulose, hydroxyalkylmethylcellulose, stearic acid and the like. In certain embodiments, the composition is provided as a solid dosage form, including a solid oral dosage form.

The compositions include those suitable for various administration routes, including oral administration. The compositions may be presented in unit dosage form and may be prepared by any of the methods well known in the art of pharmacy. Such methods include the step of bringing into association the active ingredient (e.g., a compound of the present disclosure or a pharmaceutical salt thereof) with one or more pharmaceutically acceptable excipients. The compositions may be prepared by uniformly and intimately bringing into association the active ingredient with liquid excipients or finely divided solid excipients or both, and then, if necessary, shaping the product. Techniques and formulations generally are found in Remington: The Science and Practice of Pharmacy, $21^{st}$ Edition, Lippincott Wiliams and Wilkins, Philadelphia, Pa., 2006.

Compositions described herein that are suitable for oral administration may be presented as discrete units (a unit dosage form) including but not limited to capsules, cachets or tablets each containing a predetermined amount of the active ingredient. In one embodiment, the pharmaceutical composition is a tablet.

Pharmaceutical compositions disclosed herein comprise one or more compounds disclosed herein, or a pharmaceutically acceptable salt thereof, together with a pharmaceutically acceptable excipient and optionally other therapeutic agents. Pharmaceutical compositions containing the active ingredient may be in any form suitable for the intended method of administration. When used for oral use for example, tablets, troches, lozenges, aqueous or oil suspensions, dispersible powders or granules, emulsions, hard or soft capsules, syrups or elixirs may be prepared. Compositions intended for oral use may be prepared according to any method known to the art for the manufacture of pharmaceutical compositions and such compositions may contain one or more excipients including sweetening agents, flavoring agents, coloring agents and preserving agents, in order to provide a palatable preparation. Tablets containing the active ingredient in admixture with non-toxic pharmaceutically acceptable excipients which are suitable for manufacture of tablets are acceptable. These excipients may be, for example, inert diluents, such as calcium or sodium carbonate, lactose, lactose monohydrate, croscarmellose sodium, povidone, calcium or sodium phosphate; granulating and disintegrating agents, such as maize starch, or alginic acid; binding agents, such as cellulose, microcrystalline cellulose, starch, gelatin or acacia; and lubricating agents, such as magnesium stearate, stearic acid or talc. Tablets may be uncoated or may be coated by known techniques including microencapsulation to delay disintegration and adsorption in the gastrointestinal tract and thereby provide a sustained action over a longer period. For example, a time delay material such as glyceryl monostearate or glyceryl distearate alone or with a wax may be employed.

The amount of active ingredient that may be combined with the inactive ingredients to produce a dosage form may vary depending upon the intended treatment subject and the particular mode of administration. For example, in some embodiments, a dosage form for oral administration to humans may contain approximately 1 to 1000 mg of active material formulated with an appropriate and convenient amount of a pharmaceutically acceptable excipient. In certain embodiments, the pharmaceutically acceptable excipient varies from about 5 to about 95% of the total compositions (weight:weight).

In certain embodiments, a composition comprising a compound of the present disclosure (e.g. a compound of Formula (I), (II), or (III), or a pharmaceutically acceptable salt thereof in one variation does not contain an agent that affects the rate at which the active ingredient is metabolized. Thus, it is understood that compositions comprising a compound of the present disclosure in one aspect do not comprise an agent that would affect (e.g., slow, hinder or retard) the metabolism of a compound of the present disclosure or any other active ingredient administered separately, sequentially or simultaneously with a compound of the present disclosure. It is also understood that any of the methods, kits, articles of manufacture and the like detailed herein in one aspect do not comprise an agent that would affect (e.g., slow, hinder or retard) the metabolism of a compound of the present disclosure or any other active ingredient administered separately, sequentially or simultaneously with a compound of the present disclosure.

IV. METHODS

The present disclosure provides for methods of treating diseases or conditions that are responsive to the modulation of toll-like receptors (e.g. TLR8 receptors). While not wishing to be bound by any one theory, the presently disclosed compounds are believed to modulate TLR8 receptors as agonists. As is understood by those of skill in the art, modulators of TLR8 may, to some degree, modulate other toll-like receptors (e.g. TLR7). As such, in certain embodiments, the compounds disclosed herein may also modulate TLR7 to a measureable degree. In certain embodiments, those compounds that modulate TLR8 to a higher degree than TLR7 are considered selective modulators of TLR8. Exemplary methods of measuring the each compounds respective modulation of TLR7 and TLR8 are described in the Examples provided herein. In certain embodiments, the compounds disclosed herein are selective modulators of TLR8.

In certain embodiments, a method of modulating TLR8 is provided, comprising administering a compound of the present disclosure, or a pharmaceutically acceptable salt thereof, to an individual (e.g. a human).

In certain embodiments, a method of modulating TLR8 in vitro is provided.

In certain embodiments, the present disclosure provides a compound of the present disclosure, or a pharmaceutically acceptable salt thereof, for use as a research tool, e.g., for use in identifying modulators of TLR8

In certain embodiments, the present disclosure provides methods for the treatment or prevention of diseases or conditions in an individual (e.g. a human) in need thereof, comprising administering a compound of the present disclosure or a pharmaceutically acceptable salt thereof. In certain embodiments, the methods comprise administering one or more additional therapeutic agents. Treatment with a compound of the present disclosure typically results in the stimulation of an immune response to the particular disease or condition being treated. Diseases or conditions contemplated by the present disclosure include those affected by the modulation of toll-like receptors (e.g. TLR8). In certain embodiments, a method of treating or preventing a disease or condition responsive to the modulation of TLR8 is provided, comprising administering to a human a therapeutically effective amount of a compound of the present disclosure, or a pharmaceutically acceptable salt thereof. Exemplary diseases, disorders and conditions include but are not limited to conditions involving autoimmunity, inflammation, allergy, asthma, graft rejection, graft versus host disease (GvHD), infectious diseases, cancer, and immunodeficiency.

In certain embodiments, infectious diseases include diseases such as hepatitis A, hepatitis B (HBV), hepatitis C (HCV), hepatitis D (HDV), HIV, human papillomavirus (HPV), respiratory syncytial virus (RSV), severe acute respiratory syndrome (SARS), influenza, parainfluenza, cytomegalovirus, dengue, herpes simplex virus-1, herpes simplex virus-2, *Leishmania* infection, and respiratory syncytial virus. In certain embodiments, infectious diseases include diseases such as hepatitis A, hepatitis B (HBV), hepatitis D (HDV), HIV, human papillomavirus (HPV), respiratory syncytial virus (RSV), severe acute respiratory syndrome (SARS), influenza, parainfluenza, cytomegalovirus, dengue, herpes simplex virus-1, herpes simplex virus-2, *Leishmania* infection, and respiratory syncytial virus.

In certain embodiments, a method of treating or preventing a viral infection is provided, comprising administering to an individual (e.g. a human) a therapeutically effective amount a compound of the present disclosure, or a pharmaceutically acceptable salt thereof. In one embodiment, the method can be used to induce an immune response against multiple epitopes of a viral infection in a human. Induction of an immune response against viral infection can be assessed using any technique that is known by those of skill in the art for determining whether an immune response has occurred. Suitable methods of detecting an immune response for the present disclosure include, among others, detecting a decrease in viral load or antigen in a subject's serum, detection of IFN-gamma-secreting peptide specific T cells, and detection of elevated levels of one or more liver enzymes, such as alanine transferase (ALT) and aspartate transferase (AST). In one embodiment, the detection of IFN-gamma-secreting peptide specific T cells is accomplished using an ELISPOT assay. Another embodiment includes reducing the viral load associated with HBV infection, including a reduction as measured by PCR testing.

In certain embodiments, the present invention provides a method for enhancing the efficacy of a vaccine by co-administering with the vaccine, a therapeutically effective amount of a compound of the present disclosure, or a pharmaceutically acceptable salt thereof, to an individual (e.g. a human). In certain embodiments, the compound of the present disclosure or a pharmaceutically acceptable salt thereof, may be co-administered with a vaccine to boost the immune response by allowing the production of a higher amount of antibodies or by allowing a longer lasting protection. In certain embodiments, the compounds of the present disclosure, or a pharmaceutically acceptable salt thereof, may be used as vaccine adjuvants to increase the efficacy and response to the immunization with a particular antigen. In certain embodiments, co-administering the compounds of the present disclosure, or a pharmaceutically acceptable salt thereof, with a vaccine, may influence the way a vaccine's antigen is presented to the immune system and enhance the vaccine's efficacy.

In certain embodiments, a compound of the present disclosure, or a pharmaceutically acceptable salt thereof, for use in medical therapy is provided. In certain embodiments, a compound of the present disclosure or a pharmaceutically acceptable salt thereof, for use in treating or preventing a disease or condition responsive to the modulation of TLR8, is provided. In certain embodiments, the disease or condition is a viral infection as set forth herein.

In certain embodiments, the use of a compound of the present disclosure, or a pharmaceutically acceptable salt thereof, for the manufacture of a medicament for treating or preventing a disease or condition responsive to the modulation of TLR8, is provided.

In certain embodiments, the present disclosure also provides methods for treating a hepatitis B viral infection, comprising administering to an individual (e.g. a human) infected with hepatitis B virus a therapeutically effective amount a compound of the present disclosure or a pharmaceutically acceptable salt thereof. Typically, the individual is suffering from a chronic hepatitis B infection, although it is within the scope of the present disclosure to treat people who are acutely infected with HBV.

The present disclosure also provides methods for treating a hepatitis C viral infection, comprising administering to an individual (e.g. a human) infected with hepatitis C virus a therapeutically effective amount a compound of the present disclosure or a pharmaceutically acceptable salt thereof. Typically, the individual is suffering from a chronic hepatitis C infection, although it is within the scope of the present disclosure to treat people who are acutely infected with HCV.

Treatment of HBV or HCV in accordance with the present disclosure typically results in the stimulation of an immune response against HBV or HCV in an individual (e.g. a human) being infected with HBV or HCV, respectively, and a consequent reduction in the viral load of HBV or HCV in the infected individual. Examples of immune responses include production of antibodies (e.g., IgG antibodies) and/or production of cytokines, such as interferons, that modulate the activity of the immune system. The immune system response can be a newly induced response, or can be boosting of an existing immune response. In particular, the immune system response can be seroconversion against one or more HBV or HCV antigens.

As described more fully herein, compounds of the present disclosure can be administered with one or more additional therapeutic agent(s) to an individual (e.g. a human) infected with HBV or HCV. The additional therapeutic agent(s) can be administered to the infected individual (e.g. a human) at the same time as a compound of the present disclosure or before or after administration of a compound of the present disclosure. For example, in certain embodiments, when used to treat or prevent HCV, a compound of the present disclosure may be administered with one or more additional therapeutic agent(s) selected from the group consisting of interferons, ribavirin or its analogs, HCV NS3 protease inhibitors, HCV NS4 protease inhibitors, HCV NS3/NS4 protease inhibitors, alpha-glucosidase 1 inhibitors, hepatoprotectants, nucleoside or nucleotide inhibitors of HCV NS5B polymerase, non-nucleoside inhibitors of HCV NS5B polymerase, HCV NS5A inhibitors, TLR7 agonists, cyclophilin inhibitors, HCV IRES inhibitors, pharmacokinetic enhancers, and other drugs for treating HCV, or mixtures thereof. Specific examples are more fully described below.

Further, in certain embodiments, when used to treat or prevent HBV, a compound of the present disclosure may be administered with one or more additional therapeutic agent(s) selected from the group consisting of HBV DNA polymerase inhibitors, toll-like receptor 7 modulators, toll-like receptor 8 modulators, Toll-like receptor 7 and 8 modulators, Toll-like receptor 3 modulators, interferon alpha ligands, HBsAg inhibitors, compounds targeting HbcAg, cyclophilin inhibitors, HBV therapeutic vaccines, HBV prophylactic vaccines, HBV viral entry inhibitors, NTCP inhibitors, antisense oligonucleotide targeting viral mRNA, short interfering RNAs (siRNA), hepatitis B virus E antigen inhibitors, HBx inhibitors, cccDNA inhibitors, HBV antibodies including HBV antibodies targeting the surface antigens of the hepatitis B virus, thymosin agonists, cytokines, nucleoprotein inhibitors (HBV core or capsid protein inhibitors), stimulators of retinoic acid-inducible gene 1, stimulators of NOD2, recombinant thymosin alpha-1 and hepatitis B virus replication inhibitors, and combinations thereof. Specific examples are more fully described below.

In certain embodiments, the present disclosure provides a method for ameliorating a symptom associated with an HBV infection or HCV infection, wherein the method comprises administering to an individual (e.g. a human) infected with hepatitis B virus or hepatitis C virus a therapeutically effective amount of a compound of the present disclosure, or a pharmaceutically acceptable salt thereof, wherein the therapeutically effective amount is sufficient to ameliorate a symptom associated with the HBV infection or HCV infection. Such symptoms include the presence of HBV virus particles (or HCV virus particles) in the blood, liver inflammation, jaundice, muscle aches, weakness and tiredness.

In certain embodiments, the present disclosure provides a method for reducing the rate of progression of a hepatitis B viral infection or a hepatitis C virus infection, in an individual (e.g. a human), wherein the method comprises administering to an individual (e.g. a human) infected with hepatitis B virus or hepatitis C virus a therapeutically effective amount of a compound of the present disclosure, or a pharmaceutically acceptable salt thereof, wherein the therapeutically effective amount is sufficient to reduce the rate of progression of the hepatitis B viral infection or hepatitis C viral infection. The rate of progression of the infection can be followed by measuring the amount of HBV virus particles or HCV virus particles in the blood.

In certain embodiments, the present disclosure provides a method for reducing the viral load associated with HBV infection or HCV infection, wherein the method comprises administering to an individual (e.g. a human) infected with HBV or HCV a therapeutically effective amount of a compound of the present disclosure, or a pharmaceutically acceptable salt thereof, wherein the therapeutically effective amount is sufficient to reduce the HBV viral load or the HCV viral load in the individual.

In certain embodiments, the present disclosure provides a method of inducing or boosting an immune response against hepatitis B virus or hepatitis C virus in an individual (e.g. a human), wherein the method comprises administering a therapeutically effective amount of a compound of the present disclosure, or a pharmaceutically acceptable salt thereof, to the individual, wherein a new immune response against hepatitis B virus or hepatitis C virus is induced in the individual, or a preexisting immune response against hepatitis B virus or hepatitis C virus is boosted in the individual. Seroconversion with respect to HBV or HCV can be induced in the individual. Examples of immune responses include production of antibodies, such as IgG antibody molecules, and/or production of cytokine molecules that modulate the activity of one or more components of the human immune system.

In certain embodiments, an immune response can be induced against one or more antigens of HBV or HCV. For example, an immune response can be induced against the HBV surface antigen (HBsAg), or against the small form of the HBV surface antigen (small S antigen), or against the medium form of the HBV surface antigen (medium S antigen), or against a combination thereof. Again by way of example, an immune response can be induced against the HBV surface antigen (HBsAg) and also against other HBV-derived antigens, such as the core polymerase or x-protein.

Induction of an immune response against HCV or HBV can be assessed using any technique that is known by those of skill in the art for determining whether an immune response has occurred. Suitable methods of detecting an immune response for the present disclosure include, among others, detecting a decrease in viral load in a individual's serum, such as by measuring the amount of HBV DNA or HCV DNA in a subject's blood using a PCR assay, and/or by measuring the amount of anti-HBV antibodies, or anti-HCV antibodies, in the subject's blood using a method such as an ELISA.

In certain embodiments, a compound of a compound of the present disclosure (e.g. a compound of Formula (I)), or a pharmaceutically acceptable salt thereof, for use in treating or preventing a HBV infection is provided. In certain embodiments, a compound of the present disclosure (e.g. a compound of Formula (I)), or a pharmaceutically acceptable salt thereof, for use in treating or preventing a HCV infection is provided. In certain embodiments, a compound of the present disclosure (e.g. a compound of Formula (I)), or a pharmaceutically acceptable salt thereof, for the manufacture of a medicament for treating or preventing a HBV infection is provided. In certain embodiments, a compound of the present disclosure (e.g. a compound of Formula (I)), or a pharmaceutically acceptable salt thereof, for the manufacture of a medicament for treating or preventing a HCV infection is provided.

In certain embodiments, the present disclosure also provides methods for treating a Retroviridae viral infection (e.g., an HIV viral infection) in an individual (e.g., a human), comprising administering a compound of the present disclosure, or a pharmaceutically acceptable salt thereof, to the individual.

In certain embodiments, the present disclosure also provides methods for treating a HIV infection (e.g a HIV-1 infection), comprising administering to an individual (e.g. a human) infected with HIV virus a therapeutically effective amount of a compound of the present disclosure, or a pharmaceutically acceptable salt thereof. In certain embodiments, the individual in need thereof is a human who has been infected with HIV. In certain embodiments, the individual in need thereof is a human who has been infected with HIV but who has not developed AIDS. In certain embodiments, the individual in need thereof is an individual at risk for developing AIDS. In certain embodiments, the individual in need thereof is a human who has been infected with HIV and who has developed AIDS.

In certain embodiments, a method for treating or preventing an HIV viral infection in an individual (e.g., a human), comprising administering a compound of the present disclosure, or a pharmaceutically acceptable salt thereof, to the individual is provided.

In certain embodiments, a method for inhibiting the replication of the HIV virus, treating AIDS or delaying the onset of AIDS in an individual (e.g., a human), comprising administering a compound of the present disclosure, or a pharmaceutically acceptable salt thereof, to the individual is provided.

In certain embodiments, a method for preventing an HIV infection in an individual (e.g., a human), comprising administering a compound of the present disclosure, or a pharmaceutically acceptable salt thereof, to the individual is provided. In certain embodiments, the individual is at risk of contracting the HIV virus, such as an individual who has one or more risk factors known to be associated with of contracting the HIV virus.

In certain embodiments, a method for treating an HIV infection in an individual (e.g., a human), comprising administering a compound of the present disclosure, or a pharmaceutically acceptable salt thereof, to the individual is provided.

In certain embodiments, a method for treating an HIV infection in an individual (e.g., a human), comprising administering to the individual in need thereof a therapeutically effective amount of a compound of the present disclosure, or a pharmaceutically acceptable salt thereof, in combination with a therapeutically effective amount of one or more additional therapeutic agents selected from the group consisting of HIV protease inhibiting compounds, HIV non-nucleoside inhibitors of reverse transcriptase, HIV nucleoside inhibitors of reverse transcriptase, HIV nucleotide inhibitors of reverse transcriptase, HIV integrase inhibitors, gp41 inhibitors, CXCR4 inhibitors, gp120 inhibitors, CCR5 inhibitors, capsid polymerization inhibitors, and other drugs for treating HIV, and combinations thereof is provided.

In certain embodiments, a compound of the present invention is administered to a patient where active HIV gene expression has been suppressed by administration of anti-retroviral therapy (including combination antiretroviral therapy" or "cART").

In certain embodiments, a method of reducing the latent HIV reservoir in a human infected with HIV is provided, the method comprising administering to the human a pharmaceutically effective amount of a compound of the present disclosure. In certain embodiments, the method further comprises administering one or more anti-HIV agents. In certain embodiments, the method further comprises administering antiretroviral therapy (including combination antiretroviral therapy" or "cART"). In certain embodiments, active HIV gene expression in the human has been suppressed by administration of antiretroviral therapy (including combination antiretroviral therapy" or "cART").

In certain embodiments, a compound of the present disclosure, or a pharmaceutically acceptable salt thereof for use in medical therapy of an HIV viral infection (e.g. HIV-1 or the replication of the HIV virus (e.g. HIV-1) or AIDS or delaying the onset of AIDS in an individual (e.g., a human)) is provided.

In certain embodiments, a compound of the present disclosure, or a pharmaceutically acceptable salt thereof for use in the manufacture of a medicament for treating an HIV viral infection or the replication of the HIV virus or AIDS or delaying the onset of AIDS in an individual (e.g., a human). One embodiment provides a compound of the present disclosure, or a pharmaceutically acceptable salt thereof, for use in the prophylactic or therapeutic treatment of an HIV infection or AIDS or for use in the therapeutic treatment or delaying the onset of AIDS is provided.

In certain embodiments, the use of a compound of the present disclosure (e.g. a compound of Formula (I)), or a pharmaceutically acceptable salt thereof, for the manufacture of a medicament for an HIV virus infection in an individual (e.g., a human) is provided. In certain embodiments, a compound of the present disclosure (e.g. a compound of Formula (I)), or a pharmaceutically acceptable salt thereof, for use in the prophylactic or therapeutic treatment of an HIV virus infection is provided.

In certain embodiments, in the methods of use, the administration is to an individual (e.g., a human) in need of the treatment. In certain embodiments, in the methods of use, the administration is to an individual (e.g., a human) who is at risk of developing AIDS.

Provided herein is a compound of the present disclosure (e.g. a compound of Formula (I)), or a pharmaceutically acceptable salt thereof, for use in therapy. In one embodiment, the compound of the present disclosure, or a pharmaceutically acceptable salt thereof, is for use in a method of treating an HIV viral infection or the replication of the HIV virus or AIDS or delaying the onset of AIDS in an individual (e.g., a human).

Also provided herein is a compound of the present disclosure (e.g. a compound of Formula (I)), or a pharmaceutically acceptable salt thereof, for use in a method of treating or preventing HIV in an individual in need thereof. In certain embodiments, the individual in need thereof is a human who has been infected with HIV. In certain embodiments, the individual in need thereof is a human who has been infected with HIV but who has not developed AIDS. In certain embodiments, the individual in need thereof is an individual at risk for developing AIDS. In certain embodiments, the individual in need thereof is a human who has been infected with HIV and who has developed AIDS.

Also provided herein is a compound of the present disclosure (e.g. a compound of Formula (I)), or a pharmaceutically acceptable salt thereof, for use in the therapeutic treatment or delaying the onset of AIDS.

Also provided herein is a compound of the present disclosure (e.g. a compound of Formula (I)), or a pharmaceutically acceptable salt thereof, for use in the prophylactic or therapeutic treatment of an HIV infection.

In certain embodiments, the HIV infection is an HIV-1 infection.

Additionally, the compounds of this disclosure are useful in the treatment of cancer or tumors (including dysplasias, such as uterine dysplasia). These includes hematological malignancies, oral carcinomas (for example of the lip, tongue or pharynx), digestive organs (for example esophagus, stomach, small intestine, colon, large intestine, or rectum), peritoneum, liver and biliary passages, pancreas, respiratory system such as larynx or lung (small cell and non-small cell), bone, connective tissue, skin (e.g., melanoma), breast, reproductive organs (fallopian tube, uterus, cervix, testicles, ovary, or prostate), urinary tract (e.g., bladder or kidney), brain and endocrine glands such as the thyroid. In summary, the compounds of this disclosure are employed to treat any neoplasm, including not only hematologic malignancies but also solid tumors of all kinds. In certain embodiments, the compounds are useful for treating a form of cancer selected from ovarian cancer, breast cancer, head and neck cancer, renal cancer, bladder cancer, hepatocellular cancer, and colorectal cancer.

Hematological malignancies are broadly defined as proliferative disorders of blood cells and/or their progenitors, in which these cells proliferate in an uncontrolled manner. Anatomically, the hematologic malignancies are divided into two primary groups: lymphomas—malignant masses of lymphoid cells, primarily but not exclusively in lymph nodes, and leukemias—neoplasm derived typically from lymphoid or myeloid cells and primarily affecting the bone marrow and peripheral blood. The lymphomas can be subdivided into Hodgkin's Disease and Non-Hodgkin's lymphoma (NHL). The later group comprises several distinct entities, which can be distinguished clinically (e.g. aggressive lymphoma, indolent lymphoma), histologically (e.g. follicular lymphoma, mantle cell lymphoma) or based on the origin of the malignant cell (e.g. B lymphocyte, T lymphocyte). Leukemias and related malignancies include acute myelogenous leukemia (AML), chronic myelogenous leukemia (CML), acute lymphoblastic leukemia (ALL) and chronic lymphocytic leukemia (CLL). Other hematological malignancies include the plasma cell dyscrasias including multiple myeloma, and the myelodysplastic syndromes.

In certain embodiments, the compounds of the present disclosure are useful in the treatment of B-cell lymphoma, lymphoplasmacytoid lymphoma, fallopian tube cancer, head and neck cancer, ovarian cancer, and peritoneal cancer.

In certain embodiments, the compounds of the present disclosure are useful in the treatment of hepatocellular carcinoma, gastric cancer, and/or colorectal cancer. In certain embodiments, the compounds of the present disclosure are useful in the treatment of prostate cancer, breast cancer, and/or ovarian cancer. In certain embodiments, the compounds of the present disclosure are useful in the treatment of recurrent or metastatic squamous cell carcinoma.

In certain embodiments, a method of treating a hyperproliferative disease, comprising administering to an individual (e.g. a human) in need thereof a therapeutically effective amount of a compound of the present disclosure, or a pharmaceutically acceptable salt thereof, is provided. In certain embodiments, the hyperproliferative disease is cancer. In certain embodiments, the cancer is a solid tumor. In certain embodiments, the cancer is selected from ovarian cancer, breast cancer, head and neck cancer, renal cancer, bladder cancer, hepatocellular cancer, and colorectal cancer. In certain embodiments, the cancer is a lymphoma. In certain embodiments, the cancer is Hodgkin's lymphoma. In certain embodiments, the cancer is non-Hodgkin's lymphoma. In certain embodiments, the cancer is B-cell lymphoma. In certain embodiments, the cancer is selected from B-cell lymphoma; fallopian tube cancer, head and neck cancer, ovarian cancer and peritoneal cancer. In certain embodiments, the method further comprises administering one or more additional therapeutic agents as more fully described herein.

In certain embodiments, the cancer is prostate cancer, breast cancer, ovarian cancer, hepatocellular carcinoma, gastric cancer, colorectal cancer and/or recurrent or metastatic squamous cell carcinoma. In certain embodiments, the cancer is prostate cancer, breast cancer, and/or ovarian cancer. In certain embodiments, the cancer is hepatocellular carcinoma, gastric cancer, and/or colorectal cancer. In certain embodiments, the cancer is recurrent or metastatic squamous cell carcinoma.

In some embodiments, in the methods of use, the administration is to an individual (e.g., a human) in need of the treatment.

Additional examples of diseases, disorders, or conditions include psoriasis, systemic lupus erythematosus and allergic rhinitis In one embodiment, the compound of the present disclosure, or a pharmaceutically acceptable salt thereof, is for use in a method of treating a hyperproliferative disease (e.g. cancer) in an individual (e.g., a human).

Also provided herein is the use of a compound of the present disclosure (e.g. a compound of Formula (I)) or a pharmaceutically acceptable salt thereof for the manufacture of a medicament for treating a hyperproliferative disease (e.g. cancer) is provided.

V. ADMINISTRATION

One or more of the compounds of the present disclosure (also referred to herein as the active ingredients), can be administered by any route appropriate to the condition to be treated. Suitable routes include oral, rectal, nasal, topical (including buccal and sublingual), transdermal, vaginal and parenteral (including subcutaneous, intramuscular, intravenous, intradermal, intrathecal and epidural), and the like. It will be appreciated that the preferred route may vary with for example the condition of the recipient. An advantage of certain compounds disclosed herein is that they are orally bioavailable and can be dosed orally.

A compound of the present disclosure, such as a compound of Formula (I), may be administered to an individual in accordance with an effective dosing regimen for a desired period of time or duration, such as at least about one month, at least about 2 months, at least about 3 months, at least about 6 months, or at least about 12 months or longer. In one variation, the compound is administered on a daily or intermittent schedule for the duration of the individual's life.

The dosage or dosing frequency of a compound of the present disclosure may be adjusted over the course of the treatment, based on the judgment of the administering physician.

The compound may be administered to an individual (e.g., a human) in an effective amount. In certain embodiments, the compound is administered once daily.

In certain embodiments, methods for treating or preventing a disease or condition in a human are provided, comprising administering to the human a therapeutically effective amount of a compound of the present disclosure, or a pharmaceutically acceptable salt thereof, in combination with a therapeutically effective amount of one or more (e.g., one, two, three, four, one or two, one to three, or one to four) additional therapeutic agents. As modulators of TLR8 may be used in the treatment of various diseases or condutions, the particular identity of the additional therapeutic agents will depend on the particular disease or condition being treated.

The compound of Formula (I), (II), or (III) can be administered by any useful route and means, such as by oral or parenteral (e.g., intravenous) administration. Therapeutically effective amounts of the compound of Formula (I), (II), or (III) are from about 0.00001 mg/kg body weight per day to about 10 mg/kg body weight per day, such as from about 0.0001 mg/kg body weight per day to about 10 mg/kg body weight per day, or such as from about 0.001 mg/kg body weight per day to about 1 mg/kg body weight per day, or such as from about 0.01 mg/kg body weight per day to about 1 mg/kg body weight per day, or such as from about 0.05 mg/kg body weight per day to about 0.5 mg/kg body weight per day, or such as from about 0.3 µg to about 30 mg per day, or such as from about 30 µg to about 300 µg per day.

A compound of the present disclosure may be combined with one or more additional therapeutic agents in any dosage amount of the compound of the present disclosure (e.g., from 1 mg to 1000 mg of compound). Therapeutically effective amounts of the compound of Formula (I), (II), or (III) are from about 0.01 mg per dose to about 1000 mg per dose, such as from about 0.01 mg per dose to about 100 mg per dose, or such as from about 0.1 mg per dose to about 100 mg per dose, or such as from about 1 mg per dose to about 100 mg per dose, or such as from about 1 mg per dose to about 10 mg per dose. Other therapeutically effective amounts of the compound of Formula (I), (II), or (III) are about 1 mg per dose, or about 2, 3, 4, 5, 6, 7, 8, 9, 10, 15, 20, 25, 30, 35, 40, 45, 50, 55, 60, 65, 70, 75, 80, 85, 90, 95, or about 100 mg per dose. Other therapeutically effective amounts of the compound of Formula (I), (II), or (III) are about 100 mg per dose, or about 125, 150, 175, 200, 225, 250, 275, 300, 350, 400, 450, or about 500 mg per dose. A single dose can be administered hourly, daily, or weekly. For example, a single dose can be administered once every 1 hour, 2, 3, 4, 6, 8, 12, 16 or once every 24 hours. A single dose can also be administered once every 1 day, 2, 3, 4, 5, 6, or once every 7 days. A single dose can also be administered once every 1 week, 2, 3, or once every 4 weeks. In certain embodiments, a single dose can be administered once every week. A single dose can also be administered once every month.

The frequency of dosage of the compound of Formula (I), (II), or (III) will be determined by the needs of the individual patient and can be, for example, once per day or twice, or more times, per day. Administration of the compound continues for as long as necessary to treat the HBV or HCV infection. For example, Compound I can be administered to a human being infected with HBV or HCV for a period of from 20 days to 180 days or, for example, for a period of from 20 days to 90 days or, for example, for a period of from 30 days to 60 days.

Administration can be intermittent, with a period of several or more days during which a patient receives a daily dose of the compound of Formula (I), (II), or (III) followed by a period of several or more days during which a patient does not receive a daily dose of the compound. For example, a patient can receive a dose of the compound every other day, or three times per week. Again by way of example, a patient can receive a dose of the compound each day for a period of from 1 to 14 days, followed by a period of 7 to 21 days during which the patient does not receive a dose of the compound, followed by a subsequent period (e.g., from 1 to 14 days) during which the patient again receives a daily dose of the compound. Alternating periods of administration of the compound, followed by non-administration of the compound, can be repeated as clinically required to treat the patient.

In one embodiment, pharmaceutical compositions comprising a compound of the present disclosure, or a pharmaceutically acceptable salt thereof, in combination with one or more (e.g., one, two, three, four, one or two, one to three, or one to four) additional therapeutic agents, and a pharmaceutically acceptable excipient are provided.

In one embodiment, kits comprising a compound of the present disclosure, or a pharmaceutically acceptable salt thereof, in combination with one or more (e.g., one, two, three, four, one or two, one to three, or one to four) additional therapeutic agents are provided.

In certain embodiments, a compound of the present disclosure, or a pharmaceutically acceptable salt thereof, is combined with one, two, three, four or more additional therapeutic agents. In certain embodiments, a compound of the present disclosure, or a pharmaceutically acceptable salt thereof, is combined with two additional therapeutic agents. In other embodiments, a compound of the present disclosure, or a pharmaceutically acceptable salt thereof, is combined with three additional therapeutic agents. In further embodiments, a compound of the present disclosure, or a pharmaceutically acceptable salt thereof, is combined with four additional therapeutic agents. The one, two, three, four or more additional therapeutic agents can be different therapeutic agents selected from the same class of therapeutic agents, and/or they can be selected from different classes of therapeutic agents.

In certain embodiments, when a compound of the present disclosure is combined with one or more additional therapeutic agents as described herein, the components of the composition are administered as a simultaneous or sequential regimen. When administered sequentially, the combination may be administered in two or more administrations.

In certain embodiments, a compound of the present disclosure is combined with one or more additional therapeutic agents in a unitary dosage form for simultaneous administration to a patient, for example as a solid dosage form for oral administration.

In certain embodiments, a compound of the present disclosure is administered with one or more additional therapeutic agents. Co-administration of a compound of the present disclosure with one or more additional therapeutic agents generally refers to simultaneous or sequential administration of a compound of the present disclosure and one or more additional therapeutic agents, such that therapeutically effective amounts of the compound disclosed herein and one or more additional therapeutic agents are both present in the body of the patient.

Co-administration includes administration of unit dosages of the compounds disclosed herein before or after administration of unit dosages of one or more additional therapeutic agents, for example, administration of the compound disclosed herein within seconds, minutes, or hours of the administration of one or more additional therapeutic agents. For example, in some embodiments, a unit dose of a compound of the present disclosure is administered first, followed within seconds or minutes by administration of a unit dose of one or more additional therapeutic agents. Alternatively, in other embodiments, a unit dose of one or more additional therapeutic agents is administered first, followed by administration of a unit dose of a compound of the present disclosure within seconds or minutes. In some embodiments, a unit dose of a compound of the present disclosure is administered first, followed, after a period of hours (e.g., 1-12 hours), by administration of a unit dose of one or more additional therapeutic agents. In other embodiments, a unit dose of one or more additional therapeutic agents is administered first, followed, after a period of hours (e.g., 1-12 hours), by administration of a unit dose of a compound of the present disclosure.

VI. COMBINATION THERAPY FOR HBV

In certain embodiments, a method for treating or preventing an HBV infection in a human having or at risk of having the infection is provided, comprising administering to the human a therapeutically effective amount of a compound disclosed herein, or a pharmaceutically acceptable salt thereof, in combination with a therapeutically effective amount of one or more (e.g., one, two, three, four, one or two, one to three, or one to four) additional therapeutic agents. In one embodiment, a method for treating an HBV infection in a human having or at risk of having the infection is provided, comprising administering to the human a therapeutically effective amount of a compound disclosed herein, or a pharmaceutically acceptable salt thereof, in combination with a therapeutically effective amount of one or more (e.g., one, two, three, four, one or two, one to three, or one to four) additional therapeutic agents.

In certain embodiments, the present disclosure provides a method for treating an HBV infection, comprising administering to a patient in need thereof a therapeutically effective amount of a compound disclosed herein or a pharmaceutically acceptable salt thereof, in combination with a therapeutically effective amount of one or more (e.g., one, two, three, four, one or two, one to three, or one to four) additional therapeutic agents which are suitable for treating an HBV infection.

In certain embodiments, a compound disclosed herein, or a pharmaceutically acceptable salt thereof, is combined with one, two, three, four, or more additional therapeutic agents. In certain embodiments, a compound disclosed herein, or a pharmaceutically acceptable salt thereof, is combined with two additional therapeutic agents. In other embodiments, a compound disclosed herein, or a pharmaceutically acceptable salt thereof, is combined with three additional therapeutic agents. In further embodiments, a compound disclosed herein, or a pharmaceutically acceptable salt thereof, is combined with four additional therapeutic agents. The one, two, three, four, or more additional therapeutic agents can be different therapeutic agents selected from the same class of therapeutic agents, and/or they can be selected from different classes of therapeutic agents.

Administration of HBV Combination Therapy

In certain embodiments, when a compound disclosed herein is combined with one or more additional therapeutic agents as described above, the components of the composition are administered as a simultaneous or sequential regimen. When administered sequentially, the combination may be administered in two or more administrations.

Co-administration of a compound disclosed herein with one or more additional therapeutic agents generally refers to simultaneous or sequential administration of a compound disclosed herein and one or more additional therapeutic agents, such that therapeutically effective amounts of each agent are present in the body of the patient.

Co-administration includes administration of unit dosages of the compounds disclosed herein before or after administration of unit dosages of one or more additional therapeutic agents. The compound disclosed herein may be administered within seconds, minutes, or hours of the administration of one or more additional therapeutic agents. For example, in some embodiments, a unit dose of a compound disclosed herein is administered first, followed within seconds or minutes by administration of a unit dose of one or more additional therapeutic agents. Alternatively, in other embodiments, a unit dose of one or more additional therapeutic agents is administered first, followed by administration of a unit dose of a compound disclosed herein within seconds or minutes. In some embodiments, a unit dose of a compound disclosed herein is administered first, followed, after a period of hours (e.g., 1-12 hours), by administration of a unit dose of one or more additional therapeutic agents. In other embodiments, a unit dose of one or more additional therapeutic agents is administered first, followed, after a period of hours (e.g., 1-12 hours), by administration of a unit dose of a compound disclosed herein.

In certain embodiments, a compound disclosed herein is combined with one or more additional therapeutic agents in a unitary dosage form for simultaneous administration to a patient, for example as a solid dosage form for oral administration.

In certain embodiments a compound of Formula (I) is formulated as a tablet, which may optionally contain one or more other compounds useful for treating HBV. In certain embodiments, the tablet can contain another active ingredient for treating HBV.

In certain embodiments, such tablets are suitable for once daily dosing.

HBV Combination Therapy

In the above embodiments, the additional therapeutic agent may be an anti-HBV agent. For example, the additional therapeutic agent may be selected from the group consisting of HBV combination drugs, other drugs for treating HBV, 3-dioxygenase (IDO) inhibitors, antisense oligonucleotide targeting viral mRNA, Apolipoprotein A1 modulator, arginase inhibitors, B- and T-lymphocyte attenuator inhibitors, Bruton's tyrosine kinase (BTK) inhibitors, CCR2 chemokine antagonist, CD137 inhibitors, CD160 inhibitors, CD305 inhibitors, CD4 agonist and modulator, compounds targeting HBcAg, compounds targeting hepatitis B core antigen (HBcAg), covalently closed circular DNA (cccDNA) inhibitors, cyclophilin inhibitors, cytokines, cytotoxic T-lymphocyte-associated protein 4 (ipi4) inhibitors, DNA polymerase inhibitor, Endonuclease modulator, epigenetic modifiers, Farnesoid X receptor agonist, gene modifiers or editors, HBsAg inhibitors, HBsAg secretion or assembly inhibitors, HBV antibodies, HBV DNA polymerase inhibitors, HBV replication inhibitors, HBV RNAse inhibitors, HBV vaccines, HBV viral entry inhibitors, HBx inhibitors, Hepatitis B large envelope protein modulator, Hepatitis B large envelope protein stimulator, Hepatitis B structural protein modulator, hepatitis B surface antigen (HBsAg) inhibitors, hepatitis B surface antigen (HBsAg) secretion or assembly inhibitors, hepatitis B virus E antigen inhibitors, hepatitis B virus replication inhibitors, Hepatitis virus structural protein inhibitor, HIV-1 reverse transcriptase inhibitor, Hyaluronidase inhibitor, IAPB inhibitors, IL-2 agonist, IL-7 agonist, Immunoglobulin agonist, Immunoglobulin G modulator, immunomodulators, indoleamine-2, inhibitors of ribonucleotide reductase, Interferon agonist, Interferon alpha 1 ligand, Interferon alpha 2 ligand, Interferon alpha 5 ligand modulator, Interferon alpha ligand, Interferon alpha ligand modulator, interferon alpha receptor ligands, Interferon beta ligand, Interferon ligand, Interferon receptor modulator, Interleukin-2 ligand, ipi4 inhibitors, lysine demethylase inhibitors, histone demethylase inhibitors, KDM5 inhibitors, KDM1 inhibitors, killer cell lectin-like receptor subfamily G member 1 inhibitors, lymphocyte-activation gene 3 inhibitors, lymphotoxin beta receptor activators, microRNA (miRNA) gene therapy agents, modulators of Axl, modulators of B7-H3, modulators of B7-H4, modulators of CD160, modulators of CD161, modulators of CD27, modulators of CD47, modulators of CD70, modulators of GITR, modulators of HEVEM, modulators of ICOS, modulators of Mer, modulators of NKG2A, modulators of NKG2D, modulators of OX40, modulators of SIRPalpha, modulators of TIGIT, modulators of Tim-4, modulators of Tyro, Na+-taurocholate cotransporting polypeptide (NTCP)

inhibitors, natural killer cell receptor 2B4 inhibitors, NOD2 gene stimulator, Nucleoprotein inhibitor, nucleoprotein modulators, PD-1 inhibitors, PD-L1 inhibitors, PEG-Interferon Lambda, Peptidylprolyl isomerase inhibitor, phosphatidylinositol-3 kinase (PI3K) inhibitors, recombinant scavenger receptor A (SRA) proteins, recombinant thymosin alpha-1, Retinoic acid-inducible gene 1 stimulator, Reverse transcriptase inhibitor, Ribonuclease inhibitor, RNA DNA polymerase inhibitor, short interfering RNAs (siRNA), short synthetic hairpin RNAs (sshRNAs), SLC10A1 gene inhibitor, SMAC mimetics, Src tyrosine kinase inhibitor, stimulator of interferon gene (STING) agonists, stimulators of NOD1, T cell surface glycoprotein CD28 inhibitor, T-cell surface glycoprotein CD8 modulator, Thymosin agonist, Thymosin alpha 1 ligand, Tim-3 inhibitors, TLR3 agonist, TLR7 agonist, TLR9 agonist, TLR9 gene stimulator, toll-like receptor (TLR) modulators, Viral ribonucleotide reductase inhibitor, zinc finger nucleases or synthetic nucleases (TALEN5), and combinations thereof.

In certain embodiments, a compound of Formula (I) is formulated as a tablet, which may optionally contain one or more other compounds useful for treating HBV. In certain embodiments, the tablet can contain another active ingredient for treating HBV, such as 3-dioxygenase (IDO) inhibitors, Apolipoprotein A1 modulator, arginase inhibitors, B- and T-lymphocyte attenuator inhibitors, Bruton's tyrosine kinase (BTK) inhibitors, CCR2 chemokine antagonist, CD137 inhibitors, CD160 inhibitors, CD305 inhibitors, CD4 agonist and modulator, compounds targeting HBcAg, compounds targeting hepatitis B core antigen (HBcAg), core protein allosteric modulators, covalently closed circular DNA (cccDNA) inhibitors, cyclophilin inhibitors, cytotoxic T-lymphocyte-associated protein 4 (ipi4) inhibitors, DNA polymerase inhibitor, Endonuclease modulator, epigenetic modifiers, Farnesoid X receptor agonist, HBsAg inhibitors, HBsAg secretion or assembly inhibitors, HBV DNA polymerase inhibitors, HBV replication inhibitors, HBV RNAse inhibitors, HBV viral entry inhibitors, HBx inhibitors, Hepatitis B large envelope protein modulator, Hepatitis B large envelope protein stimulator, Hepatitis B structural protein modulator, hepatitis B surface antigen (HBsAg) inhibitors, hepatitis B surface antigen (HBsAg) secretion or assembly inhibitors, hepatitis B virus E antigen inhibitors, hepatitis B virus replication inhibitors, Hepatitis B virus structural protein inhibitor, HIV-1 reverse transcriptase inhibitor, Hyaluronidase inhibitor, IAPB inhibitors, IL-2 agonist, IL-7 agonist, immunomodulators, indoleamine-2 inhibitors, inhibitors of ribonucleotide reductase, Interleukin-2 ligand, ipi4 inhibitors, lysine demethylase inhibitors, histone demethylase inhibitors, KDM1 inhibitors, KDM5 inhibitors, killer cell lectin-like receptor subfamily G member 1 inhibitors, lymphocyte-activation gene 3 inhibitors, lymphotoxin beta receptor activators, modulators of Axl, modulators of B7-H3, modulators of B7-H4, modulators of CD160, modulators of CD161, modulators of CD27, modulators of CD47, modulators of CD70, modulators of GITR, modulators of HEVEM, modulators of ICOS, modulators of Mer, modulators of NKG2A, modulators of NKG2D, modulators of OX40, modulators of SIRPalpha, modulators of TIGIT, modulators of Tim-4, modulators of Tyro, Na+-taurocholate cotransporting polypeptide (NTCP) inhibitors, natural killer cell receptor 2B4 inhibitors, NOD2 gene stimulator, Nucleoprotein inhibitor, nucleoprotein modulators, PD-1 inhibitors, PD-L1 inhibitors, Peptidylprolyl isomerase inhibitor, phosphatidylinositol-3 kinase (PI3K) inhibitors, Retinoic acid-inducible gene 1 stimulator, Reverse transcriptase inhibitor, Ribonuclease inhibitor, RNA DNA polymerase inhibitor, SLC10A1 gene inhibitor, SMAC mimetics, Src tyrosine kinase inhibitor, stimulator of interferon gene (STING) agonists, stimulators of NOD1, T cell surface glycoprotein CD28 inhibitor, T-cell surface glycoprotein CD8 modulator, Thymosin agonist, Thymosin alpha 1 ligand, Tim-3 inhibitors, TLR3 agonist, TLR7 agonist, TLR9 agonist, TLR9 gene stimulator, toll-like receptor (TLR) modulators, Viral ribonucleotide reductase inhibitor, and combinations thereof.

In certain embodiments, a compound of the present disclosure, or a pharmaceutically acceptable salt thereof, is combined with one, two, three, four or more additional therapeutic agents selected from HBV combination drugs, HBV vaccines, HBV DNA polymerase inhibitors, immunomodulators toll-like receptor (TLR) modulators, interferon alpha receptor ligands, hyaluronidase inhibitors, hepatitis b surface antigen (HBsAg) inhibitors, cytotoxic T-lymphocyte-associated protein 4 (ipi4) inhibitors, cyclophilin inhibitors, HBV viral entry inhibitors, antisense oligonucleotide targeting viral mRNA, short interfering RNAs (siRNA) and ddRNAi endonuclease modulators, ribonucelotide reductase inhibitors, HBV E antigen inhibitors, covalently closed circular DNA (cccDNA) inhibitors, farnesoid X receptor agonists, HBV antibodies, CCR2 chemokine antagonists, thymosin agonists, cytokines, nucleoprotein modulators, retinoic acid-inducible gene 1 stimulators, NOD2 stimulators, phosphatidylinositol 3-kinase (PI3K) inhibitors, indoleamine-2, 3-dioxygenase (IDO) pathway inhibitors, PD-1 inhibitors, PD-L1 inhibitors, recombinant thymosin alpha-1, bruton's tyrosine kinase (BTK) inhibitors, KDM inhibitors, HBV replication inhibitors, arginase inhibitors, and other HBV drugs.

HBV Combination Drugs

Examples of combination drugs for the treatment of HBV include TRUVADA® (tenofovir disoproxil fumarate and emtricitabine); ABX-203, lamivudine, and PEG-IFN-alpha; ABX-203adefovir, and PEG-IFNalpha; and INO-1800 (INO-9112 and RG7944).

Other HBV Drugs

Examples of other drugs for the treatment of HBV include alpha-hydroxytropolones, amdoxovir, beta-hydroxycytosine nucleosides, CCC-0975, elvucitabine, ezetimibe, cyclosporin A, gentiopicrin (gentiopicroside), JNJ-56136379, nitazoxanide, birinapant, NOV-205 (molixan, BAM-205), oligotide, mivotilate, feron, GST-HG-131, levamisole, Ka Shu Ning, alloferon, WS-007, Y-101 (Ti Fen Tai), rSIFN-co, PEG-IIFNm, KW-3, BP-Inter-014, oleanolic acid, HepB-nRNA, cTP-5 (rTP-5), HSK-II-2, HEISCO-106-1, HEISCO-106, Hepbarna, IBPB-0061A, Hepuyinfen, DasKloster 0014-01, ISA-204, Jiangantai (Ganxikang), MIV-210, OB-AI-004, PF-06, picroside, DasKloster-0039, hepulantai, IMB-2613, TCM-800B, reduced glutathione, RO-6864018, RG-7834, UB-551, and ZH-2N, and the compounds disclosed in US20150210682, (Roche), US 2016/0122344 (Roche), WO2015173164, WO2016023877, US2015252057A (Roche), WO16128335A1 (Roche), WO16120186A1 (Roche), US2016237090A (Roche), WO16107833A1 (Roche), WO16107832A1 (Roche), US2016176899A (Roche), WO16102438A1 (Roche), WO16012470A1 (Roche), US2016220586A (Roche), and US2015031687A (Roche).

HBV Vaccines

HBV vaccines include both prophylactic and therapeutic vaccines. Examples of HBV prophylactic vaccines include Vaxelis, Hexaxim, Heplisav, Mosquirix, DTwP-HBV vaccine, Bio-Hep-B, D/T/P/HBV/M (LBVP-0101; LBVW-0101), DTwP-Hepb-Hib-IPV vaccine, Heberpenta L, DTwP-HepB-Hib, V-419, CVI-HBV-001, Tetrabhay, hepatitis B prophylactic vaccine (Advax Super D), Hepatrol-07, GSK-223192A, ENGERIX B®, recombinant hepatitis B vaccine (intramuscular, Kangtai Biological Products), recombinant hepatitis B vaccine (Hansenual *polymorpha* yeast, intramuscular, Hualan Biological Engineering), recombinant hepatitis B surface antigen vaccine, Bimmugen, Euforavac, Eutravac, anrix-DTaP—IPV-Hep B, HBAI-20, Infanrix-DTaP—IPV-Hep B-Hib, Pentabio Vaksin DTP—HB-Hib, Comvac 4, Twinrix, Euvax-B, Tritanrix HB, Infanrix Hep B, Comvax, DTP-Hib-HBV vaccine, DTP-HBV vaccine, Yi Tai, Heberbiovac HB, Trivac HB, GerVax, DTwP-Hep B-Hib vaccine, Bilive, Hepavax-Gene, SUPERVAX, Comvac5, Shanvac-B, Hebsulin, Recombivax HB, Revac B mcf, Revac B+, Fendrix, DTwP-HepB-Hib, DNA-001, Shan6, rhHBsAG vaccine, and DTaP-rHB-Hib vaccine.

Examples of HBV therapeutic vaccines include HBsAG-HBIG complex, ARB-1598, Bio-Hep-B, NASVAC, abi-HB (intravenous), ABX-203, Tetrabhay, GX-110E, GS-4774, peptide vaccine (epsilonPA-44), Hepatrol-07, NASVAC (NASTERAP), IMP-321, BEVAC, Revac B mcf, Revac B+, MGN-1333, KW-2, CVI-HBV-002, AltraHepB, VGX-6200, FP-02, FP-02.2, TG-1050, NU-500, HBVax, im/TriGrid/antigen vaccine, Mega-CD40L-adjuvanted vaccine, HepB-v, RG7944 (INO-1800), recombinant VLP-based therapeutic vaccine (HBV infection, VLP Biotech), AdTG-17909, AdTG-17910 AdTG-18202, ChronVac-B, TG-1050, and Lm HBV.

HBV DNA Polymerase Inhibitors

Examples of HBV DNA polymerase inhibitors include adefovir (HEPSERA®), emtricitabine (EMTRIVA®), tenofovir disoproxil fumarate (VIREAD®), tenofovir alafenamide, tenofovir, tenofovir disoproxil, tenofovir alafenamide fumarate, tenofovir alafenamide hemifumarate, tenofovir dipivoxil, tenofovir dipivoxil fumarate, tenofovir octadecyloxyethyl ester, CMX-157, besifovir, entecavir (BARACLUDE®), entecavir maleate, telbivudine (TYZEKA®), pradefovir, clevudine, ribavirin, lamivudine (EPIVIR-HBV®), phosphazide, famciclovir, fusolin, metacavir, SNC-019754, FMCA, AGX-1009, AR-II-04-26, HIP-1302, tenofovir disoproxil aspartate, tenofovir disoproxil orotate, and HS-10234.

Immunomodulators

Examples of immunomodulators include rintatolimod, imidol hydrochloride, ingaron, dermaVir, plaquenil (hydroxychloroquine), proleukin, hydroxyurea, mycophenolate mofetil (MPA) and its ester derivative mycophenolate mofetil (MMF), WF-10, ribavirin, IL-12, INO-9112, polymer polyethyleneimine (PEI), Gepon, VGV-1, MOR-22, BMS-936559, RO-7011785, RO-6871765, and IR-103.

Toll-Like Receptor (TLR) Modulators

TLR modulators include modulators of TLR1, TLR2, TLR3, TLR4, TLR5, TLR6, TLR7, TLR8, TLR9, TLR10, TLR11, TLR12, and TLR13. Examples of TLR3 modulators include rintatolimod, poly-ICLC, RIBOXXON®, Apoxxim, RIBOXXIM®, IPH-33, MCT-465, MCT-475, and ND-1.1.

Examples of TLR7 modulators include GS-9620, GSK-2245035, imiquimod, resiquimod, DSR-6434, DSP-3025, IMO-4200, MCT-465, MEDI-9197, 3M-051, SB-9922, 3M-052, Limtop, TMX-30X, TMX-202, RG-7863, RG-7795, and the compounds disclosed in US20100143301 (Gilead Sciences), US20110098248 (Gilead Sciences), and US20090047249 (Gilead Sciences).

Examples of TLR8 modulators include motolimod, resiquimod, 3M-051, 3M-052, MCT-465, IMO-4200, VTX-763, VTX-1463, and the compounds disclosed in US20140045849 (Janssen), US20140073642 (Janssen), WO2014/056953 (Janssen), WO2014/076221 (Janssen), WO2014/128189 (Janssen), US20140350031 (Janssen), WO2014/023813 (Janssen), US20080234251 (Array Biopharma), US20080306050 (Array Biopharma), US20100029585 (Ventirx Pharma), US20110092485 (Ventirx Pharma), US20110118235 (Ventirx Pharma), US20120082658 (Ventirx Pharma), US20120219615 (Ventirx Pharma), US20140066432 (Ventirx Pharma), US20140088085 (Ventirx Pharma), US20140275167 (Novira Therapeutics), and US20130251673 (Novira Therapeutics).

Examples of TLR9 modulators include BB-001, BB-006, CYT-003, IMO-2055, IMO-2125, IMO-3100, IMO-8400, IR-103, IMO-9200, agatolimod, DIMS-9054, DV-1079, DV-1179, AZD-1419, leftolimod (MGN-1703), litenimod, and CYT-003-QbG10.

Interferon Alpha Receptor Ligands

Examples of interferon alpha receptor ligands include interferon alpha-2b (INTRON A®), pegylated interferon alpha-2a (PEGASYS®), PEGylated interferon alpha-1b, interferon alpha 1b (HAPGEN®), Veldona, Infradure, Roferon-A, YPEG-interferon alfa-2a (YPEG-rhIFNalpha-2a), P-1101, Algeron, Alfarona, Ingaron (interferon gamma), rSIFN-co (recombinant super compound interferon), Ypeginterferon alfa-2b (YPEG-rhIFNalpha-2b), MOR-22, peginterferon alfa-2b (PEG-INTRON®), Bioferon, Novaferon, Inmutag (Inferon), MULTIFERON®, interferon alfa-n1 (HUMOFERON®), interferon beta-1a (AVONEX®), Shaferon, interferon alfa-2b (Axxo), Alfaferone, interferon alfa-2b (BioGeneric Pharma), interferon-alpha 2 (CJ), Laferonum, VIPEG, BLAUFERON-A, BLAUFERON-B, Intermax Alpha, Realdiron, Lanstion, Pegaferon, PDferon-B PDferon-B, interferon alfa-2b (IFN, Laboratorios Bioprofarma), alfainterferona 2b, Kalferon, Pegnano, Feronsure, PegiHep, interferon alfa 2b (Zydus-Cadila), interferon alfa 2a, Optipeg A, Realfa 2B, Reliferon, interferon alfa-2b (Amega), interferon alfa-2b (Virchow), ropeginterferon alfa-2b, rHSA-IFN alpha-2a (recombinant human serum albumin intereferon alpha 2a fusion protein), rHSA-IFN alpha 2b, recombinant human interferon alpha-(1b, 2a, 2b), peginterferon alfa-2b (Amega), peginterferon alfa-2a, Reaferon-EC, Proquiferon, Uniferon, Urifron, interferon alfa-2b (Changchun Institute of Biological Products), Anterferon, Shanferon, Layfferon, Shang Sheng Lei Tai, INTEFEN, SINOGEN, Fukangtai, Pegstat, rHSA-IFN alpha-2b, and Interapo (Interapa).

Hyaluronidase Inhibitors

Examples of hyaluronidase inhibitors include astodrimer.

Hepatitis B Surface Antigen (HBsAg) Inhibitors

Examples of HBsAg inhibitors include HBF-0259, PBHBV-001, PBHBV-2-15, PBHBV-2-1, REP-9AC, REP-9C, REP-9, REP-2139, REP-2139-Ca, REP-2165, REP-2055, REP-2163, REP-2165, REP-2053, REP-2031 and REP-006, and REP-9AC'.

Examples of HBsAg secretion inhibitors include BM601.

Cytotoxic T-Lymphocyte-Associated Protein 4 (Ipi4) Inhibitors

Examples of Cytotoxic T-lymphocyte-associated protein 4 (ipi4) inhibitors include AGEN-2041, AGEN-1884, ipilumimab, belatacept, PSI-001, PRS-010, Probody mAbs, tremelimumab, and JHL-1155.

Cyclophilin Inhibitors

Examples of cyclophilin inhibitors include CPI-431-32, EDP-494, OCB-030, SCY-635, NVP-015, NVP-018, NVP-019, STG-175, and the compounds disclosed in U.S. Pat. No. 8,513,184 (Gilead Sciences), US20140030221 (Gilead Sciences), US20130344030 (Gilead Sciences), and US20130344029 (Gilead Sciences).

HBV Viral Entry Inhibitors

Examples of HBV viral entry inhibitors include Myrcludex B.

Antisense Oligonucleotide Targeting Viral mRNA

Examples of antisense oligonucleotide targeting viral mRNA include ISIS-HBVRx, IONIS-HBVRx, IONIS-GSK6-LRx, GSK-3389404.

Short Interfering RNAs (siRNA) and ddRNAi.

Examples of siRNA include TKM-HBV (TKM-HepB), ALN-HBV, SR-008, HepB-nRNA, and ARC-520, ARC-521, ARB-1740, ARB-1467.

Examples of DNA-directed RNA interference (ddRNAi) include BB-HB-331.

Endonuclease Modulators

Examples of endonuclease modulators include PGN-514.

Ribonucleotide Reductase Inhibitors

Examples of inhibitors of ribonucleotide reductase include Trimidox.

HBV E Antigen Inhibitors

Examples of HBV E antigen inhibitors include wogonin.

Covalently Closed Circular DNA (cccDNA) Inhibitors

Examples of cccDNA inhibitors include BSBI-25, and CHR-101.

Farnesoid X Receptor Agonist

Example of farnesoid x receptor agonist such as EYP-001.

HBV Antibodies

Examples of HBV antibodies targeting the surface antigens of the hepatitis B virus include GC-1102, XTL-17, XTL-19, KN-003, IV Hepabulin SN, and fully human monoclonal antibody therapy (hepatitis B virus infection, Humabs BioMed).

Examples of HBV antibodies, including monoclonal antibodies and polyclonal antibodies, include Zutectra, Shang Sheng Gan Di, Uman Big (Hepatitis B Hyperimmune), Omri-Hep-B, Nabi-HB, Hepatect CP, HepaGam B, igantibe, Niuliva, CT-P24, hepatitis B immunoglobulin (intravenous, pH4, HBV infection, Shanghai RAAS Blood Products), and Fovepta (BT-088).

Fully human monoclonal antibodies such as HBC-34.

CCR2 Chemokine Antagonists

Examples of CCR2 chemokine antagonists include propagermanium.

Thymosin Agonists

Examples of thymosin agonists include Thymalfasin, recombinant thymosin alpha 1 (GeneScience)

Cytokines

Examples of cytokines include recombinant IL-7, CYT-107, interleukin-2 (IL-2, Immunex), recombinant human interleukin-2 (Shenzhen Neptunus), IL-15, IL-21, IL-24, and celmoleukin.

Nucleoprotein Modulators

Nucleoprotein modulators may be either HBV core or capsid protein inhibitors. Examples of nucleoprotein modulators include AT-130, GLS4, NVR-1221, NVR-3778, BAY 41-4109, morphothiadine mesilate, JNJ-379, and DVR-23.

Capsid assembly inhibitors such as AB-423.

Examples of capsid inhibitors include the compounds disclosed in US20140275167 (Novira Therapeutics), US20130251673 (Novira Therapeutics), US20140343032 (Roche), WO2014037480 (Roche), US20130267517 (Roche), WO2014131847 (Janssen), WO2014033176 (Janssen), WO2014033170 (Janssen), WO2014033167 (Janssen), WO2015/059212 (Janssen), WO2015118057 (Janssen), WO2015011281 (Janssen), WO2014184365 (Janssen), WO2014184350 (Janssen), WO2014161888 (Janssen), WO2013096744 (Novira), US20150225355 (Novira), US20140178337 (Novira), US20150315159 (Novira), US20150197533 (Novira), US20150274652 (Novira), US20150259324, (Novira), US20150132258 (Novira), U.S. Pat. No. 9,181,288 (Novira), WO2014184350 (Janssen), WO2013144129 (Roche).

Retinoic Acid-Inducible Gene 1 Stimulators

Examples of stimulators of retinoic acid-inducible gene 1 include SB-9200, SB-40, SB-44, ORI-7246, ORI-9350, ORI-7537, ORI-9020, ORI-9198, and ORI-7170, RGT-100.

NOD2 Stimulators

Examples of stimulators of NOD2 include SB-9200.

Phosphatidylinositol 3-kinase (PI3K) Inhibitors

Examples of PI3K inhibitors include idelalisib, ACP-319, AZD-8186, AZD-8835, buparlisib, CDZ-173, CLR-457, pictilisib, neratinib, rigosertib, rigosertib sodium, EN-3342, TGR-1202, alpelisib, duvelisib, IPI-549, UCB-5857, taselisib, XL-765, gedatolisib, ME-401, VS-5584, copanlisib, CAI orotate, perifosine, RG-7666, GSK-2636771, DS-7423, panulisib, GSK-2269557, GSK-2126458, CUDC-907, PQR-309, INCB-40093, pilaralisib, BAY-1082439, puquitinib mesylate, SAR-245409, AMG-319, RP-6530, ZSTK-474, MLN-1117, SF-1126, RV-1729, sonolisib, LY-3023414, SAR-260301, TAK-117, HMPL-689, tenalisib, voxtalisib, and CLR-1401.

Indoleamine-2, 3-dioxygenase (IDO) Pathway Inhibitors

Examples of IDO inhibitors include epacadostat (INCB24360), resminostat (4SC-201), indoximod, F-001287, SN-35837, NLG-919, GDC-0919, GBV-1028, GBV-1012, NKTR-218, and the compounds disclosed in US20100015178 (Incyte), US2016137652 (Flexus Biosciences, Inc.), WO2014073738 (Flexus Biosciences, Inc.), and WO2015188085 (Flexus Biosciences, Inc.).

PD-1 Inhibitors

Examples of PD-1 inhibitors include nivolumab, pembrolizumab, pidilizumab, BGB-108, SHR-1210, PDR-001, PF-06801591, IBI-308, GB-226, STI-1110, and mDX-400.

PD-L1 Inhibitors

Examples of PD-L1 inhibitors include atezolizumab, avelumab, AMP-224, MEDI-0680, RG-7446, GX-P2, durvalumab, KY-1003, KD-033, MSB-0010718C, TSR-042, ALN-PDL, STI-A1014, CX-072, and BMS-936559.

Recombinant Thymosin Alpha-1

Examples of recombinant thymosin alpha-1 include NL-004 and PEGylated thymosin alpha-1.

Bruton's Tyrosine Kinase (BTK) Inhibitors

Examples of BTK inhibitors include ABBV-105, acalabrutinib (ACP-196), ARQ-531, BMS-986142, dasatinib, ibrutinib, GDC-0853, PRN-1008, SNS-062, ONO-4059, BGB-3111, ML-319, MSC-2364447, RDX-022, X-022, AC-058, RG-7845, spebrutinib, TAS-5315, TP-0158, TP-4207, HM-71224, KBP-7536, M-2951, TAK-020, AC-0025, and the compounds disclosed in US20140330015 (Ono Pharmaceutical), US20130079327 (Ono Pharmaceutical), and US20130217880 (Ono Pharmaceutical).

KDM Inhibitors

Examples of KDM5 inhibitors include the compounds disclosed in WO2016057924 (Genentech/Constellation Pharmaceuticals), US20140275092 (Genentech/Constellation Pharmaceuticals), US20140371195 (Epitherapeutics) and US20140371214 (Epitherapeutics)., US20160102096 (Epitherapeutics), US20140194469 (Quanticel), US20140171432, US20140213591 (Quanticel), US20160039808 (Quanticel), US20140275084 (Quanticel), WO2014164708 (Quanticel).

Examples of KDM1 inhibitors include the compounds disclosed in U.S. Pat. No. 9,186,337B2 (Oryzon Genomics), and GSK-2879552, RG-6016, ORY-2001.

HBV Replication Inhibitors

Examples of hepatitis B virus replication inhibitors include isothiafludine, IQP-HBV, RM-5038, and Xingantie.

Arginase Inhibitors

Examples of Arginase inhibitors include CB-1158, C-201, and resminostat.

HBV Combination Therapy

In a particular embodiment, a compound disclosed herein, or a pharmaceutically acceptable salt thereof, is combined with one, two, three, or four additional therapeutic agent selected from the group consisting of adefovir (HEPSERA®), tenofovir disoproxil fumarate (VIREAD®), tenofovir alafenamide, tenofovir, tenofovir disoproxil, tenofovir alafenamide fumarate, tenofovir alafenamide hemifumarate, entecavir (BARACLUDE®), telbivudine (TYZEKA®), or lamivudine (EPIVIR-HBV®). In a particular embodiment, a compound disclosed herein, or a pharmaceutically acceptable salt thereof, is combined with a first additional therapeutic agent selected from the group consisting of adefovir (HEPSERA®), tenofovir disoproxil fumarate (VIREAD®), tenofovir alafenamide, tenofovir, tenofovir disoproxil, tenofovir alafenamide fumarate, tenofovir alafenamide hemifumarate, entecavir (BARACLUDE®), telbivudine (TYZEKA®), or lamivudine (EPIVIR-HBV®). In one embodiment, pharmaceutical compositions comprising a compound disclosed herein, or a pharmaceutically acceptable salt thereof, in combination with one or more (e.g., one, two, three, four, one or two, or one to three, or one to four) additional therapeutic agents and a pharmaceutically acceptable carrier, diluent, or excipient are provided.

HBV DNA Polymerase Inhibitor Combination Therapy

In a specific embodiment, a compound disclosed herein, or a pharmaceutically acceptable salt thereof, is combined with an HBV DNA polymerase inhibitor. In another specific embodiment, a compound disclosed herein, or a pharmaceutically acceptable salt thereof, is combined with an HBV DNA polymerase inhibitor and at least one additional therapeutic agent selected from the group consisting of: immunomodulators, TLR modulators, interferon alpha receptor ligands, hyaluronidase inhibitors, recombinant IL-7, HBsAg inhibitors, HBsAg secretion or assembly inhibitors, compounds targeting HBcAg, cyclophilin inhibitors, HBV vaccines, HBV viral entry inhibitors, NTCP inhibitors, antisense oligonucleotide targeting viral mRNA, siRNA, miRNA gene therapy agents, endonuclease modulators, inhibitors of ribonucleotide reductase, hepatitis B virus E antigen inhibitors, recombinant SRA proteins, src kinase inhibitors, HBx inhibitors, cccDNA inhibitors, sshRNAs, HBV antibodies including HBV antibodies targeting the surface antigens of the hepatitis B virus and bispecific antibodies and "antibody-like" therapeutic proteins (such as DARTs®, DUOBODIES®, BITES®, XmAbs®, TandAbs®, Fab derivatives, or TCR-like antibodies), CCR2 chemokine antagonists, thymosin agonists, cytokines, nucleoprotein modulators (HBV core or capsid protein modulators), stimulators of retinoic acid-inducible gene 1, stimulators of RIG-I like receptors, stimulators of NOD2, stimulators of NOD1, Arginase inhibitors, STING agonists, PI3K inhibitors, lymphotoxin beta receptor activators, natural killer cell receptor 2B4 inhibitors, Lymphocyte-activation gene 3 inhibitors, CD160 inhibitors, cytotoxic T-lymphocyte-associated protein 4 (ipi4) inhibitors, CD137 inhibitors, Killer cell lectin-like receptor subfamily G member 1 inhibitors, TIM-3 inhibitors, B- and T-lymphocyte attenuator inhibitors, CD305 inhibitors, PD-1 inhibitors, PD-L1 inhibitors, PEG-Interferon Lambda, recombinant thymosin alpha-1, BTK inhibitors, modulators of TIGIT, modulators of CD47, modulators of SIRPalpha, modulators of ICOS, modulators of CD27, modulators of CD70, modulators of OX40, epigenetic modifiers, modulators of NKG2D, modulators of Tim-4, modulators of B7-H4, modulators of B7-H3, modulators of NKG2A, modulators of GITR, modulators of CD160, modulators of HEVEM, modulators of CD161, modulators of Axl, modulators of Mer, modulators of Tyro, gene modifiers or editors such as CRISPR (including CRISPR Cas9), zinc finger nucleases or synthetic nucleases (TALENs), IAPB inhibitors, SMAC mimetics, KDM5 inhibitors, IDO inhibitors, and hepatitis B virus replication inhibitors.

In another specific embodiment, a compound disclosed herein, or a pharmaceutically acceptable salt thereof, is combined with an HBV DNA polymerase inhibitor, one or two additional therapeutic agents selected from the group consisting of immunomodulators, TLR modulators, HBsAg inhibitors, HBsAg secretion or assembly inhibitors, HBV therapeutic vaccines, HBV antibodies including HBV antibodies targeting the surface antigens of the hepatitis B virus and bispecific antibodies and "antibody-like" therapeutic proteins (such as DARTs®, DUOBODIES®, BITES®, XmAbs®, TandAbs®, Fab derivatives, or TCR-like antibodies), cyclophilin inhibitors, stimulators of retinoic acid-inducible gene 1, stimulators of RIG-I like receptors, PD-1 inhibitors, PD-L1 inhibitors, Arginase inhibitors, PI3K inhibitors, IDO inhibitors, and stimulators of NOD2, and one or two additional therapeutic agents selected from the group consisting of HBV viral entry inhibitors, NTCP inhibitors, HBx inhibitors, cccDNA inhibitors, HBV antibodies targeting the surface antigens of the hepatitis B virus, siRNA, miRNA gene therapy agents, sshRNAs, KDM5 inhibitors, and nucleoprotein modulators (HBV core or capsid protein modulators).

In another specific embodiment, a compound disclosed herein, or a pharmaceutically acceptable salt thereof, is combined with an HBV DNA polymerase inhibitor and at least a second additional therapeutic agent selected from the group consisting of: HBV viral entry inhibitors, NTCP inhibitors, HBx inhibitors, cccDNA inhibitors, HBV antibodies targeting the surface antigens of the hepatitis B virus, siRNA, miRNA gene therapy agents, sshRNAs, KDM5 inhibitors, and nucleoprotein modulators (HBV core or capsid protein inhibitors).

HBV Drug Combination Therapy

In a particular embodiment, a compound disclosed herein, or a pharmaceutically acceptable salt thereof, is combined with a first additional therapeutic agent selected from the group consisting of adefovir (HEPSERA®), tenofovir disoproxil fumarate (VIREAD®), tenofovir alafenamide, tenofovir, tenofovir disoproxil, tenofovir alafenamide fumarate, tenofovir alafenamide hemifumarate, entecavir (BARACLUDE®), telbivudine (TYZEKA®), or lamivudine (EPIVIR-HBV®), and at least a second additional therapeutic agent selected from the group consisting of immunomodulators, TLR modulators, interferon alpha receptor ligands, hyaluronidase inhibitors, recombinant IL-7, HBsAg inhibitors, HBsAg secretion or assembly inhibitors, compounds targeting HBcAg, cyclophilin inhibitors, HBV vaccines, HBV viral entry inhibitors, NTCP inhibitors, antisense oligonucleotide targeting viral mRNA, siRNA, miRNA gene therapy agents, endonuclease modulators, inhibitors of ribonucleotide reductase, hepatitis B virus E antigen inhibitors, recombinant SRA proteins, src kinase inhibitors, HBx inhibitors, cccDNA inhibitors, sshRNAs, HBV antibodies including HBV antibodies targeting the surface antigens of the hepatitis B virus and bispecific antibodies and "antibody-like" therapeutic proteins (such as DARTs®, DUOBODIES®, BITES®, XmAbs®, TandAbs®, Fab derivatives, and TCR-like antibodies), CCR2 chemokine antagonists, thymosin agonists, cytokines, nucleoprotein modulators (HBV core or capsid protein modulators), stimulators of retinoic acid-inducible gene 1, stimulators of RIG-I like receptors, stimulators of NOD2, stimulators of NOD1, IDO inhibitors, recombinant thymosin alpha-1, Arginase inhibitors, STING agonists, PI3K inhibitors, lymphotoxin beta receptor activators, natural killer cell receptor 2B4 inhibitors, Lymphocyte-activation gene 3 inhibitors, CD160 inhibitors, ipi4 inhibitors, CD137 inhibitors, killer cell lectin-like receptor subfamily G member 1 inhibitors, TIM-3 inhibitors, B- and T-lymphocyte attenuator inhibitors, epigenetic modifiers, CD305 inhibitors, PD-1 inhibitors, PD-L1 inhibitors, PEG-Interferon Lambd, BTK inhibitors, modulators of TIGIT, modulators of CD47, modulators of SIRPalpha, modulators of ICOS, modulators of CD27, modulators of CD70, modulators of OX40, modulators of NKG2D, modulators of Tim-4, modulators of B7-H4, modulators of B7-H3, modulators of NKG2A, modulators of GITR, modulators of CD160, modulators of HEVEM, modulators of CD161, modulators of Axl, modulators of Mer, modulators of Tyro, gene modifiers or editors such as CRISPR (including CRISPR Cas9), zinc finger nucleases or synthetic nucleases (TALEN5), IAPB inhibitors, SMAC mimetics, KDM5 inhibitors, and hepatitis B virus replication inhibitors.

In a particular embodiment, a compound disclosed herein, or a pharmaceutically acceptable salt thereof, is combined with a first additional therapeutic agent selected from the group consisting of adefovir (HEPSERA®), tenofovir disoproxil fumarate (VIREAD®), tenofovir alafenamide, tenofovir, tenofovir disoproxil, tenofovir alafenamide fumarate, tenofovir alafenamide hemifumarate, entecavir (BARACLUDE®), telbivudine (TYZEKA®) or lamivudine (EPI-VIR-HBV®) and at least a second additional therapeutic agent selected from the group consisting of peginterferon alfa-2b (PEG-INTRON®), MULTIFERON®, interferon alpha 1b (HAPGEN®), interferon alpha-2b (INTRON A®), pegylated interferon alpha-2a (PEGASYS®), interferon) alfa-n1 (HUMOFERON®), ribavirin, interferon beta-1a (AVONEX®), Bioferon, Ingaron, Inmutag (Inferon), Algeron, Roferon-A, Oligotide, Zutectra, Shaferon, interferon alfa-2b (AXXO), Alfaferone, interferon alfa-2b (Bio-Generic Pharma), Feron, interferon-alpha 2 (CJ), BEVAC, Laferonum, VIPEG, BLAUFERON-B, BLAUFERON-A, Intermax Alpha, Realdiron, Lanstion, Pegaferon, PDferon-B, interferon alfa-2b (IFN, Laboratorios Bioprofarma), alfainterferona 2b, Kalferon, Pegnano, Feronsure, PegiHep, interferon alfa 2b (Zydus-Cadila), Optipeg A, Realfa 2B, Reliferon, interferon alfa-2b (Amega), interferon alfa-2b (Virchow), peginterferon alfa-2b (Amega), Reaferon-EC, Proquiferon, Uniferon, Urifron, interferon alfa-2b (Changchun Institute of Biological Products), Anterferon, Shanferon, MOR-22, interleukin-2 (IL-2, Immunex), recombinant human interleukin-2 (Shenzhen Neptunus), Layfferon, Ka Shu Ning, Shang Sheng Lei Tai, INTEFEN, SINOGEN, Fukangtai, Alloferon, and celmoleukin.

In a particular embodiment, a compound disclosed herein, or a pharmaceutically acceptable salt thereof, is combined with a first additional therapeutic agent selected from the group consisting of: adefovir (HEPSERA®), tenofovir disoproxil fumarate (VIREAD®), tenofovir alafenamide, tenofovir, tenofovir disoproxil, tenofovir alafenamide fumarate, tenofovir alafenamide hemifumarate, entecavir (BARACLUDE®), telbivudine (TYZEKA®), or lamivudine (EPI-VIR-HBV®), and at least a second additional therapeutic agent selected from the group consisting of HBV viral entry inhibitors, NTCP inhibitors, HBx inhibitors, cccDNA inhibitors, HBV antibodies targeting the surface antigens of the hepatitis B virus, siRNA, miRNA gene therapy agents, sshRNAs, KDM5 inhibitors, and nucleoprotein modulators (HBV core or capsid protein modulators).

In a particular embodiment, a compound disclosed herein, or a pharmaceutically acceptable salt thereof, is combined with a first additional therapeutic agent selected from the group consisting of adefovir (HEPSERA®), tenofovir disoproxil fumarate (VIREAD®), tenofovir alafenamide, tenofovir, tenofovir disoproxil, tenofovir alafenamide fumarate, tenofovir alafenamide hemifumarate, entecavir (BARACLUDE®), telbivudine (TYZEKA®), or lamivudine (EPI-VIR-HBV®); one, two, or three additional therapeutic agents selected from the group consisting of immunomodulators, TLR modulators, HBsAg inhibitors, HBsAg secretion or assembly inhibitors, HBV therapeutic vaccines, HBV antibodies including HBV antibodies targeting the surface antigens of the hepatitis B virus and bispecific antibodies and "antibody-like" therapeutic proteins (such as DARTs®, DUOBODIES®, BITES®, XmAbs®, TandAbs®, Fab derivatives, or TCR-like antibodies), cyclophilin inhibitors, stimulators of retinoic acid-inducible gene 1, stimulators of RIG-I like receptors, PD-1 inhibitors, PD-L1 inhibitors, Arginase inhibitors, PI3K inhibitors, IDO inhibitors, and stimulators of NOD2; and one or two additional therapeutic agents selected from the group consisting of HBV viral entry inhibitors, NTCP inhibitors, HBx inhibitors, cccDNA inhibitors, HBV antibodies targeting the surface antigens of the hepatitis B virus, siRNA, miRNA gene therapy agents, sshRNAs, KDM5 inhibitors, and nucleoprotein modulators (HBV core or capsid protein modulators).

In a particular embodiment, a compound disclosed herein, or a pharmaceutically acceptable salt thereof, is combined with a first additional therapeutic agent selected from the group consisting of adefovir (HEPSERA®), tenofovir disoproxil fumarate (VIREAD®), tenofovir alafenamide, tenofovir, tenofovir disoproxil, tenofovir alafenamide fumarate, tenofovir alafenamide hemifumarate, entecavir (BARACLUDE®), telbivudine (TYZEKA®), or lamivudine (EPI-VIR-HBV®); one or two additional therapeutic agents selected from the group consisting of immunomodulators, TLR modulators, HBsAg inhibitors, HBsAg secretion or assembly inhibitors, HBV therapeutic vaccines, HBV antibodies including HBV antibodies targeting the surface antigens of the hepatitis B virus and bispecific antibodies and "antibody-like" therapeutic proteins (such as DARTs®, DUOBODIES®, BITES®, XmAbs®, TandAbs®, Fab derivatives, or TCR-like antibodies), cyclophilin inhibitors, stimulators of retinoic acid-inducible gene 1, stimulators of RIG-I like receptors, PD-1 inhibitors, PD-L1 inhibitors, Arginase inhibitors, PI3K inhibitors, IDO inhibitors, and stimulators of NOD2; and one or two additional therapeutic agents selected from the group consisting of HBV viral entry inhibitors, NTCP inhibitors, HBx inhibitors, cccDNA inhibitors, HBV antibodies targeting the surface antigens of the hepatitis B virus, siRNA, miRNA gene therapy agents, sshRNAs, KDM5 inhibitors, and nucleoprotein modulators (HBV core or capsid protein modulators).

In a particular embodiment, a compound disclosed herein, or a pharmaceutically acceptable salt thereof, is combined with a first additional therapeutic agent selected from the group consisting of adefovir (HEPSERA®), tenofovir disoproxil fumarate (VIREAD®), tenofovir alafenamide, tenofovir, tenofovir disoproxil, tenofovir alafenamide fumarate, tenofovir alafenamide hemifumarate, entecavir (BARACLUDE®), telbivudine (TYZEKA®), or lamivudine (EPIVIR-HBV®); and one, two, three, or four additional therapeutic agents selected from the group consisting of immunomodulators, TLR7 modulators, TLR8 modulators, HBsAg inhibitors, HBsAg secretion or assembly inhibitors, HBV therapeutic vaccines, HBV antibodies including HBV antibodies targeting the surface antigens of the hepatitis B virus and bispecific antibodies and "antibody-like" therapeutic proteins (such as DARTs®, DUOBODIES®, BITES®, XmAbs®, TandAbs®, Fab derivatives, or TCR-like antibodies), cyclophilin inhibitors, stimulators of retinoic acid-inducible gene 1, stimulators of RIG-I like receptors, PD-1 inhibitors, PD-L1 inhibitors, Arginase inhibitors, PI3K inhibitors, IDO inhibitors, stimulators of NOD2 HBV viral entry inhibitors, NTCP inhibitors, HBx inhibitors, cccDNA inhibitors, siRNA, miRNA gene therapy agents, sshRNAs, KDM5 inhibitors, and nucleoprotein modulators (HBV core or capsid protein modulators).

In a particular embodiment, a compound disclosed herein, or a pharmaceutically acceptable salt thereof, is combined with compounds such as those disclosed in U.S. Publication No. 2010/0143301 (Gilead Sciences), U.S. Publication No. 2011/0098248 (Gilead Sciences), U.S. Publication No. 2009/0047249 (Gilead Sciences), U.S. Pat. No. 8,722,054 (Gilead Sciences), U.S. Publication No. 2014/0045849 (Janssen), U.S. Publication No. 2014/0073642 (Janssen), WO2014/056953 (Janssen), WO2014/076221 (Janssen), WO2014/128189 (Janssen), U.S. Publication No. 2014/0350031 (Janssen), WO2014/023813 (Janssen), U.S. Publication No. 2008/0234251 (Array Biopharma), U.S. Publication No. 2008/0306050 (Array Biopharma), U.S. Publication No. 2010/0029585 (Ventirx Pharma), U.S. Publication No. 2011/0092485 (Ventirx Pharma), US2011/0118235 (Ventirx Pharma), U.S. Publication No. 2012/0082658 (Ventirx Pharma), U.S. Publication No. 2012/0219615 (Ventirx Pharma), U.S. Publication No. 2014/0066432 (Ventirx Pharma), U.S. Publication No. 2014/0088085 (Ventirx Pharma), U.S. Publication No. 2014/0275167 (Novira Therapeutics), U.S. Publication No. 2013/0251673 (Novira Therapeutics), U.S. Pat. No. 8,513,184 (Gilead Sciences), U.S. Publication No. 2014/0030221 (Gilead Sciences), U.S. Publication No. 2013/0344030 (Gilead Sciences), U.S. Publication No. 2013/0344029 (Gilead Sciences), US20140275167 (Novira Therapeutics), US20130251673 (Novira Therapeutics), U.S. Publication No. 2014/0343032 (Roche), WO2014037480 (Roche), U.S. Publication No. 2013/0267517 (Roche), WO2014131847 (Janssen), WO2014033176 (Janssen), WO2014033170 (Janssen), WO2014033167 (Janssen), WO2015/059212 (Janssen), WO2015118057 (Janssen), WO2015011281 (Janssen), WO2014184365 (Janssen), WO2014184350 (Janssen), WO2014161888 (Janssen), WO2013096744 (Novira), US20150225355 (Novira), US20140178337 (Novira), US20150315159 (Novira), US20150197533 (Novira), US20150274652 (Novira), US20150259324, (Novira), US20150132258 (Novira), U.S. Pat. No. 9,181,288 (Novira), WO2014184350 (Janssen), WO2013144129 (Roche), US20100015178 (Incyte), US2016137652 (Flexus Biosciences, Inc.), WO2014073738 (Flexus Biosciences, Inc.), WO2015188085 (Flexus Biosciences, Inc.), U.S. Publication No. 2014/0330015 (Ono Pharmaceutical), U.S. Publication No. 2013/0079327 (Ono Pharmaceutical), U.S. Publication No. 2013/0217880 (Ono pharmaceutical), WO2016057924 (Genentech/Constellation Pharmaceuticals), US20140275092 (Genentech/Constellation Pharmaceuticals), US20140371195 (Epitherapeutics) and US20140371214 (Epitherapeutics)., US20160102096 (Epitherapeutics), US20140194469 (Quanticel), US20140171432, US20140213591 (Quanticel), US20160039808 (Quanticel), US20140275084 (Quanticel), WO2014164708 (Quanticel), U.S. Pat. No. 9,186,337B2 (Oryzon Genomics), and other drugs for treating HBV, and combinations thereof.

In certain embodiments, a compound as disclosed herein (e.g., any compound of Formula I) may be combined with one or more (e.g., one, two, three, four, one or two, one to three, or one to four) additional therapeutic agents in any dosage amount of the compound of Formula I (e.g., from 10 mg to 1000 mg of compound).

In certain embodiments, a compound disclosed herein, or a pharmaceutically acceptable salt thereof, is combined with 5-30 mg tenofovir alafenamide fumarate, tenofovir alafenamide hemifumarate, or tenofovir alafenamide. In certain embodiments, a compound disclosed herein, or a pharmaceutically acceptable salt thereof, is combined with 5-10; 5-15; 5-20; 5-25; 25-30; 20-30; 15-30; or 10-30 mg tenofovir alafenamide fumarate, tenofovir alafenamide hemifumarate, or tenofovir alafenamide. In certain embodiments, a compound disclosed herein, or a pharmaceutically acceptable salt thereof, is combined with 10 mg tenofovir alafenamide fumarate, tenofovir alafenamide hemifumarate, or tenofovir alafenamide. In certain embodiments, a compound disclosed herein, or a pharmaceutically acceptable salt thereof, is combined with 25 mg tenofovir alafenamide fumarate, tenofovir alafenamide hemifumarate, or tenofovir alafenamide. A compound as disclosed herein (e.g., a compound of Formula I) may be combined with the agents provided herein in any dosage amount of the compound (e.g., from 50 mg to 500 mg of compound) the same as if each combination of dosages were specifically and individually listed.

In certain embodiments, a compound disclosed herein, or a pharmaceutically acceptable salt thereof, is combined with 100-400 mg tenofovir disoproxil fumarate, tenofovir disoproxil hemifumarate, or tenofovir disoproxil. In certain embodiments, a compound disclosed herein, or a pharmaceutically acceptable salt thereof, is combined with 100-150; 100-200, 100-250; 100-300; 100-350; 150-200; 150-250; 150-300; 150-350; 150-400; 200-250; 200-300; 200-350; 200-400; 250-350; 250-400; 350-400 or 300-400 mg tenofovir disoproxil fumarate, tenofovir disoproxil hemifumarate, or tenofovir disoproxil. In certain embodiments, a compound disclosed herein, or a pharmaceutically acceptable salt thereof, is combined with 300 mg tenofovir disoproxil fumarate, tenofovir disoproxil hemifumarate, or tenofovir disoproxil. In certain embodiments, a compound disclosed herein, or a pharmaceutically acceptable salt thereof, is combined with 250 mg tenofovir disoproxil fumarate, tenofovir disoproxil hemifumarate, or tenofovir disoproxil. In certain embodiments, a compound disclosed herein, or a pharmaceutically acceptable salt thereof, is combined with 150 mg tenofovir disoproxil fumarate, tenofovir disoproxil hemifumarate, or tenofovir disoproxil. A compound as disclosed herein (e.g., a compound of Formula I) may be combined with the agents provided herein in any dosage amount of the compound (e.g., from 50 mg to 500 mg of compound) the same as if each combination of dosages were specifically and individually listed.

In one embodiment, kits comprising a compound disclosed herein, or a pharmaceutically acceptable salt thereof, in combination with one or more (e.g., one, two, three, four, one or two, or one to three, or one to four) additional therapeutic agents are provided.

VII. COMBINATION THERAPY FOR HCV

In certain embodiments, a method for treating or preventing an HCV infection in a human having or at risk of having the infection is provided, comprising administering to the human a therapeutically effective amount of a compound of the present disclosure, or a pharmaceutically acceptable salt thereof, in combination with a therapeutically effective amount of one or more (e.g., one, two, three, one or two, or one to three) additional therapeutic agents. In one embodiment, a method for treating an HCV infection in a human having or at risk of having the infection is provided, comprising administering to the human a therapeutically effective amount of a compound of the present disclosure, or a pharmaceutically acceptable salt thereof, in combination with a therapeutically effective amount of one or more (e.g., one, two, three, one or two, or one to three) additional therapeutic agents.

In certain embodiments, the present disclosure provides a method for treating an HCV infection, comprising administering to a patient in need thereof a therapeutically effective amount of a compound of the present disclosure, or a pharmaceutically acceptable salt thereof, in combination with a therapeutically effective amount of one or more additional therapeutic agents which are suitable for treating an HCV infection.

In the above embodiments, the additional therapeutic agent may be an anti-HCV agent. For example, in some embodiments, the additional therapeutic agent is selected from the group consisting of interferons, ribavirin or its analogs, HCV NS3 protease inhibitors, HCV NS4 protease inhibitors, HCV NS3/NS4 protease inhibitors, alpha-glucosidase 1 inhibitors, hepatoprotectants, nucleoside or nucleotide inhibitors of HCV NS5B polymerase, non-nucleoside inhibitors of HCV NS5B polymerase, HCV NS5A inhibitors, TLR7 agonists, cyclophilin inhibitors, HCV IRES inhibitors, and pharmacokinetic enhancers, compounds such as those disclosed in US2010/0310512, US2013/0102525, and WO2013/185093, or combinations thereof.

In certain embodiments a compound of the present disclosure (e.g., a compound of Formula (I)) is formulated as a tablet, which may optionally contain one or more other compounds useful for treating HCV. In certain embodiments, the tablet can contain another active ingredient for treating HCV, such as interferons, ribavirin or its analogs, HCV NS3 protease inhibitors, HCV NS4 protease inhibitors, HCV NS3/NS4 protease inhibitors, alpha-glucosidase 1 inhibitors, hepatoprotectants, nucleoside or nucleotide inhibitors of HCV NS5B polymerase, non-nucleoside inhibitors of HCV NS5B polymerase, HCV NS5A inhibitors, TLR7 agonists, cyclophilin inhibitors, HCV IRES inhibitors, and pharmacokinetic enhancers, or combinations thereof.

In certain embodiments, such tablets are suitable for once daily dosing.

In certain embodiments, the additional therapeutic agent is selected from one or more of:
(1) Interferons selected from the group consisting of pegylated rIFN-alpha 2b (PEG-Intron), pegylated rIFN-alpha 2a (Pegasys), rIFN-alpha 2b (Intron A), rIFN-alpha 2a (Roferon-A), interferon alpha (MOR-22, OPC-18, Alfaferone, Alfanative, Multiferon, subalin), interferon alfacon-1 (Infergen), interferon alpha-n1 (Wellferon), interferon alpha-n3 (Alferon), interferon-beta (Avonex, DL-8234), interferon-omega (omega DUROS, Biomed 510), albinterferon alpha-2b (Albuferon), IFN alpha XL, BLX-883 (Locteron), DA-3021, glycosylated interferon alpha-2b (AVI-005), PEG-Infergen, PEGylated interferon lambda (PEGylated IL-29), or belerofon, IFN alpha-2b XL, rIFN-alpha 2a, consensus IFN alpha, infergen, rebif, pegylated IFN-beta, oral interferon alpha, feron, reaferon, intermax alpha, r-IFN-beta, and infergen+actimmuneribavirin and ribavirin analogs, e.g., rebetol, copegus, VX-497, and viramidine (taribavirin);
(2) Ribavirin and its analogs selected from the group consisting of ribavirin (Rebetol, Copegus), and taribavirin (Viramidine);
(3) NS5A inhibitors selected from the group consisting of Compound A.1 (described below), Compound A.2 (described below), Compound A.3 (described below), ABT-267, Compound A.4 (described below), JNJ-47910382, daclatasvir (BMS-790052), ABT-267, Samatasvir, MK-8742, MK-8404, EDP-239, IDX-719, PPI-668, GSK-2336805, ACH-3102, A-831, A-689, AZD-2836 (A-831), AZD-7295 (A-689), and BMS-790052;
(4) NS5B polymerase inhibitors selected from the group consisting of sofosbuvir (GS-7977), Compound A.5 (described below), Compound A.6 (described below), ABT-333, Compound A.7 (described below), ABT-072, Compound A.8 (described below), tegobuvir (GS-9190), GS-9669, TMC647055, ABT-333, ABT-072, setrobuvir (ANA-598), IDX-21437, filibuvir (PF-868554), VX-222, IDX-375, IDX-184, IDX-102, BI-207127, valopicitabine (NM-283), PSI-6130 (R1656), PSI-7851, BCX-4678, nesbuvir (HCV-796), BILB 1941, MK-0608, NM-107, R7128, VCH-759, GSK625433, XTL-2125, VCH-916, JTK-652, MK-3281, VBY-708, A848837, GL59728, A-63890, A-48773, A-48547, BC-2329, BMS-791325, BILB-1941, AL-335, AL-516 and ACH-3422;
(5) Protease (NS3, NS3-NS4) inhibitors selected from the group consisting of Compound A.9, Compound A.10, Compound A.11, ABT-450, Compound A.12 (described below), simeprevir (TMC-435), boceprevir (SCH-503034), narlaprevir (SCH-900518), vaniprevir (MK-7009), MK-5172, danoprevir (ITMN-191), sovaprevir (ACH-1625), neceprevir (ACH-2684), Telaprevir (VX-950), VX-813, VX-500, faldaprevir (BI-201335), asunaprevir (BMS-650032), BMS-605339, VBY-376, PHX-1766, YH5531, BILN-2065, and BILN-2061;
(6) Alpha-glucosidase 1 inhibitors selected from the group consisting of celgosivir (MX-3253), Miglitol, and UT-231B;
(7) Hepatoprotectants selected from the group consisting of emericasan (IDN-6556), ME-3738, GS-9450 (LB-84451), silibilin, and MitoQ;
(8) TLR7 agonists selected from the group consisting of imiquimod, 852A, GS-9524, ANA-773, ANA-975, AZD-8848 (DSP-3025), and SM-360320;
(9) Cyclophillin inhibitors selected from the group consisting of DEBIO-025, SCY-635, and NIM811;
(10) HCV IRES inhibitors selected from the group consisting of MCI-067;
(11) Pharmacokinetic enhancers selected from the group consisting of BAS-100, SPI-452, PF-4194477, TMC-41629, GS-9350, GS-9585, and roxythromycin; and

(12) Other anti-HCV agents selected from the group consisting of thymosin alpha 1 (Zadaxin), nitazoxanide (Alinea, NTZ), BIVN-401 (virostat), PYN-17 (altirex), KPE02003002, actilon (CPG-10101), GS-9525, KRN-7000, civacir, GI-5005, XTL-6865, BIT225, PTX-111, ITX2865, TT-033i, ANA 971, NOV-205, tarvacin, EHC-18, VGX-410C, EMZ-702, AVI 4065, BMS-650032, BMS-791325, Bavituximab, MDX-1106 (ONO-4538), Oglufanide, VX-497 (merimepodib) NIM811, benzimidazole derivatives, benzo-1,2,4-thiadiazine derivatives, and phenylalanine derivatives;

Compound A.1 is an inhibitor of the HCV NS5A protein and is represented by the following chemical structure:

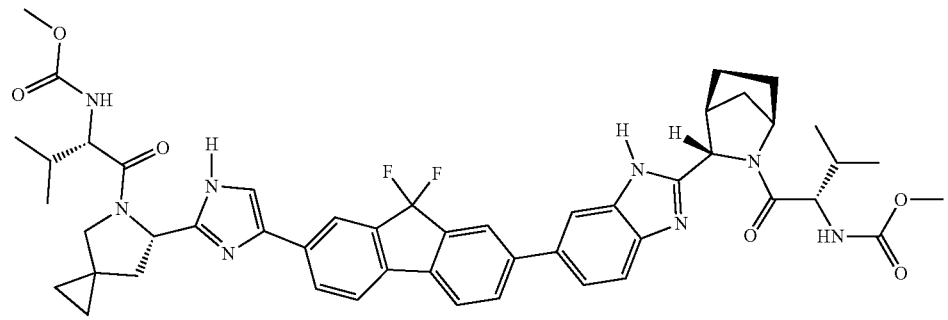

(see, e.g., U.S. Application Publication No. 20100310512 A1).

Compound A.2 is an NS5A inhibitor and is represented by the following chemical structure:

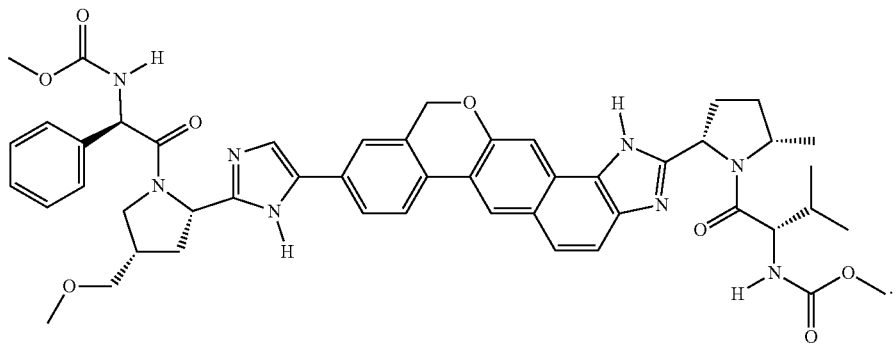

Compound A.3 is an NS5A inhibitor and is represented by the following chemical structure:

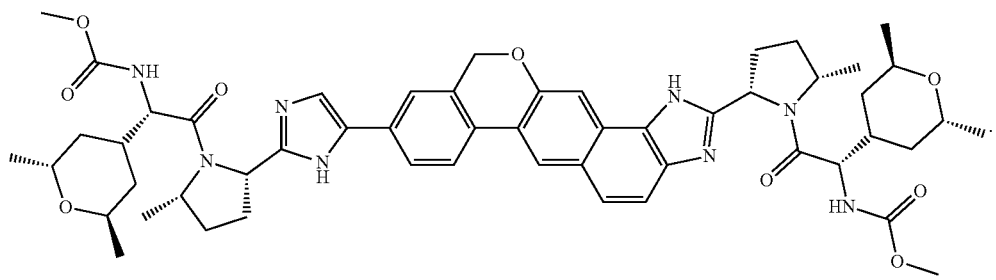

Compound A.4 is an NS5A inhibitor and is represented by the following chemical structure:

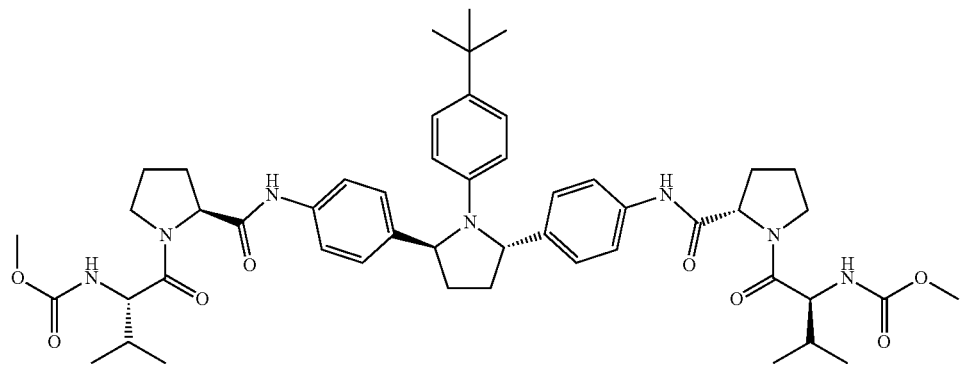 [SMILES: COC(=O)N[C@H](C(=O)N1CCC[C@H]1C(=O)Nc1ccc([C@@H]2CC[C@@H](c3ccc(NC(=O)[C@@H]4CCCN4C(=O)[C@@H](NC(=O)OC)C(C)C)cc3)N2c2ccc(C(C)(C)C)cc2)cc1)C(C)C]

(see U.S. Application Publication No. 2013/0102525 and references therein.)

Compound A.5 is an NS5B Thumb II polymerase inhibitor and is represented by the following chemical structure:

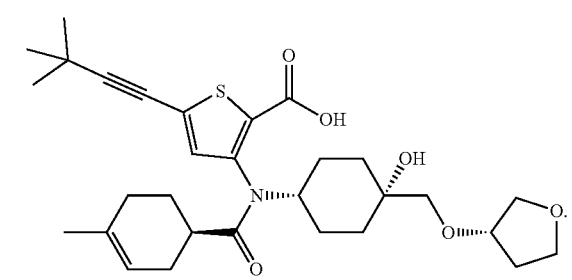 [SMILES: CC1=CC[C@H](C(=O)N(c2cc(C#CC(C)(C)C)sc2C(=O)O)[C@H]2CC[C@](O)(CO[C@H]3CCOC3)CC2)CC1]

Compound A.6 is a nucleotide inhibitor prodrug designed to inhibit replication of viral RNA by the HCV NS5B polymerase, and is represented by the following chemical structure:

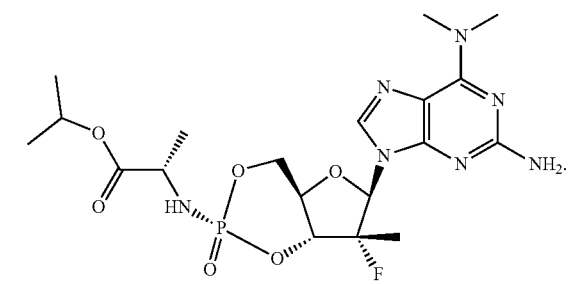 [SMILES: CC(C)OC(=O)[C@H](C)N[P@]1(=O)OC[C@H]2O[C@@H](n3cnc4c(N(C)C)nc(N)nc43)[C@](C)(F)[C@@H]2O1]

Compound A.7 is an HCV polymerase inhibitor and is represented by the following structure:

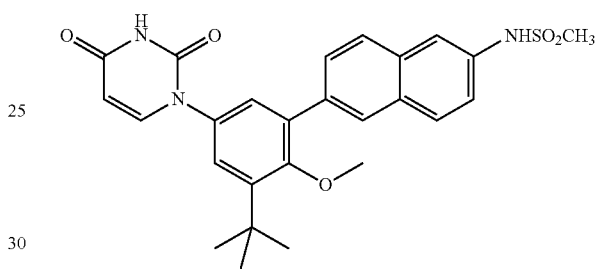

(see U.S. Application Publication No. 2013/0102525 and references therein).

Compound A.8 is an HCV polymerase inhibitor and is represented by the following structure:

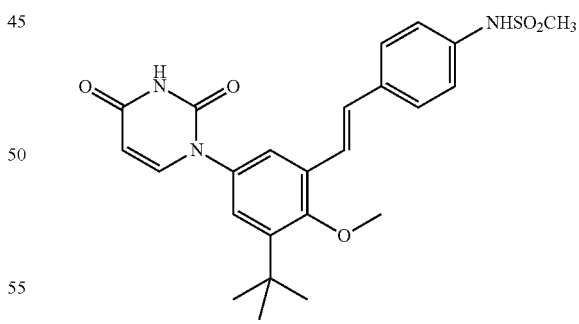

(see U.S. Application Publication No. 2013/0102525 and references therein).

Compound A.9 is an HCV protease inhibitor and is represented by the following chemical structure:

Compound A.10 is an HCV protease inhibitor and is represented by the following chemical structure:

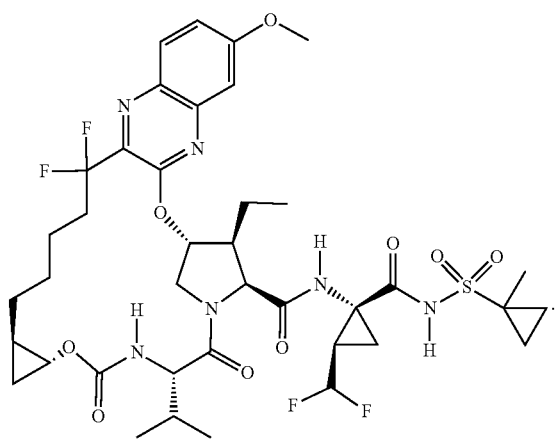

Compound A.11 is an HCV protease inhibitor and is represented by the following chemical structure:

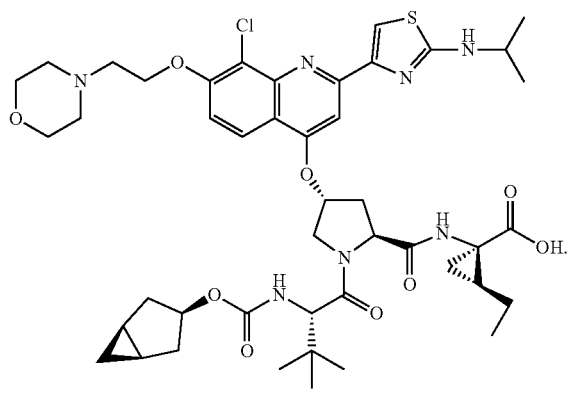

Compound A.12 is an HCV protease inhibitor and is represented by the following chemical structure:

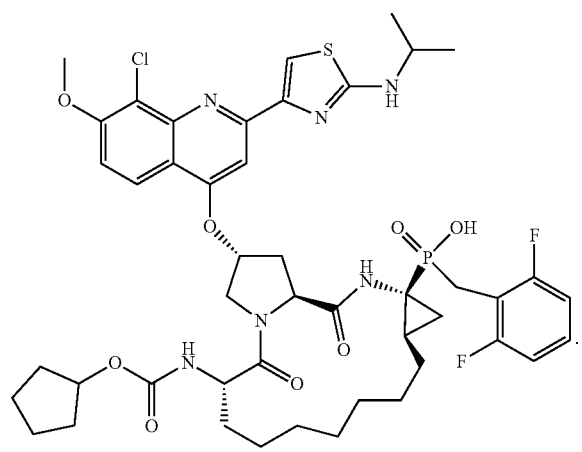 [SMILES: COc1ccc2c(O[C@@H]3C[C@H]4C(=O)N[C@]5(P(=O)(O)Cc6c(F)cccc6F)C[C@H]5CCCCCCC[C@H](NC(=O)OC5CCCC5)C(=O)N4C3)cc(-c3csc(NC(C)C)n3)nc2c1Cl]

(see U.S. Application Publication No. 2013/0102525 and references therein).

In one embodiment, the additional therapeutic agent used in combination with the pharmaceutical compositions as described herein is a HCV NS3 protease inhibitor. Non-limiting examples include the following:

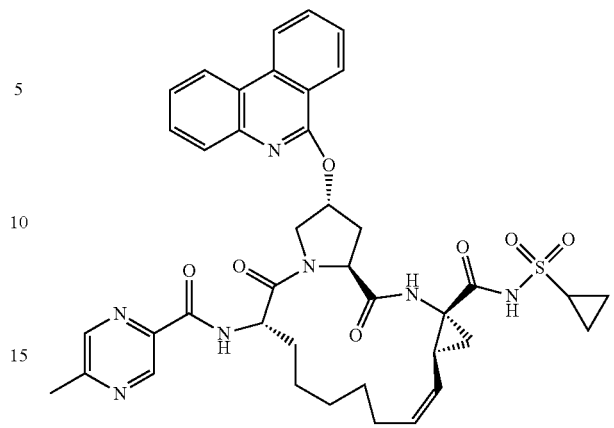

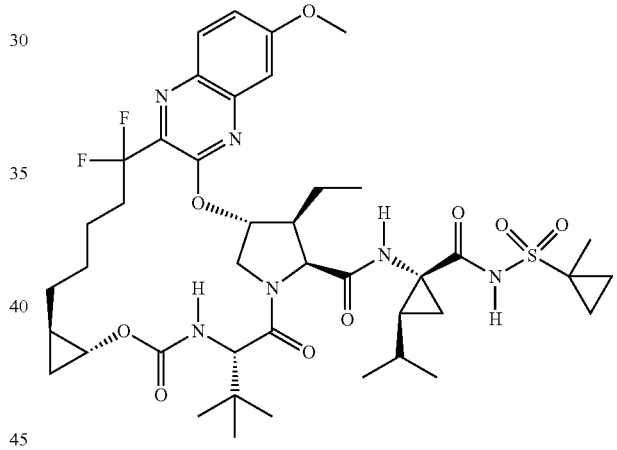

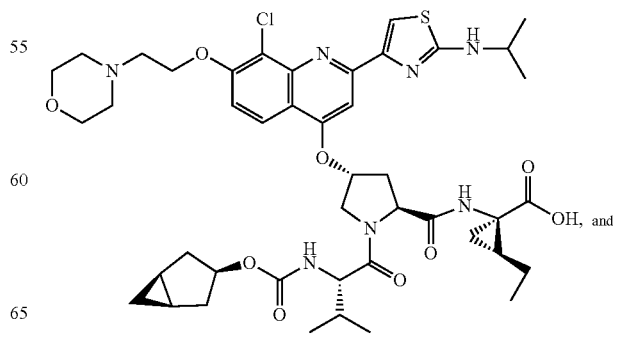

-continued
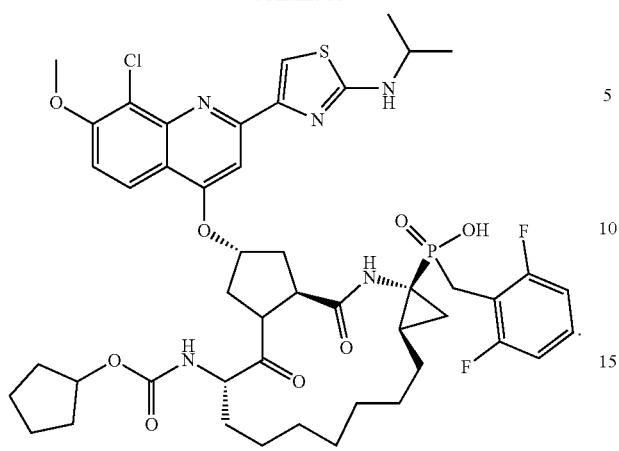
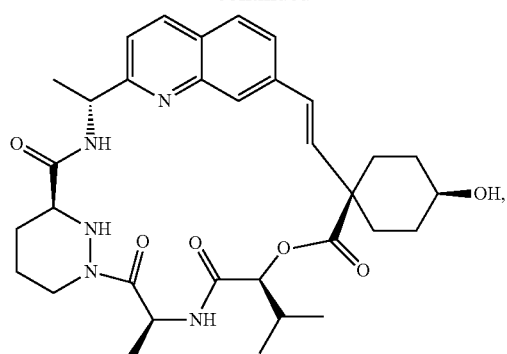
In another embodiment, the additional therapeutic agent used in combination with the pharmaceutical compositions as described herein is a cyclophillin inhibitor, including for example, a cyclophilin inhibitor disclosed in WO2013/185093. Non-limiting examples in addition to those listed above include the following:
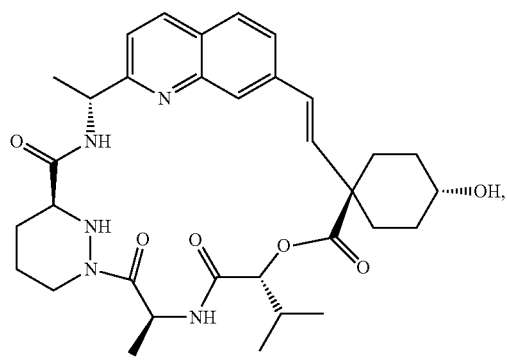
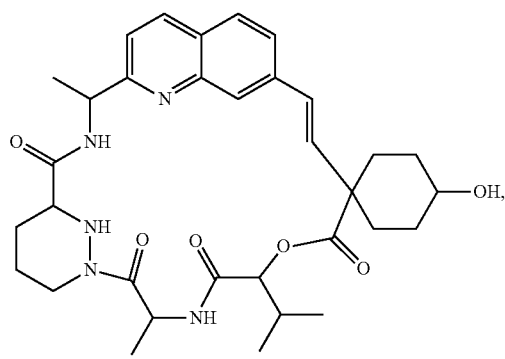
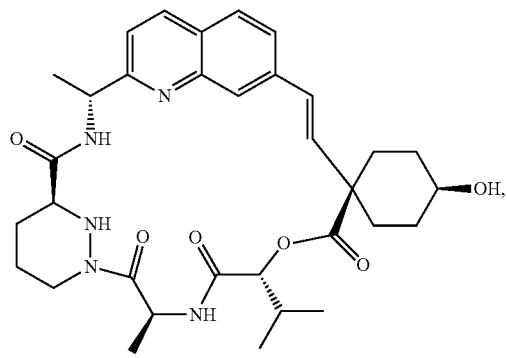
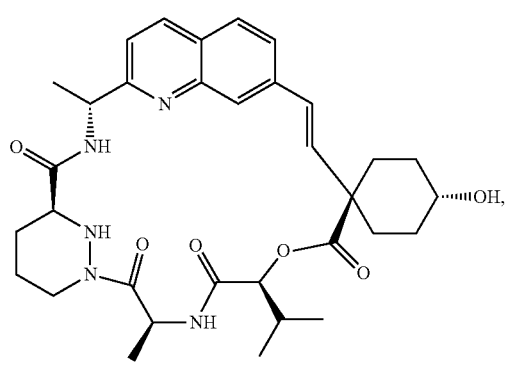
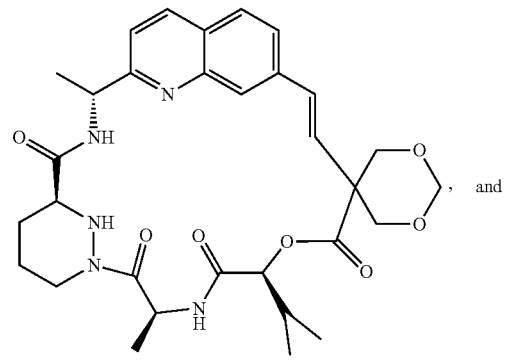, and

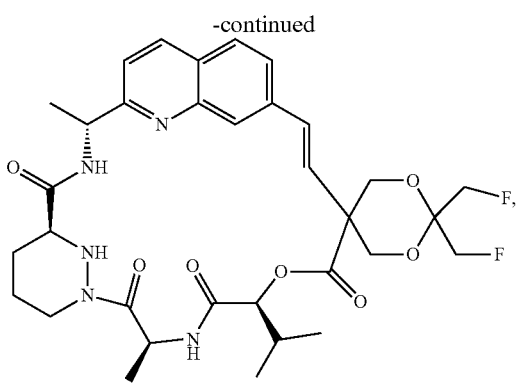

and stereoisomers and mixtures of stereoisomers thereof.

In a specific embodiment, a compound of the present disclosure, or a pharmaceutically acceptable salt thereof, is combined with a HCV NS5B polymerase inhibitor. In a specific embodiment, a compound of the present disclosure, or a pharmaceutically acceptable salt thereof, is combined with a HCV NS5B polymerase inhibitor and a HCV NS5A inhibitor. In another specific embodiment, a compound of the present disclosure, or a pharmaceutically acceptable salt thereof, is combined with a HCV NS5B polymerase inhibitor, a HCV NS3 protease inhibitor and a HCV NS5A inhibitor. In another specific embodiment, a compound of the present disclosure, or a pharmaceutically acceptable salt thereof, is combined with a HCV NS5B polymerase inhibitor, a HCV NS4 protease inhibitor and a HCV NS5A inhibitor. In another specific embodiment, a compound of the present disclosure, or a pharmaceutically acceptable salt thereof, is combined with a HCV NS5B polymerase inhibitor, a HCV NS3/NS4 protease inhibitor and a HCV NS5A inhibitor. In another specific embodiment, a compound of the present disclosure, or a pharmaceutically acceptable salt thereof, is combined with a HCV NS3 protease inhibitor and a HCV NS5A inhibitor. In another specific embodiment, a compound of the present disclosure, or a pharmaceutically acceptable salt thereof, is combined with a HCV NS4 protease inhibitor and a HCV NS5A inhibitor. In another specific embodiment, a compound of the present disclosure, or a pharmaceutically acceptable salt thereof, is combined with a HCV NS3/NS4 protease inhibitor and a HCV NS5A inhibitor. In another specific embodiment, a compound of the present disclosure, or a pharmaceutically acceptable salt thereof, is combined with a HCV NS3 protease inhibitor, a pharmacokinetic enhancer and a HCV NS5A inhibitor. In another specific embodiment, a compound of the present disclosure, or a pharmaceutically acceptable salt thereof, is combined with a HCV NS4 protease inhibitor, a pharmacokinetic enhancer and a HCV NS5A inhibitor. In another specific embodiment, a compound of the present disclosure, or a pharmaceutically acceptable salt thereof, is combined with a HCV NS3/NS4 protease inhibitor, a pharmacokinetic enhancer and a HCV NS5A inhibitor.

In a particular embodiment, a compound of the present disclosure, or a pharmaceutically acceptable salt thereof, is combined with one, two, three, four or more additional therapeutic agents selected from simeprevir, MK-8742, MK-8408, MK-5172, ABT-450, ABT-267, ABT-333, sofosbuvir, sofosbuvir+ledipasvir, sofosbuvir+GS-5816, sofosbuvir+GS-9857+ledipasvir, ABT-450+ABT-267+ritonavir, ABT-450+ABT-267+ribavirin+ritonavir, ABT-450+ABT-267+ribavirin+ABT-333+ritonavir, ABT-530+ABT-493, MK-8742+MK-5172, MK-8408+MK-3682+MK-5172, MK-8742+MK-3682+MK-5172, daclatasvir, interferon, pegylated interferon, ribavirin, samatasvir, MK-3682, ACH-3422, AL-335, IDX-21437, IDX-21459, tegobuvir, setrobuvir, valopicitabine, boceprevir, narlaprevir, vaniprevir, danoprevir, sovaprevir, neceprevir, telaprevir, faldaprevir, asunaprevir, ledipasvir, GS-5816, GS-9857, ACH-3102, ACH-3422+ACH-3102, ACH-3422+sovaprevir+ACH-3102, asunaprevir, asunaprevir+daclatasvir, AL-516, and vedroprevir.

In certain embodiments, a compound of the present disclosure, or a pharmaceutically acceptable salt thereof, is co-administered with simeprevir. In certain embodiments, a compound of the present disclosure, or a pharmaceutically acceptable salt thereof, is co-administered with MK-8742 or MK-8408. In certain embodiments, a compound of the present disclosure, or a pharmaceutically acceptable salt thereof, is co-administered with MK-5172. In certain embodiments, a compound of the present disclosure, or a pharmaceutically acceptable salt thereof, is co-administered with ABT-450, ABT-267, or ABT-333. In certain embodiments, a compound of the present disclosure, or a pharmaceutically acceptable salt thereof, is co-administered with Viekirat (a combination of ABT-450, ABT-267, and ritonavir). In certain embodiments, a compound of the present disclosure, or a pharmaceutically acceptable salt thereof, is co-administered with daclatasvir. In certain embodiments, a compound of the present disclosure, or a pharmaceutically acceptable salt thereof, is co-administered with sofosbuvir. In certain embodiments, a compound of the present disclosure, or a pharmaceutically acceptable salt thereof, is co-administered with Harvoni (sofosbuvir+ledipasvir). In certain embodiments, a compound of the present disclosure, or a pharmaceutically acceptable salt thereof, is co-administered with sofosbuvir and GS-5816. In certain embodiments, a compound of the present disclosure, or a pharmaceutically acceptable salt thereof, is co-administered with sofosbuvir+GS-9857+ledipasvir. In certain embodiments, a compound of the present disclosure, or a pharmaceutically acceptable salt thereof, is co-administered with ABT-450+ABT-267+ribavirin+ritonavir. In certain embodiments, a compound of the present disclosure, or a pharmaceutically acceptable salt thereof, is co-administered with ABT-450+ABT-267+ribavirin+ABT-333+ritonavir. In certain embodiments, a compound of the present disclosure, or a pharmaceutically acceptable salt thereof, is co-administered with ABT-530+ABT-493. In certain embodiments, a compound of the present disclosure, or a pharmaceutically acceptable salt thereof, is co-administered with MK-8408+MK-3682+MK-5172. In certain embodiments, a compound of the present disclosure, or a pharmaceutically acceptable salt thereof, is co-administered with MK-8742+MK-5172. In certain embodiments, a compound of the present disclosure, or a pharmaceutically acceptable salt thereof, is co-administered with MK-3682. In certain embodiments, a compound of the present disclosure, or a pharmaceutically acceptable salt thereof, is co-administered with ACH-3422. In certain embodiments, a compound of the present disclosure, or a pharmaceutically acceptable salt thereof, is co-administered with AL-335. In certain embodiments, a compound of the present disclosure, or a pharmaceutically acceptable salt thereof, is co-administered with ACH-3422+ACH-3102. In certain embodiments, a compound of the present disclosure, or a pharmaceutically acceptable salt thereof, is co-administered with ACH-3422+sovaprevir+ACH-3102. In certain embodiments, a compound of the present disclosure, or a pharmaceutically acceptable salt thereof, is co-administered with GS-5816. In certain embodiments, a compound of the present present disclosure, or a pharmaceutically acceptable salt thereof, is co-administered with GS-9857. In certain embodiments, a compound of the present disclosure, or a pharmaceutically acceptable salt thereof, is co-administered with IDX-21459. In certain embodiments, a compound of the present disclosure, or a pharmaceutically acceptable salt thereof, is co-administered with boceprevir. In certain embodiments, a compound of the present disclosure, or a pharmaceutically acceptable salt thereof, is co-administered with ledipasvir. In certain embodiments, a compound of the present disclosure, or a pharmaceutically acceptable salt thereof, is co-administered with AL-516.

In various methods, Compound A.1 is administered in an amount ranging from about 10 mg/day to about 200 mg/day. For example, the amount of Compound A.1 can be about 30 mg/day, about 45 mg/day, about 60 mg/day, about 90 mg/day, about 120 mg/day, about 135 mg/day, about 150 mg/day, about 180 mg/day. In some methods, Compound A.1 is administered at about 90 mg/day. In various methods, Compound A.2 is administered in an amount ranging from about 50 mg/day to about 800 mg/day. For example, the amount of Compound A.2 can be about 100 mg/day, about 200 mg/day, or about 400 mg/day. In some methods, the amount of Compound A.3 is about 10 mg/day to about 200 mg/day. For example, the amount of Compound A.3 can be about 25 mg/day, about 50 mg/day, about 75 mg/day, or about 100 mg/day.

In various methods, sofosbuvir is administered in an amount ranging from about 10 mg/day to about 1000 mg/day. For example, the amount of sofosbuvir can be about 100 mg/day, about 200 mg/day, about 300 mg/day, about 400 mg/day, about 500 mg/day, about 600 mg/day, about 700 mg/day, about 800 mg/day. In some methods, sofosbuvir is administered at about 400 mg/day.

Also provided herein is a compound of the present disclosure (e.g., a compound of Formula (I)), or a pharmaceutically acceptable salt thereof, and one or more additional therapeutic agents for treating HCV, for use in a method of treating or preventing HCV.

Also provided herein is a compound of the present disclosure (e.g., a compound of Formula (I)), or a pharmaceutically acceptable salt thereof, for use in a method of treating or preventing HCV, wherein the compound or a pharmaceutically acceptable salt thereof is administered simultaneously, separately or sequentially with one or more additional therapeutic agents for treating HCV.

VIII. COMBINATION THERAPY FOR HIV

In certain embodiments, a method for treating or preventing an HIV infection in a human having or at risk of having the infection is provided, comprising administering to the human a therapeutically effective amount of a compound of the present disclosure, or a pharmaceutically acceptable salt thereof, in combination with a therapeutically effective amount of one or more (e.g., one, two, three, one or two, or one to three) additional therapeutic agents. In one embodiment, a method for treating an HIV infection in a human having or at risk of having the infection is provided, comprising administering to the human a therapeutically effective amount of a compound of the present disclosure, or a pharmaceutically acceptable salt thereof, in combination with a therapeutically effective amount of one or more (e.g., one, two, three, one or two, or one to three) additional therapeutic agents.

In certain embodiments, the present disclosure provides a method for treating an HIV infection, comprising administering to a patient in need thereof a therapeutically effective amount of a compound of the present disclosure, or a pharmaceutically acceptable salt, thereof, in combination with a therapeutically effective amount of one or more additional therapeutic agents which are suitable for treating an HIV infection. In certain embodiments, one or more additional therapeutic agents includes, for example, one, two, three, four, one or two, one to three or one to four additional therapeutic agents.

In the above embodiments, the additional therapeutic agent may be an anti-HIV agent. For example, in some embodiments, the additional therapeutic agent is selected from the group consisting of HIV protease inhibitors, HIV non-nucleoside or non-nucleotide inhibitors of reverse transcriptase, HIV nucleoside or nucleotide inhibitors of reverse transcriptase, HIV integrase inhibitors, HIV non-catalytic site (or allosteric) integrase inhibitors, HIV entry inhibitors (e.g., CCR5 inhibitors, gp41 inhibitors (i.e., fusion inhibitors) and CD4 attachment inhibitors), CXCR4 inhibitors, gp120 inhibitors, G6PD and NADH-oxidase inhibitors, HIV vaccines, HIV maturation inhibitors, latency reversing agents (e.g., histone deacetylase inhibitors, proteasome inhibitors, protein kinase C (PKC) activators, and BRD4 inhibitors), compounds that target the HIV capsid ("capsid inhibitors"; e.g., capsid polymerization inhibitors or capsid disrupting compounds, HIV nucleocapsid p7 (NCp7) inhibitors, HIV p24 capsid protein inhibitors), pharmacokinetic enhancers, immune-based therapies (e.g., Pd-1 modulators, Pd-L1 modulators, toll like receptors modulators, IL-15 agonists), HIV antibodies, bispecific antibodies and "antibody-like" therapeutic proteins (e.g., DARTs®, Duobodies®, Bites®, XmAbs®, TandAbs®, Fab derivatives) including those targeting HIV gp120 or gp41, combination drugs for HIV, HIV p17 matrix protein inhibitors, IL-13 antagonists, Peptidyl-prolyl cis-trans isomerase A modulators, Protein disulfide isomerase inhibitors, Complement $C_5a$ receptor antagonists, DNA methyltransferase inhibitor, HIV vif gene modulators, HIV-1 viral infectivity factor inhibitors, TAT protein inhibitors, HIV-1 Nef modulators, Hck tyrosine kinase modulators, mixed lineage kinase-3 (MLK-3) inhibitors, HIV-1 splicing inhibitors, Rev protein inhibitors, Integrin antagonists, Nucleoprotein inhibitors, Splicing factor modulators, COMM domain containing protein 1 modulators, HIV Ribonuclease H inhibitors, Retrocyclin modulators, CDK-9 inhibitors, Dendritic ICAM-3 grabbing nonintegrin 1 inhibitors, HIV GAG protein inhibitors, HIV POL protein inhibitors, Complement Factor H modulators, Ubiquitin ligase inhibitors, Deoxycytidine kinase inhibitors, Cyclin dependent kinase inhibitors Protein convertase PC9 stimulators, ATP dependent RNA helicase DDX3X inhibitors, reverse transcriptase priming complex inhibitors, PI3K inhibitors, compounds such as those disclosed in WO 2013/006738 (Gilead Sciences), US 2013/0165489 (University of Pennsylvania), WO 2013/091096A1 (Boehringer Ingelheim), WO 2009/062285 (Boehringer Ingelheim), US20140221380 (Japan Tobacco), US20140221378 (Japan Tobacco), WO 2010/130034 (Boehringer Ingelheim), WO 2013/159064 (Gilead Sciences), WO 2012/145728 (Gilead Sciences), WO2012/003497 (Gilead Sciences), WO2014/100323 (Gilead Sciences), WO2012/145728 (Gilead Sciences), WO2013/159064 (Gilead Sciences) and WO 2012/003498 (Gilead Sciences) and WO 2013/006792 (Pharma Resources), and other drugs for treating HIV, and combinations thereof. In some embodiments, the additional therapeutic agent is further selected from Vif dimerization antagonists and HIV gene therapy.

In certain embodiments, the additional therapeutic is selected from the group consisting of HIV protease inhibitors, HIV non-nucleoside or non-nucleotide inhibitors of reverse transcriptase, HIV nucleoside or nucleotide inhibitors of reverse transcriptase, HIV integrase inhibitors, HIV non-catalytic site (or allosteric) integrase inhibitors, pharmacokinetic enhancers, and combinations thereof.

In certain embodiments a compound of the present disclosure is formulated as a tablet, which may optionally contain one or more other compounds useful for treating HIV. In certain embodiments, the tablet can contain another active ingredient for treating HIV, such as HIV protease inhibitors, HIV non-nucleoside or non-nucleotide inhibitors of reverse transcriptase, HIV nucleoside or nucleotide inhibitors of reverse transcriptase, HIV integrase inhibitors, HIV non-catalytic site (or allosteric) integrase inhibitors, pharmacokinetic enhancers, and combinations thereof.

In certain embodiments, such tablets are suitable for once daily dosing.

In certain embodiments, the additional therapeutic agent is selected from one or more of:

(1) Combination drugs selected from the group consisting of ATRIPLA® (efavirenz+tenofovir disoproxil fumarate+emtricitabine), COMPLERA® (EVIPLERA®, rilpivirine+tenofovir disoproxil fumarate+emtricitabine), STRIBILD® (elvitegravir+cobicistat+tenofovir disoproxil fumarate+emtricitabine), dolutegravir+abacavir sulfate+lamivudine, TRIUMEQ® (dolutegravir+abacavir+lamivudine), lamivudine+nevirapine+zidovudine, dolutegravir+rilpivirine, atazanavir sulfate+cobicistat, darunavir+cobicistat, efavirenz+lamivudine+tenofovir disoproxil fumarate, tenofovir alafenamide hemifumarate+emtricitabine+cobicistat+elvitegravir, Vacc-4x+romidepsin, darunavir+tenofovir alafenamide hemifumarate+emtricitabine+cobicistat, APH-0812, raltegravir+lamivudine, KALETRA® (ALUVIA®, lopinavir+ritonavir), atazanavir sulfate+ritonavir, COMBIVIR® (zidovudine+lamivudine, AZT+3TC), EPZICOM® (Livexa®, abacavir sulfate+lamivudine, ABC+3TC), TRIZIVIR® (abacavir sulfate+zidovudine+lamivudine, ABC+AZT+3TC), TRUVADA® (tenofovir disoproxil fumarate+emtricitabine, TDF+FTC), tenofovir+lamivudine and lamivudine+tenofovir disoproxil fumarate, as well as combinations drugs selected from dolutegravir+rilpivirine hydrochloride, atazanavir+cobicistat, tenofovir alafenamide hemifumarate+emtricitabine, tenofovir alafenamide+emtricitabine, tenofovir alafenamide hemifumarate+emtricitabine+rilpivirine, tenofovir alafenamide+emtricitabine+rilpivirine, doravirine+lamivudine+tenofovir disoproxil fumarate, doravirine+lamivudine+tenofovir disoproxil;

(2) HIV protease inhibitors selected from the group consisting of amprenavir, atazanavir, fosamprenavir, fosamprenavir calcium, indinavir, indinavir sulfate, lopinavir, ritonavir, nelfinavir, nelfinavir mesylate, saquinavir, saquinavir mesylate, tipranavir, brecanavir, darunavir, DG-17, TMB-657 (PPL-100) and TMC-310911;

(3) HIV non-nucleoside or non-nucleotide inhibitors of reverse transcriptase selected from the group consisting of delavirdine, delavirdine mesylate, nevirapine, etravirine, dapivirine, doravirine, rilpivirine, efavirenz, KM-023, VM-1500, lentinan and AIC-292;

(4) HIV nucleoside or nucleotide inhibitors of reverse transcriptase selected from the group consisting of VIDEX® and VIDEX® EC (didanosine, ddl), zidovudine, emtricitabine, didanosine, stavudine, zalcitabine, lamivudine, censavudine, abacavir, abacavir sulfate, amdoxovir, elvucitabine, alovudine, phosphazid, fozivudine tidoxil, apricitabine, amdoxovir, KP-1461, fosalvudine tidoxil, tenofovir, tenofovir disoproxil, tenofovir disoproxil fumarate, tenofovir disoproxil hemifumarate, tenofovir alafenamide, tenofovir alafenamide hemifumarate, tenofovir alafenamide fumarate, adefovir, adefovir dipivoxil, and festinavir;

(5) HIV integrase inhibitors selected from the group consisting of curcumin, derivatives of curcumin, chicoric acid, derivatives of chicoric acid, 3,5-dicaffeoylquinic acid, derivatives of 3,5-dicaffeoylquinic acid, aurintricarboxylic acid, derivatives of aurintricarboxylic acid, caffeic acid phenethyl ester, derivatives of caffeic acid phenethyl ester, tyrphostin, derivatives of tyrphostin, quercetin, derivatives of quercetin, raltegravir, elvitegravir, dolutegravir and cabotegravir, as well as HIV integrase inhibitors selected from JTK-351;

(6) HIV non-catalytic site, or allosteric, integrase inhibitors (NCINI) selected from the group consisting of CX-05168, CX-05045 and CX-14442;

(7) HIV gp41 inhibitors selected from the group consisting of enfuvirtide, sifuvirtide and albuvirtide;

(8) HIV entry inhibitors selected from the group consisting of cenicriviroc;

(9) HIV gp120 inhibitors selected from the group consisting of Radha-108 (Receptol) and BMS-663068;

(10) CCR5 inhibitors selected from the group consisting of aplaviroc, vicriviroc, maraviroc, cenicriviroc, PRO-140, Adaptavir (RAP-101), TBR-220 (TAK-220), nifeviroc (TD-0232), TD-0680, and vMIP (Haimipu);

(11) CD4 attachment inhibitors selected from the group consisting of ibalizumab;

(12) CXCR4 inhibitors selected from the group consisting of plerixafor, ALT-1188, vMIP and Haimipu;

(13) Pharmacokinetic enhancers selected from the group consisting of cobicistat and ritonavir;

(14) Immune-based therapies selected from the group consisting of dermaVir, interleukin-7, plaquenil (hydroxychloroquine), proleukin (aldesleukin, IL-2), interferon alfa, interferon alfa-2b, interferon alfa-n3, pegylated interferon alfa, interferon gamma, hydroxyurea, mycophenolate mofetil (MPA) and its ester derivative mycophenolate mofetil (MMF), WF-10, ribavirin, IL-2, IL-12, polymer polyethyleneimine (PEI), Gepon, VGV-1, MOR-22, BMS-936559, toll-like receptors modulators (TLR1, TLR2, TLR3, TLR4, TLR5, TLR6, TLR7, TLR8, TLR9, TLR10, TLR11, TLR12 and TLR13), rintatolimod and IR-103;

(15) HIV vaccines selected from the group consisting of peptide vaccines, recombinant subunit protein vaccines, live vector vaccines, DNA vaccines, virus-like particle vaccines (pseudovirion vaccine), CD4-derived peptide vaccines, vaccine combinations, rgp120 (AIDSVAX), ALVAC HIV (vCP1521)/AIDSVAX B/E (gp120) (RV144), Remune, ITV-1, Contre Vir, Ad5-ENVA-48, DCVax-001 (CDX-2401), PEP-6409, Vacc-4x, Vacc-05, VAC-3S, multiclade DNA recombinant adenovirus-5 (rAd5), Pennvax-G, VRC-HIV MAB060-00-AB, AVX-101, Tat Oyi vaccine, AVX-201, HIV-LAMP-vax, Ad35, Ad35-GRIN, NAcGM3/VSSP ISA-51, poly-ICLC adjuvanted vaccines, TatImmune, GTU-multiHIV (FIT-06), AGS-004, gp140[delta]V2.TV1+MF-59, rVSVIN HIV-1 gag vaccine, SeV-Gag vaccine, AT-20, DNK-4, Ad35-GRIN/ENV, TBC-M4, HIVAX, HIVAX-2, NYVAC-HIV-PT1, NYVAC-HIV-PT4, DNA-HIV-PT123, Vichrepol, rAAV1-PG9DP, GOVX-B11, GOVX-B21, ThV-01, TUTI-16, VGX-3300, TVI-HIV-1, Ad-4 (Ad4-env Clade C+Ad4-mGag), EN41-UGR7C, EN41-FPA2, PreVaxTat, TL-01, SAV-001, AE-H, MYM-V101, CombiHIVvac, ADVAX, MYM-V201, MVA-CMDR, ETV-01 and DNA-Ad5 gag/pol/nef/nev (HVTN505), as well as HIV vaccines selected from monomeric gp120 HIV-1 subtype C vaccine (Novartis), HIV-TriMix-mRNA, MVATG-17401, ETV-01, CDX-1401, and rcAd26.MOS1.HIV-Env;

(16) HIV antibodies, bispecific antibodies and "antibody-like" therapeutic proteins (such as DARTs®, Duobodies®, Bites®, XmAbs®, TandAbs®, Fab derivatives) including BMS-936559, TMB-360 and those targeting HIV gp120 or gp41 selected from the group consisting of bavituximab, UB-421, C$_2$F5, C2G12, C4E10, C2F5+C2G12+C4E10, 3-BNC-117, PGT145, PGT121, MDX010 (ipilimumab), VRC01, A32, 7B2, 10E8 and VRC07, as well as HIV antibodies such as VRC-07-523;

(17) latency reversing agents selected from the group consisting of Histone deacetylase inhibitors such as Romidepsin, vorinostat, panobinostat; Proteasome inhibitors such as Velcade; protein kinase C (PKC) activators such as Indolactam, Prostratin, Ingenol B and DAG-lactones, Ionomycin, GSK-343, PMA, SAHA, BRD4 inhibitors, IL-15, JQ1, disulfram, and amphotericin B;

(18) HIV nucleocapsid p7 (NCp7) inhibitors selected from the group consisting of azodicarbonamide;

(19) HIV maturation inhibitors selected from the group consisting of BMS-955176 and GSK-2838232;

(20) PI3K inhibitors selected from the group consisting of idelalisib, AZD-8186, buparlisib, CLR-457, pictilisib, neratinib, rigosertib, rigosertib sodium, EN-3342, TGR-1202, alpelisib, duvelisib, UCB-5857, taselisib, XL-765, gedatolisib, VS-5584, copanlisib, CAI orotate, perifosine, RG-7666, GSK-2636771, DS-7423, panulisib, GSK-2269557, GSK-2126458, CUDC-907, PQR-309, INCB-040093, pilaralisib, BAY-1082439, puquitinib mesylate, SAR-245409, AMG-319, RP-6530, ZSTK-474, MLN-1117, SF-1126, RV-1729, sonolisib, LY-3023414, SAR-260301 and CLR-1401;

(21) the compounds disclosed in WO 2004/096286 (Gilead Sciences), WO 2006/110157 (Gilead Sciences), WO 2006/015261 (Gilead Sciences), WO 2013/006738 (Gilead Sciences), US 2013/0165489 (University of Pennsylvania), US20140221380 (Japan Tobacco), US20140221378 (Japan Tobacco), WO 2013/006792 (Pharma Resources), WO 2009/062285 (Boehringer Ingelheim), WO 2010/130034 (Boehringer Ingelheim), WO 2013/091096A1 (Boehringer Ingelheim), WO 2013/159064 (Gilead Sciences), WO 2012/145728 (Gilead Sciences), WO2012/003497 (Gilead Sciences), WO2014/100323 (Gilead Sciences), WO2012/145728 (Gilead Sciences), WO2013/159064 (Gilead Sciences) and WO 2012/003498 (Gilead Sciences); and

(22) other drugs for treating HIV selected from the group consisting of BanLec, MK-8507, AG-1105, TR-452, MK-8591, REP 9, CYT-107, alisporivir, NOV-205, IND-02, metenkefalin, PGN-007, Acemannan, Gamimune, Prolastin, 1,5-dicaffeoylquinic acid, BIT-225, RPI-MN, VSSP, Hlviral, IMO-3100, SB-728-T, RPI-MN, VIR-576, HGTV-43, MK-1376, rHIV7-shl-TAR-CCR5RZ, MazF gene therapy, BlockAide, ABX-464, SCY-635, naltrexone and PA-1050040 (PA-040); and other drugs for treating HIV selected from AAV-eCD4-Ig gene therapy, TEV-90110, TEV-90112, TEV-90111, TEV-90113, deferiprone, and HS-10234.

In certain embodiments, the additional therapeutic agent is a compound disclosed in US 2014-0221356 (Gilead Sciences, Inc.) for example (2R,5S,13aR)—N-(2,4-difluorobenzyl)-8-hydroxy-7,9-dioxo-2,3,4,5,7,9,13,13a-octahydro-2,5-methanopyrido[1',2':4,5]pyrazino[2,1-b][1,3]oxazepine-10-carboxamide, (2S,5R,13aS)—N-(2,4-difluorobenzyl)-8-hydroxy-7,9-dioxo-2,3,4,5,7,9,13,13a-octahydro-2,5-methanopyrido[1',2':4,5]pyrazino[2,1-b][1,3]oxazepine-10-carboxamide, (1 S,4R,12aR)—N-(2,4-difluorobenzyl)-7-hydroxy-6,8-dioxo-1,2,3,4,6,8,12,12a-octahydro-1,4-methanodipyrido[1,2-a:1',2'-d]pyrazine-9-carboxamide, (1R,4S,12aR)-7-hydroxy-6,8-dioxo-N-(2,4,6-trifluorobenzyl)-1,2,3,4,6,8,12,12a-octahydro-1,4-methanodipyrido[1,2-a:1',2'-d]pyrazine-9-carboxamide, (2R,5S,13aR)-8-hydroxy-7,9-dioxo-N-(2,4,6-trifluorobenzyl)-2,3,4,5,7,9,13,13a-octahydro-2,5-methanopyrido[1',2':4,5]pyrazino[2,1-b][1,3]oxazepine-10-carboxamide, and (1R,4S,12aR)—N-(2,4-difluorobenzyl)-7-hydroxy-6,8-dioxo-1,2,3,4,6,8,12,12a-octahydro-1,4-methanodipyrido[1,2-a:1',2'-d]pyrazine-9-carboxamide, US2015-0018298 (Gilead Sciences, Inc.) and US2015-0018359 (Gilead Sciences, Inc.), In certain embodiments, a compound of the present disclosure, or a pharmaceutically acceptable salt thereof, is combined with one, two, three, four or more additional therapeutic agents. In certain embodiments, a compound of the present disclosure, or a pharmaceutically acceptable salt thereof, is combined with two additional therapeutic agents. In other embodiments, a compound of the present disclosure, or a pharmaceutically acceptable salt thereof, is combined with three additional therapeutic agents. In further embodiments, a compound of the present disclosure, or a pharmaceutically acceptable salt thereof, is combined with four additional therapeutic agents. The one, two, three, four or more additional therapeutic agents can be different therapeutic agents selected from the same class of therapeutic agents, and/or they can be selected from different classes of therapeutic agents.

In a specific embodiment, a compound of the present disclosure, or a pharmaceutically acceptable salt thereof, is combined with an HIV nucleoside or nucleotide inhibitor of reverse transcriptase and an HIV non-nucleoside inhibitor of reverse transcriptase. In another specific embodiment, a compound of the present disclosure, or a pharmaceutically acceptable salt thereof, is combined with an HIV nucleoside or nucleotide inhibitor of reverse transcriptase, and an HIV protease inhibiting compound. In a further embodiment, a compound of the present disclosure, or a pharmaceutically acceptable salt thereof, is combined with an HIV nucleoside or nucleotide inhibitor of reverse transcriptase, an HIV non-nucleoside inhibitor of reverse transcriptase, and an HIV protease inhibiting compound. In an additional embodiment, a compound of the present disclosure, or a pharmaceutically acceptable salt thereof, is combined with an HIV nucleoside or nucleotide inhibitor of reverse transcriptase, an HIV non-nucleoside inhibitor of reverse transcriptase, and a pharmacokinetic enhancer. In certain embodiments, a compound of the present disclosure, or a pharmaceutically acceptable salt thereof, is combined with one or more additional therapeutic agents selected from HIV nucleoside inhibitor of reverse transcriptase, an integrase inhibitor, and a pharmacokinetic enhancer. In another embodiment, a compound of the present disclosure, or a pharmaceutically acceptable salt thereof, is combined with two HIV nucleoside or nucleotide inhibitors of reverse transcriptase.

In a particular embodiment, a compound of the present disclosure, or a pharmaceutically acceptable salt thereof, is combined with one, two, three, four or more additional therapeutic agents selected from Triumeq® (dolutegravir+abacavir+lamivudine), dolutegravir+abacavir sulfate+lamivudine, raltegravir, Truvada® (tenofovir disoproxil fumarate+emtricitabine, TDF+FTC), maraviroc, enfuvirtide, Epzicom® (Livexa®, abacavir sulfate+lamivudine, ABC+3TC), Trizivir® (abacavir sulfate+zidovudine+lamivudine, ABC+AZT+3TC), adefovir, adefovir dipivoxil, Stribild® (elvitegravir+cobicistat+tenofovir disoproxil fumarate+emtricitabine), rilpivirine, rilpivirine hydrochloride, Complera® (Eviplera®, rilpivirine+tenofovir disoproxil fumarate+emtricitabine), Cobicistat, Atripla® (efavirenz+tenofovir disoproxil fumarate+emtricitabine), atazanavir, atazanavir sulfate, dolutegravir, elvitegravir, Aluvia® (Kaletra®, lopinavir+ritonavir), ritonavir, emtricitabine, atazanavir sulfate+ritonavir, darunavir, lamivudine, Prolastin, fosamprenavir, fosamprenavir calcium, efavirenz, Combivir® (zidovudine+lamivudine, AZT+3TC), etravirine, nelfinavir, nelfinavir mesylate, interferon, didanosine, stavudine, indinavir, indinavir sulfate, tenofovir+lamivudine, zidovudine, nevirapine, saquinavir, saquinavir mesylate, aldesleukin, zalcitabine, tipranavir, amprenavir, delavirdine, delavirdine mesylate, Radha-108 (Receptol), Hlviral, lamivudine+tenofovir disoproxil fumarate, efavirenz+lamivudine+tenofovir disoproxil fumarate, phosphazid, lamivudine+nevirapine+zidovudine, abacavir, abacavir sulfate, tenofovir, tenofovir disoproxil, tenofovir disoproxil fumarate, tenofovir alafenamide and tenofovir alafenamide hemifumarate. In certain embodiments, the one, two, three, four or more additional therapeutic agents are further selected from raltegravir+lamivudine, atazanavir sulfate+cobicistat, atazanavir+cobicistat, darunavir+cobicistat, darunavir+cobicistat, atazanavir sulfate+cobicistat, atazanavir+cobicistat.

In a particular embodiment, a compound of the present disclosure, or a pharmaceutically acceptable salt thereof, is combined with one, two, three, four or more additional therapeutic agents selected from Triumeq® (dolutegravir+abacavir+lamivudine), dolutegravir+abacavir sulfate+lamivudine, raltegravir, Truvada® (tenofovir disoproxil fumarate+emtricitabine, TDF+FTC), maraviroc, enfuvirtide, Epzicom® (Livexa®, abacavir sulfate+lamivudine, ABC+3TC), Trizivir® (abacavir sulfate+zidovudine+lamivudine, ABC+AZT+3TC), adefovir, adefovir dipivoxil, Stribild® (elvitegravir+cobicistat+tenofovir disoproxil fumarate+emtricitabine), rilpivirine, rilpivirine hydrochloride, Complera® (Eviplera®, rilpivirine+tenofovir disoproxil fumarate+emtricitabine), cobicistat, Atripla® (efavirenz+tenofovir disoproxil fumarate+emtricitabine), atazanavir, atazanavir sulfate, dolutegravir, elvitegravir, Aluvia® (Kaletra®, lopinavir+ritonavir), ritonavir, emtricitabine, atazanavir sulfate+ritonavir, darunavir, lamivudine, Prolastin, fosamprenavir, fosamprenavir calcium, efavirenz, Combivir® (zidovudine+lamivudine, AZT+3TC), etravirine, nelfinavir, nelfinavir mesylate, interferon, didanosine, stavudine, indinavir, indinavir sulfate, tenofovir+lamivudine, zidovudine, nevirapine, saquinavir, saquinavir mesylate, aldesleukin, zalcitabine, tipranavir, amprenavir, delavirdine, delavirdine mesylate, Radha-108 (Receptol), Hlviral, lamivudine+tenofovir disoproxil fumarate, efavirenz+lamivudine+tenofovir disoproxil fumarate, phosphazid, lamivudine+nevirapine+zidovudine, (2R,5S,13aR)—N-(2,4-difluorobenzyl)-8-hydroxy-7,9-dioxo-2,3,4,5,7,9,13,13a-octahydro-2,5-methanopyrido[1',2':4,5]pyrazino[2,1-b][1,3]oxazepine-10-carboxamide, (2S,5R,13aS)—N-(2,4-difluorobenzyl)-8-hydroxy-7,9-dioxo-2,3,4,5,7,9,13,13a-octahydro-2,5-methanopyrido[1',2':4,5]pyrazino[2,1-b][1,3]oxazepine-10-carboxamide, (1S,4R,12aR)—N-(2,4-difluorobenzyl)-7-hydroxy-6,8-dioxo-1,2,3,4,6,8,12,12a-octahydro-1,4-methanodipyrido[1,2-a:1',2'-d]pyrazine-9-carboxamide, (1R,4S,12aR)-7-hydroxy-6,8-dioxo-N-(2,4,6-trifluorobenzyl)-1,2,3,4,6,8,12,12a-octahydro-1,4-methanodipyrido[1,2-a:1',2'-d]pyrazine-9-carboxamide, (2R,5S,13aR)-8-hydroxy-7,9-dioxo-N-(2,4,6-trifluorobenzyl)-2,3,4,5,7,9,13,13a-octahydro-2,5-methanopyrido[1',2':4,5]pyrazino[2,1-b][1,3]oxazepine-10-carboxamide, and (1R,4S,12aR)—N-(2,4-difluorobenzyl)-7-hydroxy-6,8-dioxo-1,2,3,4,6,8,12,12a-octahydro-1,4-methanodipyrido[1,2-a:1',2'-d]pyrazine-9-carboxamide abacavir, abacavir sulfate, tenofovir, tenofovir disoproxil, tenofovir disoproxil fumarate, tenofovir alafenamide and tenofovir alafenamide hemifumarate.

In a particular embodiment, a compound of the present disclosure, or a pharmaceutically acceptable salt thereof, is combined with abacavir sulfate, tenofovir, tenofovir disoproxil, tenofovir disoproxil fumarate, tenofovir disoproxil hemifumarate, tenofovir alafenamide or tenofovir alafenamide hemifumarate.

In a particular embodiment, a compound of the present disclosure, or a pharmaceutically acceptable salt thereof, is combined with tenofovir, tenofovir disoproxil, tenofovir disoproxil fumarate, tenofovir alafenamide, or tenofovir alafenamide hemifumarate.

In a particular embodiment, a compound of the present disclosure, or a pharmaceutically acceptable salt thereof, is combined with a first additional therapeutic agent selected from the group consisting of: abacavir sulfate, tenofovir, tenofovir disoproxil, tenofovir disoproxil fumarate, tenofovir alafenamide, and tenofovir alafenamide hemifumarate and a second additional therapeutic agent selected from the group consisting of emtricitabine and lamivudine.

In a particular embodiment, a compound of the present disclosure, or a pharmaceutically acceptable salt thereof, is combined with a first additional therapeutic agent selected from the group consisting of: tenofovir, tenofovir disoproxil, tenofovir disoproxil fumarate, tenofovir alafenamide, and tenofovir alafenamide hemifumarate and a second additional therapeutic agent, wherein the second additional therapeutic agent is emtricitabine.

In certain embodiments, a compound of the present disclosure, or a pharmaceutically acceptable salt thereof, is combined with 5-30 mg tenofovir alafenamide fumarate, tenofovir alafenamide hemifumarate, or tenofovir alafenamide and 200 mg emtricitabine. In certain embodiments, a compound of the present disclosure, or a pharmaceutically acceptable salt thereof, is combined with 5-10; 5-15; 5-20; 5-25; 25-30; 20-30; 15-30; or 10-30 mg tenofovir alafenamide fumarate, tenofovir alafenamide hemifumarate, or tenofovir alafenamide and 200 mg emtricitabine. In certain embodiments, a compound of the present disclosure, or a pharmaceutically acceptable salt thereof, is combined with 10 mg tenofovir alafenamide fumarate, tenofovir alafenamide hemifumarate, or tenofovir alafenamide and 200 mg emtricitabine. In certain embodiments, a compound of the present disclosure, or a pharmaceutically acceptable salt thereof, is combined with 25 mg tenofovir alafenamide fumarate, tenofovir alafenamide hemifumarate, or tenofovir alafenamide and 200 mg emtricitabine. A compound of the present disclosure (e.g., a compound of formula (I)) may be combined with the agents provided herein in any dosage amount of the compound (e.g., from 1 mg to 500 mg of compound) the same as if each combination of dosages were specifically and individually listed.

In certain embodiments, a compound of the present disclosure, or a pharmaceutically acceptable salt thereof, is combined with 200-400 mg tenofovir disoproxil fumarate, tenofovir disoproxil hemifumarate, or tenofovir disoproxil and 200 mg emtricitabine. In certain embodiments, a compound of the present disclosure, or a pharmaceutically acceptable salt thereof, is combined with 200-250; 200-300; 200-350; 250-350; 250-400; 350-400; 300-400; or 250-400 mg tenofovir disoproxil fumarate, tenofovir disoproxil hemifumarate, or tenofovir disoproxil and 200 mg emtricitabine. In certain embodiments, a compound of the present disclosure, or a pharmaceutically acceptable salt thereof, is combined with 300 mg tenofovir disoproxil fumarate, tenofovir disoproxil hemifumarate, or tenofovir disoproxil and 200 mg emtricitabine. A compound of the present disclosure (e.g., a compound of formula (I)) may be combined with the agents provided herein in any dosage amount of the compound (e.g., from 50 mg to 500 mg of compound) the same as if each combination of dosages were specifically and individually listed. A compound of the present disclosure (e.g., a compound of Formula (I)) may be combined with the agents provided herein in any dosage amount of the compound (e.g. from about 1 mg to about 150 mg of compound) the same as if each combination of dosages were specifically and individually listed.

In certain embodiments a compound of the present disclosure, or a pharmaceutically acceptable salt thereof, is combined with (2R,5S,13aR)—N-(2,4-difluorobenzyl)-8-hydroxy-7,9-dioxo-2,3,4,5,7,9,13,13a-octahydro-2,5-methanopyrido[1',2':4,5]pyrazino[2,1-b][1,3]oxazepine-10-carboxamide, (2S,5R,13aS)—N-(2,4-difluorobenzyl)-8-hydroxy-7,9-dioxo-2,3,4,5,7,9,13,13a-octahydro-2,5-methanopyrido[1',2':4,5]pyrazino[2,1-b][1,3]oxazepine-10-carboxamide, (1S,4R,12aR)—N-(2,4-difluorobenzyl)-7-hydroxy-6,8-dioxo-1,2,3,4,6,8,12,12a-octahydro-1,4-methanodipyrido[1,2-a:1',2'-d]pyrazine-9-carboxamide, (1R,4S,12aR)-7-hydroxy-6,8-dioxo-N-(2,4,6-trifluorobenzyl)-1,2,3,4,6,8,12,12a-octahydro-1,4-methanodipyrido[1,2-a:1',2'-d]pyrazine-9-carboxamide, (2R,5S,13aR)-8-hydroxy-7,9-dioxo-N-(2,4,6-trifluorobenzyl)-2,3,4,5,7,9,13,13a-octahydro-2,5-methanopyrido[1',2':4,5]pyrazino[2,1-b][1,3]oxazepine-10-carboxamide, or (1R,4S,12aR)—N-(2,4-difluorobenzyl)-7-hydroxy-6,8-dioxo-1,2,3,4,6,8,12,12a-octahydro-1,4-methanodipyrido[1,2-a:1',2'-d]pyrazine-9-carboxamide.

Also provided herein is a compound the present disclosure (e.g., a compound of Formula (I)), or a pharmaceutically acceptable salt thereof, and one or more additional therapeutic agents for treating HIV, for use in a method of treating or preventing HIV.

Also provided herein is a compound of the present disclosure (e.g., a compound of Formula (I)), or a pharmaceutically acceptable salt thereof, for use in a method of treating or preventing HIV, wherein the compound or a pharmaceutically acceptable salt thereof is administered simultaneously, separately or sequentially with one or more additional therapeutic agents for treating HIV.

In certain embodiments, a method for treating hyperproliferative disorders such as cancer in a human is provided, comprising administering to the human a therapeutically effective amount of a compound of the present disclosure, or a pharmaceutically acceptable salt thereof, in combination with a therapeutically effective amount of one or more (e.g., one, two, three, one or two, or one to three) additional therapeutic agents. In one embodiment, a method for treating hyperproliferative disorders such as cancer in a human is provided, comprising administering to the human a therapeutically effective amount of a compound of the present disclosure, or a pharmaceutically acceptable salt thereof, in combination with a therapeutically effective amount of one or more (e.g., one, two, three, one or two, or one to three) additional therapeutic agents.

IX. COMBINATION THERAPY FOR CANCER

In certain embodiments, the present disclosure provides a method for treating hyperproliferative disorders such as cancer, comprising administering to a patient in need thereof a therapeutically effective amount of a compound of the present disclosure, or a pharmaceutically acceptable salt, thereof, in combination with a therapeutically effective amount of one or more additional therapeutic agents which are suitable for treating hyperproliferative disorders such as cancer.

In the above embodiments, the additional therapeutic agent may be an anti-cancer agent. For example, in some embodiments, the additional therapeutic agent is selected from the group consisting of chemotherapeutic agents, immunotherapeutic agents, radiotherapeutic agents, antineoplastic agents, anti-hormonal agents, anti-angiogenic agents, anti-fibrotic agents, therapeutic antibodies, tyrosine kinase inhibitors, JAK inhibitors, Hedgehog inhibitors, HDAC inhibitors, Discoidin domain receptor (DDR) inhibitors, MMP9 inhibitors, LOXL inhibitors, ASK1 inhibitors, PI3K inhibitors, BTK inhibitors, SYK inhibitors, mTOR inhibitors, AKT inhibitors, Mitogen or Extracellular Regulated Kinase (MEK) inhibitors, blockers of Raf kinases (rafk), CDK inhibitors, JNK inhibitors, MAPK inhibitors, Raf inhibitors, ROCK inhibitors, Tie2 inhibitors, Myo-inositol signaling inhibitors, phospholipase C blockers, anti-CD19 antibodies, anti-CD20 antibodies, anti-MN-14 antibodies, Anti-TRAIL DR4 and DR5 antibodies, anti-CD74 antibodies, cancer vaccines based upon the genetic makeup of an individual patient's tumor, IDH1 inhibitors, BRD4 inhibitors, TPL2 inhibitors; A2B inhibitors; TBK1 inhibitors; IKK inhibitors; BCR inhibitors, agents inhibiting the RAS/RAF/ERK pathway, protein kinase C (PKC) modulators, modulators of growth factor receptors such as epidermal growth factor receptor (EGFr), platelet derived growth factor receptor (PDGFr), erbB2, erbB4, ret, vascular endothelial growth factor receptor (VEGFr), tyrosine kinase with immunoglobulin-like and epidermal growth factor homology domains (TIE-2), insulin growth factor-I (IGFI) receptor, macrophage colony stimulating factor (cfms), BTK, ckit, cmet, fibroblast growth factor (FGF) receptors, Trk receptors (TrkA, TrkB, and TrkC), ephrin (eph) receptors, and the RET protooncogene, modulators of tyrosine kinases including cSrc, Lck, Fyn, Yes, cAbl, FAK (Focal adhesion kinase) and Bcr-Abl, modulators of PKB family kinases, modulators of TGF beta receptor kinases, inhibitors of Ras oncogene including inhibitors of farnesyltransferase, geranyl-geranyl transferase, and CAAX proteases, antisense oligonucleotides, ribozymes, Bcl-2 family protein inhibitors, proteasome inhibitors, Heat shock protein HSP90 inhibitors, combination drugs and immunotherapy, and other drugs for treating hyperproliferative disorders such as cancer, and combinations thereof.

In certain embodiments a compound of the present disclosure is formulated as a tablet, which may optionally contain one or more other compounds useful for treating cancer. In certain embodiments, the tablet can contain another active ingredient for treating cancer, such as chemotherapeutic agents, immunotherapeutic agents, radiotherapeutic agents, anti-neoplastic agents, anti-fibrotic agents, anti-hormonal agents, anti-angiogenic agents, Tyrosine kinase inhibitors, JAK inhibitors, Hedgehog inhibitors, HDAC inhibitors, Discoidin domain receptor (DDR) inhibitors, MMP9 inhibitors, LOXL inhibitors, ASK1 inhibitors, PI3K inhibitors, BTK inhibitors, SYK inhibitors, mTOR inhibitors, AKT inhibitors, Mitogen or Extracellular Regulated Kinase (MEK) inhibitors, blockers of Raf kinases (rafk), CDK inhibitors, JNK inhibitors, MAPK inhibitors, Raf inhibitors, ROCK inhibitors, Tie2 inhibitors, Myoinositol signaling inhibitors, phospholipase C blockers, IDH1 inhibitors, BRD4 inhibitors, TPL2 inhibitors; A2B inhibitors; TBK1 inhibitors; IKK inhibitors; BCR inhibitors, agents inhibiting the RAS/RAF/ERK pathway, protein kinase C (PKC) modulators, modulators of growth factor receptors such as epidermal growth factor receptor (EGFr), platelet derived growth factor receptor (PDGFr), erbB2, erbB4, ret, vascular endothelial growth factor receptor (VEGFr), tyrosine kinase with immunoglobulin-like and epidermal growth factor homology domains (TIE-2), insulin growth factor-I (IGFI) receptor, macrophage colony stimulating factor (cfms), BTK, ckit, cmet, fibroblast growth factor (FGF) receptors, Trk receptors (TrkA, TrkB, and TrkC), ephrin (eph) receptors, and the RET protooncogene, modulators of tyrosine kinases including cSrc, Lck, Fyn, Yes, cAbl, FAK (Focal adhesion kinase) and Bcr-Abl, modulators of PKB family kinases, modulators of TGF beta receptor kinases, inhibitors of Ras oncogene including inhibitors of farnesyltransferase, geranyl-geranyl transferase, and CAAX proteases, anti-sense oligonucleotides, ribozymes, Bcl-2 family protein inhibitors, proteasome inhibitors, Heat shock protein HSP90 inhibitors, combination drugs and immunotherapy, and other drugs for treating hyperproliferative disorders such as cancer, and combinations thereof.

In certain embodiments, such tablets are suitable for once daily dosing. In certain embodiments, the additional therapeutic agent is selected from one or more of:

(1) Chemotherapeutic agents selected from the group consisting of: anti-metabolites/anti-cancer agents, such as pyrimidine analogs (floxuridine, capecitabine, and cytarabine); purine analogs, folate antagonists and related inhibitors, antiproliferative/antimitotic agents including natural products such as *vinca* alkaloid (vinblastine, vincristine) and microtubule such as taxane (paclitaxel, docetaxel), vinblastin, nocodazole, epothilones and navelbine, epidipodophyllotoxins (etoposide, teniposide); DNA damaging agents (actinomycin, amsacrine, busulfan, carboplatin, chlorambucil, cisplatin, cyclophosphamide, Cytoxan, dactinomycin, daunorubicin, doxorubicin, epirubicin, iphosphamide, melphalan, merchlorehtamine, mitomycin, mitoxantrone, nitrosourea, procarbazine, taxol, taxotere, teniposide, etoposide, triethylenethiophosphoramide); antibiotics such as dactinomycin (actinomycin D), daunorubicin, doxorubicin (adriamycin), idarubicin, anthracyclines, mitoxantrone, bleomycins, plicamycin (mithramycin) and mitomycin; enzymes (L-asparaginase which systemically metabolizes L-asparagine and deprives cells which do not have the capacity to synthesize their own asparagine); antiplatelet agents; antiproliferative/antimitotic alkylating agents such as nitrogen mustards cyclophosphamide and analogs, melphalan, chlorambucil), and (hexamethylmelamine and thiotepa), alkyl nitrosoureas (BCNU) and analogs, streptozocin, trazenes-dacarbazinine (DTIC); antiproliferative/antimitotic antimetabolites such as folic acid analogs (methotrexate); platinum coordination complexes (cisplatin, oxiloplatinim, carboplatin), procarbazine, hydroxyurea, mitotane, aminoglutethimide; hormones, hormone analogs (estrogen, tamoxifen, goserelin, bicalutamide, nilutamide) and aromatase inhibitors (letrozole, anastrozole); anticoagulants (heparin, synthetic heparin salts and other inhibitors of thrombin); fibrinolytic agents (such as tissue plasminogen activator, streptokinase and urokinase), aspirin, dipyridamole, ticlopidine, clopidogrel; antimigratory agents; antisecretory agents (breveldin); immunosuppressives tacrolimus, sirolimus azathioprine, mycophenolate; compounds (TNP-470, genistein) and growth factor inhibitors (vascular endothelial growth factor inhibitors, fibroblast growth factor inhibitors); angiotensin receptor blocker, nitric oxide donors; anti-sense oligonucleotides; cell cycle inhibitors and differentiation inducers (tretinoin); inhibitors, topoisomerase inhibitors (doxorubicin (adriamycin), daunorubicin, dactinomycin, eniposide, epirubicin, idarubicin, irinotecan and mitoxantrone, topotecan, irinotecan), corticosteroids (cortisone, dexamethasone, hydrocortisone, methylpednisolone, prednisone, and prednisolone); growth factor signal transduction kinase inhibitors; dysfunction inducers, toxins such as Cholera toxin, ricin, *Pseudomonas* exotoxin, *Bordetella pertussis* adenylate cyclase toxin, or diphtheria toxin, and caspase activators, chromatin, alkylating agents such as thiotepa and cyclophosphamide (Cytoxan, Endoxan, Endoxana, Cyclostin), alkyl sulfonates such as busulfan, improsulfan and piposulfan; aziridines such as benzodopa, carboquone, meturedopa, and uredopa; emylerumines and memylamelamines including alfretamine, triemylenemelamine, triethylenephosphoramide, triethylenethiophosphoramide and trimemylolomelamine; acetogenins (especially bullatacin and bullatacinone); a camptothecin (including synthetic analogue topotecan); bryostatin; callystatin; CC-1065 (including its adozelesin, carzelesin and bizelesin synthetic analogues); cryptophycins (articularly cryptophycin 1 and cryptophycin 8); dolastatin; duocarmycin (including the synthetic analogues, KW-2189 and CBI-TMI); eleutherobin; pancratistatin; a sarcodictyin; spongistatin; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosoureas such as carmustine, chlorozotocin, foremustine, lomustine, nimustine, ranimustine; antibiotics such as the enediyne antibiotics (e.g., calicheamicin, especially calicheamicin gammaII and calicheamicin phiI1, see, e.g., Agnew, Chem. Intl. Ed. Engl, 33:183-186 (1994); dynemicin, including dynemicin A; bisphosphonates, such as clodronate; an esperamicin; as well as neocarzinostatin chromophore and related chromoprotein enediyne antibiotic chromomophores), aclacinomysins, actinomycin, authramycin, azaserine, bleomycins, cactinomycin, carabicin, carrninomycin, carzinophilin, chromomycins, dactinomycin, daunorubicin, detorubicin, 6-diazo-5-oxo-L-norleucine, doxorubicin (including morpholino-doxorubicin, cyanomorpholino-doxorubicin, 2-pyrrolino-doxorubicin, PEGylated liposomal doxorubicin and deoxydoxorubicin), epirubicin, esorubicin, idarubicin, marcellomycin, mitomycins such as mitomycin C, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as demopterin, methotrexate, pteropterin, trimetrexate; purine analogs such as fludarabine, 6-mercaptopurine, thiamiprine, thioguanine; pyrimidine analogues such as ancitabine, azacitidine, 6-azauridine, carmofur, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replinisher such as frolinic acid; aceglatone; aldophosphamide glycoside; aminolevulinic acid; eniluracil; amsacrine; hestrabucil; bisantrene; edatraxate; defofamine; demecolcine; diaziquone; elformthine; ellitinium acetate; an epothilone; etoglucid; gallium nitrate; hydroxyurea; lentinan; leucovorin; lonidamine; maytansinoids such as maytansine and ansamitocins; mitoguazone; mitoxantrone; mopidamol; nitracrine; pentostatin; phenamet; pirarubicin; losoxantrone; fluoropyrimidine; folinic acid; podophyllinic acid; 2-ethylhydrazide; procarbazine; PSK(r); razoxane; rhizoxin; sizofiran; spirogermanium; tenuazonic acid; triaziquone; 2,2',2"-tricUorotriemylamine; trichothecenes (especially T-2 toxin, verracurin A, roridin A and anguidine); urethane; vindesine; dacarbazine; mannomustine; mitobronitol; mitolactol; pipobroman; gacytosine; arabinoside ("Ara-C"); cyclophosphamide; thiopeta; taxoids, paclitaxel (Taxol) and docetaxel (Taxotere); chlorambucil; gemcitabine (Gemzar); 6-thioguanine; mercaptopurine; methotrexate; platinum analogs such as cisplatin and carboplatin; platinum; ifosfamide; mitroxantrone; vancristine; vinorelbine (Navelbine); novantrone; teniposide; edatrexate; daunomycin; aminopterin; xeoloda; ibandronate; CPT-11; topoisomerase inhibitor RFS 2000; difluoromethylornithine (DMFO); retinoids such as retinoic acid; capecitabine and FOLFIRI (fluorouracil, leucovorin, and irinotecan);

(2) Anti-hormonal agents selected from the group consisting of: anti-estrogens and selective estrogen receptor modulators (SERMs), including, for example, tamoxifen (including Nolvadex), raloxifene, droloxifene, 4-hydroxytamoxifen, trioxifene, keoxifene, LY117018, onapristone, and toremifene; inhibitors of the enzyme aromatase, which regulates estrogen production in the adrenal glands, such as, for example, 4(5)-imidazoles, aminoglutethimide, megestrol acetate, exemestane, formestane, fadrozole, vorozole, letrozole and anastrozole, and anti-androgens such as flutamide, nilutamide, bicalutamide, leuprolide, and goserelin;

(3) Anti-angiogenic agents selected from the group consisting of: retinoid acid and derivatives thereof, 2-methoxyestradiol, ANGIOSTATIN, ENDOSTATIN, suramin, squalamine, tissue inhibitors of metalloproteinase-1, tissue inhibitors of metalloproteinase-2, plasminogen activator inhibitor-1, plasminogen activator inbibitor-2, cartilage-derived inhibitors, paclitaxel (nab-paclitaxel), platelet factor 4, protamine sulphate (clupeine), sulphated chitin derivatives (prepared from queen crab shells), sulphated polysaccharide peptidoglycan complex (sp-pg), staurosporine, modulators of matrix metabolism, including for example, proline analogs ((1-azetidine-2-carboxylic acid (LACA), cishydroxyproline, d,I-3,4-dehydroproline, thiaproline, .alpha.-dipyridyl, beta-aminopropionitrile fumarate, 4-propyl-5-(4-pyridinyl)-2(3h)-oxazolone; methotrexate, mitoxantrone, heparin, interferons, 2 macroglobulin-serum, chimp-3, chymostatin, beta-cyclodextrin tetradecasulfate, eponemycin; fumagillin, gold sodium thiomalate, d-penicillamine (CDPT), beta-1-anticollagenase-serum, alpba-2-antiplasmin, bisantrene, lobenzarit disodium, n-2-carboxyphenyl-4-chloroanthronilic acid disodium or "CCA", thalidomide; angiostatic steroid, cargboxynaminolmidazole; metalloproteinase inhibitors such as BB94, antibodies, preferably monoclonal antibodies against these angiogenic growth factors: beta-FGF, alpha-FGF, FGF-5, VEGF isoforms, VEGF-C, HGF/SF, Ang-1/Ang-2 and the compounds disclosed in Ferrara N. and Alitalo, K. "Clinical application of angiogenic growth factors and their inhibitors" (1999) *Nature Medicine* 5:1359-1364;

(4) Anti-fibrotic agents selected from the group consisting of: beta-aminoproprionitrile (BAPN), primary amines reacting with the carbonyl group of the active site of the lysyl oxidases, and more particularly those which produce, after binding with the carbonyl, a product stabilized by resonance, such as the following primary amines: emylenemamine, hydrazine, phenylhydrazine, and their derivatives, semicarbazide, and urea derivatives, aminonitriles, such as beta-aminopropionitrile (BAPN), or 2-nitroethylamine, unsaturated or saturated haloamines, such as 2-bromo-ethylamine, 2-chloroethylamine, 2-trifluoroethylamine, 3-bromopropylamine, p-halobenzylamines, selenohomocysteine lactone, copper chelating agents, indirect inhibitors such as compounds blocking the aldehyde derivatives originating from the oxidative deamination of the lysyl and hydroxylysyl residues by the lysyl oxidases, such as the thiolamines, in particular D-penicillamine, or its analogues such as 2-amino-5-mercapto-5-methylhexanoic acid, D-2-amino-3-methyl-3-((2-acetamidoethyl)dithio)butanoic acid, p-2-amino-3-methyl-3-((2-aminoethyl)dithio)butanoic acid, sodium-4-((p-1-dimethyl-2-amino-2-carboxyethyl)dithio)butane sulphurate, 2-acetamidoethyl-2-acetamidoethanethiol sulphanate, sodium-4-mercaptobutanesulphinate trihydrate, the compounds disclosed in U.S. Pat. Nos. 4,965,288, 4,997,854, 4,943,593, 5,021,456; 5,5059,714; 5,120,764; 5,182,297; 5,252,608 and U.S. Patent Application No. 2004/0248871;

(5) Therapeutic antibodies selected from the group consisting of: abagovomab, adecatumumab, afutuzumab, alemtuzumab, altumomab, amatuximab, anatumomab, arcitumomab, bavituximab, bectumomab, bevacizumab, bivatuzumab, blinatumomab, brentuximab, cantuzumab, catumaxomab, cetuximab, citatuzumab, cixutumumab, clivatuzumab, conatumumab, daratumumab, drozitumab, duligotumab, dusigitumab, detumomab, dacetuzumab, dalotuzumab, ecromeximab, elotuzumab, ensituximab, ertumaxomab, etaracizumab, farietuzumab, ficlatuzumab, figitumumab, flanvotumab, futuximab, ganitumab, gemtuzumab, girentuximab, glembatumumab, ibritumomab, igovomab, imgatuzumab, indatuximab, inotuzumab, intetumumab, ipilimumab, iratumumab, labetuzumab, lexatumumab, lintuzumab, lorvotuzumab, lucatumumab, mapatumumab, matuzumab, milatuzumab, minretumomab, mitumomab, moxetumomab, narnatumab, naptumomab, necitumumab, nimotuzumab, nofetumomabn, ocaratuzumab, ofatumumab, olaratumab, onartuzumab, oportuzumab, oregovomab, panitumumab, parsatuzumab, patritumab, pemtumomab, pertuzumab, pintumomab, pritumumab, racotumumab, radretumab, rilotumumab, rituximab, robatumumab, satumomab, sibrotuzumab, siltuximab, simtuzumab, solitomab, tacatuzumab, taplitumomab, tenatumomab, teprotumumab, tigatuzumab, tositumomab, trastuzumab, tucotuzumab, ublituximab, veltuzumab, vorsetuzumab, votumumab, zalutumumab, alemtuzumab, veltuzumab, apolizumab, bevacizumab, epratuzumab, tositumomab, galiximab, ibritumomab, lumiliximab, milatuzumab, obinutuzumab, ofatumumab, CC49 and 3F8, wherein the antibody may be further labeled or combined with a radioisotope particle, such as indium In 111, yttrium Y 90, iodine 1-131;

(6); JAK inhibitors selected from the group consisting of: ruxolitinib, fedratinib, tofacitinib, baricitinib, lestaurtinib, pacritinib, momelotinib, XL019, AZD1480, INCB039110, LY2784544, BMS911543, and NS018;

(7) Hedgehog inhibitors selected from the group consisting of: saridegib;

(8) Histone deacetylase (HDAC) inhibitors selected from the group consisting of: pracinostat, romidepsin, vorinostat and panobinostat;

(9) Tyrosine kinase inhibitors selected from the group consisting of: lestaurtinib, gefitinib, erlotinib and sunitinib;

(10) Discoidin domain receptor (DDR) inhibitors selected from the group consisting of: the inhibitors disclosed in US2009/0142345, US2011/0287011, WO2013/027802, WO2013/034933, and U.S. Provisional Application No. 61/705,044;

(11) MMP9 inhibitors selected from the group consisting of: marimastat (BB-2516), cipemastat (Ro 32-3555), and the inhibitors described in WO2012/027721;

(12) LOXL inhibitors selected from the group consisting of: the antibodies described in WO2009/017833, the antibodies described in WO2009/017833, WO2009/035791 and WO/2011/097513;

(13) ASK1 inhibitors selected from the group consisting of: the compounds described in WO2011/008709 and WO/2013/112741;

(14) PI3K inhibitors selected from the group consisting of: the compounds described in U.S. Pat. No. 7,932,260, U.S. Provisional Application Nos. 61/543,176; 61/581,528; 61/745,429; 61/745,437; and 61/835,333, PI3K II, TGR-1202, AMG-319, GSK2269557, X-339, X-414, RP5090, KAR4141, XL499, OXY111A, duvelisib, IPI-443, GSK2636771, BAY 10824391, TGX221, RG-7666, CUDC-907, PQR-309, DS-7423, panulisib, AZD-8186, CLR-457, pictilisib, neratinib, rigosertib, rigosertib sodium, EN-3342, UCB-5857, taselisib, INCB-040093, pilaralisib, BAY-1082439, puquitinib mesylate, XL-765, gedatolisib, VS-5584, copanlisib, CAI orotate, alpelisib, buparlisib, BAY 80-6946, BYL719, PX-866, RG7604, MLN1117, WX-037, AEZS-129, PA799, ZSTK474, RP-6530, AS252424, LY294002, TG100115, LY294002, BEZ235, XL147 (SAR245408), SAR-245409, GDC-0941, BKM120, CH5132799, XL756, MLN-1117, SF-1126, RV-1729, sonolisib, GDC-0980, CLR-1401, perifosine and wortmannin;

(15) BTK inhibitors selected from the group consisting of: ibrutinib, HM71224, ONO-4059 and CC-292;

(16) SYK inhibitors selected from the group consisting of: tamatinib (R406), fostamatinib (R788), PRT062607, BAY-61-3606, NVP-QAB 205 AA, R112, R343, and the compounds described in U.S. Pat. No. 8,450,321;

(17) mTOR inhibitors selected from the group consisting of: temsirolimus, everolimus, ridaforolimus, deforolimus, OSI-027, AZD2014, CC-223, RAD001, LY294002, BEZ235, rapamycin, Ku-0063794, and PP242;

(18) AKT inhibitors selected from the group consisting of: perifosine, MK-2206, GDC-0068 and GSK795;

(19) MEK inhibitors selected from the group consisting of: trametinib, selumetinib, cobimetinib, MEK162, PD-325901, PD-035901, AZD6244, and CI-1040;

(20) CDK inhibitors selected from the group consisting of: AT-7519, alvocidib, palbociclib and SNS-032;

(21) JNK inhibitors selected from the group consisting of: CC-401;

(22) MAPK inhibitors selected from the group consisting of: VX-702, SB203580 and SB202190;

(23) Raf inhibitors selected from the group consisting of: PLX4720;

(24) ROCK inhibitors selected from the group consisting of: Rho-15;

(25) Tie2 inhibitors selected from the group consisting of: AMG-Tie2-1;

(26) Myo-inositol signaling inhibitors such as phospholipase C blockers and Myoinositol analogues described in Powis, G., and Kozikowski A., (1994) New Molecular Targets for Cancer Chemotherapy ed., Paul Workman and David Kerr, CRC press 1994, London;

(27) Bcl-2 family protein inhibitors selected from the group consisting of: ABT-263, ABT-199 and ABT-737;

(28) IKK inhibitors selected from the group consisting of: BMS-345541;

(29) Proteasome inhibitors selected from the group consisting of: bortezomib;

(30) Protein kinase C (PKC) inhibitors selected from the group consisting of: bryostatin 1 and enzastaurin;

(31) Heat shock protein HSP90 inhibitors selected from the group consisting of: Geldanamycin;

(32) Combination drugs selected from the group consisting of: FR (fludarabine, rituximab), FCR (fludarabine, cyclophosphamide, rituximab), R-CHOP (rituximab plus CHOP), R-CVP (rituximab plus CVP), R-FCM (rituximab plus FCM), R-ICE (rituximab-ICE), CHOP (cyclophosphamide, doxorubicin, vincristine, prednisone), CVP (cyclophosphamide, vincristine and prednisone), FCM (fludarabine, cyclophosphamide, mitoxantrone), hyperCVAD (hyperfractionated cyclophosphamide, vincristine, doxorubicin, dexamethasone, methotrexate, cytarabine), ICE (iphosphamide, carboplatin and etoposide), MCP (mitoxantrone, chlorambucil, and prednisolone), and R MCP (R MCP); and

(33) other drugs for treating cancer selected from the group consisting of aldesleukin, alvocidib, CHIR-12.12, ha20, tiuxetan, PRO131921, SGN-40, WT-1 analog peptide vaccine, WT1 126-134 peptide vaccine, autologous human tumor-derived HSPPC-96, GTOP-99 (MyVax®), antineoplaston AS2-1, antineoplaston A10, anti-thymocyte globulin, beta alethine, arsenic trioxide, amifostine, aminocamptothecin, lenalidomide, caspofungin, clofarabine, ixabepilone, cladribine, chlorambucil, Curcumin, vinorelbine, tipifarnib, tanespimycin, sildenafil citrate, denileukin diftitox, simvastatin, epoetin alfa, fenretinide, filgrastim, mesna, mitoxantrone, lenalidomide, fludarabine, mycophenolate mofetil, nelarabine, octreotide, oxaliplatin, pegfilgrastim, recombinant interleukin-12, recombinant interleukin-11, recombinant flt3 ligand, recombinant human thrombopoietin, sargramostim, lymphokine-activated killer cells, omega-3 fatty acids, recombinant interferon alfa, therapeutic allogeneic lymphocytes and cyclosporine analogs.

In a particular embodiment, a compound of the present disclosure, or a pharmaceutically acceptable salt thereof, is combined with one, two, three, four or more additional therapeutic agents selected from ibrutinib, aldesleukin, alvocidib, antineoplaston AS2-1, antineoplaston A10, anti-thymocyte globulin, amifostine trihydrate, aminocamptothecin, arsenic trioxide, beta alethine, ABT-263, ABT-199, ABT-737, BMS-345541, bortezomib, bryostatin 1, busulfan, carboplatin, campath-1H, CC-5103, carmustine, caspofungin acetate, clofarabine, cisplatin, Cladribine (Leustarin), Chlorambucil (Leukeran), Curcumin, cyclosporine, Cyclophosphamide (Cyloxan, Endoxan, Endoxana, Cyclostin), denileukin diftitox, dexamethasone, DT PACE, docetaxel, dolastatin 10, Doxorubicin (Adriamycin®, Adriblastine), doxorubicin hydrochloride, enzastaurin, epoetin alfa, etoposide, everolimus (RAD001), fenretinide, filgrastim, melphalan, mesna, flavopiridol, fludarabine (Fludara), Geldanamycin (17 AAG), ifosfamide, irinotecan hydrochloride, ixabepilone, lenalidomide (Revlimid®), lymphokine-activated killer cells, melphalan, methotrexate, mitoxantrone hydrochloride, motexafin gadolinium, mycophenolate mofetil, nelarabine, oblimersen Obatoclax, oblimersen, octreotide acetate, omega-3 fatty acids, oxaliplatin, paclitaxel, PD0332991, PEGylated liposomal doxorubicin hydrochloride, pegfilgrastim, Pentstatin (Nipent), perifosine, Prednisolone, Prednisone, selicilib, recombinant interferon alfa, recombinant interleukin-12, recombinant interleukin-11, recombinant flt3 ligand, recombinant human thrombopoietin, rituximab, sargramostim, sildenafil citrate, simvastatin, sirolimus, Styryl sulphones, tacrolimus, tanespimycin, temsirolimus, thalidomide, therapeutic allogeneic lymphocytes, thiotepa, tipifarnib, Vincristine, vincristine sulfate, vinorelbine ditartrate, Vorinostat (SAHA), vorinostat, FR (fludarabine, rituximab), CHOP (cyclophosphamide, doxorubicin, vincristine, prednisone), CVP (cyclophosphamide, vincristine and prednisone), FCM (fludarabine, cyclophosphamide, mitoxantrone), FCR (fludarabine, cyclophosphamide, rituximab), hyperCVAD (hyperfractionated cyclophosphamide, vincristine, doxorubicin, dexamethasone, methotrexate, cytarabine), ICE (iphosphamide, carboplatin and etoposide), MCP (mitoxantrone, chlorambucil, and prednisolone), R-CHOP (rituximab plus CHOP), R-CVP (rituximab plus CVP), R-FCM (rituximab plus FCM), R-ICE (rituximab-ICE), and R MCP (R MCP).

Any of the methods of treatment provided may be used to treat cancer at various stages. By way of example, the cancer stage includes but is not limited to early, advanced, locally advanced, remission, refractory, reoccurred after remission and progressive.

In addition, the subject may be a human who is undergoing one or more standard therapies, such as chemotherapy, radiotherapy, immunotherapy, surgery, or combination thereof. Accordingly, one or more anti-cancer agents may be administered before, during, or after administration of chemotherapy, radiotherapy, immunotherapy, surgery or combination thereof.

The therapeutic treatments can be supplemented or combined with any of the abovementioned therapies with stem cell transplantation or treatment. One example of modified approach is radioimmunotherapy, wherein a monoclonal antibody is combined with a radioisotope particle, such as indium In 111, yttrium Y 90, iodine I-131. Examples of combination therapies include, but are not limited to, Iodine-131 tositumomab (Bexxar®), Yttrium-90 ibritumomab tiuxetan (Zevalin®), Bexxar® with CHOP.

Other therapeutic procedures include peripheral blood stem cell transplantation, autologous hematopoietic stem cell transplantation, autologous bone marrow transplantation, antibody therapy, biological therapy, enzyme inhibitor therapy, total body irradiation, infusion of stem cells, bone marrow ablation with stem cell support, in vitro-treated peripheral blood stem cell transplantation, umbilical cord blood transplantation, immunoenzyme technique, pharmacological study, low-LET cobalt-60 gamma ray therapy, bleomycin, conventional surgery, radiation therapy, and nonmyeloablative allogeneic hematopoietic stem cell transplantation.

Also provided herein is a compound of the present disclosure (e.g., a compound of Formula (I)), or a pharmaceutically acceptable salt thereof, and one or more additional therapeutic agents for treating cancer, for use in a method of treating cancer.

Also provided herein is a compound of the present disclosure (e.g., a compound of Formula (I)), or a pharmaceutically acceptable salt thereof, for use in a method of treating cancer, wherein the compound or a pharmaceutically acceptable salt thereof is administered simultaneously, separately or sequentially with one or more additional therapeutic agents for treating cancer.

X. KITS

The present disclosure provides a kit comprising a compound of the present disclosure or a pharmaceutically acceptable salt thereof. The kit may further comprise instructions for use, e.g., for use in modulating a toll-like receptor (e.g. TLR8), such as for use in treating a disease, disorder, or condition. In certain embodiments the use is for treating a HIV, HBV, or HCV infection. In certain embodiments the use is for treating a HBV infection. The instructions for use are generally written instructions, although electronic storage media (e.g., magnetic diskette or optical disk) containing instructions are also acceptable.

The present disclosure also provides a pharmaceutical kit comprising one or more containers comprising a compound of the present disclosure or a pharmaceutically acceptable salt thereof. Optionally associated with such container(s) can be a notice in the form prescribed by a governmental agency regulating the manufacture, use or sale of pharmaceuticals, which notice reflects approval by the agency for the manufacture, use or sale for human administration. Each component (if there is more than one component) can be packaged in separate containers or some components can be combined in one container where cross-reactivity and shelf life permit. The kits may be in unit dosage forms, bulk packages (e.g., multi-dose packages) or sub-unit doses. Kits may also include multiple unit doses of the compounds and instructions for use and be packaged in quantities sufficient for storage and use in pharmacies (e.g., hospital pharmacies and compounding pharmacies).

XI. COMPOUND PREPARATION

Also provided are articles of manufacture comprising a unit dosage of a compound of the present disclosure or a pharmaceutically acceptable salt thereof, in suitable packaging for use in the methods described herein. Suitable packaging is known in the art and includes, for example, vials, vessels, ampules, bottles, jars, flexible packaging and the like. An article of manufacture may further be sterilized and/or sealed.

The embodiments are also directed to processes and intermediates useful for preparing the subject compounds or pharmaceutically acceptable salts thereof.

Many general references providing commonly known chemical synthetic schemes and conditions useful for synthesizing the disclosed compounds are available (see, e.g., Smith, March's Advanced Organic Chemistry: Reactions, Mechanisms, and Structure, 7$^{th}$ edition, Wiley-Interscience, 2013.)

Compounds as described herein can be purified by any of the means known in the art, including chromatographic means, such as high performance liquid chromatography (HPLC), preparative thin layer chromatography, flash column chromatography and ion exchange chromatography. Any suitable stationary phase can be used, including normal and reversed phases as well as ionic resins. Most typically the disclosed compounds are purified via silica gel and/or alumina chromatography. See, e.g., Introduction to Modern Liquid Chromatography, 2nd ed., ed. L. R. Snyder and J. J. Kirkland, John Wiley and Sons, 1979; and Thin Layer Chromatography, E. Stahl (ed.), Springer-Verlag, New York, 1969.

During any of the processes for preparation of the subject compounds, it may be necessary and/or desirable to protect sensitive or reactive groups on any of the molecules concerned. This may be achieved by means of conventional protecting groups as described in standard works, such as T. W. Greene and P. G. M. Wuts, "Protective Groups in Organic Synthesis," 4$^{th}$ ed., Wiley, New York 2006. The protecting groups may be removed at a convenient subsequent stage using methods known from the art.

XII. EXAMPLES

Exemplary chemical entities useful in methods of the embodiments will now be described by reference to illustrative synthetic schemes for their general preparation herein and the specific examples that follow. Artisans will recognize that, to obtain the various compounds herein, starting materials may be suitably selected so that the ultimately desired substituents will be carried through the reaction scheme with or without protection as appropriate to yield the desired product. Alternatively, it may be necessary or desirable to employ, in the place of the ultimately desired substituent, a suitable group that may be carried through the reaction scheme and replaced as appropriate with the desired substituent. Furthermore, one of skill in the art will recognize that the transformations shown in the schemes below may be performed in any order that is compatible with the functionality of the particular pendant groups. Each of the reactions depicted in the general schemes is preferably run at a temperature from about 0° C. to the reflux temperature of the organic solvent used. Unless otherwise specified, the variables are as defined above in reference to Formulas (I) or (J).

Representative syntheses of compounds of the present disclosure are described in schemes below, and the particular examples that follow.

Scheme 1 shows a representative synthesis of the compounds of the embodiments. The methodology is compatible with a wide variety of functionalities.

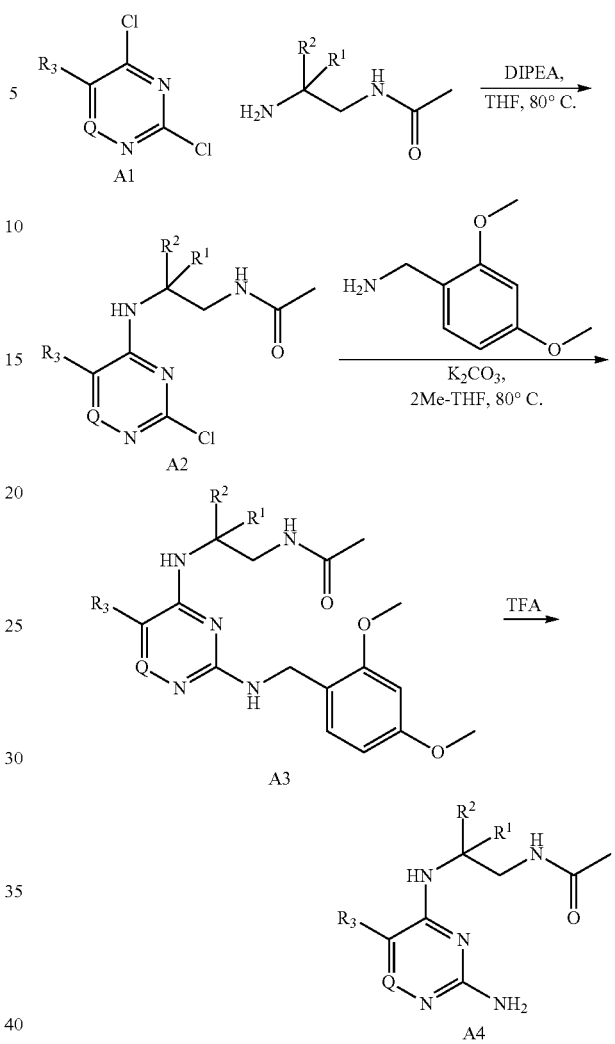

In Scheme 1, the compounds of formula A1 (where R$^3$ and Q are as defined herein or are suitably protected derivatives of R$^3$ and Q) in a suitable solvent (such as tetrahydrofuran) and (R)—N-(2-amino-2-methylhexyl)acetamide are treated with N,N-diisopropylethylamine at about 80° C. to form a compound of formula A2. The compounds of formula A2 in 2-methyl-tetrahydrofuran are treated with potassium carbonate followed by 2,4-dimethoxybenzylamine to form a compound of formula A3. The compounds of formula A3, in a solvent (such as dichloromethane) are then treated with trifluoroacetic acid to form a compound of formula A4.

Scheme 2 shows a representative synthesis of the compounds of the embodiments. The methodology is compatible with a wide variety of functionalities.

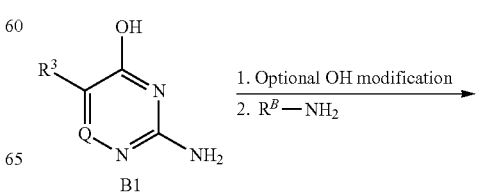

-continued

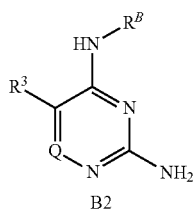

A compound of formula B1 (where Q and $R^3$ are as defined herein or are suitably protected derivatives of Q) is converted to a compound of formula B2, under suitable reaction conditions. For example, the compound of formula B1 is contacted with chloroformamidine hydrochloride under suitable conditions to provide B2. The hydroxyl group may be further modified, for example by introducing any suitable leaving group, such as a tosyl group, prior to contacting with $R^B$—$NH_2$. Further, the —OH group may be converted to a chloro group though use of a suitable reagent, such as $POCl_3$ and further contacted with $R^B$—$NH_2$. Alternatively, $R^B$—$NH_2$ may be directly coupled to B2 in the presence of a suitable coupling agent, for example, BOP reagent, under suitable conditions.

Specific embodiments of formula A1 or B1 can be found in this application herein, and additionally in references, such as WO2012/156498, WO2012/136834, WO2014/056953, WO2014/076221, WO2015/014815, WO2014/128189, WO2013/117615, and WO2014/023813. Intermediates corresponding to A1 or analogs thereof (including compounds that are outside of the variables of Formula I) may be prepared according to those references and used to prepare compounds of the present disclosure.

Except as otherwise noted, the methods and techniques of the present embodiments are generally performed according to conventional methods well known in the art and as described in various general and more specific references that are cited and discussed throughout the present specification. See, e.g., Loudon, Organic Chemistry, 5$^{th}$ edition, New York: Oxford University Press, 2009; Smith, March's Advanced Organic Chemistry: Reactions, Mechanisms, and Structure, 7$^{th}$ edition, Wiley-Interscience, 2013.

The Examples provided herein describe the synthesis of compounds disclosed herein as well as intermediates used to prepare the compounds. It is to be understood that individual steps described herein may be combined. It is also to be understood that separate batches of a compound may be combined and then carried forth in the next synthetic step.

In the following description of the Examples, specific embodiments are described. These embodiments are described in sufficient detail to enable those skilled in the art to practice certain embodiments of the present disclosure. Other embodiments may be utilized and logical and other changes may be made without departing from the scope of the disclosure. The following description is, therefore, not intended to limit the scope of the present disclosure.

The methods of the present invention generally provide a specific enantiomer or diastereomer as the desired product, although the stereochemistry of the enantiomer or diastereomer was not determined in all cases. When the stereochemistry of the specific stereocenter in the enantiomer or diastereomer is not determined, the compound is drawn without showing any stereochemistry at that specific stereocenter even though the compound can be substantially enantiomerically or disatereomerically pure.

Example 1

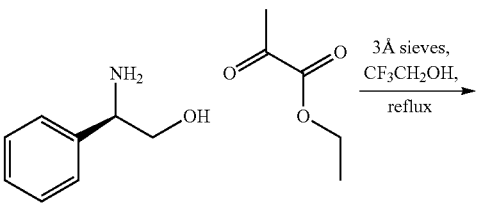

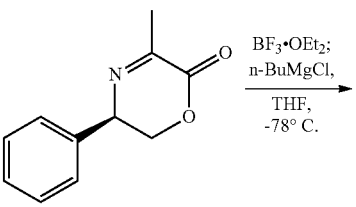

1a

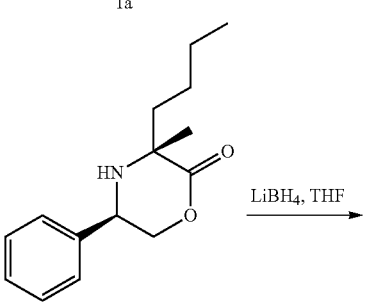

1b

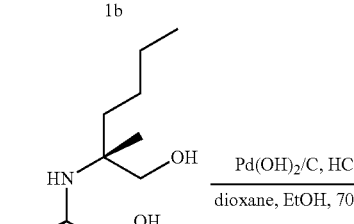

1c

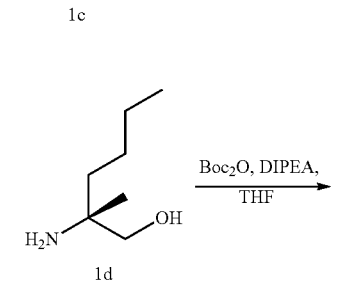

1d

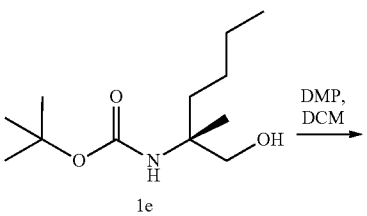

1e

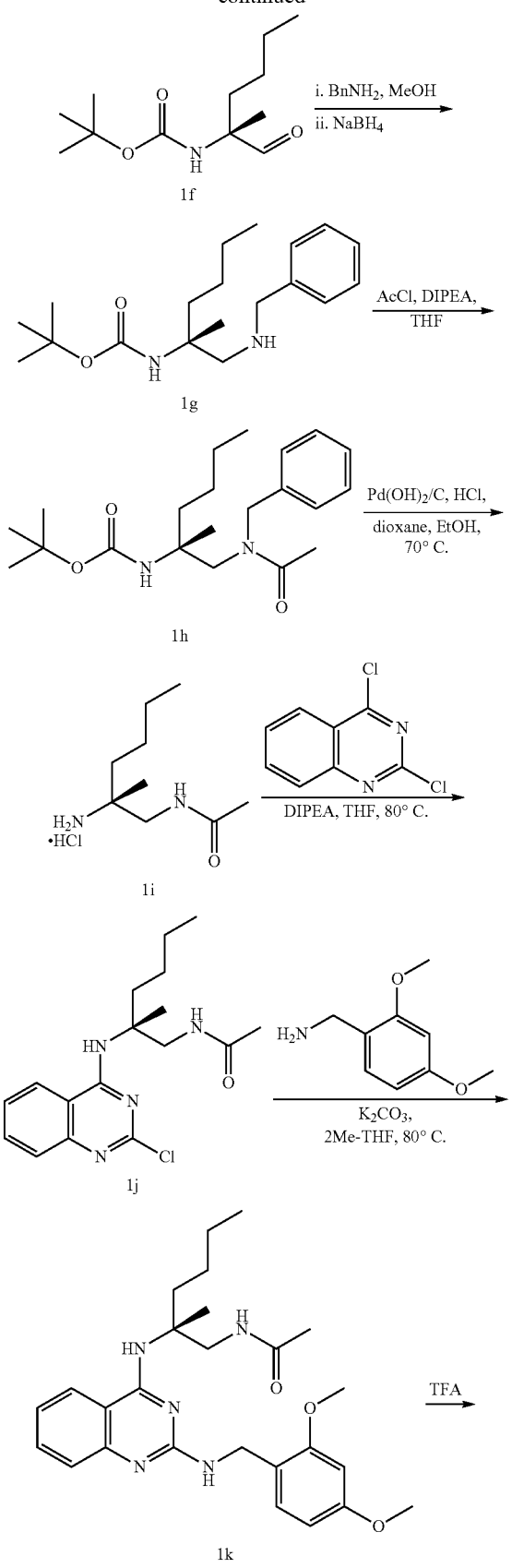

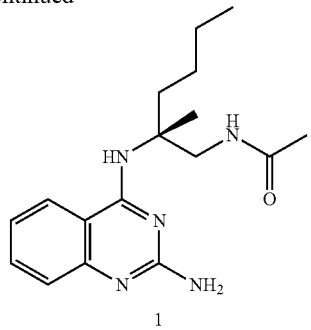

Synthesis of (R)-3-methyl-5-phenyl-5,6-dihydro-2H-1,4-oxazin-2-one (1a). To a mixture of (R)-(−)-2-phenylglycinol (23.6 g, 172 mmol, supplied by Sigma-Aldrich, 99% ee) and molecular sieves (86 g) in 2,2,2-trifluoroethanol (500 mL) was added ethyl pyruvate (19.2 mL, 172 mmol, supplied by Sigma Aldrich) and the mixture heated to reflux. After 24 h, the reaction was cooled to rt, filtered through Celite, washed with EtOAc, and concentrated in vacuo. The residue was subjected to silica gel chromatography equipped with an ELSD eluting with hexanes-EtOAc to provide 1a. LC/MS (ESI) calculated for $C_{11}H_{12}NO_2$: m/z 190.08, found 189.92 $[M+H]^+$; $t_R$=0.88 min. on LC/MS Method A. 41 NMR (400 MHz, Chloroform-d) δ 7.45-7.38 (m, 2H), 7.38-7.32 (m, 3H), 4.85 (ddd, J=10.9, 4.6, 2.4 Hz, 1H), 4.57 (dd, J=11.6, 4.5 Hz, 1H), 4.26 (dd, J=11.6, 10.9 Hz, 1H), 2.41 (d, J=2.4 Hz, 3H).

Synthesis of (3R,5R)-3-butyl-3-methyl-5-phenylmorpholin-2-one (1b). To compound 1a (14.84 g, 78.43 mmol) in THF (500 mL) at −78° C. under argon was added boron trifluoride diethyl etherate (20.5 mL, 161.11 mmol) over 30 min. After 90 min, n-butylmagnesium chloride solution (83.0 mL, 166 mmol, 2.0 M in THF) was added over 30 min. After 2 h, the reaction was warmed to rt and quenched with saturated $NH_4Cl_{(aq)}$ (300 mL). The mixture was diluted with water (200 mL) and extracted with EtOAc (300 mL×3). The organic extracts were washed with water (500 mL×3), brine (300 mL), dried over $Na_2SO_4$, and concentrated in vacuo. The residue was dissolved in DCM (150 mL), heated, and the insoluble material was removed by filtration. The filtrate was concentrated in vacuo and the residue was subjected to silica gel chromatography eluting with hexanes-EtOAc to provide compound 1b. LC/MS (ESI) calculated for $C_{15}H_{22}NO_2$: m/z 248.16, found 248.02 $[M+H]^+$; $t_R$=1.07 min. on LC/MS Method A. $^1H$ NMR (400 MHz, Chloroform-d) δ 7.51-7.28 (m, 5H), 4.44-4.31 (m, 2H), 4.27 (t, J=11.5 Hz, 1H), 2.03 (ddd, J=13.8, 11.4, 4.7 Hz, 1H), 1.74 (td, J=12.2, 11.2, 4.1 Hz, 2H), 1.46 (s, 3H), 1.43-1.20 (m, 4H), 0.99-0.85 (m, 3H).

Synthesis of (R)-2-(((R)-2-hydroxy-1-phenylethyl)amino)-2-methylhexan-1-ol (1c). To compound 1b (14.01 g, 56.64 mmol) in THF (100 mL) at 0° C. was added $LiBH_4$ solution (57 mL, 114 mmol, 2.0 M in THF) and the reaction was allowed to warm to rt. After 2 h, the mixture was cooled to 0° C. and quenched with water (500 mL). The mixture was separated and the aqueous was extracted with EtOAc (300 mL×3). The combined organics were washed with water (500 mL) and brine (100 mL), dried over $Na_2SO_4$, and concentrated under reduced pressure to provide 1c. LC/MS (ESI) calculated for $C_{15}H_{26}NO_2$: m/z 252.19, found 252.05 $[M+H]^+$; $t_R$=0.68 min. on LC/MS Method A. $^1H$ NMR (400 MHz, Chloroform-d) δ 7.33-7.22 (m, 5H), 3.85 (dd, J=9.4, 4.6 Hz, 1H), 3.60 (dd, J=10.5, 4.6 Hz, 1H), 3.43 (dd, J=10.5, 9.4 Hz, 1H), 3.37 (d, J=11.2 Hz, 1H), 3.14 (d, J=11.1 Hz, 1H), 2.31 (s, 3H), 1.37-1.23 (m, 1H), 1.23-1.00 (m, 4H), 0.96 (s, 1H), 0.78 (t, J=6.9 Hz, 3H).

Synthesis of (R)-2-amino-2-methylhexan-1-ol (1d). To a mixture of compound 1c (14.24 g, 56.65 mmol) and 20% Pd(OH)$_2$ on carbon (2.85 g) in EtOH (210 mL) was added HCl solution (21.5 mL, 86.0 mmol, 4 M in dioxane) The resulting mixture was purged with H$_2$ gas and then stirred under H$_2$ atmosphere at 70° C. After 10 h, the reaction mixture was cooled to rt, filtered through Celite, rinsed with EtOH (50 mL), and concentrated in vacuo. The residue was co-evaporated with toluene (50 mL×1) to provide compound 1d as an HCl salt. LC/MS (ESI) calculated for C$_7$H$_{18}$NO: m/z 132.13, found 131.90 [M+H]$^+$; t$_R$=0.42 min. on LC/MS Method A. $^1$H NMR (400 MHz, Methanol-d$_4$) δ 3.54 (d, J=11.4 Hz, 1H), 3.46 (d, J=11.5 Hz, 1H), 1.65 (ddd, J=14.0, 11.0, 5.8 Hz, 1H), 1.57 (dt, J=13.8, 5.4 Hz, 1H), 1.44-1.26 (m, 4H), 1.24 (s, 3H), 0.95 (t, J=7.0 Hz, 3H).

Synthesis of (R)-tert-butyl (1-hydroxy-2-methylhexan-2-yl)carbamate (1e). To a solution of 1d (1 g, 7.6 mmol) in THF (35 mL) was added sat. NaHCO$_{3(aq)}$ (35 mL) followed by di-tert-butyl dicarbonate (3.33 g, 15.24 mmol). After 24 h, the organic solvents were removed in vacuo. The resulting slurry was diluted with water (50 mL), extracted with EtOAc (100 mL), washed with brine (10 mL), dried over Na$_2$SO$_4$, and concentrated in vacuo. The residue was subjected to silica gel chromatography eluting with hexanes-EtOAc to provide 1e. LC/MS (ESI) calculated for C$_{12}$H$_{25}$NO$_3$: m/z 232.18, found 231.61 [M+H]$^+$; t$_R$=1.09 min. on LC/MS Method A. $^1$H NMR (400 MHz, Chloroform-d) δ 3.64 (d, J=11.4 Hz, 1H), 3.59 (d, J=11.5 Hz, 1H), 1.75-1.65 (m, 1H), 1.56-1.45 (m, 1H), 1.43 (s, 9H), 1.37-1.27 (m, 4H), 1.16 (s, 3H), 0.91 (t, J=7.0 Hz, 3H).

Synthesis of (R)-tert-butyl (2-methyl-1-oxohexan-2-yl)carbamate (1f). To a solution of 1e (2.1 g, 9.0 mmol) in DCM (100 mL) was added Dess-Martin periodinane (5.7 g, 14 mmol). After 2 h the reaction was quenched with sat. Na$_2$S$_2$O$_{3(aq)}$ (75 mL). The mixture was separated and the aqueous layer was extracted with DCM (100 mL). The combined organics were washed with water (100 mL) and brine (100 mL), dried over Na$_2$SO$_4$, then filtered and concentrated in vacuo. The residue was subjected to silica gel chromatography eluting with hexanes-EtOAc to provide if. LC/MS (ESI) calculated for C$_8$H$_{15}$NO$_3$: m/z 231.17, found 173.75 [M+H-(t-Bu)]$^+$; t$_R$=1.18 min. on LC/MS Method A. $^1$H NMR (400 MHz, Chloroform-d) δ 9.36 (s, 1H), 1.98-1.78 (m, 1H), 1.70-1.61 (m, 1H), 1.44 (s, 9H), 1.35 (s, 3H), 1.34-1.26 (m, 4H), 0.89 (t, J=7.1 Hz, 3H).

Synthesis of (R)-tert-butyl (1-(benzylamino)-2-methylhexan-2-yl)carbamate (1g). To a solution of if (1.9 g, 8.4 mmol) in dry MeOH (50 mL) was added benzylamine (1.0 mL, 8.35 mmol). After 18 h, sodium borohydride (500 mg, 13 mmol) was added portionwise. After 60 minutes, the mixture was concentrated in vacuo. The resulting residue was dissolved in EtOAc (50 mL), washed with 1M NaOH$_{(aq)}$ (50 mL), 10% aqueous Rochelle's salt solution (50 mL, solid supplied by Sigma-Aldrich), and brine (50 mL), dried over Na$_2$SO$_4$, then filtered and concentrated in vacuo to afford 1g. LC/MS (ESI) calculated for C$_{19}$H$_{32}$N$_2$O$_2$: m/z 321.25, found 321.03 [M+H]$^+$; t$_R$=0.94 min. on LC/MS Method A. $^1$H NMR (400 MHz, Chloroform-d) δ 7.35-7.31 (m, 5H), 3.86-3.78 (m, 2H), 2.82-2.69 (m, 1H), 2.66-2.54 (m, 1H), 1.42 (s, 9H), 1.33-1.26 (m, 3H), 1.25 (s, 3H), 1.21-1.17 (m, 1H), 0.89 (t, J=7.2 Hz, 3H).

Synthesis of (R)-tert-butyl (1-(N-benzylacetamido)-2-methylhexan-2-yl)carbamate (1h). To a solution of 1g (2.2 g, 6.9 mmol) in THF (50 mL) was added N,N-diisopropylethylamine (2.4 mL, 14 mmol) followed by acetyl chloride (0.75 mL, 11 mmol). After 60 minutes, the mixture was diluted with EtOAc (150 mL), washed with sat. NaHCO$_{3(aq)}$(100 mL) and brine (100 mL), dried over Na$_2$SO$_4$, then filtered and concentrated in vacuo. The residue was subjected to silica gel chromatography eluting with hexanes-EtOAc to provide 1h. LC/MS (ESI) calculated for C$_{21}$E134N2O$_3$: m/z 363.26, found 362.82 [M+H]$^+$; t$_R$=1.32 min. on LC/MS Method A. $^1$H NMR (400 MHz, Chloroform-d) δ 7.39-7.32 (m, 2H), 7.32-7.28 (m, 1H), 7.13-7.08 (m, 2H), 4.64 (dd, J=17.4, 8.1 Hz, 2H), 2.12 (s, 3H), 1.78-1.65 (m, 2H), 1.41 (s, 9H), 1.34-1.22 (m, 7H), 0.89 (t, J=7.0 Hz, 3H).

Synthesis of (R)—N-(2-amino-2-methylhexyl)acetamide (1i). To a solution of 1h (2.0 g, 5.4 mmol) in EtOH (55 mL) and HCl solution (2 mL, 4 M in dioxane) that was purged with Ar was added palladium hydroxide on carbon (2.0 g, 20 wt %). The mixture was purged with H$_2$ and heated to 70° C. After 24 h, the reaction mixture was filtered through Celite, rinsed with EtOAc, and concentrated in vacuo to afford 1i as an HCl salt. LC/MS (ESI) calculated for C$_9$H$_{20}$N$_2$O: m/z 173.16, found 172.92 [M+H]$^+$; t$_R$=0.50 min. on LC/MS Method A. $^1$H NMR (400 MHz, MeOH-d$_4$) δ 3.34 (d, J=4.1 Hz, 2H), 2.02 (s, 3H), 1.66-1.57 (m, 2H), 1.45-1.33 (m, 4H), 1.29 (s, 3H), 0.98 (t, J=6.9 Hz, 3H).

Synthesis of (R)—N-(2-((2-chloroquinazolin-4-yl)amino)-2-methylhexyl)acetamide (1j). To a solution of 1i (202 mg, 0.97 mmol) and 2,4-dichloroquinazoline (500 mg, 0.97 mmol, supplied by AstaTech, Inc.) in THF (4 mL) was added N,N-diisopropylethylamine (0.67 mL, 3.87 mmol). After stirring at 75° C. for 22 h, the reaction was cooled to rt, diluted with EtOAc (10 mL), washed with water (10 mL) and brine (10 mL), dried over Na$_2$SO$_4$, then filtered and concentrated in vacuo. The residue was subjected to silica gel chromatography eluting with hexanes-EtOAc to provide 1j as a mixture of isomers. LC/MS (ESI) calculated for C$_{17}$H$_{23}$ClN$_4$O: m/z 335.15, found 335.20 [M+H]$^+$; t$_R$=1.08 min. on LC/MS Method A. $^1$H NMR (400 MHz, Chloroform-d) δ 9.27 (s, 1H), 7.96 (d, J=8.2 Hz, 1H), 7.84 (d, J=8.3 Hz, 1H), 7.76-7.67 (m, 4H), 7.48 (ddt, J=8.4, 5.3, 2.6 Hz, 3H), 6.59 (s, 1H), 5.65 (s, 1H), 3.83 (dd, J=14.0, 5.0 Hz, 2H), 3.69 (dd, J=14.1, 4.1 Hz, 1H), 3.20 (dd, J=14.5, 6.1 Hz, 1H), 2.25 (t, J=12.7 Hz, 1H), 2.13 (s, 2H), 2.09 (s, 3H), 2.02-1.88 (m, 2H), 1.77-1.64 (m, 2H), 1.57 (d, J=4.6 Hz, 5H), 1.39 (s, 4H), 1.36-1.27 (m, 10H), 0.88 (td, J=7.2, 6.8, 2.8 Hz, 9H).

Synthesis of (R)—N-(2-((2-((2,4-dimethoxybenzyl)amino)quinazolin-4-yl)amino)-2-methylhexyl)acetamide (1k). To a solution of 1j (40.6 mg, 0.12 mmol) in 2-MeTHF (2 mL) was added potassium carbonate (34.5 mg, 0.24 mmol) followed by 2,4-dimethoxybenzylamine (0.04 mL, 0.24 mmol, supplied by Sigma-Aldrich). After stirring at 80° C. for 18 h, the reaction was cooled to rt, diluted with EtOAc (10 mL), washed with water (10 mL) and brine (10 mL), dried over Na$_2$SO$_4$, then filtered and concentrated in vacuo. The residue was purified by preparative HPLC (Gemini 10u C18 110A, Axia; 25% aq. acetonitrile—70% aq. acetonitrile, over 20 min. gradient) to provide 1k as a TFA salt. LC/MS (ESI) calculated for C$_{26}$H$_{35}$N$_5$O$_3$: m/z 466.27, found 466.39 [M+H]$^+$; t$_R$=0.99 min. on LC/MS Method A. $^1$H NMR (400 MHz, Chloroform-d) δ 9.51 (s, 1H), 8.72 (s, 1H), 7.85 (d, J=7.9 Hz, 1H), 7.65-7.57 (m, 1H), 7.53 (d, J=8.5 Hz, 1H), 7.30 (dd, J=7.8, 2.6 Hz, 1H), 7.11 (d, J=8.6 Hz, 1H), 6.43 (d, J=2.6 Hz, 1H), 6.37 (d, J=8.4 Hz, 1H), 6.29 (s, 1H), 4.63 (d, J=5.4 Hz, 2H), 3.91-3.83 (m, 1H), 3.82 (d, J=2.2 Hz, 3H), 3.76 (d, J=2.2 Hz, 3H), 3.01 (d, J=14.6 Hz, 1H), 2.19 (d, J=13.0 Hz, 1H), 2.11 (d, J=2.8 Hz, 3H), 1.79 (t, J=13.1 Hz, 1H), 1.47 (d, J=2.8 Hz, 3H), 1.21-1.06 (m, 4H), 0.83 (t, J=6.7 Hz, 3H). $^{19}$F NMR (377 MHz, Chloroform-d) δ −76.19.

Synthesis of (R)—N-(2-((2-aminoquinazolin-4-yl)amino)-2-methylhexyl)acetamide (1). To 1k (3.3 mg, 0.01 mmol) in DCM (1 mL) was added TFA (1.5 mL). After 4 h, the reaction mixture was concentrated in vacuo and coevaporated with MeOH (3×20 mL). The residue was suspended in MeOH and filtered. The solution was concentrated in vacuo to afford 1 as its TFA salt. LC/MS (ESI) calculated for $C_{17}H_{25}N_5O$: m/z 316.21, found 316.22 [M+H]$^+$; $t_R$=0.76 min. on LC/MS Method A. $^1$H NMR (400 MHz, Methanol-d$_4$) δ 8.57 (t, J=5.9 Hz, 1H), 8.18-8.01 (m, 1H), 7.78 (ddd, J=8.4, 7.4, 1.2 Hz, 1H), 7.42 (ddd, J=20.7, 9.8, 4.6 Hz, 2H), 3.89 (dd, J=14.3, 5.8 Hz, 1H), 3.34 (d, J=6.5 Hz, 1H), 2.23-2.10 (m, 2H), 2.03 (s, 3H), 1.57 (s, 3H), 1.36-1.31 (m, 4H), 0.91 (t, J=7.0 Hz, 3H). $^{19}$F NMR (377 MHz, Methanol-d$_4$) δ −77.51.

Example 2

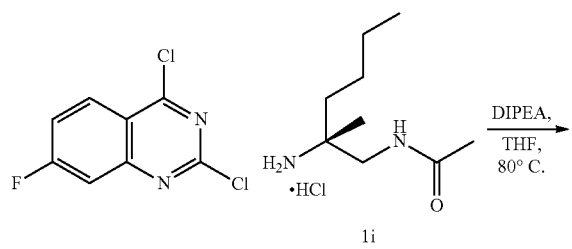

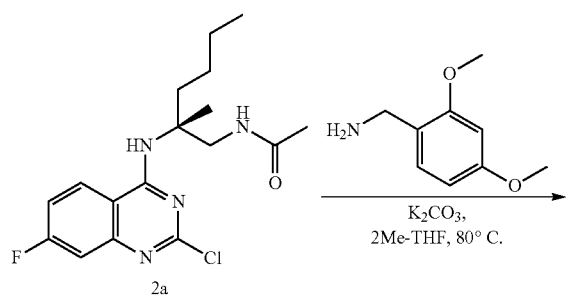

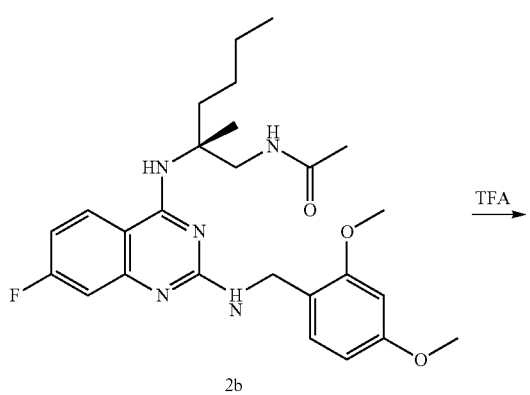

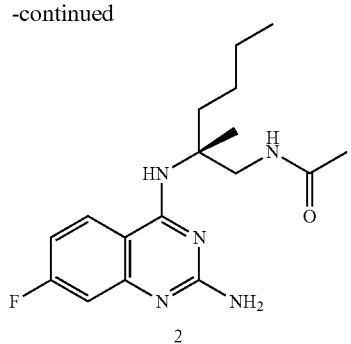

Synthesis of (R)—N-(2-((2-chloro-7-fluoroquinazolin-4-yl)amino)-2-methylhexyl)acetamide (2a). To a solution of 1i (80.8 mg, 0.39 mmol) and 2,4-dichloro-7-fluoroquinazoline (84.8 mg, 0.39 mmol, supplied by AstaTech, Inc.) in THF (1.6 mL) was added N,N-diisopropylethylamine (0.27 mL, 1.55 mmol). After stirring at 75° C. for 18 h, the reaction was cooled to rt, diluted with EtOAc (10 mL), washed with water (10 mL) and brine (10 mL), dried over Na$_2$SO$_4$, then filtered and concentrated in vacuo. The residue was subjected to silica gel chromatography eluting with hexanes-EtOAc to provide 2a. LC/MS (ESI) calculated for $C_{17}H_{22}ClFN_4O$: m/z 353.15, found 353.17 [M+H]$^+$; $t_R$=1.36 min. on LC/MS Method A.

Synthesis of (R)—N-(2-((2-((2,4-dimethoxybenzyl)amino)-7-fluoroquinazolin-4-yl)amino)-2-methylhexyl)acetamide (2b). To a solution of 2a (64 mg, 0.18 mmol) in 2-MeTHF (2 mL) was added potassium carbonate (52.7 mg, 0.36 mmol) followed by 2,4-dimethoxybenzylamine (0.06 mL, 0.36 mmol). After stirring at 80° C. for 4 d, the reaction was cooled to rt, diluted with EtOAc (10 mL), washed with water (10 mL) and brine (10 mL), dried over Na$_2$SO$_4$, then filtered and concentrated in vacuo. The residue was subjected to silica gel chromatography eluting with hexanes-EtOAc to provide 2b. LC/MS (ESI) calculated for $C_{26}H_{34}FN_5O_3$: m/z 484.27, found 484.19 [M+H]$^+$; $t_R$=1.29 min. on LC/MS Method A. $^1$H NMR (400 MHz, Chloroform-d) δ 7.59 (dd, J=9.0, 5.9 Hz, 1H), 7.20 (d, J=8.1 Hz, 1H), 6.99 (d, J=9.7 Hz, 1H), 6.80 (td, J=8.6, 2.6 Hz, 1H), 6.45 (d, J=2.3 Hz, 1H), 6.39 (dd, J=8.3, 2.4 Hz, 1H), 4.63-4.51 (m, 2H), 3.86-3.79 (m, 4H), 3.78 (s, 3H), 3.21 (dd, J=14.1, 6.4 Hz, 1H), 2.10-2.04 (m, 1H), 2.03 (s, 3H), 1.95-1.83 (m, 1H), 1.45 (s, 3H), 1.25-1.17 (m, 4H), 0.84 (t, J=7.1 Hz, 3H). $^{19}$F NMR (377 MHz, Chloroform-d) δ −108.10.

Synthesis of (R)—N-(2-((2-amino-7-fluoroquinazolin-4-yl)amino)-2-methylhexyl)acetamide (2). To 2b (36.5 mg, 0.08 mmol) was added TFA (3 mL). After 90 min, the reaction mixture was concentrated in vacuo and coevaporated with MeOH (3×20 mL). The residue was suspended in MeOH and filtered. The solution was concentrated in vacuo to afford 2 as its TFA salt. LC/MS (ESI) calculated for $C_{17}H_{24}FN_5O$: m/z 334.20, found 334.19 [M+H]$^+$; $t_R$=0.99 min. on LC/MS Method A. $^1$H NMR (400 MHz, Methanol-d$_4$) δ 8.77 (s, 1H), 8.18 (dd, J=9.1, 5.4 Hz, 1H), 7.22-7.11 (m, 2H), 3.86 (d, J=14.2 Hz, 1H), 3.33 (d, J=14.1 Hz, 1H), 2.12 (t, J=7.9 Hz, 2H), 2.02 (s, 3H), 1.55 (s, 3H), 1.37-1.26 (m, 4H), 0.90 (t, J=7.0 Hz, 3H).

Example 3

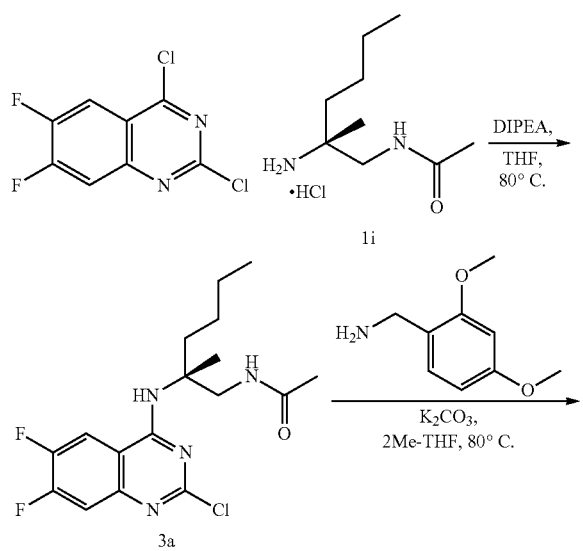

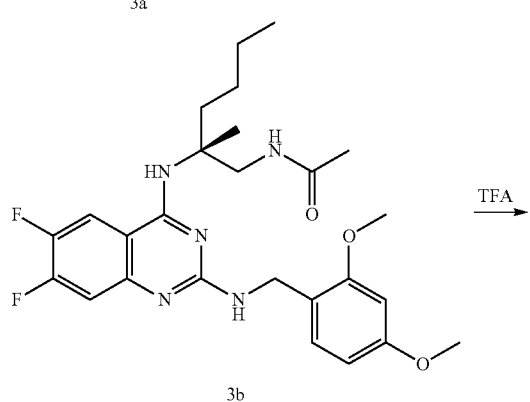

Synthesis of (R)—N-(2-((2-chloro-6,7-difluoroquinazolin-4-yl)amino)-2-methylhexyl)acetamide (3a). To a solution of 1i (80.8 mg, 0.39 mmol) and 2,4-dichloro-6,7-difluoroquinazoline (90.1 mg, 0.39 mmol, supplied by Matrix Scientific) in THF (1.6 mL) was added N,N-diisopropylethylamine (0.27 mL, 0.15 mmol). After stirring at 75° C. for 18 h, the reaction was cooled to rt, diluted with EtOAc (10 mL), washed with water (10 mL) and brine (10 mL), dried over $Na_2SO_4$, then filtered and concentrated in vacuo. The residue was subjected to silica gel chromatography eluting with hexanes-EtOAc to provide 3a. LC/MS (ESI) calculated for $C_{17}H_{21}ClF_2N_4O$: m/z 371.14, found 371.12 [M+H]$^+$; $t_R$=1.51 min. on LC/MS Method A.

Synthesis of (R)—N-(2-((2-((2,4-dimethoxybenzyl)amino)-6,7-difluoroquinazolin-4-yl)amino)-2-methylhexyl)acetamide (3b). To a solution of 3a (78.9 mg, 0.21 mmol) in 2-MeTHF (2 mL) was added potassium carbonate (61.5 mg, 0.43 mmol) followed by 2,4-dimethoxybenzylamine (0.06 mL, 0.43 mmol). After stirring at 80° C. for 4 d, the reaction was cooled to rt, diluted with EtOAc (10 mL), washed with water (10 mL) and brine (10 mL), dried over $Na_2SO_4$, then filtered and concentrated in vacuo. The residue was subjected to silica gel chromatography eluting with hexanes-EtOAc to provide 3b. LC/MS (ESI) calculated for $C_{26}H_{33}F_2N_5O_3$: m/z 502.26, found 502.25 [M+H]$^+$; $t_R$=1.32 min. on LC/MS Method A. $^1$H NMR (400 MHz, Chloroform-d) δ 7.44 (dd, J=10.9, 8.4 Hz, 1H), 7.20 (d, J=8.2 Hz, 1H), 7.10 (dd, J=11.5, 7.8 Hz, 1H), 6.75 (s, 1H), 6.45 (d, J=2.3 Hz, 1H), 6.40 (dd, J=8.3, 2.4 Hz, 1H), 6.09 (s, 1H), 5.29 (s, 1H), 4.56 (d, J=6.0 Hz, 2H), 3.85-3.78 (m, 4H), 3.78 (s, 3H), 3.17 (dd, J=14.2, 6.4 Hz, 1H), 2.12-2.06 (m, 1H), 2.05 (s, 3H), 1.94-1.83 (m, 1H), 1.46 (s, 3H), 1.27-1.19 (m, 4H), 0.85 (t, J=6.4 Hz, 3H). $^{19}$F NMR (377 MHz, Chloroform-d) δ −131.08, −144.04.

Synthesis of (R)—N-(2-((2-amino-6,7-difluoroquinazolin-4-yl)amino)-2-methylhexyl)acetamide (3). To 3b (32.9 mg, 0.07 mmol) was added TFA (3 mL). After 1 h, the reaction mixture was concentrated in vacuo and coevaporated with MeOH (3×20 mL). The residue was suspended in MeOH and filtered. The solution was concentrated in vacuo to afford 3 as its TFA salt. LC/MS (ESI) calculated for $C_{17}H_{23}F_2N_5O$: m/z 352.19, found 352.17 [M+H]$^+$; $t_R$=1.03 min. on LC/MS Method A. $^1$H NMR (400 MHz, Methanol-$d_4$) δ 8.70 (s, 1H), 8.17 (dd, J=11.0, 7.8 Hz, 1H), 7.36 (dd, J=10.6, 6.9 Hz, 1H), 3.87 (d, J=14.2 Hz, 1H), 3.38 (d, J=14.2 Hz, 1H), 2.17 (ddd, J=13.8, 9.7, 6.3 Hz, 1H), 2.06 (dd, J=10.7, 5.3 Hz, 1H), 2.02 (s, 3H), 1.54 (s, 3H), 1.35-1.27 (m, 4H), 0.91 (t, J=6.9 Hz, 3H). $^{19}$F NMR (377 MHz, Methanol-$d_4$) δ −77.84, $^-$127.42-$^-$129.14 (m), −141.96 (ddd, J=21.6, 10.9, 6.8 Hz).

Example 4

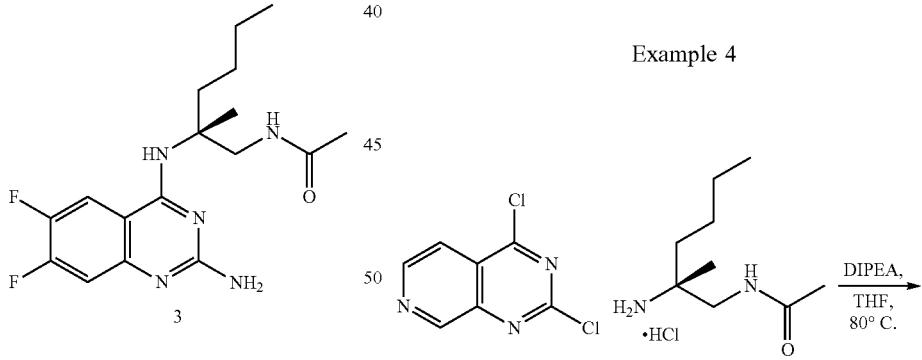

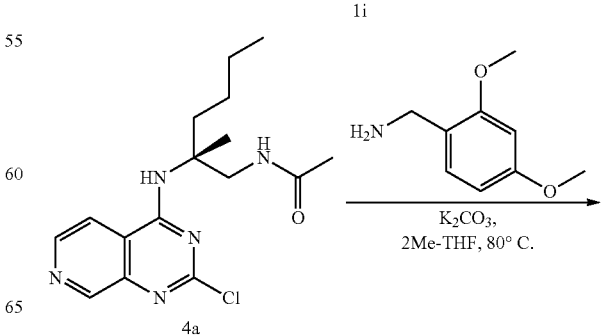

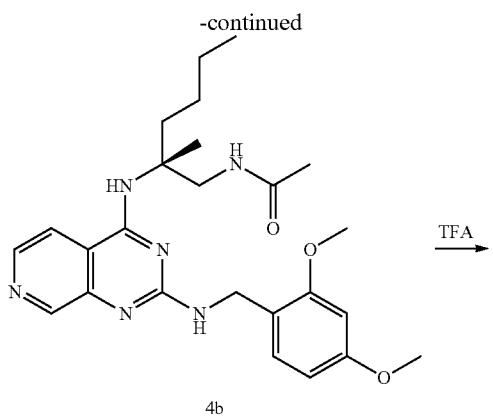

4b

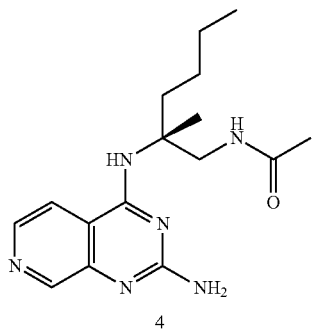

4

Synthesis of (R)—N-(2-N-(2-chloropyrido[3,4-d]pyrimidin-4-yl)amino)-2-methylhexyl)acetamide (4a). To a solution of 1i (80.8 mg, 0.39 mmol) and 2,4-dichloropyrido[3,4-d]pyrimidine (78.1 mg, 0.39 mmol, supplied by AstaTech, Inc.) in THF (1.6 mL) was added N,N-diisopropylethylamine (0.27 mL, 1.5 mmol). After stirring at 75° C. for 18 h, the reaction was cooled to rt, diluted with EtOAc (10 mL), washed with water (10 mL) and brine (10 mL), dried over Na$_2$SO$_4$, then filtered and concentrated in vacuo. The residue was subjected to silica gel chromatography eluting with hexanes-EtOAc to provide 4a. LC/MS (ESI) calculated for C$_{16}$H$_{22}$ClN$_5$O: m/z 336.15, found 336.12 [M+H]$^+$; t$_R$=1.14 min. on LC/MS Method A.

Synthesis of (R)—N-(2-((2-((2,4-dimethoxybenzyl)amino)pyrido[3,4-d]pyrimidin-4-yl)amino)-2-methylhexyl)acetamide (4b). To a solution of 4a (43.7 mg, 0.13 mmol) in 2-MeTHF (2 mL) was added potassium carbonate (36.3 mg, 0.26 mmol) followed by 2,4-dimethoxybenzylamine (0.04 mL, 0.26 mmol). After stirring at 80° C. for 18 h, the reaction was cooled to rt, diluted with EtOAc (10 mL), washed with water (10 mL) and brine (10 mL), dried over Na$_2$SO$_4$, then filtered and concentrated in vacuo. The residue was subjected to silica gel chromatography eluting with hexanes-EtOAc to provide 4b. LC/MS (ESI) calculated for C$_{25}$H$_{34}$N$_6$O$_3$: m/z 467.27, found 467.21 [M+H]$^+$; t$_R$=1.11 min. on LC/MS Method A. $^1$H NMR (400 MHz, Chloroform-d) δ 8.80 (s, 1H), 8.24 (d, J=5.5 Hz, 1H), 7.44 (d, J=5.5 Hz, 1H), 7.22 (s, 1H), 6.46 (d, J=2.3 Hz, 1H), 6.40 (d, J=8.5 Hz, 1H), 6.16 (s, 1H), 4.60 (d, J=6.0 Hz, 2H), 3.83 (s, 5H), 3.78 (s, 3H), 3.14 (dd, J=14.5, 6.3 Hz, 1H), 2.13 (t, J=14.2 Hz, 1H), 2.08 (s, 3H), 2.04 (s, 3H), 1.93-1.82 (m, 2H), 1.48 (s, 3H), 1.23 (m, 4H), 0.85 (t, J=6.7 Hz, 3H).

Synthesis of (R)—N-(2-((2-aminopyrido[3,4-d]pyrimidin-4-yl)amino)-2-methylhexyl)acetamide (4). To 4b (16.8 mg, 0.04 mmol) was added TFA (3 mL). After 24 h, the reaction mixture was concentrated in vacuo and coevaporated with MeOH (3×20 mL). The residue was suspended in MeOH and filtered. The solution was concentrated in vacuo to afford 4 as its TFA salt. LC/MS (ESI) calculated for C$_{16}$H$_{24}$N$_6$O: m/z 317.20, found 317.17 [M+H]$^+$; t$_R$=0.85 min. on LC/MS Method A. $^1$H NMR (400 MHz, Methanol-d$_4$) δ 9.17 (s, 1H), 8.79 (s, 1H), 8.56 (d, J=5.5 Hz, 1H), 8.05 (d, J=5.5 Hz, 1H), 3.87 (d, J=14.3 Hz, 1H), 3.36 (d, J=14.3 Hz, 1H), 2.23-2.07 (m, 2H), 2.02 (s, 3H), 1.57 (s, 3H), 1.38-1.31 (m, 4H), 0.91 (t, J=6.8 Hz, 3H). $^{19}$F NMR (377 MHz, Methanol-d$_4$) δ −77.93.

Example 5

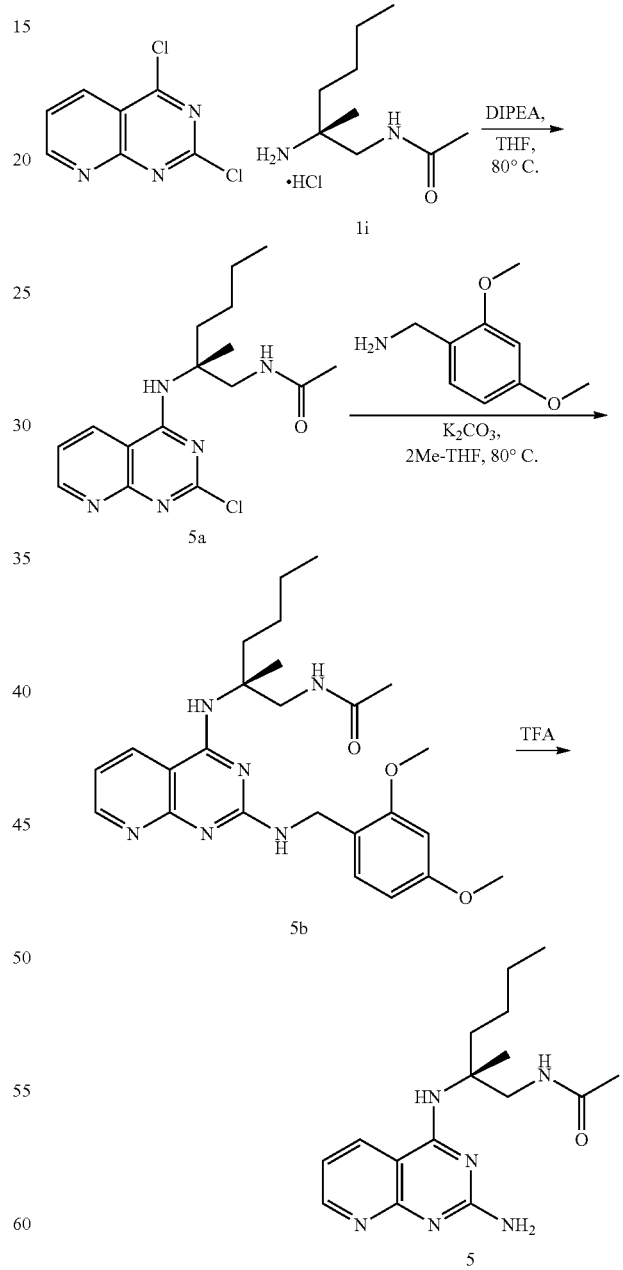

Synthesis of (R)—N-(2-N-(2-chloropyrido[2,3-d]pyrimidin-4-yl)amino)-2-methylhexyl)acetamide (5a). To a solution of 1i (106 mg, 0.50 mmol) and 2,4-dichloropyrido[2,3-d]pyrimidine (100 mg, 0.50 mmol, supplied by Combi- Blocks) in THF (2 mL) was added N,N-diisopropylethylamine (0.35 mL, 2.0 mmol). After stirring at 80° C. for 2 h, the reaction was cooled to rt, diluted with EtOAc (15 mL), washed with water (15 mL) and brine (15 mL), dried over $Na_2SO_4$, then filtered and concentrated in vacuo. The residue was subjected to silica gel chromatography eluting with hexanes-EtOAc to provide 5a. LC/MS (ESI) calculated for $C_{16}H_{22}ClN_5O$: m/z 336.15, found 336.21 [M+H]$^+$; $t_R$=0.94 min. on LC/MS Method A. $^1$H NMR (400 MHz, Chloroform-d) δ 8.96 (dd, J=4.4, 1.8 Hz, 1H), 8.49 (s, 1H), 8.38 (dd, J=8.2, 1.8 Hz, 1H), 7.41 (dd, J=8.2, 4.5 Hz, 1H), 6.72 (t, J=6.9 Hz, 1H), 3.85 (dd, J=14.5, 6.7 Hz, 1H), 3.14 (dd, J=14.5, 6.3 Hz, 1H), 2.36 (td, J=13.4, 12.7, 4.4 Hz, 1H), 2.16 (s, 3H), 1.92 (td, J=13.8, 12.8, 3.9 Hz, 1H), 1.59 (s, 3H), 1.41-1.22 (m, 4H), 0.86 (t, J=7.2 Hz, 3H).

Synthesis of (R)—N-(2-((2-((2,4-dimethoxybenzyl)amino)pyrido[2,3-d]pyrimidin-4-yl)amino)-2-methylhexyl)acetamide (5b). To a solution of 5a (128.5 mg, 0.38 mmol) in 2-MeTHF (2.5 mL) was added potassium carbonate (107 mg, 0.77 mmol) followed by 2,4-dimethoxybenzylamine (0.12 mL, 0.77 mmol). After stirring at 80° C. for 18 h, the reaction was cooled to rt, diluted with EtOAc (15 mL), washed with water (15 mL) and brine (15 mL), dried over $Na_2SO_4$, then filtered and concentrated in vacuo. The residue was subjected to silica gel chromatography eluting with hexanes-EtOAc to provide 5b. LC/MS (ESI) calculated for $C_{25}H_{34}N_6O_3$: m/z 467.27, found 467.40 [M+H]$^+$; $t_R$=0.90 min. on LC/MS Method A. $^1$H NMR (400 MHz, Chloroform-d) δ 8.36 (s, 1H), 8.17 (s, 1H), 7.17 (s, 1H), 7.00 (dd, J=8.1, 4.6 Hz, 1H), 6.46 (d, J=2.4 Hz, 1H), 6.41 (d, J=8.4 Hz, 1H), 4.76-4.48 (m, 2H), 3.85-3.80 (m, 1H), 3.79 (s, 6H), 3.15 (dd, J=14.3, 6.1 Hz, 1H), 2.18 (s, 1H), 2.11 (s, 3H), 1.84 (s, 1H), 1.51 (s, 3H), 1.17 (s, 4H), 0.83 (s, 3H).

Synthesis of (R)—N-(2-((2-aminopyrido[2,3-d]pyrimidin-4-yl)amino)-2-methylhexyl)acetamide (5). To 5b (168.5 mg, 0.36 mmol) was added TFA (3 mL). After 24 h, the reaction mixture was concentrated in vacuo and coevaporated with MeOH (3×20 mL). The residue was suspended in MeOH and filtered. The solution was concentrated in vacuo to afford 5 as its TFA salt. LC/MS (ESI) calculated for $C_{16}H_{24}N_6O$: m/z 317.20, found 317.24 [M+H]$^+$; $t_R$=0.64 min. on LC/MS Method A. $^1$H NMR (400 MHz, Methanol-$d_4$) δ 9.05 (s, 1H), 8.73 (dd, J=4.7, 1.6 Hz, 1H), 8.55 (dd, J=8.2, 1.6 Hz, 1H), 7.46 (dd, J=8.2, 4.7 Hz, 1H), 3.87 (dd, J=14.3, 5.3 Hz, 1H), 3.40-3.33 (m, 1H), 2.23-2.04 (m, 2H), 2.02 (s, 3H), 1.57 (s, 3H), 1.39-1.28 (m, 4H), 0.92 (t, J=6.9 Hz, 3H). $^{19}$F NMR (377 MHz, Methanol-$d_4$) δ −77.93.

Example 6

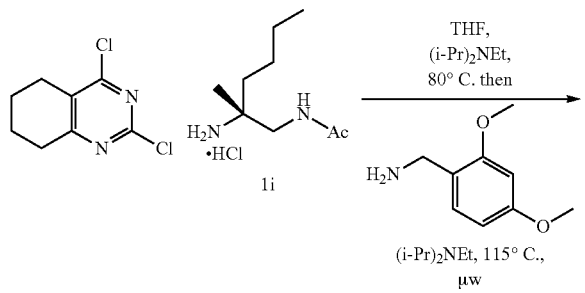

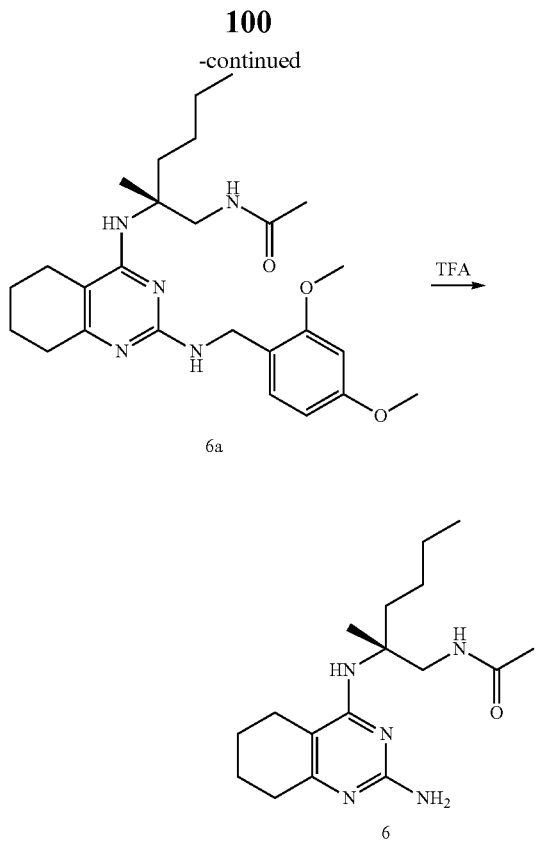

Synthesis of (R)—N-(2-((2-((2,4-dimethoxybenzyl)amino)-5,6,7,8-tetrahydroquinazolin-4-yl)amino)-2-methylhexyl)acetamide (6a)

A solution of 2,4-dichloro-5,6,7,8-tetrahydroquinazoline (supplied by Astatech, Inc.) (100 mg, 0.49 mmol) in THF (10 mL) was treated with 1i, (200 mg, 0.95 mmol) and N,N-diisopropylethylamine (0.25 mL, 1.15 mmol). After the mixture was stirred under reflux for 12 h, 2,4-dimethoxybenzylamine (0.38 mL, 2.5 mmol) and N,N-diisopropylethylamine (0.13 mL, 0.75 mmol) were added, and the mixture was heated to 115° C. for 2 h in a microwave reactor. After this time, the reaction was cooled to rt, diluted with EtOAc (100 mL), washed with water (100 mL), brine (100 mL), dried over $Na_2SO_4$, filtered and concentrated in vacuo. The resulting residue was subjected to silica gel flash chromatography eluting with 0-100% EtOAc in hexanes to provide 6a. LCMS (m/z): 470.21 [M+H]$^+$.

Synthesis of (R)—N-(2-((2-amino-5,6,7,8-tetrahydroquinazolin-4-yl)amino)-2-methylhexyl)acetamide (6). 6a (60 mg, 0.133 mmol) was dissolved in TFA (3 mL). After 60 minutes, the mixture was concentrated in vacuo. The residue was taken up in MeOH, filtered and concentrated in vacuo, to give the title compound 6 as its TFA salt.

$^1$H NMR (400 MHz, MeOH-$d_4$) 8.65 (dd, J=4.3, 1.5 Hz, 1H), 7.86-7.73 (m, 2H), 4.68-4.55 (m, 4H), 3.59 (dd, J=13.9, 4.3 Hz, 4H), 3.34-3.23 (m, 3H), 1.88 (s, 3H), 1.78-1.67 (m, 2H), 1.39 (ddd, J=7.7, 5.1, 2.4 Hz, 4H), 0.91 (ddt, J=8.3, 4.7, 3.0 Hz, 3H). $^{19}$F NMR (377 MHz, MeOH-d4) δ −77.7.

LC/MS 320.15 [M+H]$^+$; $t_R$=0.91 min. (LC/MS HPLC method A).

Example 7

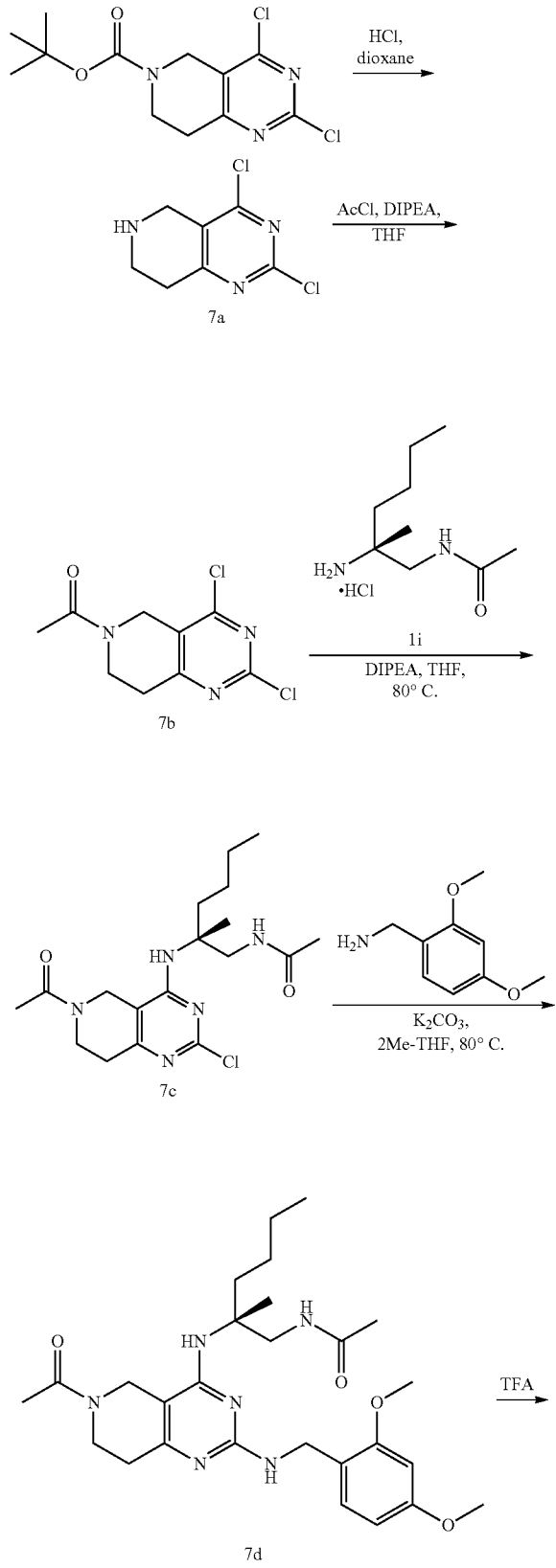

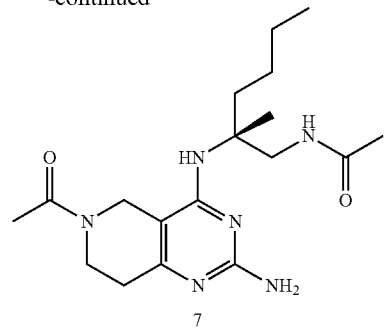

Synthesis of 2,4-dichloro-5,6,7,8-tetrahydropyrido[4,3-d]pyrimidine (7a). To a solution of tert-butyl 2,4-dichloro-7,8-dihydropyrido[4,3-d]pyrimidine-6(5H)-carboxylate (500 mg, 1.64 mmol, supplied by AstaTech, Inc.) in DCM (10 mL) was added HCl solution (1 mL, 4.0 mmol, 4 M in dioxane). After 3 d, the reaction was concentrated in vacuo to afford 7a as an HCl salt. LC/MS (ESI) calculated for $C_7H_7Cl_2N_3$: m/z 204.00, found 204.00 [M+H]$^+$; $t_R$=0.25 min. on LC/MS Method A.

Synthesis of 1-(2,4-dichloro-7,8-dihydropyrido[4,3-d]pyrimidin-6(5H)-yl)ethan-1-one (7b). To 7a (401.9 mg, 1.64 mmol) in THF (20 mL) was added triethylamine (0.55 mL, 3.95 mmol) followed by acetyl chloride (0.15 mL, 2.11 mmol). After 60 min, the mixture was concentrated in vacuo. The residue was diluted with EtOAC (30 mL) and washed with sat. NaHCO$_{3(aq)}$ (30 mL) and brine (30 mL). The combined aqueous was extracted with EtOAc (50 mL). The combined organics were dried over Na$_2$SO$_4$ and concentrated in vacuo to afford 7b LC/MS (ESI) calculated for $C_9H_9Cl_2N_3O$: m/z 246.01, found 246.14 [M+H]$^+$; $t_R$=0.68 min. on LC/MS Method A.

Synthesis of (R)—N-(2-((6-acetyl-2-chloro-5,6,7,8-tetrahydropyrido[4,3-d]pyrimidin-4-yl)amino)-2-methylhexyl)acetamide (7c). To a solution of 7b (420.7 mg, 1.64 mmol) and 1i (363.9 mg, 1.64 mmol) in NMP (6.5 mL) was added N,N-diisopropylethylamine (0.60 mL, 3.29 mmol). After stirring at 150° C. for 18 h, the reaction was cooled to rt, diluted with EtOAc (30 mL) and washed with water (30 mL). The aqueous was extracted with EtOAc (30 mL). The Combined organics were washed with brine (3×50 mL), dried over Na$_2$SO$_4$, then filtered and concentrated in vacuo. The residue was subjected to silica gel chromatography eluting with EtOAc-MeOH to provide 7c as a mixture of products. LC/MS (ESI) calculated for $C_{18}H_{28}ClN_5O_2$: m/z 382.19, found 382.29 [M+H]$^+$; $t_R$=0.88 min. on LC/MS Method A.

Synthesis of (R)—N-(2-((6-acetyl-2-((2,4-dimethoxybenzyl)amino)-5,6,7,8-tetrahydropyrido[4,3-d]pyrimidin-4-yl)amino)-2-methylhexyl)acetamide (7d). To a solution of 7c (418.1 mg, 1.10 mmol) in 2-MeTHF (10 mL) was added potassium carbonate (303.9 mg, 2.19 mmol) followed by 2,4-dimethoxybenzylamine (0.82 mL, 5.47 mmol) in a sealed vessel. After stirring at 150° C. for 18 h, the reaction was cooled to rt, diluted with EtOAc (20 mL) and washed with water (15 mL) and brine (15 mL). The combined aqueous was extracted with EtOAc (50 mL). The combined organics were dried over Na$_2$SO$_4$, then filtered and concentrated in vacuo. The residue was purified by preparative HPLC (Gemini 10u C18 110A, Axia; 25% aq. acetonitrile—45% aq. acetonitrile, over 12 min. gradient) to provide 7d as a TFA salt. LC/MS (ESI) calculated for $C_{27}H_{40}N_6O_4$: m/z 513.31, found 513.46 [M+H]$^+$; $t_R$=0.88 min. on LC/MS Method A. $^1$H NMR (400 MHz, Chloroform-d) δ 9.12 (dt, J=70.2, 5.8 Hz, 1H), 7.54 (d, J=168.2 Hz, 1H), 7.07 (d, J=8.3 Hz, 1H), 6.46-6.40 (m, 1H), 6.37 (dt, J=8.3, 2.1 Hz, 1H), 6.16 (dt, J=72.4, 6.6 Hz, 1H), 4.52 (d, J=5.8 Hz, 2H), 4.41-4.22 (m, 1H), 3.81 (s, 3H), 3.77 (s, 3H), 3.69 (dt, J=21.6, 6.8 Hz, 3H), 2.97 (ddd, J=38.6, 14.6, 6.3 Hz, 1H), 2.82 (t, J=5.1 Hz, 1H), 2.73 (t, J=6.0 Hz, 1H), 2.21 (d, J=34.6 Hz, 3H), 2.07 (d, J=2.4 Hz, 3H), 2.05-1.97 (m, 1H), 1.81-1.67 (m, 1H), 1.39 (d, J=11.7 Hz, 3H), 1.21-0.98 (m, 4H), 0.85 (t, J=6.6 Hz, 3H). $^{19}$F NMR (377 MHz, Chloroform-d) δ −76.33.

Synthesis of (R)—N-(2-((6-acetyl-2-amino-5,6,7,8-tetrahydropyrido[4,3-d]pyrimidin-4-yl)amino)-2-methylhexyl)acetamide (7). To 7d (53.6 mg, 0.11 mmol) was added TFA (3 mL). After 3 h, the reaction mixture was concentrated in vacuo and coevaporated with MeOH (3×20 mL). The residue was suspended in MeOH and filtered. The solution was concentrated in vacuo to afford 7 as its TFA salt. LC/MS (ESI) calculated for $C_{18}H_{30}N_6O_2$: m/z 363.24, found 363.36 [M+H]$^+$; $t_R$=0.65 min. on LC/MS Method A. $^1$H NMR (400 MHz, Methanol-d$_4$) δ 7.53 (d, J=154.6 Hz, 1H), 4.41-4.20 (m, 2H), 4.02-3.60 (m, 5H), 3.20 (dd, J=31.3, 14.2 Hz, 1H), 2.70 (dt, J=47.8, 5.9 Hz, 2H), 2.22 (d, J=18.5 Hz, 3H), 2.17-2.07 (m, 1H), 2.02 (d, J=5.5 Hz, 3H), 2.00-1.92 (m, 1H), 1.49 (d, J=15.4 Hz, 3H), 1.38-1.15 (m, 4H), 0.91 (td, J=7.1, 3.3 Hz, 3H). $^{19}$F NMR (377 MHz, Methanol-d$_4$) δ −77.86.

Example 8

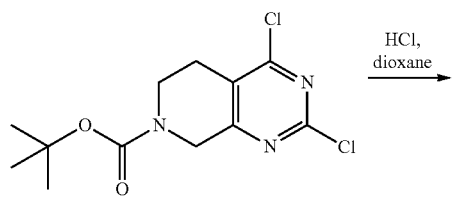

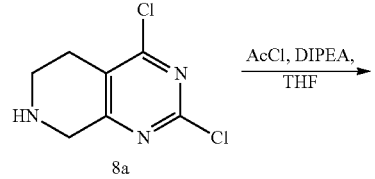

8a

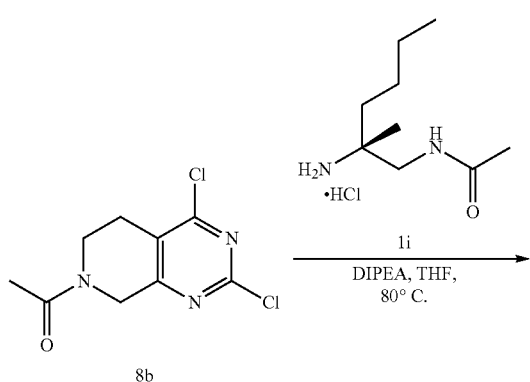

8b

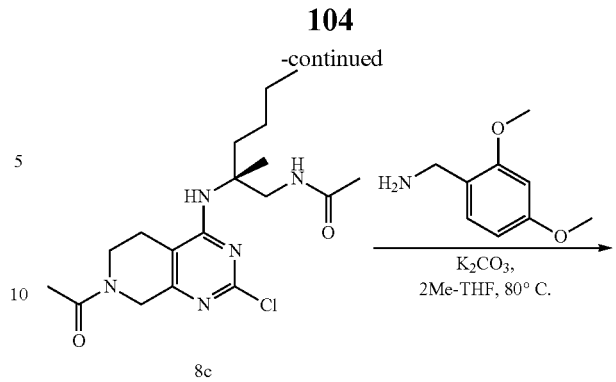

8c

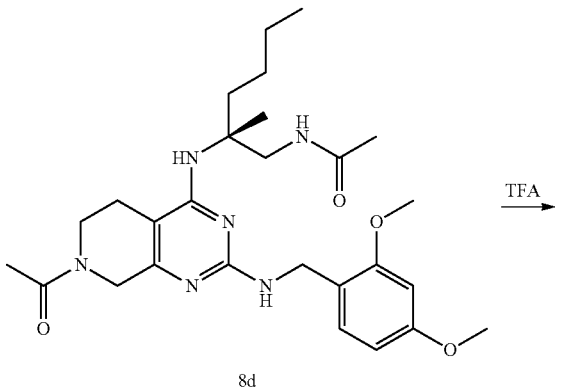

8d

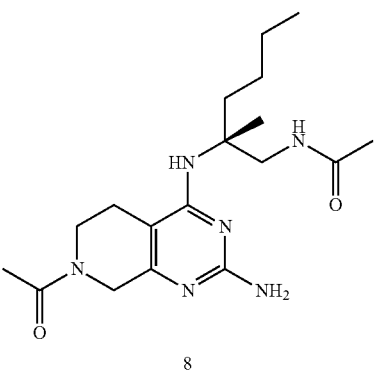 [SMILES: CCCC[C@](C)(CNC(C)=O)Nc1nc(N)nc2c1CCN(C(C)=O)C2]

8

Synthesis of 2,4-dichloro-5,6,7,8-tetrahydropyrido[3,4-d]pyrimidine (8a). To a solution of tert-butyl 2,4-dichloro-5,6-dihydropyrido[3,4-d]pyrimidine-7(8H)-carboxylate (500 mg, 1.64 mmol, supplied by AstaTech, Inc.) in DCM (10 mL) was added HCl solution (2 mL, 8.0 mmol, 4 M in dioxane). After 18 h, the reaction was concentrated in vacuo to afford 8a as an HCl salt. LC/MS (ESI) calculated for $C_7H_7Cl_2N_3$: m/z 204.00, found 204.00 [M+H]$^+$; $t_R$=0.38 min. on LC/MS Method A.

Synthesis of 1-(2,4-dichloro-5,8-dihydropyrido[3,4-d]pyrimidin-7(6H)-yl)ethan-1-one (8b). To 8a in THF (20 mL) was added triethylamine (0.55 mL, 3.95 mmol) followed by acetyl chloride (0.14 mL, 1.97 mmol). After 60 min, the mixture was concentrated in vacuo. The residue was diluted with EtOAC (30 mL) and washed with sat. NaHCO$_{3(aq)}$ (30 mL) and brine (30 mL). The combined aqueous was extracted with EtOAc (50 mL). The combined organics were dried over Na$_2$SO$_4$ and concentrated in vacuo to afford 8b. LC/MS (ESI) calculated for $C_9H_9Cl_2N_3O$: m/z 246.01, found 246.76 [M+H]$^+$; $t_R$=0.74 min. on LC/MS Method A.

Synthesis of (R)—N-(2-((7-acetyl-2-chloro-5,6,7,8-tetrahydropyrido[3,4-d]pyrimidin-4-yl)amino)-2-methylhexyl)acetamide (8c). To a solution of 8b (550.1 mg, 1.64 mmol)

and 1i (360.4 mg, 1.64 mmol) in NMP (6.5 mL) was added N,N-diisopropylethylamine (0.60 mL, 3.29 mmol). After stirring at 150° C. for 18 h, the reaction was cooled to rt, diluted with EtOAc (30 mL) and washed with water (30 mL). The aqueous was extracted with EtOAc (30 mL). The Combined organics were washed with brine (3×50 mL), dried over $Na_2SO_4$, then filtered and concentrated in vacuo. The residue was subjected to silica gel chromatography eluting with EtOAc-MeOH to provide 8c as a mixture of products. LC/MS (ESI) calculated for $C_{18}H_{28}ClN_5O_2$: m/z 382.19, found 382.29 [M+H]$^+$; $t_R$=0.88 min. on LC/MS Method A.

Synthesis of (R)—N-(2-((7-acetyl-2-((2,4-dimethoxybenzyl)amino)-5,6,7,8-tetrahydropyrido[3,4-d]pyrimidin-4-yl)amino)-2-methylhexyl)acetamide (8d). To a solution of 8c (173.9 mg, 0.46 mmol) in 2-MeTHF (4.5 mL) was added potassium carbonate (131.7 mg, 0.91 mmol) followed by 2,4-dimethoxybenzylamine (0.35 mL, 2.28 mmol) in a sealed vessel. After stirring at 150° C. for 18 h, the reaction was cooled to rt, diluted with EtOAc (30 mL), washed with water (25 mL) and brine (25 mL), dried over $Na_2SO_4$, then filtered and concentrated in vacuo. The residue was purified by preparative HPLC (Gemini 10u C18 110A, Axia; 25% aq. acetonitrile—45% aq. acetonitrile, over 15 min. gradient) to provide 8d as a TFA salt. LC/MS (ESI) calculated for $C_{27}H_{40}N_6O_4$: m/z 513.31, found 513.41 [M+H]$^+$; $t_R$=0.89 min. on LC/MS Method A. $^1$H NMR (400 MHz, Chloroform-d) δ 7.93-7.68 (m, 1H), 7.36 (d, J=39.2 Hz, 1H), 7.05 (dd, J=8.3, 4.7 Hz, 1H), 6.45 (dd, J=4.4, 2.3 Hz, 1H), 6.38 (dd, J=8.2, 2.7 Hz, 1H), 4.51 (dd, J=12.8, 7.0 Hz, 4H), 3.80 (d, J=6.1 Hz, 3H), 3.78 (d, J=3.4 Hz, 3H), 3.76-3.66 (m, 2H), 3.07 (dd, J=14.6, 6.2 Hz, 1H), 2.47-2.29 (m, 2H), 2.21 (s, 3H), 2.13 (d, J=16.1 Hz, 3H), 2.09-2.01 (m, 1H), 1.85-1.72 (m, 1H), 1.45 (d, J=2.3 Hz, 3H), 1.32-1.16 (m, 4H), 0.87 (td, J=7.0, 3.7 Hz, 3H). $^{19}$F NMR (377 MHz, Chloroform-d) δ −76.44.

Synthesis of (R)—N-(2-((7-acetyl-2-amino-5,6,7,8-tetrahydropyrido[3,4-d]pyrimidin-4-yl)amino)-2-methylhexyl)acetamide (8). To 8d (65.5 mg, 0.13 mmol) was added TFA (3 mL). After 3 h, the reaction mixture was concentrated in vacuo and coevaporated with MeOH (3×20 mL). The residue was suspended in MeOH and filtered. The solution was concentrated in vacuo to afford 7 as its TFA salt. LC/MS (ESI) calculated for $C_{18}H_{30}N_6O_2$: m/z 363.33, found 363.36 [M+H]$^+$; $t_R$=0.65 min. on LC/MS Method A. $^1$H NMR (400 MHz, Methanol-d$_4$) δ 7.55 (d, J=23.4 Hz, 1H), 4.50 (d, J=1.8 Hz, 2H), 3.93-3.70 (m, 5H), 3.18 (dd, J=14.2, 4.7 Hz, 1H), 2.41 (dt, J=38.3, 6.0 Hz, 2H), 2.19 (d, J=12.0 Hz, 3H), 2.13-2.05 (m, 1H), 2.01 (d, J=5.8 Hz, 3H), 2.00-1.90 (m, 1H), 1.48 (d, J=3.0 Hz, 3H), 1.41-1.15 (m, 4H), 0.90 (t, J=7.0 Hz, 3H). $^{19}$F NMR (377 MHz, Methanol-d$_4$) δ −77.91.

Example 9

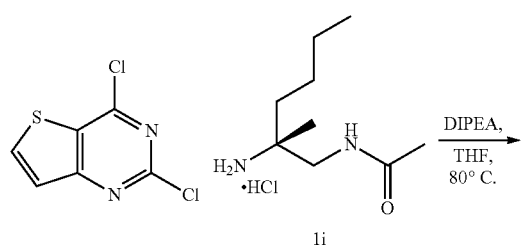

Synthesis of (R)—N-(2-N-(2-chlorothieno[3,2-d]pyrimidin-4-yl)amino)hexyl)acetamide (9a). To a solution of 1i (204 mg, 0.98 mmol) and 2,4-dichlorothieno[3,2-d]pyrimidine (200 mg, 0.975 mmol, supplied by Synthonix) in 2,4-dioxane (4 mL) was added $Na_2CO_3$ (420 mg, 3.90 mmol). After stirring at 85° C. for 3 d, the reaction was cooled to rt, diluted with EtOAc (20 mL), washed with water (20 mL) and brine (20 mL), dried over $Na_2SO_4$, then filtered and concentrated in vacuo. The residue was subjected to silica gel chromatography eluting with hexanes-EtOAc to provide 9a. LC/MS (ESI) calculated for $C_{15}H_{21}ClN_4OS$: m/z 341.11, found 341.12 [M+H]$^+$; $t_R$=1.26 min. on LC/MS Method A. $^1$H NMR (400 MHz, Chloroform-d) δ 7.71 (d, J=5.3 Hz, 1H), 7.32 (d, J=5.3 Hz, 1H), 5.72 (s, 1H), 3.84 (dd, J=13.9, 5.4 Hz, 1H), 3.70 (dd, J=13.9, 4.8 Hz, 1H), 1.88 (td, J=13.1, 11.6, 3.2 Hz, 1H), 1.66 (td, J=14.2, 12.3, 4.4 Hz, 1H), 1.35 (s, 3H), 1.31 (tt, J=6.2, 3.3 Hz, 4H), 0.90 (t, J=6.7 Hz, 3H).

Synthesis of (R)—N-(2-((2-((2,4-dimethoxybenzyl)amino)thieno[3,2-d]pyrimidin-4-yl)amino)hexyl)acetamide (9b). To a solution of 9a (188.7 mg, 0.55 mmol) in 2-MeTHF (4 mL) was added potassium carbonate (158 mg, 0.11 mmol) followed by 2,4-dimethoxybenzylamine (0.17 mL, 1.11 mmol). After stirring at 85° C. for 18 h, the reaction was

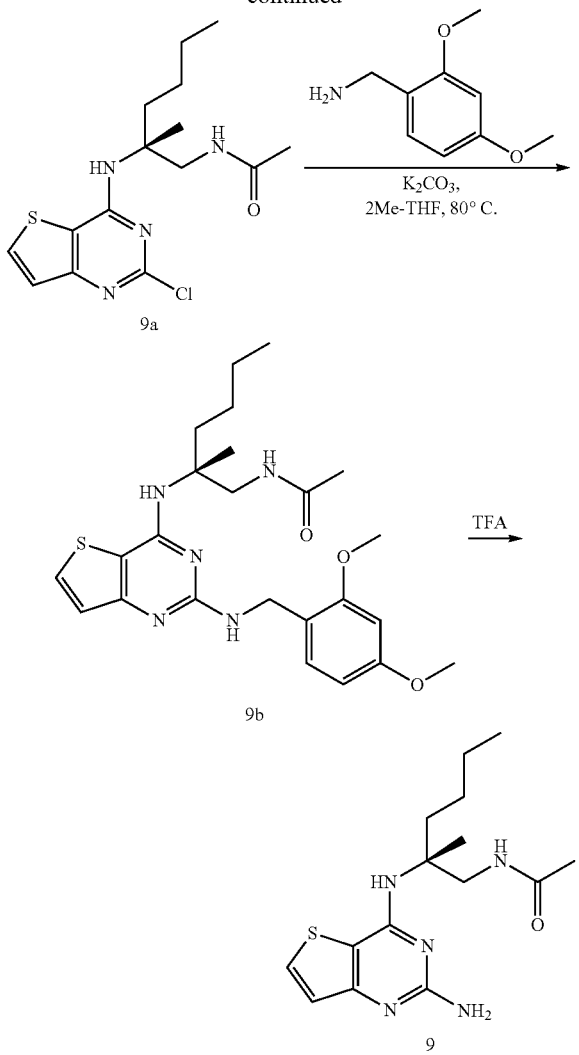

cooled to rt, washed with water (10 mL) and brine (10 mL), dried over Na$_2$SO$_4$, then filtered and concentrated in vacuo. The residue was subjected to silica gel chromatography eluting with hexanes-EtOAc to provide 9b. LC/MS (ESI) calculated for C$_{24}$H$_{33}$N$_5$O$_3$S: m/z 472.23, found 472.23 [M+H]$^+$; t$_R$=1.23 min. on LC/MS Method A. $^1$H NMR (400 MHz, Chloroform-d) δ 7.55 (d, J=5.3 Hz, 1H), 7.24 (s, 1H), 7.12 (d, J=5.3 Hz, 1H), 6.45 (d, J=2.4 Hz, 1H), 6.40 (dd, J=8.2, 2.4 Hz, 1H), 4.57 (dd, J=5.9, 1.5 Hz, 4H), 3.88 (dd, J=14.0, 6.0 Hz, 1H), 3.82 (s, 3H), 3.78 (s, 3H), 3.56 (dd, J=14.1, 5.8 Hz, 1H), 1.92 (s, 3H), 1.78 (dq, J=15.1, 8.6, 7.8 Hz, 1H), 1.35 (s, 4H), 1.34-1.25 (m, 7H), 0.94-0.86 (m, 3H).

Synthesis of (R)—N-(2-N-(2-aminothieno[3,2-d]pyrimidin-4-yl)amino)hexyl)acetamide (9). To 9b (12.9 mg, 0.03 mmol) was added TFA (3 mL). After 2 h, the reaction mixture was concentrated in vacuo and coevaporated with MeOH (3×20 mL). The residue was suspended in MeOH and filtered. The solution was concentrated in vacuo to afford 9 as its TFA salt. LC/MS (ESI) calculated for C$_{15}$H$_{23}$N$_5$OS: m/z 322.16, found 322.16 [M+H]$^+$; t$_R$=0.92 min. on LC/MS Method A. $^1$H NMR (400 MHz, Methanol-d$_4$) δ 8.09 (d, J=5.4 Hz, 1H), 7.19 (d, J=5.4 Hz, 1H), 4.08 (d, J=13.7 Hz, 1H), 3.77 (d, J=13.7 Hz, 1H), 2.09-2.01 (m, 1H), 1.91 (s, 3H), 1.58-1.47 (m, 1H), 1.35-1.29 (m, 4H), 1.28 (s, 3H), 0.92 (t, J=6.8 Hz, 3H). $^{19}$F NMR (377 MHz, Methanol-d$_4$) δ −77.85.

Example 10

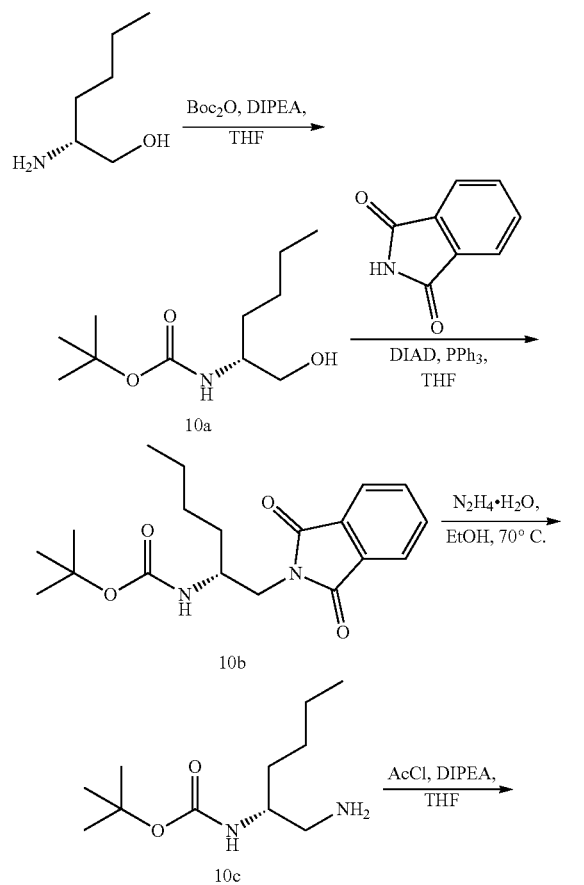

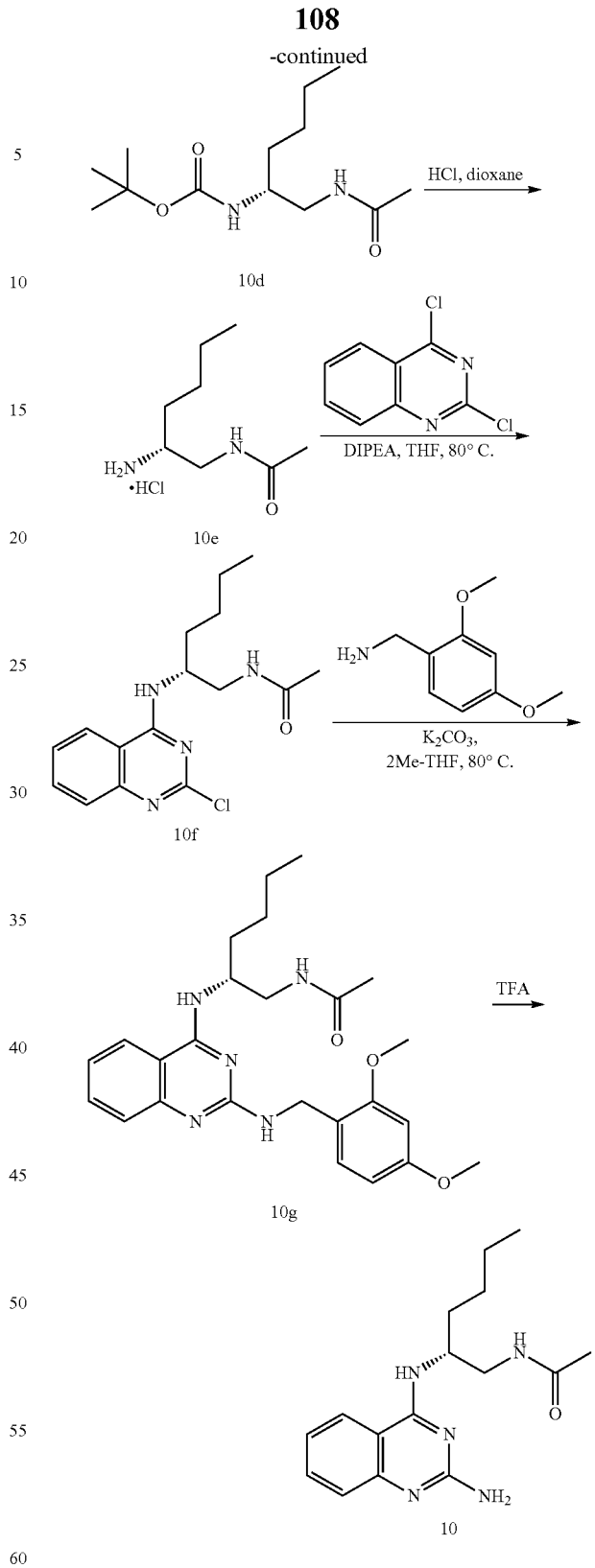

Synthesis of tert-butyl (R)-(1-hydroxyhexan-2-yl)carbamate (18a). To a solution of (R)-norleucinol (4.0 g, 34.1 mmol, supplied by Astatech Inc.) in DCM (150 mL) was added di-tert-butyl dicarbonate (14.9 g, 68.3 mmol) followed by N,N-diisopropylethylamine (6.0 mL, 34.1 mmol). After stirring at 40° C. for 18 h, the reaction was cooled to ambient temperature, washed with water (75 mL) and brine (75 mL), dried over $Na_2SO_4$, and concentrated in vacuo. The residue was subjected to silica gel chromatography equipped with an ELSD eluting with hexanes-EtOAc to provide 10a. LC/MS (ESI) calculated for $C_{11}H_{23}NO_3$: m/z 218.17, found 217.70 [M+H]$^+$; $t_R$=0.93 min. on LC/MS Method A. $^1$H NMR (400 MHz, Chloroform-d) δ 4.59 (s, 1H), 3.67 (dd, J=10.5, 3.4 Hz, 1H), 3.61 (s, 1H), 3.53 (dd, J=10.5, 5.7 Hz, 1H), 2.18 (s, 1H), 1.57-1.47 (m, 1H), 1.45 (s, 9H), 1.43-1.38 (m, 1H), 1.39-1.29 (m, 4H), 0.97-0.83 (m, 3H).

Synthesis of tert-butyl (R)-(1-(1,3-dioxoisoindolin-2-yl)hexan-2-yl)carbamate (10b). To a solution of 10a (7.10 g, 32.1 mmol) in THF (33 mL) was added triphenylphosphine (10.5 g, 42.5 mmol), followed by phthalimide (6.3 g, 42.5 mmol) and diisopropyl azodicarboxylate (8.4 mL, 42.5 mmol). After stirring at ambient temperature for 18 h, the reaction was diluted with EtOAc (75 mL), washed with water (75 mL) and brine (100 mL), dried over $Na_2SO_4$, then filtered and concentrated in vacuo. The residue was then triturated with ether and filtered and concentrated in vacuo several times. The residue was subjected to silica gel chromatography eluting with hexanes-EtOAc to provide 10b. LC/MS (ESI) calculated for $C_{19}H_{26}N_2O_4$: m/z 347.19, found 346.37 [M+H]$^+$; $t_R$=1.01 min. on LC/MS Method A. $^1$H NMR (400 MHz, Chloroform-d) δ 7.84 (dd, J=5.5, 3.1 Hz, 2H), 7.70 (dd, J=5.3, 3.0 Hz, 2H), 4.52 (d, J=9.5 Hz, 1H), 3.97 (s, 1H), 3.79-3.53 (m, 2H), 1.64-1.27 (m, 6H), 1.22 (s, 9H), 0.91 (t, J=7.1 Hz, 3H).

Synthesis of tert-butyl (R)-(1-aminohexan-2-yl)carbamate (10c). To a solution of 10b (1.21 g, 3.49 mmol) in EtOH (35 mL) was added hydrazine monohydrate (0.34 mL, 6.98 mmol). After stirring at 80° C. for 18 h, the reaction was cooled to ambient temperature, diluted with ether (50 mL), filtered, rinsed with ether (30 mL), and concentrated in vacuo to yield 10c. $^1$H NMR (400 MHz, Chloroform-d) δ 3.52 (s, 1H), 2.78 (dd, J=13.1, 4.5 Hz, 1H), 2.63 (dd, J=13.1, 6.8 Hz, 1H), 1.44 (s, 9H), 1.40-1.27 (m, J=3.7 Hz, 6H), 0.89 (t, J=6.3 Hz, 3H).

Synthesis of tert-butyl (R)-(1-acetamidohexan-2-yl)carbamate (10d). To a solution of 10c (0.68 g, 3.15 mmol) in THF (100 mL) was added N,N-diisopropylethylamine (0.88 mL, 6.31 mmol) followed by acetyl chloride (0.337 mL, 4.72 mmol). After stirring at ambient temperature for 1 h, the reaction was diluted with EtOAc (120 mL), washed with sat. sodium bicarbonate solution (150 mL) and brine (75 mL), dried over $Na_2SO_4$, then filtered and concentrated in vacuo to afford crude 10d. LC/MS (ESI) calculated for $C_{13}H_{26}N_2O_3$: m/z 259.19, found 258.81 [M+H]$^+$; $t_R$=0.90 min. on LC/MS Method A. $^1$H NMR (400 MHz, Chloroform-d) δ 3.72-3.50 (m, 1H), 3.30-3.09 (m, 2H), 1.90 (s, 3H), 1.38 (s, 9H), 1.34-1.09 (m, 6H), 0.83 (t, J=6.8, 6.1 Hz, 3H).

Synthesis of (R)—N-(2-aminohexyl)acetamide (10e). To a solution of 10d (813 mg, 3.15 mmol) in DCM (6 mL) was added HCl solution (3.2 mL, 4 M in dioxane). After stirring at ambient temperature for 18 h, the solution was concentrated in vacuo to afford crude 10e as an HCL salt. LC/MS (ESI) calculated for $C_8H_{18}N_2O$: m/z 159.14, found 159.98 [M+H]$^+$; $t_R$=0.49 min. on LC/MS Method A. $^1$H NMR (400 MHz, Chloroform-d) δ 3.14-3.04 (m, 1H), 2.10 (s, 3H), 1.80-1.61 (m, 2H), 1.29-1.23 (m, 4H), 0.96-0.82 (m, 3H).

Synthesis of (R)—N-(2-((2-((2,4-dimethoxybenzyl)amino)quinazolin-4-yl)amino)hexyl)acetamide (10g). To a solution of 2,4-dichloroquinazoline (100 mg, 0.502 mmol) and 10e (107.6 mg, 0.502 mmol) in THF (2 mL) was added N,N-diisopropylethylamine (0.18 mL, 1.0 mmol). After stirring at 75° C. for 18 h, 2,4-dimethoxybenzylamine (0.17 mL, 1.1 mmol) was added followed by N,N-diisopropylethylamine (0.20 mL, 1.1 mmol). The reaction was heated in a microwave reactor at 125° C. for 30 min, the solution was diluted with EtOAc (60 mL), washed with water (50 mL) and brine (60 mL), dried of $Na_2SO_4$, filtered and concentrated in vacuo. The residue was subjected to silica gel chromatography eluting in hexanes-EtOAc followed by EtOAc-MeOH to provide 10g as an isomeric mixture. LC/MS (ESI) calculated for $C_{25}H_{33}N_5O_3$: m/z 452.26, found 452.37 [M+H]$^+$; $t_R$=1.01 min. on LC/MS Method A. $^1$H NMR (400 MHz, Chloroform-d) δ 7.62 (t, J=7.7 Hz, 1H), 7.51 (d, J=7.9 Hz, 1H), 7.45 (d, J=8.4 Hz, 1H), 7.21 (t, J=9.3 Hz, 1H), 7.12 (t, J=7.5 Hz, 1H), 6.44 (d, J=2.3 Hz, 1H), 6.39 (dd, J=8.1, 2.3 Hz, 1H), 4.59 (d, J=5.8 Hz, 2H), 4.41-4.13 (m, 1H), 3.84 (d, J=2.8 Hz, 3H), 3.77 (d, J=1.5 Hz, 3H), 3.66-3.51 (m, 1H), 3.37 (dt, J=15.0, 4.2 Hz, 1H), 1.94 (dd, J=29.2, 2.2 Hz, 3H), 1.75-1.64 (m, 1H), 1.63-1.52 (m, 1H), 1.47-1.34 (m, 2H), 1.33-1.28 (m, 2H), 0.90 (dt, J=29.0, 7.1 Hz, 3H).

Synthesis of (R)—N-(2-((2-aminoquinazolin-4-yl)amino)hexyl)acetamide (10). To 10g (67.3 mg, 0.15 mmol) was added TFA (3 mL). After 90 min, the reaction mixture was concentrated in vacuo and coevaporated with MeOH (3×20 mL). The residue was purified by preparative HPLC (Gemini 10u C18 110A, Axia; 20% aq. acetonitrile—40% aq. acetonitrile, over 10 min. gradient) to afford 10 as its TFA salt. LC/MS (ESI) calculated for $C_{16}H_{23}N_5O$: m/z 302.19, found 302.24 [M+H]$^+$; $t_R$=0.64 min. on LC/MS Method A. $^1$H NMR (400 MHz, Methanol-d$_4$) δ 8.03 (dt, J=8.4, 1.0 Hz, 1H), 7.77 (ddt, J=8.4, 7.2, 1.1 Hz, 1H), 7.42 (tdd, J=7.2, 2.4, 1.2 Hz, 2H), 4.23 (tt, J=9.1, 4.6 Hz, 1H), 3.82 (dd, J=13.4, 4.6 Hz, 1H), 3.58 (dd, J=13.6, 8.4 Hz, 1H), 1.92 (s, 3H), 1.63 (ddt, J=14.0, 9.3, 4.8 Hz, 1H), 1.51 (dtd, J=13.8, 9.3, 4.1 Hz, 1H), 1.46-1.28 (m, 4H), 0.93 (t, J=6.6 Hz, 3H). $^{19}$F NMR (377 MHz, Methanol-d$_4$) δ -77.86.

Example 11

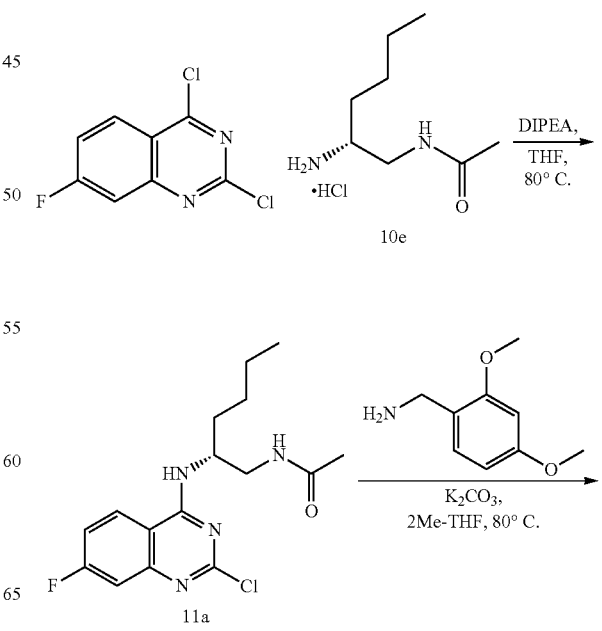

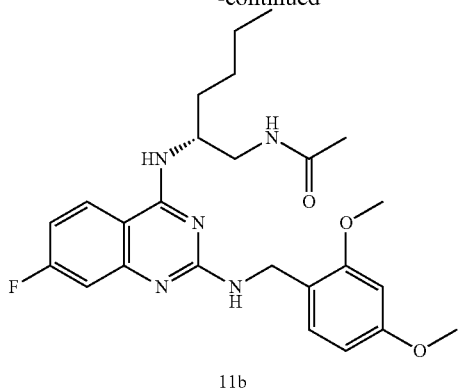

11b

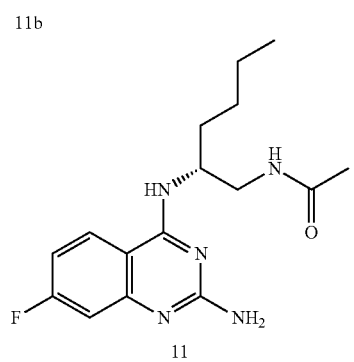

11

Synthesis of (R)—N-(2-N-(2-((2,4-dimethoxybenzyl)amino)-7-fluoroquinazolin-4-yl)amino)hexyl)acetamide (11b). To a solution of 2,4-dichloro-7-fluoroquinazoline (100 mg, 0.46 mmol) and 10e (90 mg, 0.46 mmol) in THF (2 mL) was added N,N-diisopropylethylamine (0.32 mL, 1.8 mmol). After stirring at 75° C. for 18 h, 2,4-dimethoxybenzylamine (0.21 mL, 1.4 mmol) was added followed by N,N-diisopropylethylamine (0.25 mL, 1.4 mmol). The reaction was heated in a microwave reactor at 125° C. for 30 min, diluted with EtOAc (70 mL), washed with water (50 mL) and brine (50 mL), dried of Na$_2$SO$_4$, filtered, and concentrated in vacuo. The residue was subjected to silica gel chromatography eluting in hexanes-EtOAc followed by EtOAc-MeOH to provide 11b (LC/MS (ESI) calculated for C$_{25}$H$_{32}$FN$_5$O$_3$: m/z 470.25, found 470.34 [M+H]$^+$; t$_R$=0.99 min. on LC/MS Method A. $^1$H NMR (400 MHz, Chloroform-d) δ 7.55 (dd, J=9.0, 6.0 Hz, 1H), 7.24 (d, J=8.6 Hz, 1H), 7.03 (d, J=11.1 Hz, 1H), 6.79 (t, J=8.9 Hz, 1H), 6.45 (d, J=2.3 Hz, 1H), 6.40 (dd, J=8.2, 1.9 Hz, 1H), 4.59 (d, J=5.8 Hz, 2H), 3.83 (s, 3H), 3.78 (s, 3H), 3.75-3.68 (m, 1H), 3.62 (d, J=11.3 Hz, 1H), 3.35 (d, J=14.1 Hz, 1H), 1.85 (s, 3H), 1.74-1.64 (m, 1H), 1.64-1.52 (m, 1H), 1.40-1.29 (m, 4H), 0.94-0.84 (m, 3H).

Synthesis of (R)—N-(2-((2-amino-7-fluoroquinazolin-4-yl)amino)hexyl)acetamide (11). To 11b (73.7 mg, 0.16 mmol) was added TFA (3 mL). After 90 min, the reaction mixture was concentrated in vacuo and coevaporated with MeOH (3×20 mL). The residue was purified by preparative HPLC (Gemini 10u C18 110A, Axia; 20% aq. acetonitrile—40% aq. acetonitrile, over 10 min. gradient) to afford 11 as its TFA salt. LC/MS (ESI) calculated for C$_{16}$H$_{22}$FN$_5$O: m/z 320.18, found 320.28 [M+H]$^+$; t$_R$=0.70 min. on LC/MS Method A. $^1$H NMR (400 MHz, Methanol-d$_4$) δ 8.10 (dd, J=9.0, 5.4 Hz, 1H), 7.18 (ddd, J=18.6, 9.1, 2.5 Hz, 2H), 4.22 (dq, J=12.9, 4.5 Hz, 1H), 3.81 (dd, J=13.4, 4.6 Hz, 1H), 3.56 (dd, J=13.4, 8.3 Hz, 1H), 1.92 (s, 3H), 1.69-1.56 (m, 1H), 1.56-1.45 (m, 1H), 1.45-1.29 (m, 4H), 0.93 (t, J=7.0 Hz, 3H). $^{19}$F NMR (377 MHz, Methanol-d$_4$) δ −77.85, −103.53-104.38 (m).

Example 12

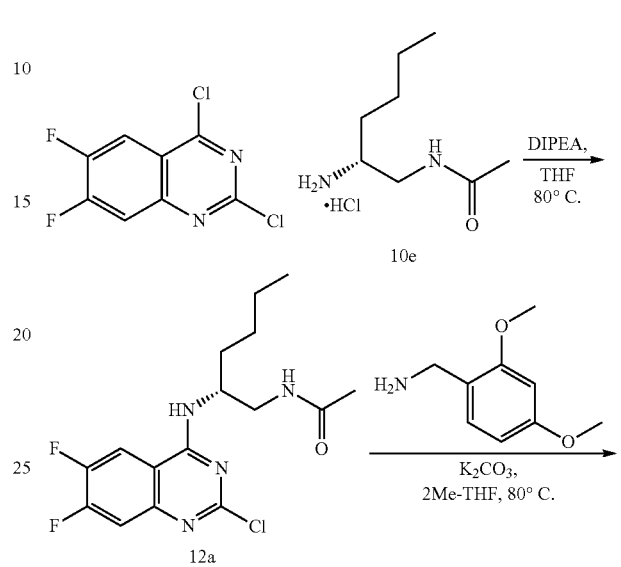

10e

12a

12b

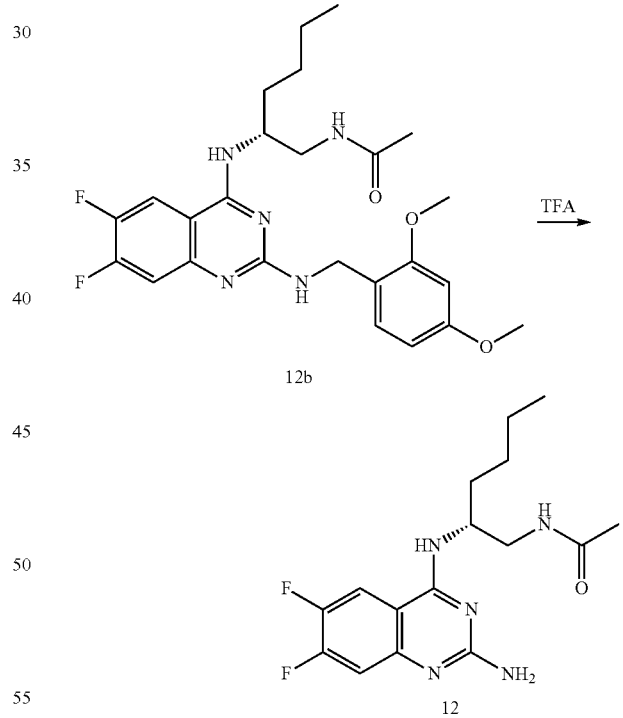

12

Synthesis of (R)—N-(2-((2-chloro-6,7-difluoroquinazolin-4-yl)amino)hexyl)acetamide (12a). To a solution of 2,4-dichloro-6,7-difluoroquinazoline (1.00 g, 0.43 mmol) and 10e (91 mg, 0.47 mmol) in THF (2.4 mL) was added N,N-diisopropylethylamine (0.15 mL, 0.85 mmol). After stirring at ambient temperature for 18 h, the solution was diluted with EtOAc (75 mL), washed with water (50 mL) and brine (60 mL), dried over Na$_2$SO$_4$, filtered and concentrated in vacuo to provide crude 12a. LC/MS (ESI) calculated for C$_{16}$H$_{19}$ClF$_2$N$_4$O: m/z 357.12, found 357.23

[M+H]+; $t_R$=1.09 min. on LC/MS Method A. $^1$H NMR (400 MHz, Chloroform-d) δ 7.46 (dd, J=10.7, 7.6 Hz, 1H), 7.31 (dd, J=15.2, 8.7 Hz, 1H), 4.47-4.30 (m, 1H), 3.66 (dt, J=9.2, 2.9 Hz, 1H), 3.39 (ddd, J=14.4, 5.1, 3.1 Hz, 1H), 1.99 (s, 3H), 1.74 (t, J=9.0 Hz, 1H), 1.59 (t, J=6.2 Hz, 1H), 1.40-1.31 (m, 4H), 0.86-0.77 (m, 3H).

Synthesis of (R)—N-(2-N-(2-((2,4-dimethoxybenzyl)amino)-6,7-difluoroquinazolin-4-yl)amino)hexyl)acetamide (12b). To a solution of 12a (152 mg, 0.43 mmol) in THF (3 mL) was added 2,4-dimethoxybenzylamine (0.19 mL, 1.28 mmol) followed by N,N-diisopropylethylamine (0.22 mL, 1.28 mmol). The reaction was heated in a microwave reactor at 140° C. for 1 h, the solution was diluted with hexanes-EtOAc (1:3, 75 mL), washed with water (2×50 mL) and brine (75 mL), dried over Na$_2$SO$_4$, filtered and concentrated in vacuo. The residue was subjected to silica gel chromatography eluting in hexanes-EtOAc followed by EtOAc-MeOH to provide 12b. LC/MS (ESI) calculated for C$_{25}$H$_{31}$F$_2$N$_5$O$_3$: m/z 488.24, found 488.33 [M+H]+; $t_R$=1.16 min. on LC/MS Method A. $^1$H NMR (400 MHz, Chloroform-d) δ 7.45 (dt, J=10.8, 7.7 Hz, 1H), 7.23 (d, J=8.3 Hz, 1H), 7.18-7.07 (m, 1H), 6.45 (d, J=2.3 Hz, 1H), 6.40 (dd, J=8.2, 2.4 Hz, 1H), 4.56 (dd, J=5.9, 3.0 Hz, 2H), 4.41-4.30 (m, 1H), 3.82 (s, 3H), 3.77 (s, 3H), 3.56-3.45 (m, 1H), 3.33 (dt, J=14.0, 4.1 Hz, 1H), 1.83 (s, 3H), 1.76-1.61 (m, 1H), 1.60-1.49 (m, 1H), 1.36-1.28 (m, 4H), 0.87 (t, J=6.8 Hz, 3H).

Synthesis of (R)—N-(2-((2-amino-6,7-difluoroquinazolin-4-yl)amino)hexyl)acetamide (12). To 12b (26.0 mg, 0.05 mmol) was added TFA (3 mL). After 90 min, the reaction mixture was concentrated in vacuo and coevaporated with MeOH (3×20 mL. The residue was suspended in MeOH and filtered. The solution was concentrated in vacuo to afford 12 as its TFA salt. LC/MS (ESI) calculated for C$_{16}$H$_{21}$F$_2$N$_5$O: m/z 338.17, found 338.30 [M+H]+; $t_R$=0.74 min. on LC/MS Method A. $^1$H NMR (400 MHz, Methanol-d$_4$) δ 8.21 (dd, J=10.9, 7.9 Hz, 1H), 7.37 (dd, J=10.6, 6.8 Hz, 1H), 4.66 (qd, J=7.4, 4.1 Hz, 1H), 3.57 (dd, J=13.9, 4.2 Hz, 1H), 3.30-3.20 (m, 1H), 1.88 (s, 3H), 1.70 (pd, J=7.8, 6.9, 3.2 Hz, 2H), 1.46-1.31 (m, 4H), 0.99-0.85 (m, 3H). $^{19}$F NMR (377 MHz, Methanol-d$_4$) δ −77.76, −126.95-−128.53 (m), −142.19 (ddd, J=21.6, 11.0, 7.0 Hz).

Example 13

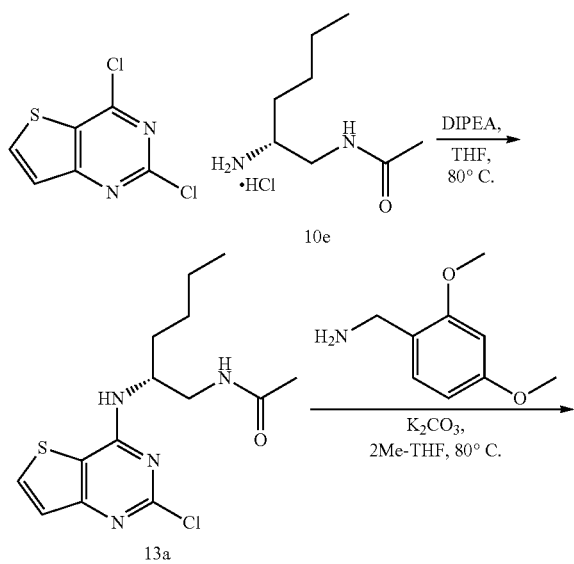

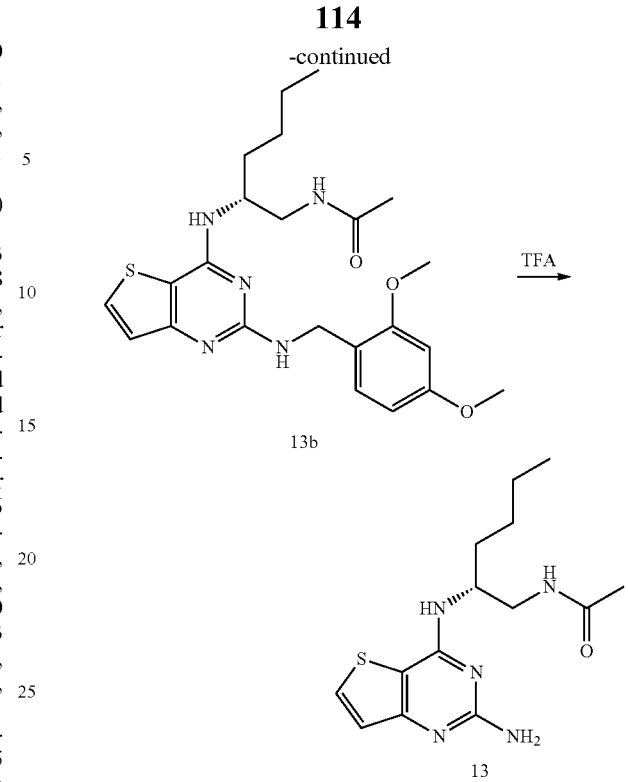

Synthesis of (R)—N-(2-((2-((2,4-dimethoxybenzyl)amino)thieno[3,2-d]pyrimidin-4-yl)amino)hexyl)acetamide (13b). To a solution of 2,4-dichlorothieno[3,2-d]pyrimidine (100 mg, 0.49 mmol) and 10a (77 mg, 0.49 mmol) in THF (3 mL) was added N,N-diisopropylethylamine (0.340 mL, 1.951 mmol). After stirring at 80° C. for 18 h, 2,4-dimethoxybenzylamine (0.293 mL, 1.951 mmol) was added followed by N,N-diisopropylethylamine (0.255 mL, 1.45 mmol). The reaction was heated in a microwave reactor at 155° C. for 2 h, diluted with EtOAc (60 mL) and washed with water (60 mL). The aqueous was extracted with EtOAc (50 mL), and the combined organic layers were washed with brine (60 mL), dried over Na$_2$SO$_4$, and concentrated in vacuo. The residue was subjected to silica gel chromatography, eluting in hexanes-EtOAc followed by EtOAc-MeOH to provide 13b as an isomeric mixture. LC/MS (ESI) calculated for C$_{23}$H$_{31}$N$_5$O$_3$S: m/z 458.22, found 458.30 [M+H]+; $t_R$=0.93 min. on LC/MS Method A. $^1$H NMR (400 MHz, Chloroform-d) δ 7.56-7.49 (m, 1H), 7.25-7.21 (m, 1H), 7.09 (dd, J=5.4, 2.5 Hz, 1H), 6.45 (d, J=2.4 Hz, 1H), 6.40 (dd, J=8.2, 2.4 Hz, 1H), 4.67-4.46 (m, 2H), 4.45-4.29 (m, 1H), 3.82 (s, 3H), 3.78 (s, 3H), 3.75-3.63 (m, 1H), 3.46-3.34 (m, 1H), 1.80 (s, 3H), 1.65-1.43 (m, 2H), 1.40-1.29 (m, 4H), 0.94-0.84 (m, 3H).

Synthesis of (R)—N-(2-N-(2-aminothieno[3,2-d]pyrimidin-4-yl)amino)hexyl)acetamide (13). To 13b (46.4 mg, 0.10 mmol) was added TFA (3 mL). After 90 min, the reaction mixture was concentrated in vacuo and coevaporated with MeOH (3×20 mL). The residue was purified by preparative HPLC (Gemini 10u C18 110A, Axia; 20% aq. acetonitrile—40% aq. acetonitrile, over 10 min. gradient) to afford 13 as its TFA salt. LC/MS (ESI) calculated for C$_{14}$H$_{21}$N$_5$OS: m/z 308.15, found 308.20 [M+H]+; $t_R$=0.65 min. on LC/MS Method A. $^1$H NMR (400 MHz, Methanol-d$_4$) δ 8.07 (d, J=5.4 Hz, 1H), 7.17 (d, J=5.4 Hz, 1H), 4.17 (ddt, J=9.5, 7.7, 4.7 Hz, 1H), 3.79 (dd, J=13.5, 4.8 Hz, 1H), 3.50 (dd, J=13.5, 7.7 Hz, 1H), 1.91 (s, 3H), 1.60 (ddd, J=13.8, 9.3, 4.5 Hz, 1H), 1.53-1.44 (m, 1H), 1.44-1.27 (m, 5H), 0.92 (t, J=6.9 Hz, 3H). $^{19}$F NMR (377 MHz, Methanol-d$_4$) δ −77.89.

Example 14

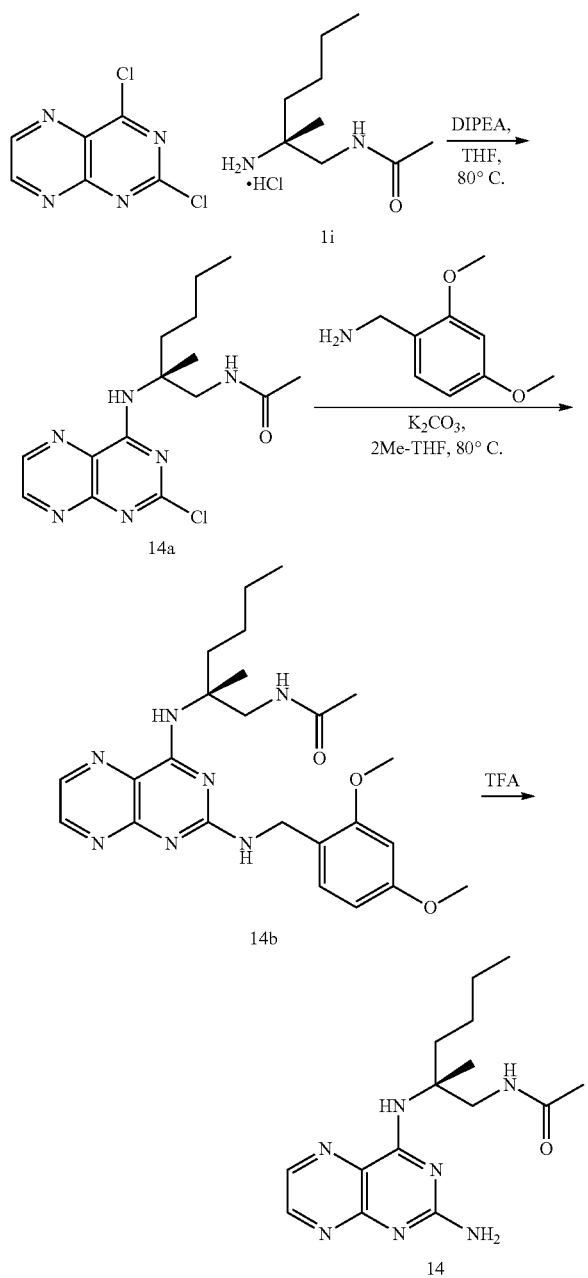

Synthesis of (R)—N-(2-((2-((2,4-dimethoxybenzyl)amino)pteridin-4-yl)amino)-2-methylhexyl)acetamide (14b). To a solution of 1i (100 mg, 0.58 mmol) and 2,4-dichloropteridine (96 mg, 0.58 mmol, supplied by AstaTech, Inc.) in THF (2.5 mL) was added N,N-diisopropylethylamine (0.25 mL, 1.9 mmol). The mixture was heated in a microwave reactor at 100° C. for 30 min. To the mixture was then added 2,4-dimethoxybenzylamine (0.15 mL, 0.96 mmol) and heated in a microwave reactor at 120° C. for 30 min. The reaction was diluted with EtOAc (15 mL), washed with water (15 mL) and brine (15 mL), dried over Na$_2$SO$_4$, then filtered and concentrated in vacuo. The residue was subjected to silica gel chromatography eluting with hexanes-EtOAc followed by EtOAc-MeOH to provide 14b. LC/MS (ESI) calculated for C$_{24}$H$_{33}$N$_7$O$_3$: m/z 468.26, found 468.35 [M+H]$^+$; t$_R$=0.96 min. on LC/MS Method A. $^1$H NMR (400 MHz, Chloroform-d) δ 8.75-8.25 (m, 1H), 8.10 (d, J=14.5 Hz, 1H), 7.24 (dd, J=83.8, 8.2 Hz, 1H), 7.08-6.86 (m, 1H), 6.52-6.29 (m, 2H), 4.63 (d, J=26.6 Hz, 2H), 3.83 (s, 3H), 3.77 (d, J=8.0 Hz, 3H), 3.74-3.64 (m, 2H), 1.95 (d, J=24.8 Hz, 3H), 1.63 (t, J=12.8 Hz, 1H), 1.39 (s, 3H), 1.34-1.16 (m, 5H), 0.90-0.81 (m, 3H).

Synthesis of (R)—N-(2-((2-aminopteridin-4-yl)amino)-2-methylhexyl)acetamide (14). To 14b (52.2 mg, 0.11 mmol) was added TFA (3 mL). After 5 h, the reaction mixture was concentrated in vacuo and coevaporated with MeOH (3×20 mL). The residue was suspended in MeOH and filtered. The solution was concentrated in vacuo to afford as its TFA salt. LC/MS (ESI) calculated for C$_{15}$H$_{23}$N$_7$O: m/z 318.20, found 318.45 [M+H]$^+$; t$_R$=0.67 min. on LC/MS Method A. $^1$H NMR (400 MHz, Methanol-d$_4$) δ 8.77 (d, J=2.4 Hz, 2H), 8.65 (d, J=2.3 Hz, 1H), 3.93 (d, J=14.1 Hz, 1H), 3.52 (d, J=14.1 Hz, 1H), 2.25-2.12 (m, 1H), 1.96 (s, 4H), 1.56 (s, 3H), 1.36 (td, J=8.4, 6.9, 4.8 Hz, 4H), 0.96-0.87 (m, 3H).

HPLC Methods

Method for LC/MS HPLC (Method A): HPLC LC/MS chromatograms were generated using a Thermo Scientific LCQ LC/MS system eluting with a Kinetex 2.6u C18 100 A, 5×30 mm HPLC column, using a 1.85 minute gradient elution from 2% aq. acetonitrile—98% aq. acetonitrile with 0.1% formic acid modifier.

Method for LC/MS HPLC (Method B): HPLC LC/MS chromatograms were generated using a Thermo Scientific LCQ LC/MS system eluting with a Kinetex 2.6u C18 100 A, 5×30 mm HPLC column, using a 2.85 minute gradient elution from 2% aq. acetonitrile—98% aq. acetonitrile with 0.1% formic acid modifier.

Cells and Reagents

Cryopreserved human PBMCs isolated from healthy donors were purchased from StemCell Technologies (Vancouver, Canada). Cell culture medium used was RPMI with L-Glutamine (Mediatech, Manassas, Va.) supplemented with 10% fetal bovine serum (Hyclone, GE Healthcare, Logan, Utah) and Penicillin-Streptomycin (Mediatech). Human TNFα, IL12p40, and IFNα2a 384-well Assay capture plates, standards, buffers and processing reagents were obtained from MesoScale Discovery Technologies (MSD; Rockville, Md.).

Cryopreserved human PBMCs (1×10e8 cells/ml) were thawed at 37° C. and resuspended in 25 mL warm cell culture medium. The cells were pelleted at 200×g (Beckman Avanti J-E) for 5 min and resuspended in 20 mL of fresh culture media. Cells were counted using a Cellometer (Nexcelcom Bioscience), adjusted to 2×10e6 cells, and incubated for 2 hours in an incubator set at 37° C., 5% CO2 to recover from cryopreservation. Compounds were serially diluted in DMSO at half-log steps to generate a 10-point dose range. Using a Bravo pipette equipped with a 384 well head (Agilent), 0.4 μL of compound was transferred to each well of a 384 well black, clear bottom plate (Greiner Bio-One, Germany) containing 30 μL of cell culture medium. Recovered PBMCs were then dispensed into the assay plate at 50 μL per well (100 k cells/well) using the MicroFlow multichannel dispenser (Biotek). Final DMSO concentration was 0.5%. DMSO was used as the negative control. The plates were incubated for 24 hours at 37° C. PBMCs in the assay plate were pelleted by centrifugation (Beckman Avanti J-E) at 200×g for 5 min.

Using a Biomek FX 384 well pipetting station (Beckman), conditioned culture medium (CCM) from the assay plate was transferred to MSD capture plates customized for each cytokine. For IFNα and IL12-p40 detection, 254, and 204, of CCM were added directly to each capture plate, respectively. For TNFα detection, CCM was diluted 1:9 in fresh culture medium, and 204, of diluted CCM was used. Serially diluted calibration standards for each cytokine were used to generate standard curves and establish assay linearity. The plates were sealed and incubated overnight at 4° C. in a plate shaker (Titer Plate) set at 200 rpm. On the following day, antibodies specific for each cytokine were diluted 1:50 in MSD Diluent 100 antibody dilution buffer. Diluted antibodies were added to corresponding capture plates at 10 µL/well, and incubated at RT for 1-2 hrs in the shaker. The plates were washed with PBST buffer (3×, 60 µl/well) using a Biotek Multiflow plate washer. MSD Read Buffer diluted to 2× in deionized water and 35 µL/well was added via Biomek FX instrument. The plates were read immediately in a MSD6000 reader. Data were normalized to positive and negative controls in each assay plate. $AC_{50}$ values represent compound concentrations at half-maximal effect based on normalized percent activation and calculated by non-linear regression using Pipeline Pilot software (Accelrys, San Diego, Calif.).

Results of the cytokine profiling assay are reported in Table 1.

| Example # | TNFa $AC_{50}$ (nM) | IL12p40 $AC_{50}$ (nM) | IFNa $AC_{50}$ (nM) |
|---|---|---|---|
| 1 | 62.95 | 52.19 | >50000 |
| 2 | 40.87 | 8.83 | >50000 |
| 3 | 811.93 | 703.37 | >50000 |
| 4 | 110.35 | 131.73 | >50000 |
| 5 | 542.65 | 363.52 | >50000 |
| 6 | 10177 | 9580.7 | >50000 |
| 7 | 2496 | 2323.2 | >50000 |
| 8 | 4612.3 | 3628 | >50000 |
| 9 | 1100 | 854.68 | >50000 |
| 10 | 1674 | 1315 | >50000 |
| 11 | 561 | 433 | >50000 |
| 12 | 10192 | 11998 | >50000 |
| 13 | 9519 | 8288 | >50000 |
| 14 | 1914 | 1896 | >50000 |

The present disclosure provides reference to various embodiments and techniques. However, it should be understood that many variations and modifications may be made while remaining within the spirit and scope of the present disclosure.

What is claimed is:

1. A compound of Formula I

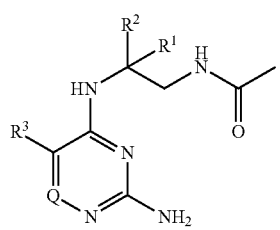

Formula I or a pharmaceutically acceptable salt thereof, wherein:
$R^1$ is —H, $C_{1-4}$ alkyl, or $C_{1-4}$ haloalkyl;
$R^2$ is $C_{1-6}$ alkyl or $C_{1-6}$ haloalkyl;
Q is $CR^4$;
$R^3$ and $R^4$ are taken together to form a 6-membered cycloalkyl, wherein:
the 6-membered cycloalkyl is optionally substituted with 1 to 3 $R^5$;
each $R^5$ is independently halogen, —OH, —NH$_2$, —CN, $C_{1-4}$ alkyl optionally substituted with 1 to 3 $R^Z$, $C_{1-4}$ haloalkyl, $C_{1-4}$ alkoxy, —C(O)OH, —C(O)C$_{1-4}$ alkyl, —C(O)OC$_{1-4}$ alkyl, —C(O)NH$_2$, —C(O)NH(C$_{1-4}$ alkyl), —C(O)N(C$_{1-4}$ alkyl)$_2$, —N(H)C(O)C$_{1-4}$ alkyl, —S(O)$_2$C$_{1-4}$ alkyl, or 5 to 6 membered heteroaryl having 1 to 3 heteroatoms selected from oxygen, nitrogen, and sulfur optionally substituted with 1 to 3 $R^Z$; and
each $R^Z$ is independently —NH$_2$, $C_{1-4}$ alkyl, halogen, —CN, —OC$_{1-4}$ alkyl, $C_{1-4}$ haloalkyl, or —C(O)NH$_2$.

2. The compound of claim 1, or a pharmaceutically acceptable salt thereof, wherein $R^1$ is —H or $C_{1-4}$ alkyl.

3. The compound of claim 1, or a pharmaceutically acceptable salt thereof, wherein $R^1$ is methyl.

4. The compound of claim 1, or a pharmaceutically acceptable salt thereof, wherein $R^2$ is $C_{3-6}$ alkyl.

5. The compound of claim 1, or a pharmaceutically acceptable salt thereof, wherein
$R^1$ is —H or $C_{1-4}$ alkyl;
$R^2$ is $C_{3-6}$ alkyl; and
$R^3$ and $R^4$ are taken together to form a 6-membered cycloalkyl.

6. The compound of claim 1, or a pharmaceutically acceptable salt thereof, wherein Formula I is represented by Formula II

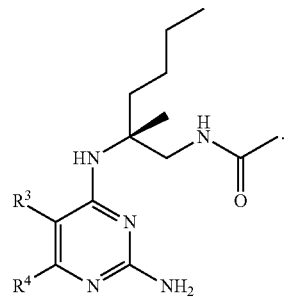

Formula II

7. The compound of claim 1, or a pharmaceutically acceptable salt thereof, wherein Formula I is represented by Formula III

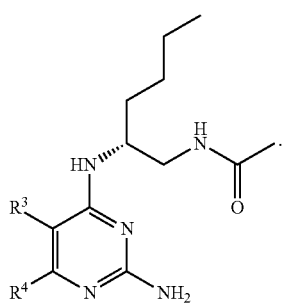

Formula III

8. The compound of claim 1, having the structure

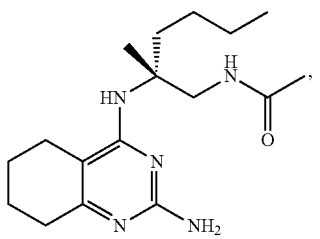 [SMILES: CCCC[C@](C)(CNC(C)=O)Nc1nc(N)nc2c1CCCC2]

or a pharmaceutically acceptable salt thereof.

9. A pharmaceutical composition comprising a compound of claim 1, or a pharmaceutically acceptable salt thereof, and a pharmaceutically acceptable excipient.

10. The pharmaceutical composition of claim 9, further comprising one or more additional therapeutic agents.

11. A kit comprising a compound of claim 1, or a pharmaceutically acceptable salt thereof.

* * * * *